(12) United States Patent
Dickhaut et al.

(10) Patent No.: US 9,179,680 B2
(45) Date of Patent: Nov. 10, 2015

(54) SUBSTITUTED PYRIMIDINIUM COMPOUNDS FOR COMBATING ANIMAL PESTS

(75) Inventors: Joachim Dickhaut, Heidelberg (DE); Florian Kaiser, Mannheim (DE); Arun Narine, Mannheim (DE); Wolfgang Von Deyn, Neustadt (DE); Karsten Koerber, Eppelheim (DE); Prashant Deshmukh, Mannheim (DE); Gemma Veitch, Basel (CH); Nina Gertrud Bandur, Mannheim (DE); Juergen Langewald, Mannheim (DE); Deborah L. Culbertson, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/009,601

(22) PCT Filed: Apr. 4, 2012

(86) PCT No.: PCT/EP2012/056209
§ 371 (c)(1),
(2), (4) Date: Oct. 3, 2013

(87) PCT Pub. No.: WO2012/136724
PCT Pub. Date: Oct. 11, 2012

(65) Prior Publication Data
US 2014/0031206 A1 Jan. 30, 2014

Related U.S. Application Data

(60) Provisional application No. 61/472,221, filed on Apr. 6, 2011, provisional application No. 61/525,857, filed on Aug. 22, 2011.

(30) Foreign Application Priority Data

Apr. 27, 2011 (EP) .................................. 11163813

(51) Int. Cl.
*A01N 43/90* (2006.01)
*C07D 487/04* (2006.01)
*A61K 31/519* (2006.01)
*C07D 471/04* (2006.01)

(52) U.S. Cl.
CPC .............. *A01N 43/90* (2013.01); *A61K 31/519* (2013.01); *C07D 471/04* (2013.01); *C07D 487/04* (2013.01)

(58) Field of Classification Search
None
See application file for complete search history.

(56) References Cited

FOREIGN PATENT DOCUMENTS

| WO | WO 2009/099929 | 8/2009 |
| WO | WO 2011/017334 | 2/2011 |
| WO | WO 2011/017342 | 2/2011 |
| WO | WO 2011/017347 | 2/2011 |
| WO | WO 2011/017351 | 2/2011 |

OTHER PUBLICATIONS

International Search Report dated Jul. 11, 2012, prepared in International Application No. PCT/EP2012/056209.
International Preliminary Report on Patentability dated Aug. 6, 2013, prepared in International Application No. PCT/EP2012/056209.

*Primary Examiner* — Mina Haghighatian
*Assistant Examiner* — Erin Hirt
(74) *Attorney, Agent, or Firm* — Brinks Gilson & Lione

(57) ABSTRACT

Substituted imine compounds of formula (I),

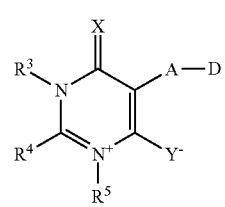

wherein
D is $C(R^2)=N\sim Z-R^1$ or $C(=Y^1)NR^AY^2R^B$
and the other symbols have the meanings given in the description, their N-oxides and salts are useful for combating animal pests.

20 Claims, No Drawings

SUBSTITUTED PYRIMIDINIUM COMPOUNDS FOR COMBATING ANIMAL PESTS

This application is a National Stage application of International Application No. PCT/EP2012/056209, filed Apr. 4, 2012, which claims the benefit of U.S. Provisional Application No. 61/472,221, filed Apr. 6, 2011, and U.S. Provisional Application No. 61/525,857, filed Aug. 22, 2011, the entire contents of which are hereby incorporated herein by reference. This application also claims priority under 35 U.S.C. §119 to European Patent Application No. 11163813.6, filed Apr. 27, 2011, the entire contents of which is hereby incorporated herein by reference.

The invention relates to substituted pyrimidine compounds and salts thereof, to methods for preparing these compounds and to compositions comprising such compounds. The invention also relates to the use of the substituted pyrimidine compounds, of their salts or of compositions comprising them for combating animal pests. Furthermore the invention relates to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

WO 2009/099929, WO 2011/017334, WO 2011/017347, WO 2011/017342 and WO 2011/017351 disclose pesticides having a mesoionic pyrimidine structure. However, the known compounds are not completely satisfactory in many cases, in terms, for example, of application rate, spectrum of activity, duration of activity, tendency to form resistance or economic aspects of the preparation process.

It is therefore a constant object to provide further pesticidal mesoionic pyrimidine compounds which, at least in some aspects, offer advantages over the known compounds.

It has been found that particular mesoionic pyrimidine compounds carrying substituted pyrimidine group are particularly suitable for controlling pests. Accordingly, in one aspect of the invention there is provided a substituted pyrimidine compound of formula (I),

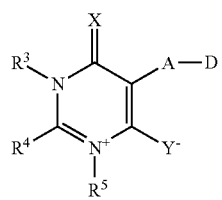
(I)

wherein

D is $C(R^2)=N\sim Z-R^1$ or $C(=Y^1)NR^AY^2R^B$

X is O or S;

Y, $Y^1$, $Y^2$ are independently O or S;

Z is O, $S(O)_n$, N—$R^a$ or a direct bond;

A is phenyl, naphthyl or a 5- or 6-membered heteroaromatic ring system, or a 8-10-membered heteroaromatic bicyclic ring system, each unsubstituted or substituted with up to 6 substituents $R^b$;

$R^A$ is H, $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl or $C_3$-$C_6$-cycloalkenyl, each unsubstituted or substituted with at least one substituent independently selected from $R^r$; or $Q^1$;

$R^B$ is H, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —Si($R^f$)$_3$, —S(O)$_m$$R^h$, —S(O)$_n$N($R^d$)$_2$, —C(=O)OR$^g$, —C(=O)N($R^d$)$_2$, —C(=S)R$^e$, —C(=S)OR$^g$, —C(=S)N($R^d$)$_2$, —C(=NR$^d$)R$^e$, or $Q^1$ $R^1$ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —N($R^d$)$_2$, —N($R^d$)C(=O)R$^e$, —Si($R^f$)$_3$, —OR$^g$, —SR$^g$, —S(O)$_m$R$^h$, —S(O)$_n$N($R^d$)$_2$, —C(=O)R$^e$, —C(=O)OR$^g$, —C(=O)N($R^d$)$_2$, —C(=S)R$^e$, —C(=S)OR$^g$, —C(=S)N($R^d$)$_2$, —C(=NR$^d$)R$^e$, or $Q^1$;

with the proviso that $R^1$ is not —OR$^g$, CN or nitro if Z is O;

$R^2$ is NR$^j$R$^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, C(=O)R$^e$, —C(=O)OR$^g$, —C(=O)N($R^d$)$_2$, C(=S)R$^e$, —C(=S)OR$^g$, —C(=S)N($R^d$)$_2$, C(=NR$^d$)R$^e$, halogen, cyano, O-$Q^1$ or S-$Q^1$;

$R^3$, $R^4$ is each independently, $C_1$-$C_8$-alkyl, $C_2$-$C_8$-alkenyl, $C_2$-$C_8$-alkynyl, $C_3$-$C_{10}$-cycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_3$-$C_8$-cycloalkenyl, $C_1$-$C_8$-alkoxy, $C_3$-$C_8$-cycloalkoxy, $C_4$-$C_{10}$-cycloalkylalkoxy, $C_2$-$C_8$-alkenyloxy, $C_2$-$C_8$-alkynyloxy, $C_1$-$C_8$-alkylthio, $C_1$-$C_8$-alkylsulfinyl, $C_1$-$C_8$-alkylsulfonyl, $C_3$-$C_8$-cycloalkylsulfonyl, cycloalkylalkylthio, $C_4$-$C_{10}$-cycloalkylalkylsulfinyl, $C_4$-$C_{10}$-cycloalkylalkylsulfonyl, $C_2$-$C_8$-alkenylthio, $C_2$-$C_8$-alkenylsulfinyl, $C_2$-$C_8$-alkenylsulfonyl, $C_2$-$C_8$-alkynylthio, $C_2$-$C_8$-alkynylsulfinyl or $C_2$-$C_8$-alkynylsulfonyl, each unsubstituted or substituted with at least one substituent $R^r$; or is halogen, cyano, hydroxy, amino, nitro, $SF_5$, OCN, SCN, CHO, C(=O)OH, C(=O)NH$_2$, C(=S)NH$_2$, SO$_2$NH$_2$, C(=O)R$^l$, C(=O)OR$^l$, NHR$^l$, NR$^j$R$^m$, C(=O)NR$^j$R$^m$, C(=S)NR$^j$R$^m$, SO$_2$NR$^j$R$^m$, OC(=O)R$^m$, OC(=O)OR$^l$, OC(=O)NR$^j$R$^m$, N(R$^m$)C(=O)R$^m$, N(R$^m$)C(=O)OR$^l$, N(R$^n$)C(=O)N(R$^m$)$_2$, NR$^m$SO$_2$R$^l$, NR$^m$SO$_2$N(R$^m$)$_2$, Si($R^f$)$_3$, C(=NR$^m$)R$^m$, C(=NOR$^m$)R$^m$, C(=NNR$^m$$_2$)R$^m$, C(=NN(C(=O)R$^l$)R$^m$)R$^m$, C(=NN(C=O)OR$^l$)(R$^m$)$_2$, ON=C(R$^m$)$_2$, ON(R$^m$)$_2$, S(=O)(=NR$^m$)R$^m$, SO$_2$NR$^m$C(=O)N(R$^m$)$_2$, P(=X$^1$)(R$^l$)$_2$, OP(=X$^1$)R$^l$$_2$, OP(=X$^1$)(OR$^l$)R$^l$, OP(=X$^1$)(OR$^l$)OR$^l$, N=C(R$^m$)$_2$, NR$^m$N=C(R$^m$)$_2$, NR$^m$N(R$^m$)$_2$, NR$^m$C(=X$^2$)N(R$^m$)$_2$, NR$^m$C(=NR$^m$)N(R$^m$)$_2$, NR$^m$NR$^m$C(=X$^1$)N(R$^m$)$_2$, NR$^m$NR$^m$SO$_2$N(R$^m$)$_2$, $Z^1Q^2$ or $Z^1Q^3Z^1Q^2$;

or $R^3$ and $R^4$ together with the contiguous linking nitrogen and carbon atoms form a 5- to 7-membered ring, each ring containing ring members selected from carbon atoms and up to 3 heteroatoms independently selected from up to 2O, up to 2S, and up to 3 N, wherein up to 2 carbon atom ring members are independently selected from C(=O) and C(=S) and the sulfur atom ring members are independently selected from S(=O)$_n$, each ring unsubstituted or substituted with up to 3 substituents independently selected from the group consisting of halogen, cyano, hydroxy, amino, nitro, C(=O)OH, C(=O)NH$_2$, SO$_2$NH$_2$, C$_1$-C$_4$-alkyl, C$_1$-C$_4$-haloalkyl, C$_2$-C$_4$-alkenyl, C$_2$-C$_4$-haloalkenyl, C$_2$-C$_4$-alkynyl, C$_2$-C$_4$-haloalkynyl, C$_3$-C$_7$-cycloalkyl, C$_3$-C$_7$-halocycloalkyl, C$_4$-C$_8$-alkylcycloalkyl, C$_4$-C$_8$-haloalkylcycloalkyl, C$_4$-C$_8$-cycloalkylalkyl, C$_4$-C$_8$-halocycloalkylalkyl, C$_1$-C$_6$-alkoxy, C$_1$-C$_6$-haloalkoxy, C$_2$-C$_6$-alkoxycarbonyl, C$_2$-C$_6$-haloalkoxycarbonyl, C$_2$-C$_6$-alkylcarbonyl and C$_2$-C$_6$-haloalkylcarbonyl;

R$^5$ is (CR$^{5a}$R$^{5b}$)$_a$R$^{5c}$, or

R$^5$ is C$_3$-C$_6$ cycloalkyl unsubstituted or substituted with 1 to 4 substituents selected from the group consisting of halogen, C$_1$-C$_2$ alkyl, 1 cyclopropyl and 1 CF$_3$;

a is 0, 1, 2 or 3;

each R$^{5a}$ and R$^{5b}$ is independently H, halogen, cyano, hydroxy, amino, nitro, OCN, SCN, CHO, C(=O)OH, C(=O)NH$_2$, C(=S)NH$_2$ or SO$_2$NH$_2$, or C$_1$-C$_6$ alkyl, C$_2$-C$_6$-alkenyl, C$_2$-C$_6$-alkynyl, C$_3$-C$_8$-cycloalkyl, C$_4$-C$_8$-alkylcycloalkyl, C$_4$-C$_8$-cycloalkylalkyl, C$_6$-C$_{12}$-cycloalkylcycloalkyl, C$_5$-C$_8$-alkylcycloalkylalkyl, C$_3$-C$_6$-cycloalkenyl, C$_1$-C$_6$-alkoxy, C$_3$-C$_6$-cycloalkoxy, C$_4$-C$_8$-cycloalkylalkoxy, C$_2$-C$_6$-alkenyloxy or C$_2$-C$_6$-alkynyloxy, each unsubstituted or substituted with at least one substituent R$^r$;

R$^{5c}$ is H, halogen, cyano, hydroxy, amino, nitro, OCN, SCN, CHO, C(=O)OH, C(=O)NH$_2$, C(=S)NH$_2$, SO$_2$NH$_2$, C(=O)R$^l$, C(=O)OR$^l$, NHR$^l$, NR$^l$R$^l$, C(=O)NR$^l$R$^m$, C(=S)NR$^l$R$^m$, SO$_2$NR$^l$R$^m$, OC(=O)R$^m$, OC(=O)OR$^l$, OC(=O)N(R$^m$)$_2$, N(R$^m$)C(=O)R$^m$, N(R$^m$)C(=O)OR$^l$, N(R$^m$)C(=O)N(R$^n$)$_2$, OSO$_2$R$^l$, OSO$_2$N(R$^n$)$_2$, NR$^m$SO$_2$R$^l$, NR$^m$SO$_2$N(R$^n$)$_2$ or Si(R$_f$)$_3$, or C$_1$-C$_8$-alkyl, C$_2$-C$_8$-alkenyl, C$_2$-C$_8$-alkynyl, C$_3$-C$_{10}$-cycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_3$-C$_8$-cycloalkenyl, C$_1$-C$_8$-alkylthio, C$_1$-C$_8$-alkylsulfinyl, C$_1$-C$_8$-alkylsulfonyl, C$_3$-C$_8$-cycloalkylthio, C$_3$-C$_8$-cycloalkylsulfinyl, C$_3$-C$_8$-cycloalkylsulfonyl, C$_4$-C$_{10}$-cycloalkylalkylthio, C$_4$-C$_{10}$-cycloalkylalkylsulfinyl, C$_4$-C$_{10}$-cycloalkylalkylsulfonyl, C$_2$-C$_8$-alkenylthio, C$_2$-C$_8$-alkenylsulfinyl, C$_2$-C$_8$-alkenylsulfonyl, C$_2$-C$_8$-alkynylthio, C$_2$-C$_8$-alkynylsulfinyl or C$_2$-C$_8$-alkynylsulfonyl, each unsubstituted or substituted with at least one substituent R$^r$, or Q$^2$;

each R$^a$ is independently H, CN, C$_1$-C$_{10}$-alkyl which is unsubstituted or substituted with one or more radicals R$^c$, C$_3$-C$_8$-cycloalkyl which is unsubstituted or substituted with one or more radicals R$^c$, C$_2$-C$_{10}$-alkenyl which is unsubstituted or substituted with one or more radicals R$^c$, C$_2$-C$_{10}$-alkynyl which is unsubstituted or substituted with one or more radicals R$^c$, —N(R$^d$)$_2$, —Si(R$^f$)$_3$, —OR$^g$, —SR$^g$, —S(O)$_m$R$^h$, —S(O)$_m$N(R$^d$)$_2$, —C(=O)R$^e$, —C(=O)OR$^g$, —C(=O)N(R$^d$)$_2$, —C(=S)R$^e$, —C(=S)OR$^g$, —C(=S)N(R$^d$)$_2$, —C(=NR$^d$)R$^e$ or Q$^1$;

or R$^1$ and R$^a$ together form a group =C(R")$_2$, =S(O)$_m$R$^h$, =S(O)$_m$N(R$^d$)$_2$, =NR$^d$ or =NOR$^g$;

or R$^1$ and R$^a$ together form a C$_2$-C$_7$ alkylene chain, thus forming, together with the nitrogen atom to which they are bonded, a 3-, 4-, 5-, 6-, 7- or 8-membered ring, where the alkylene chain is optionally interrupted by 1 or 2 O, S and/or NR$^p$ and/or 1 or 2 of the CH$_2$ groups of the alkylene chain are optionally replaced by a group C=O, C=S and/or C=NR$^d$, and/or the alkylene chain is unsubstituted or substituted with one or more radicals selected from the group consisting of halogen, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl and Q$^1$;

each R$^b$ is independently halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the carbon atoms of the aforementioned aliphatic and cyclo-aliphatic radicals are unsubstituted or substituted with one or more R$^c$, Si(R$^f$)$_3$, OR$^g$, OS(O)$_n$R$^h$, —S(O)$_n$R$^h$, S(O)$_n$N(R$^d$)$_2$, N(R$^d$)$_2$, C(=O)R$^e$, C(=O)OR$^g$, —C(=NR$^d$)R$^e$, C(=O)N(R$^d$)$_2$, C(=S)N(R$^d$)$_2$ or Q$^4$;

each R$^c$ is independently, halogen, cyano, azido, nitro, —SCN, SF$_5$, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$ haloalkynyl, Si(R$^f$)$_3$, OR$^o$, OSO$_2$R$^o$, S(O)$_n$R", S(O)$_n$N(R$^p$)$_2$, NR$^p$)$_2$, C(=O)N(R$^p$)$^2$, C(=S)N(R$^p$)$_2$, C(=O)OR$^o$, Q$^1$ or two R$^c$ present on one carbon atom together form =O, =C(R")$_2$, =S, =S(O)$_n$R", =S(O)$_m$N(R$^p$)$_2$, =NR$^p$, =NOR$^o$, =NNR$^p$, or two R$^c$ form a 3-, 4-, 5-, 6-, 7- or 8-membered saturated or partly unsaturated carbocyclic or heterocyclic ring together with the carbon atoms to which the two R$^c$ are bonded to;

each R$^d$ is independently hydrogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$ haloalkynyl, S(O)$_m$R", —S(O)$_m$N(R$^p$)$_2$, C(=O)R$^m$, C(=O)OR$^o$, C(=O)N(R$^p$)$_2$, C(=S)R", C(=S)SR$^o$, C(=S)N(R$^p$)$_2$, C(=NR$^p$)R" or Q$^1$; or two R$^d$ together are a C$_2$-C$_7$ alkylene chain, forming a 3- to 8-membered saturated, partly saturated or aromatic heterocyclic ring together with the nitrogen atom they are bonded to, wherein the alkylene chain optionally contain 1 or 2 oxygen atoms, sulfur atoms or nitrogen atoms, and wherein the alkylene chain is unsubstituted or substituted with at least one substituent selected from halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$ haloalkynyl and Q$^1$;

each R$^e$ is independently C$_1$-C$_6$-alkyl, C$_1$-C$_6$-haloalkyl, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$ haloalkynyl, Si(R$^f$)$_3$, OR$^o$, OSO$_2$R", S(O)$_n$R", S(O)$_n$N(R$^p$)$_2$, N(R$^p$)$_2$, C(=O)N(R$^p$)$^2$, C(=S)N(R$^p$)$_2$, C(=O)OR$^o$ or Q$^1$;

each R$^f$ is independently hydrogen, halogen, C$_1$-C$_6$-alkyl, C$_1$-C$_6$-haloalkyl, C$_1$-C$_6$-alkoxyalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxyalkyl, C$_1$-C$_6$-haloalkoxyalkyl or phenyl which is unsubstituted or substituted with one or more substituents R$^g$;

each R$^g$ is independently H, C$_1$-C$_6$-alkyl, C$_1$-C$_6$-haloalkyl, C$_1$-C$_6$-alkylsulfinyl, C$_1$-C$_6$-alkylsulfonyl, C$_3$-C$_8$-cycloalkyl, C$_4$-C$_8$-alkylcycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, —Si(R$^f$)$_3$, S(O)$_n$R$^o$, —S(O)$_n$NR$^p$$_2$, —C(=O)R$^o$, C(=O)N(R$^p$)$_2$, C(=S)N(R$^p$)$_2$, C(=O)OR$^o$ or Q$^1$;

each $R^h$ is independently $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^f$)$_3$, S(O)$_n$R$^o$, —S(O)$_n$NR$^p{}_2$, N(R$^p$)$_2$, —N=C(R$^n$)$_2$, —C(=O)R$^o$, C(=O)N(R$^p$)$_2$, C(=S)N(R$^p$)$_2$, C(=O)OR$^d$ or Q$^1$;

$R^i$ is independently cyano, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals are unsubstituted or substituted with one or more substituents N(R$^d$)$_2$, Si(R$^f$)$_3$, OR$^g$, S(O)$_n$R$^h$, C(=O)R$^e$, C(=O)N(R$^d$)$_2$, C(=O)OR$^g$, C(=S)R$^e$, C(=S)N(R$^d$)$_2$, C(=S)SR$^g$, C(=NR$^d$)R$^e$ or Q$^1$;

$R^k$ is independently H or R'; or $R^i$ and $R^k$ together are =C(R$^n$)$_2$, =S(O)$_n$R$^h$, =S(O)$_n$NC(R$^d$)$_2$, =NR$^d$ or =NOR$^g$;

each $R^l$ is independently $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl or $C_3$-$C_6$-cycloalkenyl, each unsubstituted or substituted with at least one substituent independently selected from R$^r$; or Q$^1$;

each $R^m$ is independently H or R$^l$;

each $R^n$ is independently $C_1$-$C_4$ alkyl, $C_1$-$C_6$ cycloalkyl, $C_1$-$C_4$ alkoxyalkyl, phenyl or benzyl;

each $R^o$ is independently H, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or may carry 1 or 2 radicals selected from 1 or 2 $C_1$-$C_4$-alkoxy groups and (=O); or is Q$^5$;

each $R^p$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals are unsubstituted, partially or fully halogenated and/or optionally carry 1 or 2 radicals selected from 1 or 2 $C_1$-$C_4$-alkoxy groups and (=O); or is Q$^5$; or two groups $R^p$ are together a $C_2$-$C_6$ alkylene chain forming a 3- to 7-membered saturated, partly saturated or unsaturated ring together with the nitrogen atom they are bonded to, wherein the alkylene chain optionally contains 1 or 2 heteroatoms selected from oxygen, sulfur, nitrogen, S(O), s(O)$_2$ and NO and is unsubstituted or substituted with one or more halogen, $C_1$-$C_4$-haloalkyl, $C_1$-$C_4$-alkoxy and $C_1$-$C_4$-haloalkoxy;

each $R^q$ is independently H, halogen, cyano, azido, nitro, SCN, SF$_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic group and cyclo-aliphatic radicals are unsubstituted or substituted with one or more R$^t$, Si(R$^f$)$_3$, OR$^o$, OS(O)$_n$R$^o$, S(O)$_n$N(R$^p$)$_2$, N(R$^p$)$_2$, C(=O)R$^o$, C(=O)OR$^o$, —C(=NR$^p$)R$^o$, C(=O)N(R$^p$)$_2$, C(=S)N(R$^p$)$_2$, phenyl, unsubstituted or substituted with halogen, cyano, nitro, $C_1$-$C_6$-alkyl, $C_1$-$C_6$-haloalkyl, $C_1$-$C_6$-alkoxy or $C_1$-$C_6$-haloalkoxy or is Q$^4$; or two $R^p$ together on one atom of a partly saturated heterocyclic are =O, =C(R$^n$)$_2$, =S(O)$_m$R$^n$, =S(O)$_m$N(R$^p$)$_2$, =NR$^p$, =NOR$^o$ or =NN(R$^p$)$_2$; or two $R^q$ on adjacent carbon atoms form a bridge selected from CH$_2$CH$_2$CH$_2$CH$_2$, CH=CH—CH=CH, N=CH—CH=CH, CH=N—CH=CH, N=CH—N=CH, OCH$_2$CH$_2$CH$_2$, OCH=CHCH$_2$, CH$_2$OCH$_2$CH$_2$, OCH$_2$CH$_2$O, OCH$_2$OCH$_2$, CH$_2$CH$_2$CH$_2$, CH=CHCH$_2$, CH$_2$CH$_2$O, CH=CHO, CH$_2$OCH$_2$, CH$_2$C(=O)O, C(=O)OCH$_2$, O(CH$_2$)O, SCH$_2$CH$_2$CH$_2$, SCH=CHCH$_2$, CH$_2$SCH$_2$CH$_2$, SCH$_2$CH$_2$S, SCH$_2$SCH$_2$, CH$_2$CH$_2$S, CH=CHS, CH$_2$SCH$_2$, CH$_2$C(=S)S, C(=S)SCH$_2$, S(CH$_2$)S, CH$_2$CH$_2$NR$^p$, CH$_2$CH=N, CH=CH—NR$^p$, OCH=N, SCH=N and form together with the carbon atoms to which the two $R^q$ are bonded to a 5-membered or 6-membered partly saturated or unsaturated, aromatic carbocyclic or heterocyclic ring, wherein the ring is unsubstituted or substituted with one or two substituents selected from =O, OH, CH$_3$, OCH$_3$, halogen, halomethyl and halomethoxy;

each $R^r$ is independently halogen, cyano, nitro, CHO, C(=O)OH, C(=O)NH$_2$, C(=O)R$^s$, C(=O)OR$^s$, C(=O)N(R$^s$)$_2$, OR$^s$, S(O)$_n$R$^s$, SO$_2$N(R$^f$)$_2$, Si(R$^s$)$_3$ or Z$^1$Q$^2$;

each $R^s$ is independently $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl or $C_3$-$C_6$-cycloalkenyl, each unsubstituted or substituted with at least one substituent independently selected from the group consisting of halogen, cyano, nitro, CHO, C(=O)OH, C(=O)NH$_2$, $C_1$-$C_4$ alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_3$-$C_6$-cycloalkylamino, $C_2$-$C_4$-alkoxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl and $C_3$-$C_6$-trialkylsilyl; or is phenyl or a 5- or 6-membered heteroaromatic ring, each unsubstituted or substituted with at least one substituent independently selected from the group consisting of $C_1$-$C_6$-alkyl, $C_1$-$C_6$-haloalkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl, $C_3$-$C_6$-cycloalkenyl, halogen, cyano, nitro, CHO, C(=O)OH, C(=O)NH$_2$, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_3$-$C_6$-cycloalkylamino, $C_2$-$C_4$-alkoxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl and $C_3$-$C_6$-trialkylsilyl;

each $R^t$ is independently hydrogen, halogen, cyano, nitro, OH, SH, SCN, SF$_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkyl, $C_3$-$C_8$-cycloalkyl, wherein the four last mentioned aliphatic and cyclo-aliphatic radicals are unsubstituted, partially or fully halogenated and/or substituted with (=O) and/or carry 1 or 2 radicals selected from $C_1$-$C_4$-alkoxy; $Q^5$; or two $R^t$ present on the same carbon atom are together =O, =CH($C_1$-$C_4$), =C($C_1$-$C_4$-alkyl) $C_1$-$C_4$-alkyl, =N($C_1$-$C_6$-alkyl) or =NO($C_1$-$C_6$-alkyl);

each $R^u$ is independently $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl, $C_3$-$C_6$-cycloalkenyl, $C_2$-$C_6$-alkylcarbonyl or $C_2$-$C_6$-alkoxycarbonyl, each unsubstituted or substituted with at least one substituent independently selected from the group consisting of halogen, cyano, nitro, CHO, C(=O)OH, C(=O)NH$_2$, C(=O)R$^n$, C(=O)OR$^n$, C(=O)N(R$^p$)$_2$, OR$^o$, S(O)$_n$R$^o$, SO$_2$N(R$^p$)$_2$ and Si(R$^f$)$_3$; or is H;

each $R^v$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent $R^r$;

each $Q^1$ is independently phenyl which is unsubstituted or substituted with 1, 2, 3, 4 or 5 radicals $R^q$, or a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring is unsubstituted or substituted with one or more radicals $R^q$;

each $Q^2$ is independently a 3- to 10-membered ring or a 7- to 11-membered ring system, each ring or ring system containing ring members selected from carbon atoms and up to 4 heteroatoms independently selected from up to 2O, up to 2S, and up to 4N, wherein up to 3 carbon atom ring members are independently selected from C(=O) and C(=S) and the sulfur atom ring members are independently selected from S(=O)$_x$(=NR$^p$)$_z$, each ring or ring system unsubstituted or substituted with up to 5 substituents $R^r$ each $Q^3$ is independently a 3- to 10-membered ring or a 7- to 11-membered ring system, each ring or ring system containing ring members selected from carbon atoms and up to 4 heteroatoms independently selected from up to 2O, up to 2S, and up to 4N, wherein up to 3 carbon atom ring members are independently selected from C(=O) and C(=S) and the sulfur atom ring members are independently selected from S(=O)$_x$(=NR$^p$)$_z$, each ring or ring system unsubstituted or substituted with up to 4 substituents $R^r$;

each $Q^4$ is independently phenyl, unsubstituted or substituted with at least one substituent selected from halogen, cyano, nitro, $C_1$-$C_6$-alkyl, $C_1$-$C_6$-haloalkyl, $C_1$-$C_6$-alkoxy and $C_1$-$C_6$-haloalkoxy, a 3-, 4-, 5-, 6- or 7-membered saturated, partly saturated or unsaturated aromatic heterocyclic ring comprising 1, 2 or 3 heteroatoms or heteroatom groups selected from oxygen, nitrogen, sulfur, NO, SO and SO$_2$ unsubstituted or substituted with k substituents selected independently from halogen, cyano, NO$_2$, $C_1$-$C_6$-alkyl, $C_1$-$C_6$-haloalkyl, $C_1$-$C_6$-alkoxy and $C_1$-$C_6$-haloalkoxy;

each $Q^5$ is independently phenyl, benzyl, pyridyl, phenoxy, which are unsubstituted, partially or fully halogenated and/or carry 0, 1, 2 or 3 substituents selected from $C_1$-$C_6$-alkyl, $C_1$-$C_6$-haloalkyl, $C_1$-$C_6$-alkoxy, $C_1$-$C_6$-haloalkoxy, ($C_1$-$C_6$-alkoxy)carbonyl, ($C_1$-$C_6$-alkyl)amino and di-($C_1$-$C_6$-alkyl)amino, each $Z^1$ is independently a direct bond, O, S(O)$_n$, NR$^u$, CH(R$^u$), C(R$^u$)=C(R$^u$), C=C, C(R$^u$)$_2$O, OC(R$^u$)$_2$, C(=X$^1$), C(=X$^1$)E, EC(=X$^1$), C(=NOR$^u$) or C(=NN(R$^u$)$_2$);

each $X^1$ is independently O, S or NR$^v$;

each E is independently O, S or NR$^v$;

each k is independently an integer from 0 to 6 each m is independently 1 or 2;

each n is independently 0, 1 or 2;

x and z in each case are independently 0, 1 or 2, provided that the sum x+z is 0, 1 or 2 for each ring; and N-oxides and salts thereof.

The substituted pyrimidine compounds of formula (I), their N-oxides and their agriculturally or veterinarily acceptable salts are highly active against animal pests, especially harmful arthropodes and nematodes, in particular against harmful insects and acaridae.

Accordingly, the invention provides substituted pyrimidine compounds of formula (I), N-oxides and agriculturally or veterinarily useful salts thereof.

Moreover, the invention provides and includes the following embodiments:

agricultural and veterinary compositions comprising at least one compound of formula (I), N-oxide or salt thereof;

the use of at least one compound of formula (I), N-oxide or salt thereof for combating animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of formula (I), N-oxide or salt thereof;

a method for protecting crops from attack or infestation by animal pests, which comprises contacting a crop with a pesticidally effective amount of at least one compound of the formula (I), N-oxide or salt thereof;

a method for protecting seeds from soil insects and seedlings' roots and shoots from soil and foliar insects comprising contacting the seeds before sowing and/or after pregermination with at least one compound of formula (I), N-oxide or salt thereof;

seeds comprising at least one compound of formula (I), N-oxide or salt thereof;

the use of at least one compound of formula (I), N-oxide or veterinarily acceptable salt thereof for combating parasites in and on animals.

a method for treating or protecting animals against infestation or infection by parasites which comprises orally, topically or parenterally administering or applying to the animals a parasiticidally effective amount of at least one compound of formula (I), N-oxide or veterinarily acceptable salt thereof;

a process for the preparation of a composition for treating or protecting animals against infestation or infection by parasites which comprises mixing a parasiticidally effective amount of at least one compound of formula (I), N-oxide or a veterinarily acceptable salt thereof with at least one veterinarily acceptable carrier;

the use of at least one compound of formula (I), N-oxide or veterinarily acceptable salt thereof for the preparation of a medicament for treating, controlling, preventing or protecting animals against infestation or infection by parasites;

a compound of formula (I), N-oxide or salt thereof as a medicament, in particular for use in a method for treating animals against infestation or infection by parasites.

The invention also provides plant propagation materials, in particular seeds, comprising at least one compound of formula (I), N-oxide or agriculturally acceptable salt thereof. The term "at least one compound of formula (I), N-oxide or salt thereof" means at least one compound selected from the group consisting of compounds of formula (I), N-oxides of the compounds of formula (I), salts of the compounds of formula (I) and salts of the N-oxides of the compounds of formula (I). Likewise "a compound of the invention" means a compound of formula (I), an N-oxide of a compound of formula (I), a salt of a compound of formula (I) or a salt of an N-oxide of a compound of formula (I). The compounds of formula (I) encompass every possible stereoisomer of the compounds of formula (I), e.g. single enantiomers or diastereomers, as well as mixtures thereof.

The compounds of formula (I) may be amorphous or may exist in one ore more different crystalline states (polymorphs) or modifications which may have a different macroscopic properties such as stability, or show different biological properties such as activity against certain pests. The invention encompasses both amorphous and crystalline compounds of formula (I), mixtures of different crystalline states or modifications of the respective compound (I), as well as amorphous or crystalline salts thereof. Salts of the compounds of formula (I) are preferably agriculturally and/or veterinarily acceptable salts. They can be formed in a customary method, e.g. by reacting the compound with an acid of the anion in question, if the compound of formula (I) has a basic functionality, or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula (I) with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" means fluoro, chloro, bromo and iodo.

The term "partially or fully halogenated" means that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl and 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted with fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bonded to the remainder of the molecule via an oxygen atom or a sulfur atom, respectively.

The term "$C_2$-$C_m$-alkenyl" as used herein refers to a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like the specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include: Oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl and hexahydro-1,4-dioxepinyl.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro [1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl. 3-, 4-, 5-, 6- or 7-membered aromatic heterocyclyl is 5- or 6-membered aromatic heterocyclyl(hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

$C_2$-$C_7$-alkylene is divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

If not otherwise specified, all symbols and indices have the meaning given in formula (I). In the following listing of preferred embodiments, if not otherwise stated, a reference to a compound of formula (I) shall include N-oxides and salts thereof.

In one preferred embodiment D is $C(R^2)=N\sim ZR^1$.
In another preferred embodiment D is $C(=Y^1)NR^4OH$.
In one preferred embodiment, the substituted pyrimidine compound of formula (I) is a compound of formula (I-1),

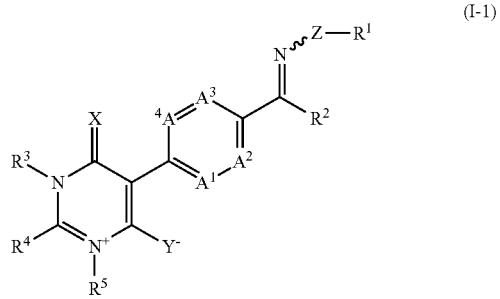

(I-1)

wherein
each $A^1$, $A^2$, $A^3$, $A^4$ is independently N or C—$R^b$,
with the proviso that no more than two of $A^1$, $A^2$, $A^3$ and $A^4$ are N.

In another preferred embodiment, the substituted pyrimidine compound of formula (I) is a compound of formula (I-2),

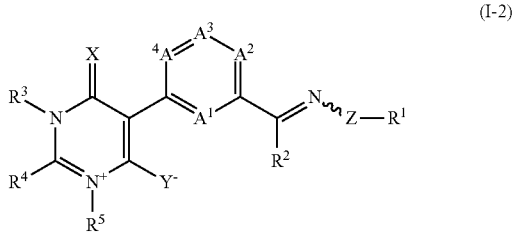

(I-2)

wherein
each $A^1$, $A^2$, $A^3$, $A^4$ is independently N or C—$R^b$,
with the proviso that no more than two of $A^1$, $A^2$, $A^3$ and $A^4$ are N.

In another preferred embodiment, the substituted pyrimidine compound of formula (I) is a compound of formula (I-3),

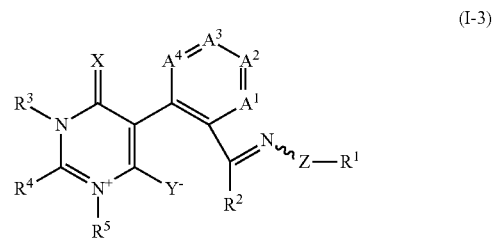

(I-3)

wherein
each $A^1$, $A^2$, $A^3$, $A^4$ is independently N or C—$R^b$,
with the proviso that no more than two of $A^1$, $A^2$, $A^3$ and $A^4$ are N.

Further preferred are compounds of formulae (I-1), (I-2), (I-3), (I-4), (I-5) or (I-6), wherein
X is O;
Y is O and
each $A^1$, $A^2$, $A^3$, $A^4$ is independently N or C—$R^b$,
with the proviso that no more than one of $A^1$, $A^2$, $A^3$ and $A^4$ is N.

In another preferred embodiment, the substituent pyrimidine compound of formula (I) is a compound of formula (I-4),

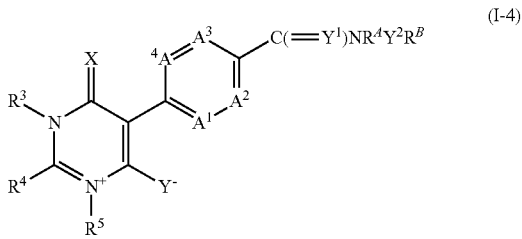

(I-4)

wherein
each $A^1$, $A^2$, $A^3$, $A^4$ is independently N or C—$R^b$,
with the proviso that no more than two of $A^1$, $A^2$, $A^3$ and $A^4$ are N.

In another preferred embodiment, the substituted imine compound of formula (I) is a compound of formula (I-5),

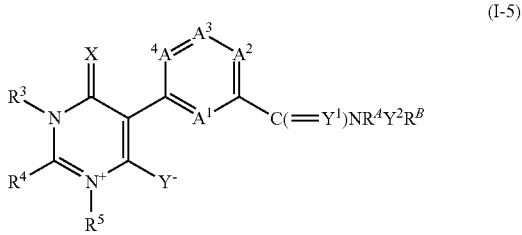

(I-5)

wherein
each $A^1$, $A^2$, $A^3$, $A^4$ is independently N or C—$R^b$,
with the proviso that no more than two of $A^1$, $A^2$, $A^3$ and $A^4$ are N.

In another preferred embodiment, the substituted imine compound of formula (I) is a compound of formula (I-6),

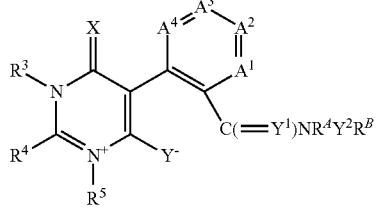
(I-6)

wherein each $A^1$, $A^2$, $A^3$, $A^4$ is independently N or C—$R^b$, with the proviso that no more than two of $A^1$, $A^2$, $A^3$ and $A^4$ are N.

Further preferred are compounds of formulae (I), (I-1), (I-2) and (I-6), wherein $R^2$ is $NR^iR^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, halogen, cyano, O-$Q^1$ or S-$Q^1$.

Further preferred or compounds of formula (I), (I-4), (I-5) and (I-6), wherein $Y^1$, $Y^2$ are O and $R^A$, $R^B$ are independently H or $CH_3$, preferably H.

Further preferred are compounds of formula (I), (I-1), (I-2), (I-3), (I-4), (I-5) and (I-6), wherein $R^3$, $R^4$ are independently hydrogen, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cycloaliphatic radicals are unsubstituted or substituted with one or more $R^r$;

$R^3$ and $R^4$ together with the nitrogen and carbon atom to which they are bonded, form any of the following substituted heterocyclic ring systems E-1 to E-9:

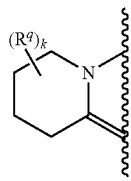
E-1

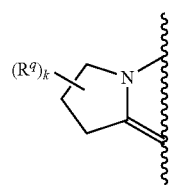
E-2

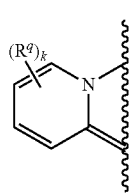
E-3

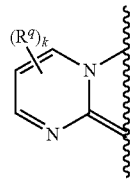
E-4

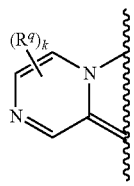
E-5

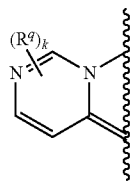
E-6

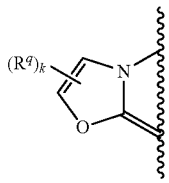
E-7

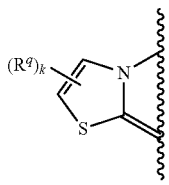
E-8

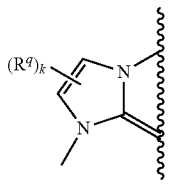
E-9

$R^5$ is $CR^{5a}R^{5b}R^{5c}$;

$R^{5a}$ is hydrogen, halogen, cyano or $C_1$-$C_4$ alkyl;

$R^{5b}$ is hydrogen, halogen or —$CH_3$;

$R^{5c}$ is a heterocyclic ring system:

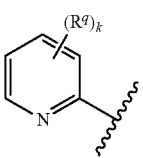
D-1

-continued
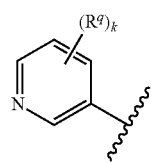 D-2
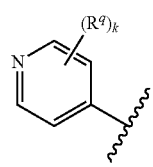 D-3
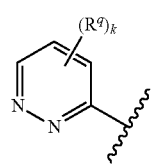 D-4
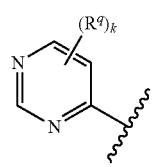 D-5
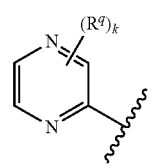 D-6
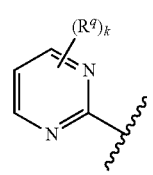 D-7
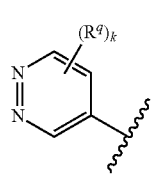 D-8
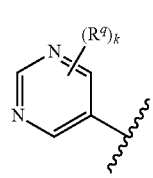 D-9
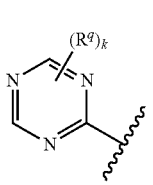 D-10
-continued
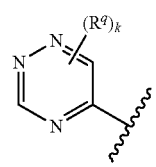 D-11
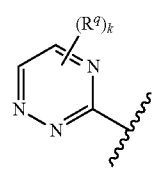 D-12
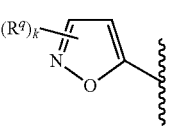 D-13
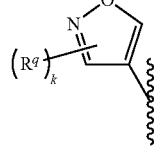 D-14
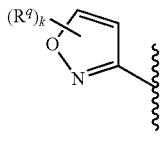 D-15
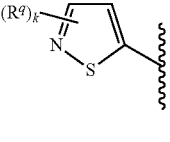 D-16
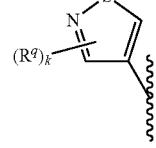 D-17
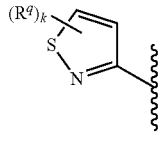 D-18
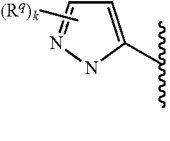 D-19
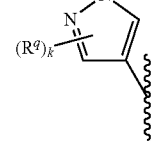 D-20

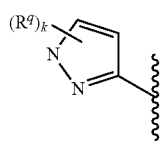 D-21
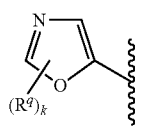 D-22
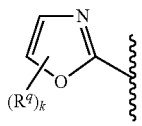 D-23
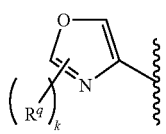 D-24
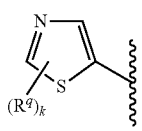 D-25
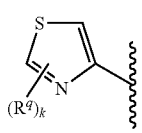 D-26
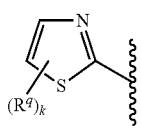 D-27
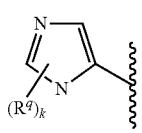 D-28
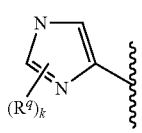 D-29
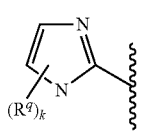 D-30
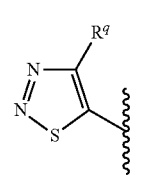 D-31
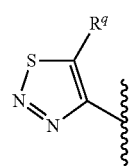 D-32
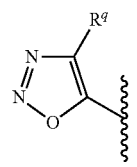 D-33
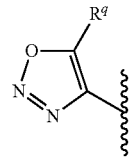 D-34
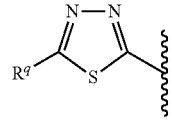 D-35
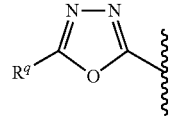 D-36
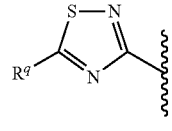 D-37
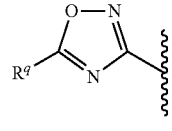 D-38
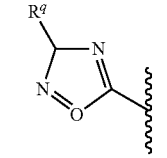 D-39
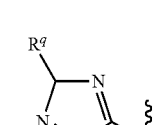 D-40
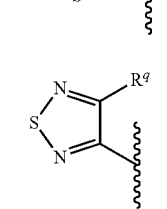 D-41

-continued
D-42 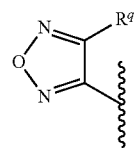
D-43 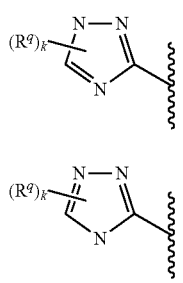
D-44
D-45 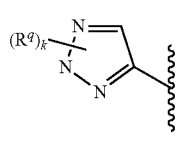
D-46 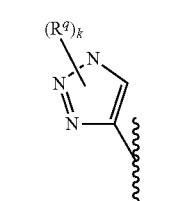
D-47 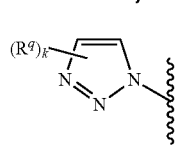
D-48 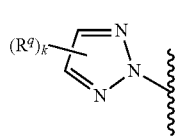
D-49 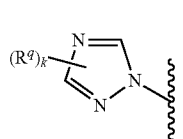
D-50 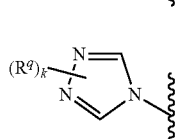
D-51 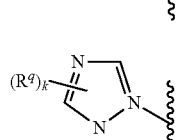
D-52 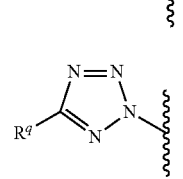
-continued
D-53 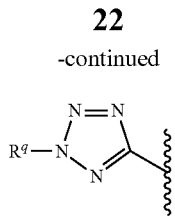
D-54
D-55 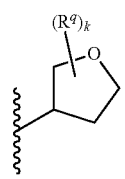
and
each k is independently 0, 1, 2, 3 or 4.
In a further preferred embodiment, the compound of formula (I) is a compound of formulae (I-7), (I-8), (I-9), (I-10), (I-11) or (I-12),
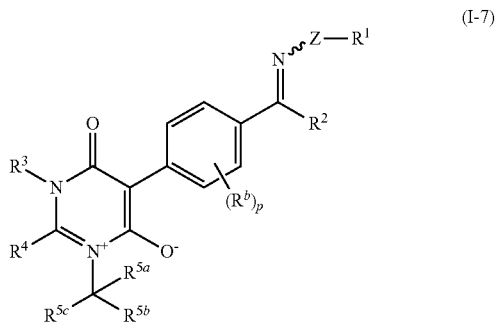 (I-7)
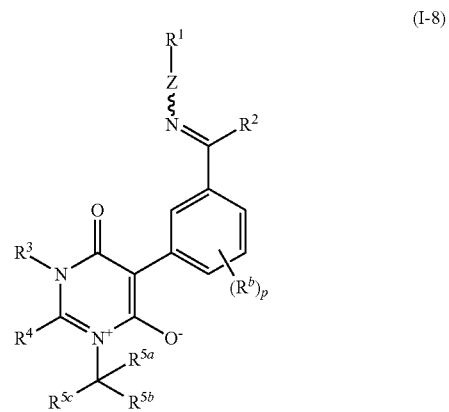 (I-8)

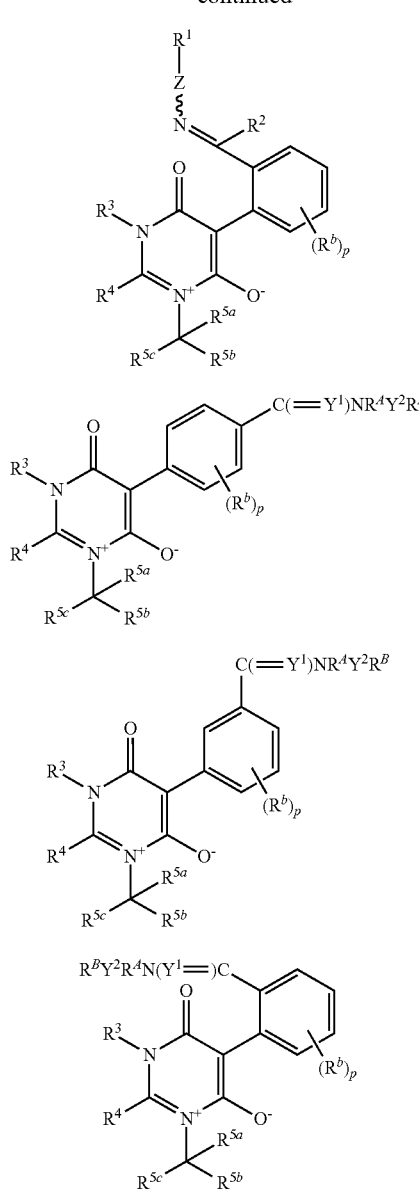

R³, R⁴ is independently hydrogen, $C_1$-$C_6$-alkyl, $C_1$-$C_6$-haloalkyl, $C_3$-$C_6$-cycloalkyl or $C_3$-$C_6$-halocycloalkyl; or R³ and R⁴ together with the nitrogen and carbon atom to which they are bonded, form any of the following substituted heterocyclic ring systems E-1 E-2, E-3 or E-9:

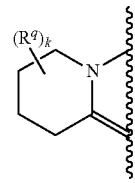

E-1

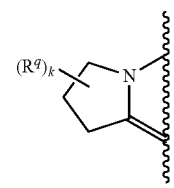

E-2

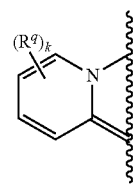

E-3

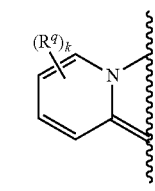

E-8

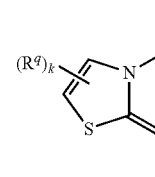

$R^{5a}$ is hydrogen, halogen, cyano or $C_1$-$C_4$ alkyl;
$R^{5b}$ is hydrogen, halogen or —CH₃;
$R^{5c}$ is a heterocyclic ring system:

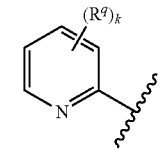

D-1

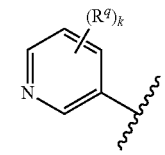

D-2

D-3 wherein
$Y^1, Y^2$ are independently O or S;
$R^A R^B$ are independently H, $(C_1$-$C_6)$-alkyl, benzyl or phenyl;
Z is O, N—$R^a$ or a direct bond;
R¹ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —N($R^d$)₂, —N($R^d$)C(=O)$R^e$, —Si($R^f$)₃, —OR$^g$, —SR$^g$, —S(O)$_m$R$^h$, —S(O)$_n$N($R^d$)₂, —C(=O)$R^e$, —C(=O)OR$^g$, —C(=O)N($R^d$)₂, —C(=S)$R^e$, —C(=S)OR$^g$, —C(=S)N($R^d$)₂ or —C(=NR$^d$)R$^e$; with the proviso that R¹ is not —OR$^g$, CN or nitro if Z is O;
R² is NR$^i$R$^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, O-Q¹ or S-Q¹;

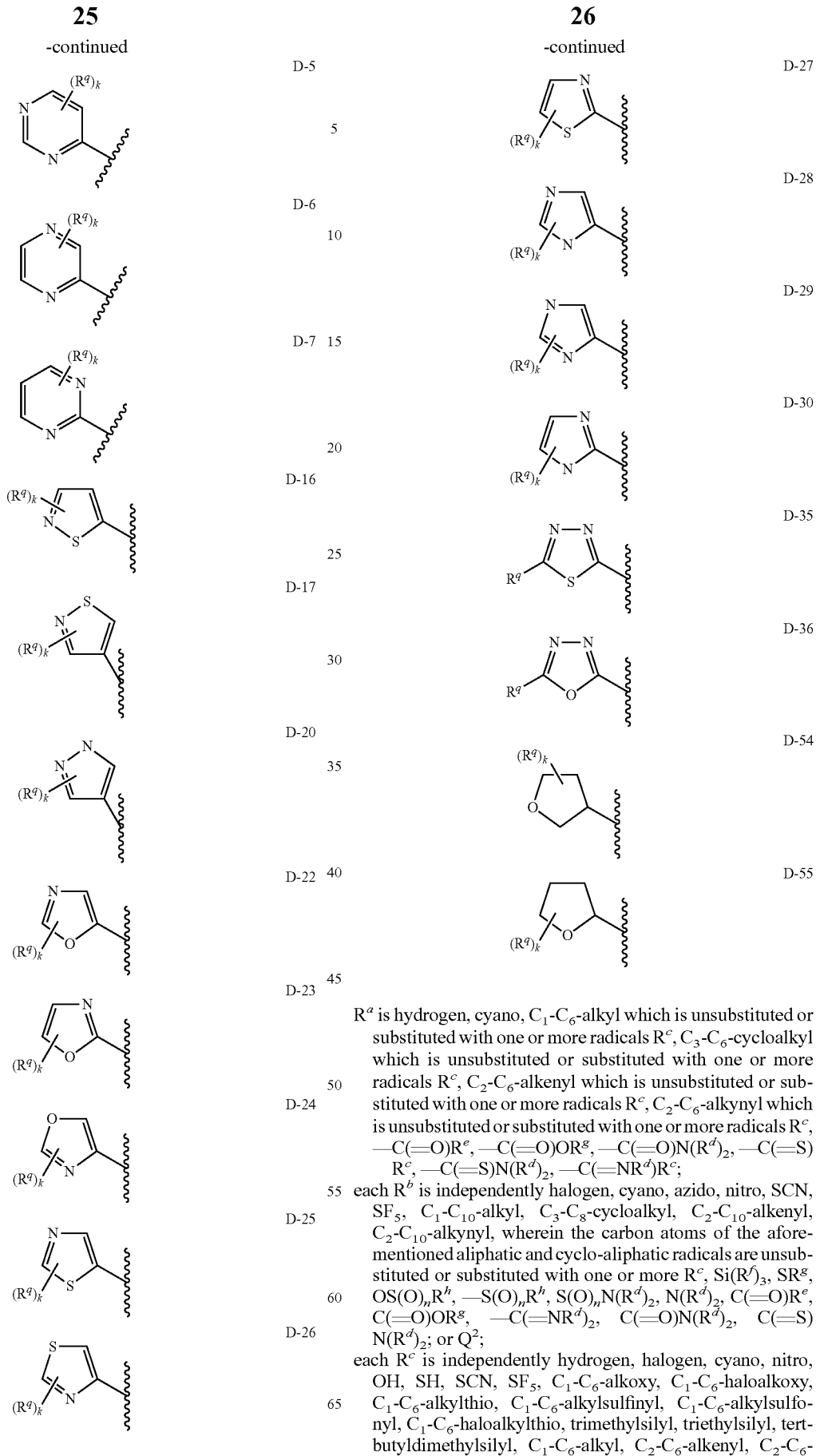

$R^a$ is hydrogen, cyano, $C_1$-$C_6$-alkyl which is unsubstituted or substituted with one or more radicals $R^c$, $C_3$-$C_6$-cycloalkyl which is unsubstituted or substituted with one or more radicals $R^c$, $C_2$-$C_6$-alkenyl which is unsubstituted or substituted with one or more radicals $R^c$, $C_2$-$C_6$-alkynyl which is unsubstituted or substituted with one or more radicals $R^c$, —C(=O)$R^e$, —C(=O)O$R^g$, —C(=O)N($R^d$)$_2$, —C(=S)$R^e$, —C(=S)N($R^d$)$_2$, —C(=N$R^d$)$R^e$;

each $R^b$ is independently halogen, cyano, azido, nitro, SCN, SF$_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals are unsubstituted or substituted with one or more $R^c$, Si($R^f$)$_3$, S$R^g$, OS(O)$_n R^h$, —S(O)$_n R^h$, S(O)$_n$N($R^d$)$_2$, N($R^d$)$_2$, C(=O)$R^e$, C(=O)O$R^g$, —C(=N$R^d$)$_2$, C(=O)N($R^d$)$_2$, C(=S)N($R^d$)$_2$; or $Q^2$;

each $R^c$ is independently hydrogen, halogen, cyano, nitro, OH, SH, SCN, SF$_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$- alkynyl, $C_3$-$C_8$-cycloalkyl, wherein the four last mentioned aliphatic and cyclo-aliphatic radicals are unsubstituted, partially or fully halogenated and/or substituted with (=O) and/or carries 1 or 2 radicals selected from $C_1$-$C_4$ alkoxy; or is $Q^5$; or two $R^c$ present on the same carbon atom are together =O, =CH($C_1$-$C_4$), =C($C_1$-$C_4$-alkyl)$C_1$-$C_4$-alkyl, =N($C_1$-$C_6$-alkyl) or =NO($C_1$-$C_6$-alkyl);

each $R^d$, $R^e$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals are unsubstituted, partially or fully halogenated and/or carries 1 or 2 radicals selected from $C_1$-$C_4$-alkoxy, $Q^5$; or two $R^d$ are together a $C_2$-$C_6$ alkylene chain forming a 3- to 7-membered saturated, partly saturated or unsaturated ring together with the nitrogen atom they are bonded to, wherein the alkylene chain may contain 1 or 2 heteroatoms selected from oxygen, sulfur and nitrogen, and is unsubstituted or substituted with halogen, $C_1$-$C_4$-haloalkyl, $C_1$-$C_4$-alkoxy and/or $C_1$-$C_4$-haloalkoxy, wherein the nitrogen and/or the sulfur atom(s) of the heterocyclic ring is optionally oxidized;

each $R^e$, $R^f$ is independently $C_1$-$C_6$ alkyl or phenyl;

each $R^g$ is independently H, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy, phenyl, benzyl, pyridyl, phenoxy, wherein the last four radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^h$ is independently $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy, phenyl, benzyl, pyridyl, phenoxy, wherein the last four radicals are unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^i$ is independently hydrogen, halogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals are unsubstituted, partially or fully halogenated and/or oxygenated and/or carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy); ($C_1$-$C_6$-alkoxy)carbonyl; or two $R^i$ present together on one atom of a partly saturated atom are =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or two $R^i$ on two adjacent carbon atoms are together a $C_2$-$C_6$ alkylene chain which forms together with the carbon atom they are bonded to a 3-, 4-, 5-, 6- or 7-membered saturated, partly saturated or unsaturated aromatic, wherein the alkylene chain may contain 1 or 2 heteroatoms selected from oxygen, sulfur and nitrogen, and is unsubstituted or substituted with halogen, $C_1$-$C_4$-haloalkyl, $C_1$-$C_4$-alkoxy and/or $C_1$-$C_4$-haloalkoxy, and wherein the nitrogen and/or the sulfur atom(s) of the heterocyclic ring are optionally oxidized;

each m is independently 1 or 2;

each n is independently 0, 1 or 2; and each p is independently 0, 1, 2, 3 or 4; and $Q^4$ and $Q^5$ have the meaning given above.

Further preferred compounds of formula (I), (I-1), (I-2), (I-3), (I-4), (I-5), (I-6), (I-7), (I-8), (I-9), (I-10), (I-11) and (I-12) are compounds, wherein $Y^1$, $Y^2$ are O;

$R^A$ is H, $CH_3$, $C_2H_5$, benzyl or phenyl;

$R^B$ is H or $C_1$-$C_6$-alkyl;

$R^1$ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —N($R^d$)$_2$, —N($R^d$)C(=O)$R^e$, —Si($R^f$)$_3$, —O$R^g$, —S$R^g$, —S(O)$_n$$R^h$, —S(O), N($R^d$)$_2$, —C(=O)$R^e$, —C(=O)O$R^g$, —C(=O)N($R^d$)$_2$, —C(=S)$R^d$, —C(=S)O$R^h$, —C(=S)N($R^d$)$R^e$, —C(=N$R^d$)$R^g$;

with the proviso that $R^1$ is not —O$R^g$, CN or nitro if Z is O;

$R^2$ is N$R^i$$R^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, O-$Q^4$ or S-$Q^4$;

$R^3$, $R^4$ are independently hydrogen, $C_1$-$C_6$-alkyl or $C_1$-$C_6$-haloalkyl; or $R^3$ and $R^4$ together with the nitrogen and carbon atom to which they are bound, form any of the following substituted heterocyclic ring systems E-1 E-2, E-3 or E-9:

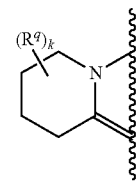

E-1

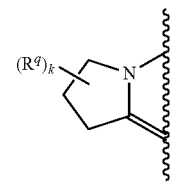

E-2

-continued

E-3
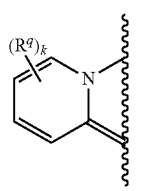

E-8
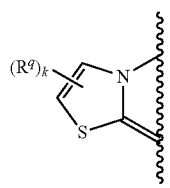

$R^5$ is $CR^{5a}R^{5b}R^{5c}$
$R^{5a}$ is hydrogen, fluoro, chloro, cyano or methyl;
$R^{5b}$ is hydrogen;
$R^{5c}$ is a substituted heterocyclic ring system:

D-2
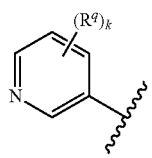

D-22
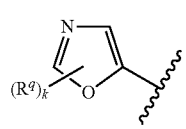

D-25
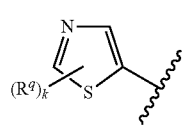

D-28
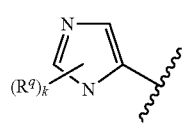

D-54
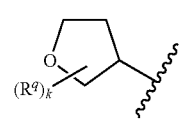

$R^a$ is hydrogen, $C_1$-$C_6$-alkyl which may be partially or fully halogenated, $C_3$-$C_6$-cycloalkyl which is unsubstituted or partially or fully halogenated, $C_2$-$C_6$-alkenyl which is unsubstituted or partially or fully halogenated, $C_2$-$C_6$-alkynyl which is unsubstituted or partially or fully halogenated, —C(=O)R$^e$, —C(=O)OR$^g$, —C(=O)N(R$^d$)$_2$, —C(=S)R$^e$ or —C(=S)N(R$^d$)$_2$;

each $R^b$ is independently H, CN, nitro, SCN, $C_1$-$C_6$-alkyl, $C_3$-$C_6$-cycloalkyl, $C_2$-$C_6$-alkenyl, $C_2$-$C_6$-alkynyl, wherein the carbon atoms of the aforementioned aliphatic and cyclo-aliphatic radicals are unsubstituted or partially or fully halogenated, OR$^g$, OS(O)$_n$R$^h$, —S(O)$_n$R$^h$, S(O)$_n$N(R$^d$)$_2$, C(=O)R$^e$, C(=O)OR$^g$, C(=O)N(R$^d$)$_2$ or C(=S)N(R$^d$)$_2$.

In a further preferred embodiment, the compound of formula (I), (I-1), (I-2), (I-3), (I-4), (I-5), (I-6), (I-7), (I-8), (I-9), (I-10), (I-11) or (I-12) is a compound, wherein $Y^1$ is O;

$R^A$ is H or $CH_3$;

$R^B$ is H $R^1$ is H, CN, nitro, $C_1$-$C_6$-alkyl which is unsubstituted or substituted with one or more radicals R$^c$, $C_3$-$C_6$-cycloalkyl which is unsubstituted or substituted with one or more radicals R$^c$, $C_2$-$C_6$-alkenyl which is unsubstituted or substituted with one or more radicals R$^c$, $C_2$-$C_6$-alkynyl which is unsubstituted or substituted with one or more radicals R$^c$,
—N(R$^d$)$_2$, —N(R$^d$)C(=O)R$^e$, —S(O)$_n$R$^b$, —S(O)$_n$N(R$^d$)$_2$, —C(=O)R$^e$,
—C(=O)OR$^g$, —C(=O)N(R$^d$)$_2$, —C(=S)R$^e$, —C(=S)N(R$^d$)$_2$;

$R^2$ is NR$^i$R$^k$, $R^3$ and $R^4$ together with the nitrogen and carbon atom to which they are bonded, form any of the following substituted heterocyclic ring systems E-1 E-2, E-3 or E-8:

E-1
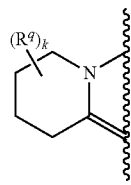

E-2
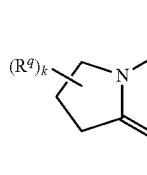

E-3
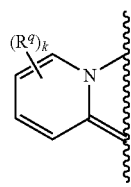

E-8
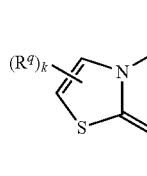

$R^5$ is $CR^{5a}R^{5b}R^{5c}$ $R^{5a}$ is hydrogen or methyl;

$R^{5b}$ is hydrogen;

$R^{5c}$ is a substituted heterocyclic ring system D-2a, D-25a or D-54a:

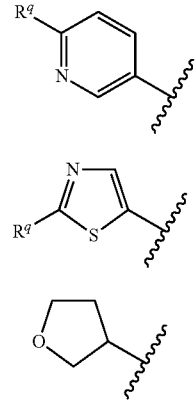

D-2a

D-25a

D-54a $R^a$ is hydrogen, $C_1$-$C_6$-alkyl which may be partially or fully halogenated, —C(=O)$R^e$, —C(=O)O$R^g$ or —C(=O)N($R^d$)$_2$;

each $R^b$ is independently hydrogen, halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl or $C_1$-$C_6$-haloalkylthio;

each $R^q$ is independently H, fluoro, chloro, bromo, CN, methyl, trifluoromethyl, methoxy, difluoromethoxy, trifluoromethoxy, thiomethoxy or trifluorothiomethoxy.

In a further preferred embodiment, the compound of formula (I) is a compound of formulae (I-13), (I-14) or (I-15), (I-16), (I-17) or (I-18,)

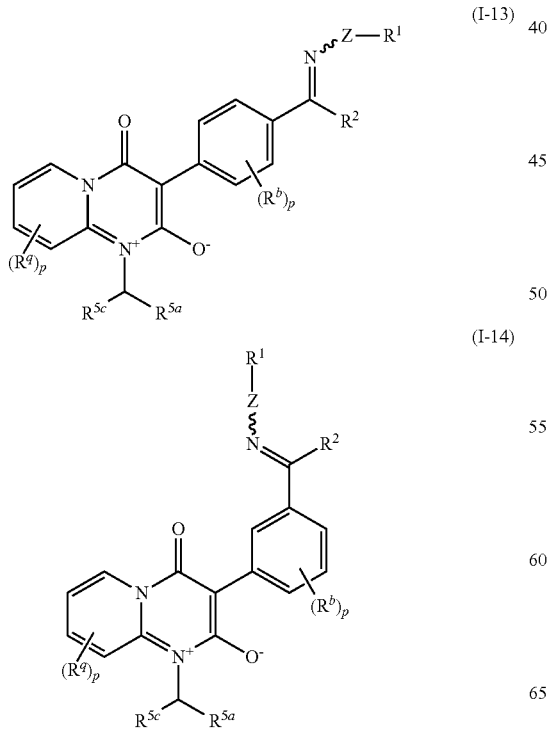

(I-13)

(I-14)

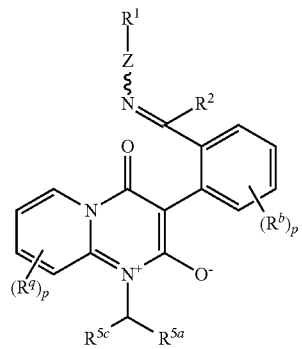

(I-15)

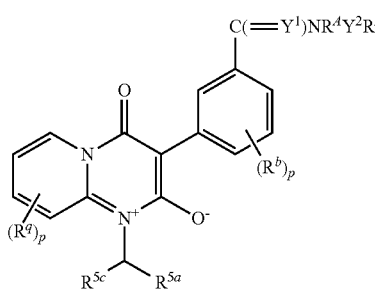

(I-16)

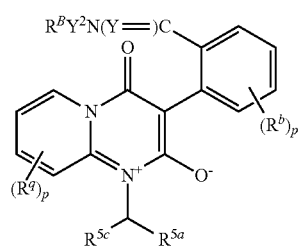

(I-17)

(I-18)

wherein
$Y^1$, $Y^2$ are independently O or S;
$R^A$, $R^B$ are independently H, ($C_1$-$C_6$)-alkyl, benzyl or phenyl;
$R^1$ is hydrogen, cyano, nitro, $C_1$-$C_6$-alkyl which may be partially or fully halogenated and/or is unsubstituted or substituted with one or more radicals $R^c$, $C_3$-$C_6$-cycloalkyl which may be partially or fully halogenated and/or is unsubstituted or substituted with one or more radicals $R^c$, $C_2$-$C_6$-alkenyl which may be partially or fully halogenated and/or is unsubstituted or substituted with one or more radicals $R^c$, $C_2$-$C_6$-alkynyl which may be partially or fully halogenated and/or is unsubstituted or substituted with one or more radicals $R^c$, —N($R^d$)$_2$, —N($R^d$)C(=O)$R^e$, —S(O)$_m R^h$, —S(O)$_n$N($R^d$)$_2$, —C(=O)$R^e$, —C(=O)O$R^h$, —C(=O)N($R^d$)$_2$, —C(=S)$R^e$, —C(=S)N($R^d$)$_2$;

$R^2$ is $NR^i R^k$;

$R^{5a}$ is hydrogen or methyl;

$R^{5c}$ is a substituted heterocyclic ring system D-2a, D-25a or D-54a;

$R^a$ is hydrogen or $C_1$-$C_4$-alkyl;

each $R^b$ is independently hydrogen, halogen, cyano, nitro, methyl, trifluoromethyl, methoxy, difluoromethoxy, trifluoromethoxy, thiomethoxy or trifluorothiomethoxy;

each $R^c$ is independently H, $C_1$-$C_6$-alkyl, $C_2$-$C_6$-alkenyl, $C_2$-$C_6$-alkynyl, $C_3$-$C_6$-cycloalkyl, wherein the four last mentioned aliphatic and cyclo-aliphatic radicals are unsubstituted or partially or fully halogenated, phenyl, benzyl, pyridyl, wherein the last three radicals are unsubstituted or partially or fully halogenated;

each $R^h$ is independently $C_1$-$C_6$-alkyl, $C_2$-$C_6$-alkenyl, $C_2$-$C_6$-alkynyl, $C_3$-$C_6$-cycloalkyl, wherein the four last mentioned aliphatic and cyclo-aliphatic radicals are unsubstituted or partially or fully halogenated, phenyl, benzyl, pyridyl, wherein the last three radicals may be unsubstituted, partially or fully halogenated;

each $R^d$ is independently hydrogen, cyano, $C_1$-$C_6$-alkoxy, $C_1$-$C_6$-haloalkoxy, $C_1$-$C_6$-alkylthio, $C_1$-$C_6$-haloalkylthio; benzyl, $C_1$-$C_6$-alkyl, $C_2$-$C_6$-alkenyl, $C_2$-$C_6$-alkynyl, $C_3$-$C_6$-cycloalkyl, wherein the four last mentioned aliphatic and cyclo-aliphatic radicals may be unsubstituted, partially or fully halogenated;

each $R^q$ is independently hydrogen, fluoro, chloro, bromo, methyl or trifluoromethyl and each p is independently 0, 1, 2, 3, or 4.

In a further preferred embodiment, the compound of formula (I) is a compound of formula (I-13a),

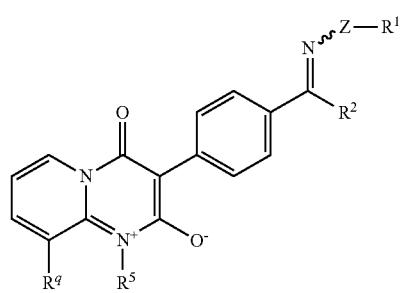

(I-13a)

wherein the symbols and indices have the same meaning as in formula (I-13), in particular a compound listed in Table 1.

TABLE 1

Compounds of formula (I-13a)

R51 is 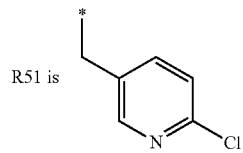

R52 is 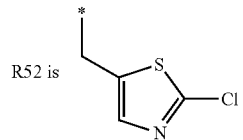

R53 is 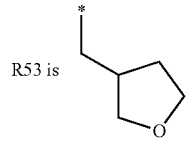

| No. | $R^5$ | $R^q$ | Z | $R^1$ | $R^2$ |
|---|---|---|---|---|---|
| 1 | R51 | H | — | H | NH—O—H |
| 2 | R51 | H | — | H | NH—O—CH$_3$ |
| 3 | R51 | H | — | H | NH—O—C$_6$H$_5$ |
| 4 | R51 | H | — | H | NH$_2$ |
| 5 | R51 | H | — | H | NH(CH$_3$) |
| 6 | R51 | H | — | H | N(CH$_3$)$_2$ |
| 7 | R51 | H | — | H | NH(C$_6$H$_5$) |
| 8 | R51 | H | — | CH$_3$ | NH—O—H |
| 9 | R51 | H | — | CH$_3$ | NH—O—CH$_3$ |
| 10 | R51 | H | — | CH$_3$ | NH—O—C$_6$H$_5$ |
| 11 | R51 | H | — | CH$_3$ | NH$_2$ |
| 12 | R51 | H | — | CH$_3$ | NH(CH$_3$) |
| 13 | R51 | H | — | CH$_3$ | N(CH$_3$)$_2$ |
| 14 | R51 | H | — | CH$_3$ | NH(C$_6$H$_5$) |
| 15 | R51 | H | — | C$_2$H$_5$ | NH—O—H |
| 16 | R51 | H | — | C$_2$H$_5$ | NH—O—CH$_3$ |
| 17 | R51 | H | — | C$_2$H$_5$ | NH—O—C$_6$H$_5$ |
| 18 | R51 | H | — | C$_2$H$_5$ | NH$_2$ |
| 19 | R51 | H | — | C$_2$H$_5$ | NH(CH$_3$) |
| 20 | R51 | H | — | C$_2$H$_5$ | N(CH$_3$)$_2$ |
| 21 | R51 | H | — | C$_2$H$_5$ | NH(C$_6$H$_5$) |
| 22 | R51 | H | — | CH(CH$_3$)$_2$ | NH—O—H |
| 23 | R51 | H | — | CH(CH$_3$)$_2$ | NH—O—CH$_3$ |
| 24 | R51 | H | — | CH(CH$_3$)$_2$ | NH—O—C$_6$H$_5$ |
| 25 | R51 | H | — | CH(CH$_3$)$_2$ | NH$_2$ |
| 26 | R51 | H | — | CH(CH$_3$)$_2$ | NH(CH$_3$) |
| 27 | R51 | H | — | CH(CH$_3$)$_2$ | N(CH$_3$)$_2$ |
| 28 | R51 | H | — | CH(CH$_3$)$_2$ | NH(C$_6$H$_5$) |
| 29 | R51 | H | — | CH$_2$CF$_3$ | NH—O—H |
| 30 | R51 | H | — | CH$_2$CF$_3$ | NH—O—CH$_3$ |
| 31 | R51 | H | — | CH$_2$CF$_3$ | NH—O—C$_6$H$_5$ |
| 32 | R51 | H | — | CH$_2$CF$_3$ | NH$_2$ |
| 33 | R51 | H | — | CH$_2$CF$_3$ | NH(CH$_3$) |
| 34 | R51 | H | — | CH$_2$CF$_3$ | N(CH$_3$)$_2$ |
| 35 | R51 | H | — | CH$_2$CF$_3$ | NH(C$_6$H$_5$) |
| 36 | R51 | H | — | CH$_2$-cyclo-C$_3$H$_5$ | NH—O—H |
| 37 | R51 | H | — | CH$_2$-cyclo-C$_3$H$_5$ | NH—O—CH$_3$ |
| 38 | R51 | H | — | CH$_2$-cyclo-C$_3$H$_5$ | NH—O—C$_6$H$_5$ |
| 39 | R51 | H | — | CH$_2$-cyclo-C$_3$H$_5$ | NH$_2$ |
| 40 | R51 | H | — | CH$_2$-cyclo-C$_3$H$_5$ | NH(CH$_3$) |
| 41 | R51 | H | — | CH$_2$-cyclo-C$_3$H$_5$ | N(CH$_3$)$_2$ |
| 42 | R51 | H | — | CH$_2$-cyclo-C$_3$H$_5$ | NH(C$_6$H$_5$) |
| 43 | R51 | H | — | C$_6$H$_5$ | NH—O—H |
| 44 | R51 | H | — | C$_6$H$_5$ | NH—O—CH$_3$ |
| 45 | R51 | H | — | C$_6$H$_5$ | NH—O—C$_6$H$_5$ |
| 46 | R51 | H | — | C$_6$H$_5$ | NH$_2$ |
| 47 | R51 | H | — | C$_6$H$_5$ | NH(CH$_3$) |
| 48 | R51 | H | — | C$_6$H$_5$ | N(CH$_3$)$_2$ |
| 49 | R51 | H | — | C$_6$H$_5$ | NH(C$_6$H$_5$) |
| 50 | R51 | H | O | H | NH—O—H |
| 51 | R51 | H | O | H | NH—O—CH$_3$ |
| 52 | R51 | H | O | H | NH—O—C$_6$H$_5$ |
| 53 | R51 | H | O | H | NH$_2$ |

TABLE 1-continued

Compounds of formula (I-13a)

R51 is: *-CH2- attached to pyridine with Cl (5-position methyl, 2-chloropyridine)

R52 is: *-CH2- attached to 2-chlorothiazole

R53 is: *-CH2- attached to tetrahydrofuran-3-yl

| No. | R⁵ | Rq | Z | R¹ | R² |
|---|---|---|---|---|---|
| 54 | R51 | H | O | H | NH(CH₃) |
| 55 | R51 | H | O | H | N(CH₃)₂ |
| 56 | R51 | H | O | H | NH(C₆H₅) |
| 57 | R51 | H | O | CH₃ | NH—O—H |
| 58 | R51 | H | O | CH₃ | NH—O—CH₃ |
| 59 | R51 | H | O | CH₃ | NH—O—C₆H₅ |
| 60 | R51 | H | O | CH₃ | NH₂ |
| 61 | R51 | H | O | CH₃ | NH(CH₃) |
| 62 | R51 | H | O | CH₃ | N(CH₃)₂ |
| 63 | R51 | H | O | CH₃ | NH(C₆H₅) |
| 64 | R51 | H | O | C₂H₅ | NH—O—H |
| 65 | R51 | H | O | C₂H₅ | NH—O—CH₃ |
| 66 | R51 | H | O | C₂H₅ | NH—O—C₆H₅ |
| 67 | R51 | H | O | C₂H₅ | NH₂ |
| 68 | R51 | H | O | C₂H₅ | NH(CH₃) |
| 69 | R51 | H | O | C₂H₅ | N(CH₃)₂ |
| 70 | R51 | H | O | C₂H₅ | NH(C₆H₅) |
| 71 | R51 | H | O | CH(CH₃)₂ | NH—O—H |
| 72 | R51 | H | O | CH(CH₃)₂ | NH—O—CH₃ |
| 73 | R51 | H | O | CH(CH₃)₂ | NH—O—C₆H₅ |
| 74 | R51 | H | O | CH(CH₃)₂ | NH₂ |
| 75 | R51 | H | O | CH(CH₃)₂ | NH(CH₃) |
| 76 | R51 | H | O | CH(CH₃)₂ | N(CH₃)₂ |
| 77 | R51 | H | O | CH(CH₃)₂ | NH(C₆H₅) |
| 78 | R51 | H | O | CH₂CF₃ | NH—O—H |
| 79 | R51 | H | O | CH₂CF₃ | NH—O—CH₃ |
| 80 | R51 | H | O | CH₂CF₃ | NH—O—C₆H₅ |
| 81 | R51 | H | O | CH₂CF₃ | NH₂ |
| 82 | R51 | H | O | CH₂CF₃ | NH(CH₃) |
| 83 | R51 | H | O | CH₂CF₃ | N(CH₃)₂ |
| 84 | R51 | H | O | CH₂CF₃ | NH(C₆H₅) |
| 85 | R51 | H | O | CH₂-cyclo-C₃H₅ | NH—O—H |
| 86 | R51 | H | O | CH₂-cyclo-C₃H₅ | NH—O—CH₃ |
| 87 | R51 | H | O | CH₂-cyclo-C₃H₅ | NH—O—C₆H₅ |
| 88 | R51 | H | O | CH₂-cyclo-C₃H₅ | NH₂ |
| 89 | R51 | H | O | CH₂-cyclo-C₃H₅ | NH(CH₃) |
| 90 | R51 | H | O | CH₂-cyclo-C₃H₅ | N(CH₃)₂ |
| 91 | R51 | H | O | CH₂-cyclo-C₃H₅ | NH(C₆H₅) |
| 92 | R51 | H | O | C₆H₅ | NH—O—H |
| 93 | R51 | H | O | C₆H₅ | NH—O—CH₃ |
| 94 | R51 | H | O | C₆H₅ | NH—O—C₆H₅ |
| 95 | R51 | H | O | C₆H₅ | NH₂ |
| 96 | R51 | H | O | C₆H₅ | NH(CH₃) |
| 97 | R51 | H | O | C₆H₅ | N(CH₃)₂ |
| 98 | R51 | H | O | C₆H₅ | NH(C₆H₅) |
| 99 | R51 | H | NH | H | NH—O—H |
| 100 | R51 | H | NH | H | NH—O—CH₃ |
| 101 | R51 | H | NH | H | NH—O—C₆H₅ |
| 102 | R51 | H | NH | H | NH₂ |
| 103 | R51 | H | NH | H | NH(CH₃) |
| 104 | R51 | H | NH | H | N(CH₃)₂ |
| 105 | R51 | H | NH | H | NH(C₆H₅) |
| 106 | R51 | H | NH | CH₃ | NH—O—H |
| 107 | R51 | H | NH | CH₃ | NH—O—CH₃ |
| 108 | R51 | H | NH | CH₃ | NH—O—C₆H₅ |
| 109 | R51 | H | NH | CH₃ | NH₂ |
| 110 | R51 | H | NH | CH₃ | NH(CH₃) |
| 111 | R51 | H | NH | CH₃ | N(CH₃)₂ |
| 112 | R51 | H | NH | CH₃ | NH(C₆H₅) |
| 113 | R51 | H | NH | C₂H₅ | NH—O—H |
| 114 | R51 | H | NH | C₂H₅ | NH—O—CH₃ |
| 115 | R51 | H | NH | C₂H₅ | NH—O—C₆H₅ |
| 116 | R51 | H | NH | C₂H₅ | NH₂ |
| 117 | R51 | H | NH | C₂H₅ | NH(CH₃) |
| 118 | R51 | H | NH | C₂H₅ | N(CH₃)₂ |
| 119 | R51 | H | NH | C₂H₅ | NH(C₆H₅) |
| 120 | R51 | H | NH | CH(CH₃)₂ | NH—O—H |
| 121 | R51 | H | NH | CH(CH₃)₂ | NH—O—CH₃ |
| 122 | R51 | H | NH | CH(CH₃)₂ | NH—O—C₆H₅ |
| 123 | R51 | H | NH | CH(CH₃)₂ | NH₂ |
| 124 | R51 | H | NH | CH(CH₃)₂ | NH(CH₃) |
| 125 | R51 | H | NH | CH(CH₃)₂ | N(CH₃)₂ |
| 126 | R51 | H | NH | CH(CH₃)₂ | NH(C₆H₅) |
| 127 | R51 | H | NH | CH₂CF₃ | NH—O—H |
| 128 | R51 | H | NH | CH₂CF₃ | NH—O—CH₃ |
| 129 | R51 | H | NH | CH₂CF₃ | NH—O—C₆H₅ |
| 130 | R51 | H | NH | CH₂CF₃ | NH₂ |
| 131 | R51 | H | NH | CH₂CF₃ | NH(CH₃) |
| 132 | R51 | H | NH | CH₂CF₃ | N(CH₃)₂ |
| 133 | R51 | H | NH | CH₂CF₃ | NH(C₆H₅) |
| 134 | R51 | H | NH | CH₂-cyclo-C₃H₅ | NH—O—H |
| 135 | R51 | H | NH | CH₂-cyclo-C₃H₅ | NH—O—CH₃ |
| 136 | R51 | H | NH | CH₂-cyclo-C₃H₅ | NH—O—C₆H₅ |
| 137 | R51 | H | NH | CH₂-cyclo-C₃H₅ | NH₂ |
| 138 | R51 | H | NH | CH₂-cyclo-C₃H₅ | NH(CH₃) |
| 139 | R51 | H | NH | CH₂-cyclo-C₃H₅ | N(CH₃)₂ |
| 140 | R51 | H | NH | CH₂-cyclo-C₃H₅ | NH(C₆H₅) |
| 141 | R51 | H | NH | C₆H₅ | NH—O—H |
| 142 | R51 | H | NH | C₆H₅ | NH—O—CH₃ |
| 143 | R51 | H | NH | C₆H₅ | NH—O—C₆H₅ |
| 144 | R51 | H | NH | C₆H₅ | NH₂ |
| 145 | R51 | H | NH | C₆H₅ | NH(CH₃) |
| 146 | R51 | H | NH | C₆H₅ | N(CH₃)₂ |
| 147 | R51 | H | NH | C₆H₅ | NH(C₆H₅) |
| 148 | R51 | CH₃ | — | H | NH—O—H |
| 149 | R51 | CH₃ | — | H | NH—O—CH₃ |
| 150 | R51 | CH₃ | — | H | NH—O—C₆H₅ |
| 151 | R51 | CH₃ | — | H | NH₂ |
| 152 | R51 | CH₃ | — | H | NH(CH₃) |
| 153 | R51 | CH₃ | — | H | N(CH₃)₂ |
| 154 | R51 | CH₃ | — | H | NH(C₆H₅) |
| 155 | R51 | CH₃ | — | CH₃ | NH—O—H |
| 156 | R51 | CH₃ | — | CH₃ | NH—O—CH₃ |
| 157 | R51 | CH₃ | — | CH₃ | NH—O—C₆H₅ |
| 158 | R51 | CH₃ | — | CH₃ | NH₂ |
| 159 | R51 | CH₃ | — | CH₃ | NH(CH₃) |

TABLE 1-continued

Compounds of formula (I-13a)

R51 is 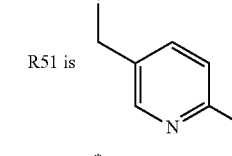

R52 is 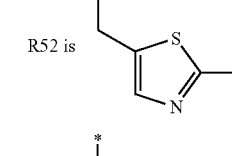

R53 is 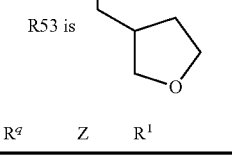

| No. | $R^5$ | $R^q$ | Z | $R^1$ | $R^2$ |
|---|---|---|---|---|---|
| 160 | R51 | $CH_3$ | — | $CH_3$ | $N(CH_3)_2$ |
| 161 | R51 | $CH_3$ | — | $CH_3$ | $NH(C_6H_5)$ |
| 162 | R51 | $CH_3$ | — | $C_2H_5$ | $NH-O-H$ |
| 163 | R51 | $CH_3$ | — | $C_2H_5$ | $NH-O-CH_3$ |
| 164 | R51 | $CH_3$ | — | $C_2H_5$ | $NH-O-C_6H_5$ |
| 165 | R51 | $CH_3$ | — | $C_2H_5$ | $NH_2$ |
| 166 | R51 | $CH_3$ | — | $C_2H_5$ | $NH(CH_3)$ |
| 167 | R51 | $CH_3$ | — | $C_2H_5$ | $N(CH_3)_2$ |
| 168 | R51 | $CH_3$ | — | $C_2H_5$ | $NH(C_6H_5)$ |
| 169 | R51 | $CH_3$ | — | $CH(CH_3)_2$ | $NH-O-H$ |
| 170 | R51 | $CH_3$ | — | $CH(CH_3)_2$ | $NH-O-CH_3$ |
| 171 | R51 | $CH_3$ | — | $CH(CH_3)_2$ | $NH-O-C_6H_5$ |
| 172 | R51 | $CH_3$ | — | $CH(CH_3)_2$ | $NH_2$ |
| 173 | R51 | $CH_3$ | — | $CH(CH_3)_2$ | $NH(CH_3)$ |
| 174 | R51 | $CH_3$ | — | $CH(CH_3)_2$ | $N(CH_3)_2$ |
| 175 | R51 | $CH_3$ | — | $CH(CH_3)_2$ | $NH(C_6H_5)$ |
| 176 | R51 | $CH_3$ | — | $CH_2CF_3$ | $NH-O-H$ |
| 177 | R51 | $CH_3$ | — | $CH_2CF_3$ | $NH-O-CH_3$ |
| 178 | R51 | $CH_3$ | — | $CH_2CF_3$ | $NH-O-C_6H_5$ |
| 179 | R51 | $CH_3$ | — | $CH_2CF_3$ | $NH_2$ |
| 180 | R51 | $CH_3$ | — | $CH_2CF_3$ | $NH(CH_3)$ |
| 181 | R51 | $CH_3$ | — | $CH_2CF_3$ | $N(CH_3)_2$ |
| 182 | R51 | $CH_3$ | — | $CH_2CF_3$ | $NH(C_6H_5)$ |
| 183 | R51 | $CH_3$ | — | $CH_2$-cyclo-$C_3H_5$ | $NH-O-H$ |
| 184 | R51 | $CH_3$ | — | $CH_2$-cyclo-$C_3H_5$ | $NH-O-CH_3$ |
| 185 | R51 | $CH_3$ | — | $CH_2$-cyclo-$C_3H_5$ | $NH-O-C_6H_5$ |
| 186 | R51 | $CH_3$ | — | $CH_2$-cyclo-$C_3H_5$ | $NH_2$ |
| 187 | R51 | $CH_3$ | — | $CH_2$-cyclo-$C_3H_5$ | $NH(CH_3)$ |
| 188 | R51 | $CH_3$ | — | $CH_2$-cyclo-$C_3H_5$ | $N(CH_3)_2$ |
| 189 | R51 | $CH_3$ | — | $CH_2$-cyclo-$C_3H_5$ | $NH(C_6H_5)$ |
| 190 | R51 | $CH_3$ | — | $C_6H_5$ | $NH-O-H$ |
| 191 | R51 | $CH_3$ | — | $C_6H_5$ | $NH-O-CH_3$ |
| 192 | R51 | $CH_3$ | — | $C_6H_5$ | $NH-O-C_6H_5$ |
| 193 | R51 | $CH_3$ | — | $C_6H_5$ | $NH_2$ |
| 194 | R51 | $CH_3$ | — | $C_6H_5$ | $NH(CH_3)$ |
| 195 | R51 | $CH_3$ | — | $C_6H_5$ | $N(CH_3)_2$ |
| 196 | R51 | $CH_3$ | — | $C_6H_5$ | $NH(C_6H_5)$ |
| 197 | R51 | $CH_3$ | O | H | $NH-O-H$ |
| 198 | R51 | $CH_3$ | O | H | $NH-O-CH_3$ |
| 199 | R51 | $CH_3$ | O | H | $NH-O-C_6H_5$ |
| 200 | R51 | $CH_3$ | O | H | $NH_2$ |
| 201 | R51 | $CH_3$ | O | H | $NH(CH_3)$ |
| 202 | R51 | $CH_3$ | O | H | $N(CH_3)_2$ |
| 203 | R51 | $CH_3$ | O | H | $NH(C_6H_5)$ |
| 204 | R51 | $CH_3$ | O | $CH_3$ | $NH-O-H$ |
| 205 | R51 | $CH_3$ | O | $CH_3$ | $NH-O-CH_3$ |
| 206 | R51 | $CH_3$ | O | $CH_3$ | $NH-O-C_6H_5$ |
| 207 | R51 | $CH_3$ | O | $CH_3$ | $NH_2$ |
| 208 | R51 | $CH_3$ | O | $CH_3$ | $NH(CH_3)$ |
| 209 | R51 | $CH_3$ | O | $CH_3$ | $N(CH_3)_2$ |
| 210 | R51 | $CH_3$ | O | $CH_3$ | $NH(C_6H_5)$ |
| 211 | R51 | $CH_3$ | O | $C_2H_5$ | $NH-O-H$ |
| 212 | R51 | $CH_3$ | O | $C_2H_5$ | $NH-O-CH_3$ |
| 213 | R51 | $CH_3$ | O | $C_2H_5$ | $NH-O-C_6H_5$ |
| 214 | R51 | $CH_3$ | O | $C_2H_5$ | $NH_2$ |
| 215 | R51 | $CH_3$ | O | $C_2H_5$ | $NH(CH_3)$ |
| 216 | R51 | $CH_3$ | O | $C_2H_5$ | $N(CH_3)_2$ |
| 217 | R51 | $CH_3$ | O | $C_2H_5$ | $NH(C_6H_5)$ |
| 218 | R51 | $CH_3$ | O | $CH(CH_3)_2$ | $NH-O-H$ |
| 219 | R51 | $CH_3$ | O | $CH(CH_3)_2$ | $NH-O-CH_3$ |
| 220 | R51 | $CH_3$ | O | $CH(CH_3)_2$ | $NH-O-C_6H_5$ |
| 221 | R51 | $CH_3$ | O | $CH(CH_3)_2$ | $NH_2$ |
| 222 | R51 | $CH_3$ | O | $CH(CH_3)_2$ | $NH(CH_3)$ |
| 223 | R51 | $CH_3$ | O | $CH(CH_3)_2$ | $N(CH_3)_2$ |
| 224 | R51 | $CH_3$ | O | $CH(CH_3)_2$ | $NH(C_6H_5)$ |
| 225 | R51 | $CH_3$ | O | $CH_2CF_3$ | $NH-O-H$ |
| 226 | R51 | $CH_3$ | O | $CH_2CF_3$ | $NH-O-CH_3$ |
| 227 | R51 | $CH_3$ | O | $CH_2CF_3$ | $NH-O-C_6H_5$ |
| 228 | R51 | $CH_3$ | O | $CH_2CF_3$ | $NH_2$ |
| 229 | R51 | $CH_3$ | O | $CH_2CF_3$ | $NH(CH_3)$ |
| 230 | R51 | $CH_3$ | O | $CH_2CF_3$ | $N(CH_3)_2$ |
| 231 | R51 | $CH_3$ | O | $CH_2CF_3$ | $NH(C_6H_5)$ |
| 232 | R51 | $CH_3$ | O | $CH_2$-cyclo-$C_3H_5$ | $NH-O-H$ |
| 233 | R51 | $CH_3$ | O | $CH_2$-cyclo-$C_3H_5$ | $NH-O-CH_3$ |
| 234 | R51 | $CH_3$ | O | $CH_2$-cyclo-$C_3H_5$ | $NH-O-C_6H_5$ |
| 235 | R51 | $CH_3$ | O | $CH_2$-cyclo-$C_3H_5$ | $NH_2$ |
| 236 | R51 | $CH_3$ | O | $CH_2$-cyclo-$C_3H_5$ | $NH(CH_3)$ |
| 237 | R51 | $CH_3$ | O | $CH_2$-cyclo-$C_3H_5$ | $N(CH_3)_2$ |
| 238 | R51 | $CH_3$ | O | $CH_2$-cyclo-$C_3H_5$ | $NH(C_6H_5)$ |
| 239 | R51 | $CH_3$ | O | $C_6H_5$ | $NH-O-H$ |
| 240 | R51 | $CH_3$ | O | $C_6H_5$ | $NH-O-CH_3$ |
| 241 | R51 | $CH_3$ | O | $C_6H_5$ | $NH-O-C_6H_5$ |
| 242 | R51 | $CH_3$ | O | $C_6H_5$ | $NH_2$ |
| 243 | R51 | $CH_3$ | O | $C_6H_5$ | $NH(CH_3)$ |
| 244 | R51 | $CH_3$ | O | $C_6H_5$ | $N(CH_3)_2$ |
| 245 | R51 | $CH_3$ | O | $C_6H_5$ | $NH(C_6H_5)$ |
| 246 | R51 | $CH_3$ | NH | H | $NH-O-H$ |
| 247 | R51 | $CH_3$ | NH | H | $NH-O-CH_3$ |
| 248 | R51 | $CH_3$ | NH | H | $NH-O-C_6H_5$ |
| 249 | R51 | $CH_3$ | NH | H | $NH_2$ |
| 250 | R51 | $CH_3$ | NH | H | $NH(CH_3)$ |
| 251 | R51 | $CH_3$ | NH | H | $N(CH_3)_2$ |
| 252 | R51 | $CH_3$ | NH | H | $NH(C_6H_5)$ |
| 253 | R51 | $CH_3$ | NH | $CH_3$ | $NH-O-H$ |
| 254 | R51 | $CH_3$ | NH | $CH_3$ | $NH-O-CH_3$ |
| 255 | R51 | $CH_3$ | NH | $CH_3$ | $NH-O-C_6H_5$ |
| 256 | R51 | $CH_3$ | NH | $CH_3$ | $NH_2$ |
| 257 | R51 | $CH_3$ | NH | $CH_3$ | $NH(CH_3)$ |
| 258 | R51 | $CH_3$ | NH | $CH_3$ | $N(CH_3)_2$ |
| 259 | R51 | $CH_3$ | NH | $CH_3$ | $NH(C_6H_5)$ |
| 260 | R51 | $CH_3$ | NH | $C_2H_5$ | $NH-O-H$ |
| 261 | R51 | $CH_3$ | NH | $C_2H_5$ | $NH-O-CH_3$ |
| 262 | R51 | $CH_3$ | NH | $C_2H_5$ | $NH-O-C_6H_5$ |
| 263 | R51 | $CH_3$ | NH | $C_2H_5$ | $NH_2$ |
| 264 | R51 | $CH_3$ | NH | $C_2H_5$ | $NH(CH_3)$ |
| 265 | R51 | $CH_3$ | NH | $C_2H_5$ | $N(CH_3)_2$ |

TABLE 1-continued

Compounds of formula (I-13a)

R51 is 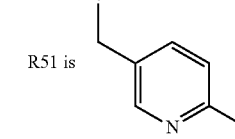

R52 is 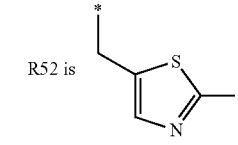

R53 is 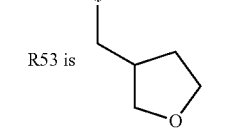

| No. | $R^5$ | $R^q$ | Z | $R^1$ | $R^2$ |
|---|---|---|---|---|---|
| 266 | R51 | $CH_3$ | NH | $C_2H_5$ | $NH(C_6H_5)$ |
| 267 | R51 | $CH_3$ | NH | $CH(CH_3)_2$ | NH—O—H |
| 268 | R51 | $CH_3$ | NH | $CH(CH_3)_2$ | NH—O—$CH_3$ |
| 269 | R51 | $CH_3$ | NH | $CH(CH_3)_2$ | NH—O—$C_6H_5$ |
| 270 | R51 | $CH_3$ | NH | $CH(CH_3)_2$ | $NH_2$ |
| 271 | R51 | $CH_3$ | NH | $CH(CH_3)_2$ | $NH(CH_3)$ |
| 272 | R51 | $CH_3$ | NH | $CH(CH_3)_2$ | $N(CH_3)_2$ |
| 273 | R51 | $CH_3$ | NH | $CH(CH_3)_2$ | $NH(C_6H_5)$ |
| 274 | R51 | $CH_3$ | NH | $CH_2CF_3$ | NH—O—H |
| 275 | R51 | $CH_3$ | NH | $CH_2CF_3$ | NH—O—$CH_3$ |
| 276 | R51 | $CH_3$ | NH | $CH_2CF_3$ | NH—O—$C_6H_5$ |
| 277 | R51 | $CH_3$ | NH | $CH_2CF_3$ | $NH_2$ |
| 278 | R51 | $CH_3$ | NH | $CH_2CF_3$ | $NH(CH_3)$ |
| 279 | R51 | $CH_3$ | NH | $CH_2CF_3$ | $N(CH_3)_2$ |
| 280 | R51 | $CH_3$ | NH | $CH_2CF_3$ | $NH(C_6H_5)$ |
| 281 | R51 | $CH_3$ | NH | $CH_2$-cyclo-$C_3H_5$ | NH—O—H |
| 282 | R51 | $CH_3$ | NH | $CH_2$-cyclo-$C_3H_5$ | NH—O—$CH_3$ |
| 283 | R51 | $CH_3$ | NH | $CH_2$-cyclo-$C_3H_5$ | NH—O—$C_6H_5$ |
| 284 | R51 | $CH_3$ | NH | $CH_2$-cyclo-$C_3H_5$ | $NH_2$ |
| 285 | R51 | $CH_3$ | NH | $CH_2$-cyclo-$C_3H_5$ | $NH(CH_3)$ |
| 286 | R51 | $CH_3$ | NH | $CH_2$-cyclo-$C_3H_5$ | $N(CH_3)_2$ |
| 287 | R51 | $CH_3$ | NH | $CH_2$-cyclo-$C_3H_5$ | $NH(C_6H_5)$ |
| 288 | R51 | $CH_3$ | NH | $C_6H_5$ | NH—O—H |
| 289 | R51 | $CH_3$ | NH | $C_6H_5$ | NH—O—$CH_3$ |
| 290 | R51 | $CH_3$ | NH | $C_6H_5$ | NH—O—$C_6H_5$ |
| 291 | R51 | $CH_3$ | NH | $C_6H_5$ | $NH_2$ |
| 292 | R51 | $CH_3$ | NH | $C_6H_5$ | $NH(CH_3)$ |
| 293 | R51 | $CH_3$ | NH | $C_6H_5$ | $N(CH_3)_2$ |
| 294 | R51 | $CH_3$ | NH | $C_6H_5$ | $NH(C_6H_5)$ |
| 295 | R52 | H | — | H | NH—O—H |
| 296 | R52 | H | — | H | NH—O—$CH_3$ |
| 297 | R52 | H | — | H | NH—O—$C_6H_5$ |
| 298 | R52 | H | — | H | $NH_2$ |
| 299 | R52 | H | — | H | $NH(CH_3)$ |
| 300 | R52 | H | — | H | $N(CH_3)_2$ |
| 301 | R52 | H | — | H | $NH(C_6H_5)$ |
| 302 | R52 | H | — | $CH_3$ | NH—O—H |
| 303 | R52 | H | — | $CH_3$ | NH—O—$CH_3$ |
| 304 | R52 | H | — | $CH_3$ | NH—O—$C_6H_5$ |
| 305 | R52 | H | — | $CH_3$ | $NH_2$ |
| 306 | R52 | H | — | $CH_3$ | $NH(CH_3)$ |
| 307 | R52 | H | — | $CH_3$ | $N(CH_3)_2$ |
| 308 | R52 | H | — | $CH_3$ | $NH(C_6H_5)$ |
| 309 | R52 | H | — | $C_2H_5$ | NH—O—H |
| 310 | R52 | H | — | $C_2H_5$ | NH—O—$CH_3$ |
| 311 | R52 | H | — | $C_2H_5$ | NH—O—$C_6H_5$ |
| 312 | R52 | H | — | $C_2H_5$ | $NH_2$ |
| 313 | R52 | H | — | $C_2H_5$ | $NH(CH_3)$ |
| 314 | R52 | H | — | $C_2H_5$ | $N(CH_3)_2$ |
| 315 | R52 | H | — | $C_2H_5$ | $NH(C_6H_5)$ |
| 316 | R52 | H | — | $CH(CH_3)_2$ | NH—O—H |
| 317 | R52 | H | — | $CH(CH_3)_2$ | NH—O—$CH_3$ |
| 318 | R52 | H | — | $CH(CH_3)_2$ | NH—O—$C_6H_5$ |
| 319 | R52 | H | — | $CH(CH_3)_2$ | $NH_2$ |
| 320 | R52 | H | — | $CH(CH_3)_2$ | $NH(CH_3)$ |
| 321 | R52 | H | — | $CH(CH_3)_2$ | $N(CH_3)_2$ |
| 322 | R52 | H | — | $CH(CH_3)_2$ | $NH(C_6H_5)$ |
| 323 | R52 | H | — | $CH_2CF_3$ | NH—O—H |
| 324 | R52 | H | — | $CH_2CF_3$ | NH—O—$CH_3$ |
| 325 | R52 | H | — | $CH_2CF_3$ | NH—O—$C_6H_5$ |
| 326 | R52 | H | — | $CH_2CF_3$ | $NH_2$ |
| 327 | R52 | H | — | $CH_2CF_3$ | $NH(CH_3)$ |
| 328 | R52 | H | — | $CH_2CF_3$ | $N(CH_3)_2$ |
| 329 | R52 | H | — | $CH_2CF_3$ | $NH(C_6H_5)$ |
| 330 | R52 | H | — | $CH_2$-cyclo-$C_3H_5$ | NH—O—H |
| 331 | R52 | H | — | $CH_2$-cyclo-$C_3H_5$ | NH—O—$CH_3$ |
| 332 | R52 | H | — | $CH_2$-cyclo-$C_3H_5$ | NH—O—$C_6H_5$ |
| 333 | R52 | H | — | $CH_2$-cyclo-$C_3H_5$ | $NH_2$ |
| 334 | R52 | H | — | $CH_2$-cyclo-$C_3H_5$ | $NH(CH_3)$ |
| 335 | R52 | H | — | $CH_2$-cyclo-$C_3H_5$ | $N(CH_3)_2$ |
| 336 | R52 | H | — | $CH_2$-cyclo-$C_3H_5$ | $NH(C_6H_5)$ |
| 337 | R52 | H | — | $C_6H_5$ | NH—O—H |
| 338 | R52 | H | — | $C_6H_5$ | NH—O—$CH_3$ |
| 339 | R52 | H | — | $C_6H_5$ | NH—O—$C_6H_5$ |
| 340 | R52 | H | — | $C_6H_5$ | $NH_2$ |
| 341 | R52 | H | — | $C_6H_5$ | $NH(CH_3)$ |
| 342 | R52 | H | — | $C_6H_5$ | $N(CH_3)_2$ |
| 343 | R52 | H | — | $C_6H_5$ | $NH(C_6H_5)$ |
| 344 | R52 | H | O | H | NH—O—H |
| 345 | R52 | H | O | H | NH—O—$CH_3$ |
| 346 | R52 | H | O | H | NH—O—$C_6H_5$ |
| 347 | R52 | H | O | H | $NH_2$ |
| 348 | R52 | H | O | H | $NH(CH_3)$ |
| 349 | R52 | H | O | H | $N(CH_3)_2$ |
| 350 | R52 | H | O | H | $NH(C_6H_5)$ |
| 351 | R52 | H | O | $CH_3$ | NH—O—H |
| 352 | R52 | H | O | $CH_3$ | NH—O—$CH_3$ |
| 353 | R52 | H | O | $CH_3$ | NH—O—$C_6H_5$ |
| 354 | R52 | H | O | $CH_3$ | $NH_2$ |
| 355 | R52 | H | O | $CH_3$ | $NH(CH_3)$ |
| 356 | R52 | H | O | $CH_3$ | $N(CH_3)_2$ |
| 357 | R52 | H | O | $CH_3$ | $NH(C_6H_5)$ |
| 358 | R52 | H | O | $C_2H_5$ | NH—O—H |
| 359 | R52 | H | O | $C_2H_5$ | NH—O—$CH_3$ |
| 360 | R52 | H | O | $C_2H_5$ | NH—O—$C_6H_5$ |
| 361 | R52 | H | O | $C_2H_5$ | $NH_2$ |
| 362 | R52 | H | O | $C_2H_5$ | $NH(CH_3)$ |
| 363 | R52 | H | O | $C_2H_5$ | $N(CH_3)_2$ |
| 364 | R52 | H | O | $C_2H_5$ | $NH(C_6H_5)$ |
| 365 | R52 | H | O | $CH(CH_3)_2$ | NH—O—H |
| 366 | R52 | H | O | $CH(CH_3)_2$ | NH—O—$CH_3$ |
| 367 | R52 | H | O | $CH(CH_3)_2$ | NH—O—$C_6H_5$ |
| 368 | R52 | H | O | $CH(CH_3)_2$ | $NH_2$ |
| 369 | R52 | H | O | $CH(CH_3)_2$ | $NH(CH_3)$ |
| 370 | R52 | H | O | $CH(CH_3)_2$ | $N(CH_3)_2$ |
| 371 | R52 | H | O | $CH(CH_3)_2$ | $NH(C_6H_5)$ |

TABLE 1-continued

Compounds of formula (I-13a)

R51 is 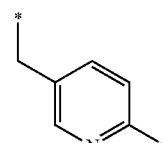

R52 is 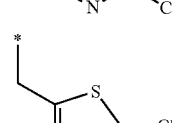

R53 is 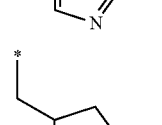

| No. | R⁵ | R$^q$ | Z | R¹ | R² |
|---|---|---|---|---|---|
| 372 | R52 | H | O | CH₂CF₃ | NH—O—H |
| 373 | R52 | H | O | CH₂CF₃ | NH—O—CH₃ |
| 374 | R52 | H | O | CH₂CF₃ | NH—O—C₆H₅ |
| 375 | R52 | H | O | CH₂CF₃ | NH₂ |
| 376 | R52 | H | O | CH₂CF₃ | NH(CH₃) |
| 377 | R52 | H | O | CH₂CF₃ | N(CH₃)₂ |
| 378 | R52 | H | O | CH₂CF₃ | NH(C₆H₅) |
| 379 | R52 | H | O | CH₂-cyclo-C₃H₅ | NH—O—H |
| 380 | R52 | H | O | CH₂-cyclo-C₃H₅ | NH—O—CH₃ |
| 381 | R52 | H | O | CH₂-cyclo-C₃H₅ | NH—O—C₆H₅ |
| 382 | R52 | H | O | CH₂-cyclo-C₃H₅ | NH₂ |
| 383 | R52 | H | O | CH₂-cyclo-C₃H₅ | NH(CH₃) |
| 384 | R52 | H | O | CH₂-cyclo-C₃H₅ | N(CH₃)₂ |
| 385 | R52 | H | O | CH₂-cyclo-C₃H₅ | NH(C₆H₅) |
| 386 | R52 | H | O | C₆H₅ | NH—O—H |
| 387 | R52 | H | O | C₆H₅ | NH—O—CH₃ |
| 388 | R52 | H | O | C₆H₅ | NH—O—C₆H₅ |
| 389 | R52 | H | O | C₆H₅ | NH₂ |
| 390 | R52 | H | O | C₆H₅ | NH(CH₃) |
| 391 | R52 | H | O | C₆H₅ | N(CH₃)₂ |
| 392 | R52 | H | O | C₆H₅ | NH(C₆H₅) |
| 393 | R52 | H | NH | H | NH—O—H |
| 394 | R52 | H | NH | H | NH—O—CH₃ |
| 395 | R52 | H | NH | H | NH—O—C₆H₅ |
| 396 | R52 | H | NH | H | NH₂ |
| 397 | R52 | H | NH | H | NH(CH₃) |
| 398 | R52 | H | NH | H | N(CH₃)₂ |
| 399 | R52 | H | NH | H | NH(C₆H₅) |
| 400 | R52 | H | NH | CH₃ | NH—O—H |
| 401 | R52 | H | NH | CH₃ | NH—O—CH₃ |
| 402 | R52 | H | NH | CH₃ | NH—O—C₆H₅ |
| 403 | R52 | H | NH | CH₃ | NH₂ |
| 404 | R52 | H | NH | CH₃ | NH(CH₃) |
| 405 | R52 | H | NH | CH₃ | N(CH₃)₂ |
| 406 | R52 | H | NH | CH₃ | NH(C₆H₅) |
| 407 | R52 | H | NH | C₂H₅ | NH—O—H |
| 408 | R52 | H | NH | C₂H₅ | NH—O—CH₃ |
| 409 | R52 | H | NH | C₂H₅ | NH—O—C₆H₅ |
| 410 | R52 | H | NH | C₂H₅ | NH₂ |
| 411 | R52 | H | NH | C₂H₅ | NH(CH₃) |
| 412 | R52 | H | NH | C₂H₅ | N(CH₃)₂ |
| 413 | R52 | H | NH | C₂H₅ | NH(C₆H₅) |
| 414 | R52 | H | NH | CH(CH₃)₂ | NH—O—H |
| 415 | R52 | H | NH | CH(CH₃)₂ | NH—O—CH₃ |
| 416 | R52 | H | NH | CH(CH₃)₂ | NH—O—C₆H₅ |
| 417 | R52 | H | NH | CH(CH₃)₂ | NH₂ |
| 418 | R52 | H | NH | CH(CH₃)₂ | NH(CH₃) |
| 419 | R52 | H | NH | CH(CH₃)₂ | N(CH₃)₂ |
| 420 | R52 | H | NH | CH(CH₃)₂ | NH(C₆H₅) |
| 421 | R52 | H | NH | CH₂CF₃ | NH—O—H |
| 422 | R52 | H | NH | CH₂CF₃ | NH—O—CH₃ |
| 423 | R52 | H | NH | CH₂CF₃ | NH—O—C₆H₅ |
| 424 | R52 | H | NH | CH₂CF₃ | NH₂ |
| 425 | R52 | H | NH | CH₂CF₃ | NH(CH₃) |
| 426 | R52 | H | NH | CH₂CF₃ | N(CH₃)₂ |
| 427 | R52 | H | NH | CH₂CF₃ | NH(C₆H₅) |
| 428 | R52 | H | NH | CH₂-cyclo-C₃H₅ | NH—O—H |
| 429 | R52 | H | NH | CH₂-cyclo-C₃H₅ | NH—O—CH₃ |
| 430 | R52 | H | NH | CH₂-cyclo-C₃H₅ | NH—O—C₆H₅ |
| 431 | R52 | H | NH | CH₂-cyclo-C₃H₅ | NH₂ |
| 432 | R52 | H | NH | CH₂-cyclo-C₃H₅ | NH(CH₃) |
| 433 | R52 | H | NH | CH₂-cyclo-C₃H₅ | N(CH₃)₂ |
| 434 | R52 | H | NH | CH₂-cyclo-C₃H₅ | NH(C₆H₅) |
| 435 | R52 | H | NH | C₆H₅ | NH—O—H |
| 436 | R52 | H | NH | C₆H₅ | NH—O—CH₃ |
| 437 | R52 | H | NH | C₆H₅ | NH—O—C₆H₅ |
| 438 | R52 | H | NH | C₆H₅ | NH₂ |
| 439 | R52 | H | NH | C₆H₅ | NH(CH₃) |
| 440 | R52 | H | NH | C₆H₅ | N(CH₃)₂ |
| 441 | R52 | H | NH | C₆H₅ | NH(C₆H₅) |
| 442 | R52 | CH₃ | — | H | NH—O—H |
| 443 | R52 | CH₃ | — | H | NH—O—CH₃ |
| 444 | R52 | CH₃ | — | H | NH—O—C₆H₅ |
| 445 | R52 | CH₃ | — | H | NH₂ |
| 446 | R52 | CH₃ | — | H | NH(CH₃) |
| 447 | R52 | CH₃ | — | H | N(CH₃)₂ |
| 448 | R52 | CH₃ | — | H | NH(C₆H₅) |
| 449 | R52 | CH₃ | — | CH₃ | NH—O—H |
| 450 | R52 | CH₃ | — | CH₃ | NH—O—CH₃ |
| 451 | R52 | CH₃ | — | CH₃ | NH—O—C₆H₅ |
| 452 | R52 | CH₃ | — | CH₃ | NH₂ |
| 453 | R52 | CH₃ | — | CH₃ | NH(CH₃) |
| 454 | R52 | CH₃ | — | CH₃ | N(CH₃)₂ |
| 455 | R52 | CH₃ | — | CH₃ | NH(C₆H₅) |
| 456 | R52 | CH₃ | — | C₂H₅ | NH—O—H |
| 457 | R52 | CH₃ | — | C₂H₅ | NH—O—CH₃ |
| 458 | R52 | CH₃ | — | C₂H₅ | NH—O—C₆H₅ |
| 459 | R52 | CH₃ | — | C₂H₅ | NH₂ |
| 460 | R52 | CH₃ | — | C₂H₅ | NH(CH₃) |
| 461 | R52 | CH₃ | — | C₂H₅ | N(CH₃)₂ |
| 462 | R52 | CH₃ | — | C₂H₅ | NH(C₆H₅) |
| 463 | R52 | CH₃ | — | CH(CH₃)₂ | NH—O—H |
| 464 | R52 | CH₃ | — | CH(CH₃)₂ | NH—O—CH₃ |
| 465 | R52 | CH₃ | — | CH(CH₃)₂ | NH—O—C₆H₅ |
| 466 | R52 | CH₃ | — | CH(CH₃)₂ | NH₂ |
| 467 | R52 | CH₃ | — | CH(CH₃)₂ | NH(CH₃) |
| 468 | R52 | CH₃ | — | CH(CH₃)₂ | N(CH₃)₂ |
| 469 | R52 | CH₃ | — | CH(CH₃)₂ | NH(C₆H₅) |
| 470 | R52 | CH₃ | — | CH₂CF₃ | NH—O—H |
| 471 | R52 | CH₃ | — | CH₂CF₃ | NH—O—CH₃ |
| 472 | R52 | CH₃ | — | CH₂CF₃ | NH—O—C₆H₅ |
| 473 | R52 | CH₃ | — | CH₂CF₃ | NH₂ |
| 474 | R52 | CH₃ | — | CH₂CF₃ | NH(CH₃) |
| 475 | R52 | CH₃ | — | CH₂CF₃ | N(CH₃)₂ |
| 476 | R52 | CH₃ | — | CH₂CF₃ | NH(C₆H₅) |
| 477 | R52 | CH₃ | — | CH₂-cyclo-C₃H₅ | NH—O—H |

TABLE 1-continued

Compounds of formula (I-13a)

R51 is 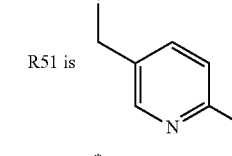

R52 is 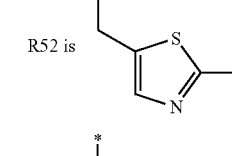

R53 is 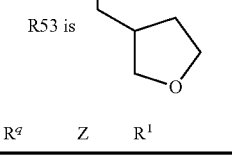

| No. | R⁵ | Rᵍ | Z | R¹ | R² |
|---|---|---|---|---|---|
| 478 | R52 | CH₃ | — | CH₂-cyclo-C₃H₅ | NH—O—CH₃ |
| 479 | R52 | CH₃ | — | CH₂-cyclo-C₃H₅ | NH—O—C₆H₅ |
| 480 | R52 | CH₃ | — | CH₂-cyclo-C₃H₅ | NH₂ |
| 481 | R52 | CH₃ | — | CH₂-cyclo-C₃H₅ | NH(CH₃) |
| 482 | R52 | CH₃ | — | CH₂-cyclo-C₃H₅ | N(CH₃)₂ |
| 483 | R52 | CH₃ | — | CH₂-cyclo-C₃H₅ | NH(C₆H₅) |
| 484 | R52 | CH₃ | — | C₆H₅ | NH—O—H |
| 485 | R52 | CH₃ | — | C₆H₅ | NH—O—CH₃ |
| 486 | R52 | CH₃ | — | C₆H₅ | NH—O—C₆H₅ |
| 487 | R52 | CH₃ | — | C₆H₅ | NH₂ |
| 488 | R52 | CH₃ | — | C₆H₅ | NH(CH₃) |
| 489 | R52 | CH₃ | — | C₆H₅ | N(CH₃)₂ |
| 490 | R52 | CH₃ | — | C₆H₅ | NH(C₆H₅) |
| 491 | R52 | CH₃ | O | H | NH—O—H |
| 492 | R52 | CH₃ | O | H | NH—O—CH₃ |
| 493 | R52 | CH₃ | O | H | NH—O—C₆H₅ |
| 494 | R52 | CH₃ | O | H | NH₂ |
| 495 | R52 | CH₃ | O | H | NH(CH₃) |
| 496 | R52 | CH₃ | O | H | N(CH₃)₂ |
| 497 | R52 | CH₃ | O | H | NH(C₆H₅) |
| 498 | R52 | CH₃ | O | CH₃ | NH—O—H |
| 499 | R52 | CH₃ | O | CH₃ | NH—O—CH₃ |
| 500 | R52 | CH₃ | O | CH₃ | NH—O—C₆H₅ |
| 501 | R52 | CH₃ | O | CH₃ | NH₂ |
| 502 | R52 | CH₃ | O | CH₃ | NH(CH₃) |
| 503 | R52 | CH₃ | O | CH₃ | N(CH₃)₂ |
| 504 | R52 | CH₃ | O | CH₃ | NH(C₆H₅) |
| 505 | R52 | CH₃ | O | C₂H₅ | NH—O—H |
| 506 | R52 | CH₃ | O | C₂H₅ | NH—O—CH₃ |
| 507 | R52 | CH₃ | O | C₂H₅ | NH—O—C₆H₅ |
| 508 | R52 | CH₃ | O | C₂H₅ | NH₂ |
| 509 | R52 | CH₃ | O | C₂H₅ | NH(CH₃) |
| 510 | R52 | CH₃ | O | C₂H₅ | N(CH₃)₂ |
| 511 | R52 | CH₃ | O | C₂H₅ | NH(C₆H₅) |
| 512 | R52 | CH₃ | O | CH(CH₃)₂ | NH—O—H |
| 513 | R52 | CH₃ | O | CH(CH₃)₂ | NH—O—CH₃ |
| 514 | R52 | CH₃ | O | CH(CH₃)₂ | NH—O—C₆H₅ |
| 515 | R52 | CH₃ | O | CH(CH₃)₂ | NH₂ |
| 516 | R52 | CH₃ | O | CH(CH₃)₂ | NH(CH₃) |
| 517 | R52 | CH₃ | O | CH(CH₃)₂ | N(CH₃)₂ |
| 518 | R52 | CH₃ | O | CH(CH₃)₂ | NH(C₆H₅) |
| 519 | R52 | CH₃ | O | CH₂CF₃ | NH—O—H |
| 520 | R52 | CH₃ | O | CH₂CF₃ | NH—O—CH₃ |
| 521 | R52 | CH₃ | O | CH₂CF₃ | NH—O—C₆H₅ |
| 522 | R52 | CH₃ | O | CH₂CF₃ | NH₂ |
| 523 | R52 | CH₃ | O | CH₂CF₃ | NH(CH₃) |
| 524 | R52 | CH₃ | O | CH₂CF₃ | N(CH₃)₂ |
| 525 | R52 | CH₃ | O | CH₂CF₃ | NH(C₆H₅) |
| 526 | R52 | CH₃ | O | CH₂-cyclo-C₃H₅ | NH—O—H |
| 527 | R52 | CH₃ | O | CH₂-cyclo-C₃H₅ | NH—O—CH₃ |
| 528 | R52 | CH₃ | O | CH₂-cyclo-C₃H₅ | NH—O—C₆H₅ |
| 529 | R52 | CH₃ | O | CH₂-cyclo-C₃H₅ | NH₂ |
| 530 | R52 | CH₃ | O | CH₂-cyclo-C₃H₅ | NH(CH₃) |
| 531 | R52 | CH₃ | O | CH₂-cyclo-C₃H₅ | N(CH₃)₂ |
| 532 | R52 | CH₃ | O | CH₂-cyclo-C₃H₅ | NH(C₆H₅) |
| 533 | R52 | CH₃ | O | C₆H₅ | NH—O—H |
| 534 | R52 | CH₃ | O | C₆H₅ | NH—O—CH₃ |
| 535 | R52 | CH₃ | O | C₆H₅ | NH—O—C₆H₅ |
| 536 | R52 | CH₃ | O | C₆H₅ | NH₂ |
| 537 | R52 | CH₃ | O | C₆H₅ | NH(CH₃) |
| 538 | R52 | CH₃ | O | C₆H₅ | N(CH₃)₂ |
| 539 | R52 | CH₃ | O | C₆H₅ | NH(C₆H₅) |
| 540 | R52 | CH₃ | NH | H | NH—O—H |
| 541 | R52 | CH₃ | NH | H | NH—O—CH₃ |
| 542 | R52 | CH₃ | NH | H | NH—O—C₆H₅ |
| 543 | R52 | CH₃ | NH | H | NH₂ |
| 544 | R52 | CH₃ | NH | H | NH(CH₃) |
| 545 | R52 | CH₃ | NH | H | N(CH₃)₂ |
| 546 | R52 | CH₃ | NH | H | NH(C₆H₅) |
| 547 | R52 | CH₃ | NH | CH₃ | NH—O—H |
| 548 | R52 | CH₃ | NH | CH₃ | NH—O—CH₃ |
| 549 | R52 | CH₃ | NH | CH₃ | NH—O—C₆H₅ |
| 550 | R52 | CH₃ | NH | CH₃ | NH₂ |
| 551 | R52 | CH₃ | NH | CH₃ | NH(CH₃) |
| 552 | R52 | CH₃ | NH | CH₃ | N(CH₃)₂ |
| 553 | R52 | CH₃ | NH | CH₃ | NH(C₆H₅) |
| 554 | R52 | CH₃ | NH | C₂H₅ | NH—O—H |
| 555 | R52 | CH₃ | NH | C₂H₅ | NH—O—CH₃ |
| 556 | R52 | CH₃ | NH | C₂H₅ | NH—O—C₆H₅ |
| 557 | R52 | CH₃ | NH | C₂H₅ | NH₂ |
| 558 | R52 | CH₃ | NH | C₂H₅ | NH(CH₃) |
| 559 | R52 | CH₃ | NH | C₂H₅ | N(CH₃)₂ |
| 560 | R52 | CH₃ | NH | C₂H₅ | NH(C₆H₅) |
| 561 | R52 | CH₃ | NH | CH(CH₃)₂ | NH—O—H |
| 562 | R52 | CH₃ | NH | CH(CH₃)₂ | NH—O—CH₃ |
| 563 | R52 | CH₃ | NH | CH(CH₃)₂ | NH—O—C₆H₅ |
| 564 | R52 | CH₃ | NH | CH(CH₃)₂ | NH₂ |
| 565 | R52 | CH₃ | NH | CH(CH₃)₂ | NH(CH₃) |
| 566 | R52 | CH₃ | NH | CH(CH₃)₂ | N(CH₃)₂ |
| 567 | R52 | CH₃ | NH | CH(CH₃)₂ | NH(C₆H₅) |
| 568 | R52 | CH₃ | NH | CH₂CF₃ | NH—O—H |
| 569 | R52 | CH₃ | NH | CH₂CF₃ | NH—O—CH₃ |
| 570 | R52 | CH₃ | NH | CH₂CF₃ | NH—O—C₆H₅ |
| 571 | R52 | CH₃ | NH | CH₂CF₃ | NH₂ |
| 572 | R52 | CH₃ | NH | CH₂CF₃ | NH(CH₃) |
| 573 | R52 | CH₃ | NH | CH₂CF₃ | N(CH₃)₂ |
| 574 | R52 | CH₃ | NH | CH₂CF₃ | NH(C₆H₅) |
| 575 | R52 | CH₃ | NH | CH₂-cyclo-C₃H₅ | NH—O—H |
| 576 | R52 | CH₃ | NH | CH₂-cyclo-C₃H₅ | NH—O—CH₃ |
| 577 | R52 | CH₃ | NH | CH₂-cyclo-C₃H₅ | NH—O—C₆H₅ |
| 589 | R52 | CH₃ | NH | CH₂-cyclo-C₃H₅ | NH₂ |
| 579 | R52 | CH₃ | NH | CH₂-cyclo-C₃H₅ | NH(CH₃) |
| 580 | R52 | CH₃ | NH | CH₂-cyclo-C₃H₅ | N(CH₃)₂ |
| 581 | R52 | CH₃ | NH | CH₂-cyclo-C₃H₅ | NH(C₆H₅) |
| 582 | R52 | CH₃ | NH | C₆H₅ | NH—O—H |
| 583 | R52 | CH₃ | NH | C₆H₅ | NH—O—CH₃ |

TABLE 1-continued

Compounds of formula (I-13a)

R51 is 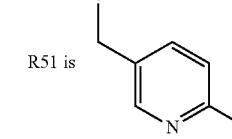

R52 is 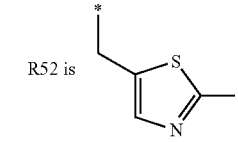

R53 is 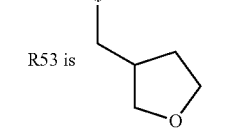

| No. | $R^5$ | $R^q$ | Z | $R^1$ | $R^2$ |
|---|---|---|---|---|---|
| 584 | R52 | $CH_3$ | NH | $C_6H_5$ | NH—O—$C_6H_5$ |
| 585 | R52 | $CH_3$ | NH | $C_6H_5$ | $NH_2$ |
| 586 | R52 | $CH_3$ | NH | $C_6H_5$ | $NH(CH_3)$ |
| 587 | R52 | $CH_3$ | NH | $C_6H_5$ | $N(CH_3)_2$ |
| 588 | R52 | $CH_3$ | NH | $C_6H_5$ | $NH(C_6H_5)$ |
| 589 | R53 | H | — | H | NH—O—H |
| 590 | R53 | H | — | H | NH—O—$CH_3$ |
| 591 | R53 | H | — | H | NH—O—$C_6H_5$ |
| 592 | R53 | H | — | H | $NH_2$ |
| 593 | R53 | H | — | H | $NH(CH_3)$ |
| 594 | R53 | H | — | H | $N(CH_3)_2$ |
| 595 | R53 | H | — | H | $NH(C_6H_5)$ |
| 596 | R53 | H | — | $CH_3$ | NH—O—H |
| 597 | R53 | H | — | $CH_3$ | NH—O—$CH_3$ |
| 598 | R53 | H | — | $CH_3$ | NH—O—$C_6H_5$ |
| 599 | R53 | H | — | $CH_3$ | $NH_2$ |
| 600 | R53 | H | — | $CH_3$ | $NH(CH_3)$ |
| 601 | R53 | H | — | $CH_3$ | $N(CH_3)_2$ |
| 602 | R53 | H | — | $CH_3$ | $NH(C_6H_5)$ |
| 603 | R53 | H | — | $C_2H_5$ | NH—O—H |
| 604 | R53 | H | — | $C_2H_5$ | NH—O—$CH_3$ |
| 605 | R53 | H | — | $C_2H_5$ | NH—O—$C_6H_5$ |
| 606 | R53 | H | — | $C_2H_5$ | $NH_2$ |
| 607 | R53 | H | — | $C_2H_5$ | $NH(CH_3)$ |
| 608 | R53 | H | — | $C_2H_5$ | $N(CH_3)_2$ |
| 609 | R53 | H | — | $C_2H_5$ | $NH(C_6H_5)$ |
| 610 | R53 | H | — | $CH(CH_3)_2$ | NH—O—H |
| 611 | R53 | H | — | $CH(CH_3)_2$ | NH—O—$CH_3$ |
| 612 | R53 | H | — | $CH(CH_3)_2$ | NH—O—$C_6H_5$ |
| 613 | R53 | H | — | $CH(CH_3)_2$ | $NH_2$ |
| 614 | R53 | H | — | $CH(CH_3)_2$ | $NH(CH_3)$ |
| 615 | R53 | H | — | $CH(CH_3)_2$ | $N(CH_3)_2$ |
| 616 | R53 | H | — | $CH(CH_3)_2$ | $NH(C_6H_5)$ |
| 617 | R53 | H | — | $CH_2CF_3$ | NH—O—H |
| 618 | R53 | H | — | $CH_2CF_3$ | NH—O—$CH_3$ |
| 619 | R53 | H | — | $CH_2CF_3$ | NH—O—$C_6H_5$ |
| 620 | R53 | H | — | $CH_2CF_3$ | $NH_2$ |
| 621 | R53 | H | — | $CH_2CF_3$ | $NH(CH_3)$ |
| 622 | R53 | H | — | $CH_2CF_3$ | $N(CH_3)_2$ |
| 623 | R53 | H | — | $CH_2CF_3$ | $NH(C_6H_5)$ |
| 624 | R53 | H | — | $CH_2$-cyclo-$C_3H_5$ | NH—O—H |
| 625 | R53 | H | — | $CH_2$-cyclo-$C_3H_5$ | NH—O—$CH_3$ |
| 626 | R53 | H | — | $CH_2$-cyclo-$C_3H_5$ | NH—O—$C_6H_5$ |
| 627 | R53 | H | — | $CH_2$-cyclo-$C_3H_5$ | $NH_2$ |
| 628 | R53 | H | — | $CH_2$-cyclo-$C_3H_5$ | $NH(CH_3)$ |
| 629 | R53 | H | — | $CH_2$-cyclo-$C_3H_5$ | $N(CH_3)_2$ |
| 630 | R53 | H | — | $CH_2$-cyclo-$C_3H_5$ | $NH(C_6H_5)$ |
| 631 | R53 | H | — | $C_6H_5$ | NH—O—H |
| 632 | R53 | H | — | $C_6H_5$ | NH—O—$CH_3$ |
| 633 | R53 | H | — | $C_6H_5$ | NH—O—$C_6H_5$ |
| 634 | R53 | H | — | $C_6H_5$ | $NH_2$ |
| 635 | R53 | H | — | $C_6H_5$ | $NH(CH_3)$ |
| 636 | R53 | H | — | $C_6H_5$ | $N(CH_3)_2$ |
| 637 | R53 | H | — | $C_6H_5$ | $NH(C_6H_5)$ |
| 638 | R53 | H | O | H | NH—O—H |
| 639 | R53 | H | O | H | NH—O—$CH_3$ |
| 640 | R53 | H | O | H | NH—O—$C_6H_5$ |
| 641 | R53 | H | O | H | $NH_2$ |
| 642 | R53 | H | O | H | $NH(CH_3)$ |
| 643 | R53 | H | O | H | $N(CH_3)_2$ |
| 644 | R53 | H | O | H | $NH(C_6H_5)$ |
| 645 | R53 | H | O | $CH_3$ | NH—O—H |
| 646 | R53 | H | O | $CH_3$ | NH—O—$CH_3$ |
| 647 | R53 | H | O | $CH_3$ | NH—O—$C_6H_5$ |
| 648 | R53 | H | O | $CH_3$ | $NH_2$ |
| 649 | R53 | H | O | $CH_3$ | $NH(CH_3)$ |
| 650 | R53 | H | O | $CH_3$ | $N(CH_3)_2$ |
| 651 | R53 | H | O | $CH_3$ | $NH(C_6H_5)$ |
| 652 | R53 | H | O | $C_2H_5$ | NH—O—H |
| 653 | R53 | H | O | $C_2H_5$ | NH—O—$CH_3$ |
| 654 | R53 | H | O | $C_2H_5$ | NH—O—$C_6H_5$ |
| 655 | R53 | H | O | $C_2H_5$ | $NH_2$ |
| 656 | R53 | H | O | $C_2H_5$ | $NH(CH_3)$ |
| 657 | R53 | H | O | $C_2H_5$ | $N(CH_3)_2$ |
| 658 | R53 | H | O | $C_2H_5$ | $NH(C_6H_5)$ |
| 659 | R53 | H | O | $CH(CH_3)_2$ | NH—O—H |
| 660 | R53 | H | O | $CH(CH_3)_2$ | NH—O—$CH_3$ |
| 661 | R53 | H | O | $CH(CH_3)_2$ | $NH_2$ |
| 662 | R53 | H | O | $CH(CH_3)_2$ | $NH(CH_3)$ |
| 663 | R53 | H | O | $CH(CH_3)_2$ | $NH(CH_3)$ |
| 664 | R53 | H | O | $CH(CH_3)_2$ | $N(CH_3)_2$ |
| 665 | R53 | H | O | $CH(CH_3)_2$ | $NH(C_6H_5)$ |
| 666 | R53 | H | O | $CH_2CF_3$ | NH—O—H |
| 667 | R53 | H | O | $CH_2CF_3$ | NH—O—$CH_3$ |
| 668 | R53 | H | O | $CH_2CF_3$ | NH—O—$C_6H_5$ |
| 669 | R53 | H | O | $CH_2CF_3$ | $NH_2$ |
| 670 | R53 | H | O | $CH_2CF_3$ | $NH(CH_3)$ |
| 671 | R53 | H | O | $CH_2CF_3$ | $N(CH_3)_2$ |
| 672 | R53 | H | O | $CH_2CF_3$ | $NH(C_6H_5)$ |
| 673 | R53 | H | O | $CH_2$-cyclo-$C_3H_5$ | NH—O—H |
| 674 | R53 | H | O | $CH_2$-cyclo-$C_3H_5$ | NH—O—$CH_3$ |
| 675 | R53 | H | O | $CH_2$-cyclo-$C_3H_5$ | NH—O—$C_6H_5$ |
| 676 | R53 | H | O | $CH_2$-cyclo-$C_3H_5$ | $NH_2$ |
| 677 | R53 | H | O | $CH_2$-cyclo-$C_3H_5$ | $NH(CH_3)$ |
| 678 | R53 | H | O | $CH_2$-cyclo-$C_3H_5$ | $N(CH_3)_2$ |
| 679 | R53 | H | O | $CH_2$-cyclo-$C_3H_5$ | $NH(C_6H_5)$ |
| 680 | R53 | H | O | $C_6H_5$ | NH—O—H |
| 681 | R53 | H | O | $C_6H_5$ | NH—O—$CH_3$ |
| 682 | R53 | H | O | $C_6H_5$ | NH—O—$C_6H_5$ |
| 683 | R53 | H | O | $C_6H_5$ | $NH_2$ |
| 684 | R53 | H | O | $C_6H_5$ | $NH(CH_3)$ |
| 685 | R53 | H | O | $C_6H_5$ | $N(CH_3)_2$ |
| 686 | R53 | H | O | $C_6H_5$ | $NH(C_6H_5)$ |
| 687 | R53 | H | NH | H | NH—O—H |
| 688 | R53 | H | NH | H | NH—O—$CH_3$ |
| 689 | R53 | H | NH | H | NH—O—$C_6H_5$ |

TABLE 1-continued

Compounds of formula (I-13a)

R51 is 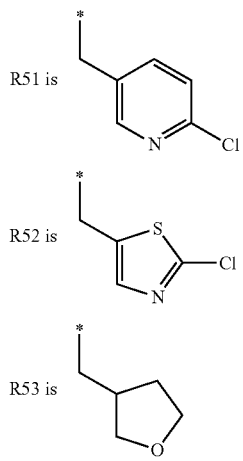

R52 is

R53 is

| No. | R⁵ | R^q | Z | R¹ | R² |
|---|---|---|---|---|---|
| 690 | R53 | H | NH | H | NH$_2$ |
| 691 | R53 | H | NH | H | NH(CH$_3$) |
| 692 | R53 | H | NH | H | N(CH$_3$)$_2$ |
| 693 | R53 | H | NH | H | NH(C$_6$H$_5$) |
| 694 | R53 | H | NH | CH$_3$ | NH—O—H |
| 695 | R53 | H | NH | CH$_3$ | NH—O—CH$_3$ |
| 696 | R53 | H | NH | CH$_3$ | NH—O—C$_6$H$_5$ |
| 697 | R53 | H | NH | CH$_3$ | NH$_2$ |
| 698 | R53 | H | NH | CH$_3$ | NH(CH$_3$) |
| 699 | R53 | H | NH | CH$_3$ | N(CH$_3$)$_2$ |
| 700 | R53 | H | NH | CH$_3$ | NH(C$_6$H$_5$) |
| 701 | R53 | H | NH | C$_2$H$_5$ | NH—O—H |
| 702 | R53 | H | NH | C$_2$H$_5$ | NH—O—CH$_3$ |
| 703 | R53 | H | NH | C$_2$H$_5$ | NH—O—C$_6$H$_5$ |
| 704 | R53 | H | NH | C$_2$H$_5$ | NH$_2$ |
| 705 | R53 | H | NH | C$_2$H$_5$ | NH(CH$_3$) |
| 706 | R53 | H | NH | C$_2$H$_5$ | N(CH$_3$)$_2$ |
| 707 | R53 | H | NH | C$_2$H$_5$ | NH(C$_6$H$_5$) |
| 708 | R53 | H | NH | CH(CH$_3$)$_2$ | NH—O—H |
| 709 | R53 | H | NH | CH(CH$_3$)$_2$ | NH—O—CH$_3$ |
| 710 | R53 | H | NH | CH(CH$_3$)$_2$ | NH—O—C$_6$H$_5$ |
| 711 | R53 | H | NH | CH(CH$_3$)$_2$ | NH$_2$ |
| 712 | R53 | H | NH | CH(CH$_3$)$_2$ | NH(CH$_3$) |
| 713 | R53 | H | NH | CH(CH$_3$)$_2$ | N(CH$_3$)$_2$ |
| 714 | R53 | H | NH | CH(CH$_3$)$_2$ | NH(C$_6$H$_5$) |
| 715 | R53 | H | NH | CH$_2$CF$_3$ | NH—O—H |
| 716 | R53 | H | NH | CH$_2$CF$_3$ | NH—O—CH$_3$ |
| 717 | R53 | H | NH | CH$_2$CF$_3$ | NH—O—C$_6$H$_5$ |
| 718 | R53 | H | NH | CH$_2$CF$_3$ | NH$_2$ |
| 719 | R53 | H | NH | CH$_2$CF$_3$ | NH(CH$_3$) |
| 720 | R53 | H | NH | CH$_2$CF$_3$ | N(CH$_3$)$_2$ |
| 721 | R53 | H | NH | CH$_2$CF$_3$ | NH(C$_6$H$_5$) |
| 722 | R53 | H | NH | CH$_2$-cyclo-C$_3$H$_5$ | NH—O—H |
| 723 | R53 | H | NH | CH$_2$-cyclo-C$_3$H$_5$ | NH—O—CH$_3$ |
| 724 | R53 | H | NH | CH$_2$-cyclo-C$_3$H$_5$ | NH—O—C$_6$H$_5$ |
| 725 | R53 | H | NH | CH$_2$-cyclo-C$_3$H$_5$ | NH$_2$ |
| 726 | R53 | H | NH | CH$_2$-cyclo-C$_3$H$_5$ | NH(CH$_3$) |
| 727 | R53 | H | NH | CH$_2$-cyclo-C$_3$H$_5$ | N(CH$_3$)$_2$ |
| 728 | R53 | H | NH | CH$_2$-cyclo-C$_3$H$_5$ | NH(C$_6$H$_5$) |
| 729 | R53 | H | NH | C$_6$H$_5$ | NH—O—H |
| 730 | R53 | H | NH | C$_6$H$_5$ | NH—O—CH$_3$ |
| 731 | R53 | H | NH | C$_6$H$_5$ | NH—O—C$_6$H$_5$ |
| 732 | R53 | H | NH | C$_6$H$_5$ | NH$_2$ |
| 733 | R53 | H | NH | C$_6$H$_5$ | NH(CH$_3$) |
| 734 | R53 | H | NH | C$_6$H$_5$ | N(CH$_3$)$_2$ |
| 735 | R53 | H | NH | C$_6$H$_5$ | NH(C$_6$H$_5$) |
| 736 | R53 | CH$_3$ | — | H | NH—O—H |
| 737 | R53 | CH$_3$ | — | H | NH—O—CH$_3$ |
| 738 | R53 | CH$_3$ | — | H | NH—O—C$_6$H$_5$ |
| 739 | R53 | CH$_3$ | — | H | NH$_2$ |
| 740 | R53 | CH$_3$ | — | H | NH(CH$_3$) |
| 741 | R53 | CH$_3$ | — | H | N(CH$_3$)$_2$ |
| 742 | R53 | CH$_3$ | — | H | NH(C$_6$H$_5$) |
| 743 | R53 | CH$_3$ | — | CH$_3$ | NH—O—H |
| 744 | R53 | CH$_3$ | — | CH$_3$ | NH—O—CH$_3$ |
| 745 | R53 | CH$_3$ | — | CH$_3$ | NH—O—C$_6$H$_5$ |
| 746 | R53 | CH$_3$ | — | CH$_3$ | NH$_2$ |
| 747 | R53 | CH$_3$ | — | CH$_3$ | NH(CH$_3$) |
| 748 | R53 | CH$_3$ | — | CH$_3$ | N(CH$_3$)$_2$ |
| 749 | R53 | CH$_3$ | — | CH$_3$ | NH(C$_6$H$_5$) |
| 750 | R53 | CH$_3$ | — | C$_2$H$_5$ | NH—O—H |
| 751 | R53 | CH$_3$ | — | C$_2$H$_5$ | NH—O—CH$_3$ |
| 752 | R53 | CH$_3$ | — | C$_2$H$_5$ | NH—O—C$_6$H$_5$ |
| 753 | R53 | CH$_3$ | — | C$_2$H$_5$ | NH$_2$ |
| 754 | R53 | CH$_3$ | — | C$_2$H$_5$ | NH(CH$_3$) |
| 755 | R53 | CH$_3$ | — | C$_2$H$_5$ | N(CH$_3$)$_2$ |
| 756 | R53 | CH$_3$ | — | C$_2$H$_5$ | NH(C$_6$H$_5$) |
| 757 | R53 | CH$_3$ | — | CH(CH$_3$)$_2$ | NH—O—H |
| 758 | R53 | CH$_3$ | — | CH(CH$_3$)$_2$ | NH—O—CH$_3$ |
| 759 | R53 | CH$_3$ | — | CH(CH$_3$)$_2$ | NH—O—C$_6$H$_5$ |
| 760 | R53 | CH$_3$ | — | CH(CH$_3$)$_2$ | NH$_2$ |
| 761 | R53 | CH$_3$ | — | CH(CH$_3$)$_2$ | NH(CH$_3$) |
| 762 | R53 | CH$_3$ | — | CH(CH$_3$)$_2$ | N(CH$_3$)$_2$ |
| 763 | R53 | CH$_3$ | — | CH(CH$_3$)$_2$ | NH(C$_6$H$_5$) |
| 764 | R53 | CH$_3$ | — | CH$_2$CF$_3$ | NH—O—H |
| 765 | R53 | CH$_3$ | — | CH$_2$CF$_3$ | NH—O—CH$_3$ |
| 766 | R53 | CH$_3$ | — | CH$_2$CF$_3$ | NH—O—C$_6$H$_5$ |
| 767 | R53 | CH$_3$ | — | CH$_2$CF$_3$ | NH$_2$ |
| 768 | R53 | CH$_3$ | — | CH$_2$CF$_3$ | NH(CH$_3$) |
| 769 | R53 | CH$_3$ | — | CH$_2$CF$_3$ | N(CH$_3$)$_2$ |
| 770 | R53 | CH$_3$ | — | CH$_2$CF$_3$ | NH(C$_6$H$_5$) |
| 771 | R53 | CH$_3$ | — | CH$_2$-cyclo-C$_3$H$_5$ | NH—O—H |
| 772 | R53 | CH$_3$ | — | CH$_2$-cyclo-C$_3$H$_5$ | NH—O—CH$_3$ |
| 773 | R53 | CH$_3$ | — | CH$_2$-cyclo-C$_3$H$_5$ | NH—O—C$_6$H$_5$ |
| 774 | R53 | CH$_3$ | — | CH$_2$-cyclo-C$_3$H$_5$ | NH$_2$ |
| 775 | R53 | CH$_3$ | — | CH$_2$-cyclo-C$_3$H$_5$ | NH(CH$_3$) |
| 776 | R53 | CH$_3$ | — | CH$_2$-cyclo-C$_3$H$_5$ | N(CH$_3$)$_2$ |
| 777 | R53 | CH$_3$ | — | CH$_2$-cyclo-C$_3$H$_5$ | NH(C$_6$H$_5$) |
| 778 | R53 | CH$_3$ | — | C$_6$H$_5$ | NH—O—H |
| 779 | R53 | CH$_3$ | — | C$_6$H$_5$ | NH—O—CH$_3$ |
| 780 | R53 | CH$_3$ | — | C$_6$H$_5$ | NH—O—C$_6$H$_5$ |
| 781 | R53 | CH$_3$ | — | C$_6$H$_5$ | NH$_2$ |
| 781 | R53 | CH$_3$ | — | C$_6$H$_5$ | NH(CH$_3$) |
| 783 | R53 | CH$_3$ | — | C$_6$H$_5$ | N(CH$_3$)$_2$ |
| 784 | R53 | CH$_3$ | — | C$_6$H$_5$ | NH(C$_6$H$_5$) |
| 785 | R53 | CH$_3$ | O | H | NH—O—H |
| 786 | R53 | CH$_3$ | O | H | NH—O—CH$_3$ |
| 787 | R53 | CH$_3$ | O | H | NH—O—C$_6$H$_5$ |
| 788 | R53 | CH$_3$ | O | H | NH$_2$ |
| 789 | R53 | CH$_3$ | O | H | NH(CH$_3$) |
| 790 | R53 | CH$_3$ | O | H | N(CH$_3$)$_2$ |
| 791 | R53 | CH$_3$ | O | H | NH(C$_6$H$_5$) |
| 792 | R53 | CH$_3$ | O | CH$_3$ | NH—O—H |
| 793 | R53 | CH$_3$ | O | CH$_3$ | NH—O—CH$_3$ |
| 794 | R53 | CH$_3$ | O | CH$_3$ | NH—O—C$_6$H$_5$ |
| 795 | R53 | CH$_3$ | O | CH$_3$ | NH$_2$ |

TABLE 1-continued

Compounds of formula (I-13a)

R51 is: *-CH2- attached to 5-position of 2-chloropyridine

R52 is: *-CH2- attached to 5-position of 2-chlorothiazole

R53 is: *-CH2- attached to 3-position of tetrahydrofuran

| No. | $R^5$ | $R^q$ | Z | $R^1$ | $R^2$ |
|---|---|---|---|---|---|
| 796 | R53 | $CH_3$ | O | $CH_3$ | $NH(CH_3)$ |
| 797 | R53 | $CH_3$ | O | $CH_3$ | $N(CH_3)_2$ |
| 798 | R53 | $CH_3$ | O | $CH_3$ | $NH(C_6H_5)$ |
| 799 | R53 | $CH_3$ | O | $C_2H_5$ | NH—O—H |
| 800 | R53 | $CH_3$ | O | $C_2H_5$ | NH—O—$CH_3$ |
| 801 | R53 | $CH_3$ | O | $C_2H_5$ | NH—O—$C_6H_5$ |
| 802 | R53 | $CH_3$ | O | $C_2H_5$ | $NH_2$ |
| 803 | R53 | $CH_3$ | O | $C_2H_5$ | $NH(CH_3)$ |
| 804 | R53 | $CH_3$ | O | $C_2H_5$ | $N(CH_3)_2$ |
| 805 | R53 | $CH_3$ | O | $C_2H_5$ | $NH(C_6H_5)$ |
| 806 | R53 | $CH_3$ | O | $CH(CH_3)_2$ | NH—O—H |
| 807 | R53 | $CH_3$ | O | $CH(CH_3)_2$ | NH—O—$CH_3$ |
| 808 | R53 | $CH_3$ | O | $CH(CH_3)_2$ | NH—O—$C_6H_5$ |
| 809 | R53 | $CH_3$ | O | $CH(CH_3)_2$ | $NH_2$ |
| 810 | R53 | $CH_3$ | O | $CH(CH_3)_2$ | $NH(CH_3)$ |
| 811 | R53 | $CH_3$ | O | $CH(CH_3)_2$ | $N(CH_3)_2$ |
| 812 | R53 | $CH_3$ | O | $CH(CH_3)_2$ | $NH(C_6H_5)$ |
| 813 | R53 | $CH_3$ | O | $CH_2CF_3$ | NH—O—H |
| 814 | R53 | $CH_3$ | O | $CH_2CF_3$ | NH—O—$CH_3$ |
| 815 | R53 | $CH_3$ | O | $CH_2CF_3$ | NH—O—$C_6H_5$ |
| 816 | R53 | $CH_3$ | O | $CH_2CF_3$ | $NH_2$ |
| 817 | R53 | $CH_3$ | O | $CH_2CF_3$ | $NH(CH_3)$ |
| 818 | R53 | $CH_3$ | O | $CH_2CF_3$ | $N(CH_3)_2$ |
| 819 | R53 | $CH_3$ | O | $CH_2CF_3$ | $NH(C_6H_5)$ |
| 820 | R53 | $CH_3$ | O | $CH_2$-cyclo-$C_3H_5$ | NH—O—H |
| 821 | R53 | $CH_3$ | O | $CH_2$-cyclo-$C_3H_5$ | NH—O—$CH_3$ |
| 822 | R53 | $CH_3$ | O | $CH_2$-cyclo-$C_3H_5$ | NH—O—$C_6H_5$ |
| 823 | R53 | $CH_3$ | O | $CH_2$-cyclo-$C_3H_5$ | $NH_2$ |
| 824 | R53 | $CH_3$ | O | $CH_2$-cyclo-$C_3H_5$ | $NH(CH_3)$ |
| 825 | R53 | $CH_3$ | O | $CH_2$-cyclo-$C_3H_5$ | $N(CH_3)_2$ |
| 826 | R53 | $CH_3$ | O | $CH_2$-cyclo-$C_3H_5$ | $NH(C_6H_5)$ |
| 827 | R53 | $CH_3$ | O | $C_6H_5$ | NH—O—H |
| 828 | R53 | $CH_3$ | O | $C_6H_5$ | NH—O—$CH_3$ |
| 829 | R53 | $CH_3$ | O | $C_6H_5$ | NH—O—$C_6H_5$ |
| 830 | R53 | $CH_3$ | O | $C_6H_5$ | $NH_2$ |
| 831 | R53 | $CH_3$ | O | $C_6H_5$ | $NH(CH_3)$ |
| 832 | R53 | $CH_3$ | O | $C_6H_5$ | $N(CH_3)_2$ |
| 833 | R53 | $CH_3$ | O | $C_6H_5$ | $NH(C_6H_5)$ |
| 834 | R53 | $CH_3$ | NH | H | NH—O—H |
| 835 | R53 | $CH_3$ | NH | H | NH—O—$CH_3$ |
| 836 | R53 | $CH_3$ | NH | H | NH—O—$C_6H_5$ |
| 837 | R53 | $CH_3$ | NH | H | $NH_2$ |
| 838 | R53 | $CH_3$ | NH | H | $NH(CH_3)$ |
| 839 | R53 | $CH_3$ | NH | H | $N(CH_3)_2$ |
| 840 | R53 | $CH_3$ | NH | H | $NH(C_6H_5)$ |
| 841 | R53 | $CH_3$ | NH | $CH_3$ | NH—O—H |
| 842 | R53 | $CH_3$ | NH | $CH_3$ | NH—O—$CH_3$ |
| 843 | R53 | $CH_3$ | NH | $CH_3$ | NH—O—$C_6H_5$ |
| 844 | R53 | $CH_3$ | NH | $CH_3$ | $NH_2$ |
| 845 | R53 | $CH_3$ | NH | $CH_3$ | $NH(CH_3)$ |
| 846 | R53 | $CH_3$ | NH | $CH_3$ | $N(CH_3)_2$ |
| 847 | R53 | $CH_3$ | NH | $CH_3$ | $NH(C_6H_5)$ |
| 848 | R53 | $CH_3$ | NH | $C_2H_5$ | NH—O—H |
| 849 | R53 | $CH_3$ | NH | $C_2H_5$ | NH—O—$CH_3$ |
| 850 | R53 | $CH_3$ | NH | $C_2H_5$ | NH—O—$C_6H_5$ |
| 851 | R53 | $CH_3$ | NH | $C_2H_5$ | $NH_2$ |
| 852 | R53 | $CH_3$ | NH | $C_2H_5$ | $NH(CH_3)$ |
| 853 | R53 | $CH_3$ | NH | $C_2H_5$ | $N(CH_3)_2$ |
| 854 | R53 | $CH_3$ | NH | $C_2H_5$ | $NH(C_6H_5)$ |
| 855 | R53 | $CH_3$ | NH | $CH(CH_3)_2$ | NH—O—H |
| 856 | R53 | $CH_3$ | NH | $CH(CH_3)_2$ | NH—O—$CH_3$ |
| 857 | R53 | $CH_3$ | NH | $CH(CH_3)_2$ | NH—O—$C_6H_5$ |
| 858 | R53 | $CH_3$ | NH | $CH(CH_3)_2$ | $NH_2$ |
| 859 | R53 | $CH_3$ | NH | $CH(CH_3)_2$ | $NH(CH_3)$ |
| 860 | R53 | $CH_3$ | NH | $CH(CH_3)_2$ | $N(CH_3)_2$ |
| 861 | R53 | $CH_3$ | NH | $CH(CH_3)_2$ | $NH(C_6H_5)$ |
| 862 | R53 | $CH_3$ | NH | $CH_2CF_3$ | NH—O—H |
| 863 | R53 | $CH_3$ | NH | $CH_2CF_3$ | NH—O—$CH_3$ |
| 864 | R53 | $CH_3$ | NH | $CH_2CF_3$ | NH—O—$C_6H_5$ |
| 865 | R53 | $CH_3$ | NH | $CH_2CF_3$ | $NH_2$ |
| 866 | R53 | $CH_3$ | NH | $CH_2CF_3$ | $NH(CH_3)$ |
| 867 | R53 | $CH_3$ | NH | $CH_2CF_3$ | $N(CH_3)_2$ |
| 868 | R53 | $CH_3$ | NH | $CH_2CF_3$ | $NH(C_6H_5)$ |
| 869 | R53 | $CH_3$ | NH | $CH_2$-cyclo-$C_3H_5$ | NH—O—H |
| 870 | R53 | $CH_3$ | NH | $CH_2$-cyclo-$C_3H_5$ | NH—O—$CH_3$ |
| 871 | R53 | $CH_3$ | NH | $CH_2$-cyclo-$C_3H_5$ | NH—O—$C_6H_5$ |
| 872 | R53 | $CH_3$ | NH | $CH_2$-cyclo-$C_3H_5$ | $NH_2$ |
| 873 | R53 | $CH_3$ | NH | $CH_2$-cyclo-$C_3H_5$ | $NH(CH_3)$ |
| 874 | R53 | $CH_3$ | NH | $CH_2$-cyclo-$C_3H_5$ | $N(CH_3)_2$ |
| 875 | R53 | $CH_3$ | NH | $CH_2$-cyclo-$C_3H_5$ | $NH(C_6H_5)$ |
| 876 | R53 | $CH_3$ | NH | $C_6H_5$ | NH—O—H |
| 877 | R53 | $CH_3$ | NH | $C_6H_5$ | NH—O—$CH_3$ |
| 878 | R53 | $CH_3$ | NH | $C_6H_5$ | NH—O—$C_6H_5$ |
| 879 | R53 | $CH_3$ | NH | $C_6H_5$ | $NH_2$ |
| 880 | R53 | $CH_3$ | NH | $C_6H_5$ | $NH(CH_3)$ |
| 881 | R53 | $CH_3$ | NH | $C_6H_5$ | $N(CH_3)_2$ |
| 882 | R53 | $CH_3$ | NH | $C_6H_5$ | $NH(C_6H_5)$ |

In a further preferred embodiment, the compound of formula (I) is a compound of formula (I-14a),

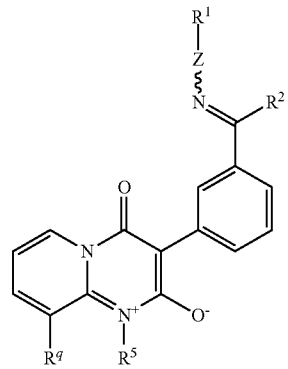

(I-14a)

wherein the symbols and indices have the same meaning as in formula (I-14), in particular a compound listed in Table 2.

TABLE 2

Compounds of formula (I-14a)

R51 is [5-methylene-2-chloropyridine]

R52 is [5-methylene-2-chlorothiazole]

R53 is [3-methylene-tetrahydrofuran]

| No. | R⁵ | Rq | Z | R¹ | R² |
|-----|-----|----|---|-----|------|
| 1 | R51 | H | — | H | NH—O—H |
| 2 | R51 | H | — | H | NH—O—CH₃ |
| 3 | R51 | H | — | H | NH—O—C₆H₅ |
| 4 | R51 | H | — | H | NH₂ |
| 5 | R51 | H | — | H | NH(CH₃) |
| 6 | R51 | H | — | H | N(CH₃)₂ |
| 7 | R51 | H | — | H | NH(C₆H₅) |
| 8 | R51 | H | — | CH₃ | NH—O—H |
| 9 | R51 | H | — | CH₃ | NH—O—CH₃ |
| 10 | R51 | H | — | CH₃ | NH—O—C₆H₅ |
| 11 | R51 | H | — | CH₃ | NH₂ |
| 12 | R51 | H | — | CH₃ | NH(CH₃) |
| 13 | R51 | H | — | CH₃ | N(CH₃)₂ |
| 14 | R51 | H | — | CH₃ | NH(C₆H₅) |
| 15 | R51 | H | — | C₂H₅ | NH—O—H |
| 16 | R51 | H | — | C₂H₅ | NH—O—CH₃ |
| 17 | R51 | H | — | C₂H₅ | NH—O—C₆H₅ |
| 18 | R51 | H | — | C₂H₅ | NH₂ |
| 19 | R51 | H | — | C₂H₅ | NH(CH₃) |
| 20 | R51 | H | — | C₂H₅ | N(CH₃)₂ |
| 21 | R51 | H | — | C₂H₅ | NH(C₆H₅) |
| 22 | R51 | H | — | CH(CH₃)₂ | NH—O—H |
| 23 | R51 | H | — | CH(CH₃)₂ | NH—O—CH₃ |
| 24 | R51 | H | — | CH(CH₃)₂ | NH—O—C₆H₅ |
| 25 | R51 | H | — | CH(CH₃)₂ | NH₂ |
| 26 | R51 | H | — | CH(CH₃)₂ | NH(CH₃) |
| 27 | R51 | H | — | CH(CH₃)₂ | N(CH₃)₂ |
| 28 | R51 | H | — | CH(CH₃)₂ | NH(C₆H₅) |
| 29 | R51 | H | — | CH₂CF₃ | NH—O—H |
| 30 | R51 | H | — | CH₂CF₃ | NH—O—CH₃ |
| 31 | R51 | H | — | CH₂CF₃ | NH—O—C₆H₅ |
| 32 | R51 | H | — | CH₂CF₃ | NH₂ |
| 33 | R51 | H | — | CH₂CF₃ | NH(CH₃) |
| 34 | R51 | H | — | CH₂CF₃ | N(CH₃)₂ |
| 35 | R51 | H | — | CH₂CF₃ | NH(C₆H₅) |
| 36 | R51 | H | — | CH₂-cyclo-C₃H₅ | NH—O—H |
| 37 | R51 | H | — | CH₂-cyclo-C₃H₅ | NH—O—CH₃ |
| 38 | R51 | H | — | CH₂-cyclo-C₃H₅ | NH—O—C₆H₅ |
| 39 | R51 | H | — | CH₂-cyclo-C₃H₅ | NH₂ |
| 40 | R51 | H | — | CH₂-cyclo-C₃H₅ | NH(CH₃) |
| 41 | R51 | H | — | CH₂-cyclo-C₃H₅ | N(CH₃)₂ |
| 42 | R51 | H | — | CH₂-cyclo-C₃H₅ | NH(C₆H₅) |
| 43 | R51 | H | — | C₆H₅ | NH—O—H |
| 44 | R51 | H | — | C₆H₅ | NH—O—CH₃ |
| 45 | R51 | H | — | C₆H₅ | NH—O—C₆H₅ |
| 46 | R51 | H | — | C₆H₅ | NH₂ |
| 47 | R51 | H | — | C₆H₅ | NH(CH₃) |
| 48 | R51 | H | — | C₆H₅ | N(CH₃)₂ |
| 49 | R51 | H | — | C₆H₅ | NH(C₆H₅) |
| 50 | R51 | H | O | H | NH—O—H |
| 51 | R51 | H | O | H | NH—O—CH₃ |
| 52 | R51 | H | O | H | NH—O—C₆H₅ |
| 53 | R51 | H | O | H | NH₂ |
| 54 | R51 | H | O | H | NH(CH₃) |
| 55 | R51 | H | O | H | N(CH₃)₂ |
| 56 | R51 | H | O | H | NH(C₆H₅) |
| 57 | R51 | H | O | CH₃ | NH—O—H |
| 58 | R51 | H | O | CH₃ | NH—O—CH₃ |
| 59 | R51 | H | O | CH₃ | NH—O—C₆H₅ |
| 60 | R51 | H | O | CH₃ | NH₂ |
| 61 | R51 | H | O | CH₃ | NH(CH₃) |
| 62 | R51 | H | O | CH₃ | N(CH₃)₂ |
| 63 | R51 | H | O | CH₃ | NH(C₆H₅) |
| 64 | R51 | H | O | C₂H₅ | NH—O—H |
| 65 | R51 | H | O | C₂H₅ | NH—O—CH₃ |
| 66 | R51 | H | O | C₂H₅ | NH—O—C₆H₅ |
| 67 | R51 | H | O | C₂H₅ | NH₂ |
| 68 | R51 | H | O | C₂H₅ | NH(CH₃) |
| 69 | R51 | H | O | C₂H₅ | N(CH₃)₂ |
| 70 | R51 | H | O | C₂H₅ | NH(C₆H₅) |
| 71 | R51 | H | O | CH(CH₃)₂ | NH—O—H |
| 72 | R51 | H | O | CH(CH₃)₂ | NH—O—CH₃ |
| 73 | R51 | H | O | CH(CH₃)₂ | NH—O—C₆H₅ |
| 74 | R51 | H | O | CH(CH₃)₂ | NH₂ |
| 75 | R51 | H | O | CH(CH₃)₂ | NH(CH₃) |
| 76 | R51 | H | O | CH(CH₃)₂ | N(CH₃)₂ |

TABLE 2-continued

Compounds of formula (I-14a)

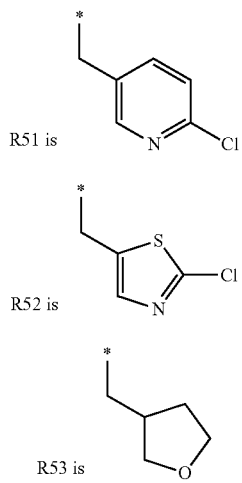

R51 is

R52 is

R53 is

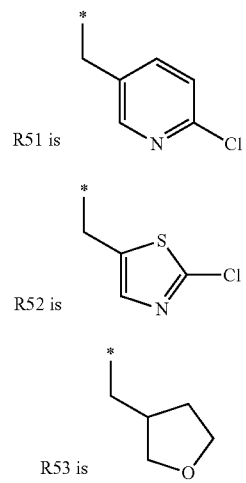

R51 is

R52 is

R53 is

| No. | R⁵ | Rᵍ | Z | R¹ | R² |
|---|---|---|---|---|---|
| 77 | R51 | H | O | CH(CH₃)₂ | NH(C₆H₅) |
| 78 | R51 | H | O | CH₂CF₃ | NH—O—H |
| 79 | R51 | H | O | CH₂CF₃ | NH—O—CH₃ |
| 80 | R51 | H | O | CH₂CF₃ | NH—O—C₆H₅ |
| 81 | R51 | H | O | CH₂CF₃ | NH₂ |
| 82 | R51 | H | O | CH₂CF₃ | NH(CH₃) |
| 83 | R51 | H | O | CH₂CF₃ | N(CH₃)₂ |
| 84 | R51 | H | O | CH₂CF₃ | NH(C₆H₅) |
| 85 | R51 | H | O | CH₂-cyclo-C₃H₅ | NH—O—H |
| 86 | R51 | H | O | CH₂-cyclo-C₃H₅ | NH—O—CH₃ |
| 87 | R51 | H | O | CH₂-cyclo-C₃H₅ | NH—O—C₆H₅ |
| 88 | R51 | H | O | CH₂-cyclo-C₃H₅ | NH₂ |
| 89 | R51 | H | O | CH₂-cyclo-C₃H₅ | NH(CH₃) |
| 90 | R51 | H | O | CH₂-cyclo-C₃H₅ | N(CH₃)₂ |
| 91 | R51 | H | O | CH₂-cyclo-C₃H₅ | NH(C₆H₅) |
| 92 | R51 | H | O | C₆H₅ | NH—O—H |
| 93 | R51 | H | O | C₆H₅ | NH—O—CH₃ |
| 94 | R51 | H | O | C₆H₅ | NH—O—C₆H₅ |
| 95 | R51 | H | O | C₆H₅ | NH₂ |
| 96 | R51 | H | O | C₆H₅ | NH(CH₃) |
| 97 | R51 | H | O | C₆H₅ | N(CH₃)₂ |
| 98 | R51 | H | O | C₆H₅ | NH(C₆H₅) |
| 99 | R51 | H | NH | H | NH—O—H |
| 100 | R51 | H | NH | H | NH—O—CH₃ |
| 101 | R51 | H | NH | H | NH—O—C₆H₅ |
| 102 | R51 | H | NH | H | NH₂ |
| 103 | R51 | H | NH | H | NH(CH₃) |
| 104 | R51 | H | NH | H | N(CH₃)₂ |
| 105 | R51 | H | NH | H | NH(C₆H₅) |
| 106 | R51 | H | NH | CH₃ | NH—O—H |
| 107 | R51 | H | NH | CH₃ | NH—O—CH₃ |
| 108 | R51 | H | NH | CH₃ | NH—O—C₆H₅ |
| 109 | R51 | H | NH | CH₃ | NH₂ |
| 110 | R51 | H | NH | CH₃ | NH(CH₃) |
| 111 | R51 | H | NH | CH₃ | N(CH₃)₂ |
| 112 | R51 | H | NH | CH₃ | NH(C₆H₅) |
| 113 | R51 | H | NH | C₂H₅ | NH—O—H |
| 114 | R51 | H | NH | C₂H₅ | NH—O—CH₃ |
| 115 | R51 | H | NH | C₂H₅ | NH—O—C₆H₅ |
| 116 | R51 | H | NH | C₂H₅ | NH₂ |
| 117 | R51 | H | NH | C₂H₅ | NH(CH₃) |
| 118 | R51 | H | NH | C₂H₅ | N(CH₃)₂ |
| 119 | R51 | H | NH | C₂H₅ | NH(C₆H₅) |
| 120 | R51 | H | NH | CH(CH₃)₂ | NH—O—H |
| 121 | R51 | H | NH | CH(CH₃)₂ | NH—O—CH₃ |
| 122 | R51 | H | NH | CH(CH₃)₂ | NH—O—C₆H₅ |
| 123 | R51 | H | NH | CH(CH₃)₂ | NH₂ |
| 124 | R51 | H | NH | CH(CH₃)₂ | NH(CH₃) |
| 125 | R51 | H | NH | CH(CH₃)₂ | N(CH₃)₂ |
| 126 | R51 | H | NH | CH(CH₃)₂ | NH(C₆H₅) |
| 127 | R51 | H | NH | CH₂CF₃ | NH—O—H |
| 128 | R51 | H | NH | CH₂CF₃ | NH—O—CH₃ |
| 129 | R51 | H | NH | CH₂CF₃ | NH—O—C₆H₅ |
| 130 | R51 | H | NH | CH₂CF₃ | NH₂ |
| 131 | R51 | H | NH | CH₂CF₃ | NH(CH₃) |
| 132 | R51 | H | NH | CH₂CF₃ | N(CH₃)₂ |
| 133 | R51 | H | NH | CH₂CF₃ | NH(C₆H₅) |
| 134 | R51 | H | NH | CH₂-cyclo-C₃H₅ | NH—O—H |
| 135 | R51 | H | NH | CH₂-cyclo-C₃H₅ | NH—O—CH₃ |
| 136 | R51 | H | NH | CH₂-cyclo-C₃H₅ | NH—O—C₆H₅ |
| 137 | R51 | H | NH | CH₂-cyclo-C₃H₅ | NH₂ |
| 138 | R51 | H | NH | CH₂-cyclo-C₃H₅ | NH(CH₃) |
| 139 | R51 | H | NH | CH₂-cyclo-C₃H₅ | N(CH₃)₂ |
| 140 | R51 | H | NH | CH₂-cyclo-C₃H₅ | NH(C₆H₅) |
| 141 | R51 | H | NH | C₆H₅ | NH—O—H |
| 142 | R51 | H | NH | C₆H₅ | NH—O—CH₃ |
| 143 | R51 | H | NH | C₆H₅ | NH—O—C₆H₅ |
| 144 | R51 | H | NH | C₆H₅ | NH₂ |
| 145 | R51 | H | NH | C₆H₅ | NH(CH₃) |
| 146 | R51 | H | NH | C₆H₅ | N(CH₃)₂ |
| 147 | R51 | H | NH | C₆H₅ | NH(C₆H₅) |
| 148 | R51 | CH₃ | — | H | NH—O—H |
| 149 | R51 | CH₃ | — | H | NH—O—CH₃ |
| 150 | R51 | CH₃ | — | H | NH—O—C₆H₅ |
| 151 | R51 | CH₃ | — | H | NH₂ |
| 152 | R51 | CH₃ | — | H | NH(CH₃) |
| 153 | R51 | CH₃ | — | H | N(CH₃)₂ |
| 154 | R51 | CH₃ | — | H | NH(C₆H₅) |
| 155 | R51 | CH₃ | — | CH₃ | NH—O—H |
| 156 | R51 | CH₃ | — | CH₃ | NH—O—CH₃ |
| 157 | R51 | CH₃ | — | CH₃ | NH—O—C₆H₅ |
| 158 | R51 | CH₃ | — | CH₃ | NH₂ |
| 159 | R51 | CH₃ | — | CH₃ | NH(CH₃) |
| 160 | R51 | CH₃ | — | CH₃ | N(CH₃)₂ |
| 161 | R51 | CH₃ | — | CH₃ | NH(C₆H₅) |
| 162 | R51 | CH₃ | — | C₂H₅ | NH—O—H |
| 163 | R51 | CH₃ | — | C₂H₅ | NH—O—CH₃ |
| 164 | R51 | CH₃ | — | C₂H₅ | NH—O—C₆H₅ |
| 165 | R51 | CH₃ | — | C₂H₅ | NH₂ |
| 166 | R51 | CH₃ | — | C₂H₅ | NH(CH₃) |
| 167 | R51 | CH₃ | — | C₂H₅ | N(CH₃)₂ |
| 168 | R51 | CH₃ | — | C₂H₅ | NH(C₆H₅) |
| 169 | R51 | CH₃ | — | CH(CH₃)₂ | NH—O—H |
| 170 | R51 | CH₃ | — | CH(CH₃)₂ | NH—O—CH₃ |
| 171 | R51 | CH₃ | — | CH(CH₃)₂ | NH—O—C₆H₅ |
| 172 | R51 | CH₃ | — | CH(CH₃)₂ | NH₂ |
| 173 | R51 | CH₃ | — | CH(CH₃)₂ | NH(CH₃) |
| 174 | R51 | CH₃ | — | CH(CH₃)₂ | N(CH₃)₂ |
| 175 | R51 | CH₃ | — | CH(CH₃)₂ | NH(C₆H₅) |
| 176 | R51 | CH₃ | — | CH₂CF₃ | NH—O—H |
| 177 | R51 | CH₃ | — | CH₂CF₃ | NH—O—CH₃ |
| 178 | R51 | CH₃ | — | CH₂CF₃ | NH—O—C₆H₅ |
| 179 | R51 | CH₃ | — | CH₂CF₃ | NH₂ |
| 180 | R51 | CH₃ | — | CH₂CF₃ | NH(CH₃) |

TABLE 2-continued

Compounds of formula (I-14a)

R51 is 5-(6-chloropyridin-3-yl)methyl group (*-CH2-pyridine-Cl)

R52 is 5-(2-chloro-1,3-thiazol-5-yl)methyl group (*-CH2-thiazole-Cl)

R53 is (tetrahydrofuran-3-yl)methyl group

| No. | $R^5$ | $R^q$ | Z | $R^1$ | $R^2$ |
|---|---|---|---|---|---|
| 181 | R51 | $CH_3$ | — | $CH_2CF_3$ | $N(CH_3)_2$ |
| 182 | R51 | $CH_3$ | — | $CH_2CF_3$ | $NH(C_6H_5)$ |
| 183 | R51 | $CH_3$ | — | $CH_2$-cyclo-$C_3H_5$ | NH—O—H |
| 184 | R51 | $CH_3$ | — | $CH_2$-cyclo-$C_3H_5$ | NH—O—$CH_3$ |
| 185 | R51 | $CH_3$ | — | $CH_2$-cyclo-$C_3H_5$ | NH—O—$C_6H_5$ |
| 186 | R51 | $CH_3$ | — | $CH_2$-cyclo-$C_3H_5$ | $NH_2$ |
| 187 | R51 | $CH_3$ | — | $CH_2$-cyclo-$C_3H_5$ | $NH(CH_3)$ |
| 188 | R51 | $CH_3$ | — | $CH_2$-cyclo-$C_3H_5$ | $N(CH_3)_2$ |
| 189 | R51 | $CH_3$ | — | $CH_2$-cyclo-$C_3H_5$ | $NH(C_6H_5)$ |
| 190 | R51 | $CH_3$ | — | $C_6H_5$ | NH—O—H |
| 191 | R51 | $CH_3$ | — | $C_6H_5$ | NH—O—$CH_3$ |
| 192 | R51 | $CH_3$ | — | $C_6H_5$ | NH—O—$C_6H_5$ |
| 193 | R51 | $CH_3$ | — | $C_6H_5$ | $NH_2$ |
| 194 | R51 | $CH_3$ | — | $C_6H_5$ | $NH(CH_3)$ |
| 195 | R51 | $CH_3$ | — | $C_6H_5$ | $N(CH_3)_2$ |
| 196 | R51 | $CH_3$ | — | $C_6H_5$ | $NH(C_6H_5)$ |
| 197 | R51 | $CH_3$ | O | H | NH—O—H |
| 198 | R51 | $CH_3$ | O | H | NH—O—$CH_3$ |
| 199 | R51 | $CH_3$ | O | H | NH—O—$C_6H_5$ |
| 200 | R51 | $CH_3$ | O | H | $NH_2$ |
| 201 | R51 | $CH_3$ | O | H | $NH(CH_3)$ |
| 202 | R51 | $CH_3$ | O | H | $N(CH_3)_2$ |
| 203 | R51 | $CH_3$ | O | H | $NH(C_6H_5)$ |
| 204 | R51 | $CH_3$ | O | $CH_3$ | NH—O—H |
| 205 | R51 | $CH_3$ | O | $CH_3$ | NH—O—$CH_3$ |
| 206 | R51 | $CH_3$ | O | $CH_3$ | NH—O—$C_6H_5$ |
| 207 | R51 | $CH_3$ | O | $CH_3$ | $NH_2$ |
| 208 | R51 | $CH_3$ | O | $CH_3$ | $NH(CH_3)$ |
| 209 | R51 | $CH_3$ | O | $CH_3$ | $N(CH_3)_2$ |
| 210 | R51 | $CH_3$ | O | $CH_3$ | $NH(C_6H_5)$ |
| 211 | R51 | $CH_3$ | O | $C_2H_5$ | NH—O—H |
| 212 | R51 | $CH_3$ | O | $C_2H_5$ | NH—O—$CH_3$ |
| 213 | R51 | $CH_3$ | O | $C_2H_5$ | NH—O—$C_6H_5$ |
| 214 | R51 | $CH_3$ | O | $C_2H_5$ | $NH_2$ |
| 215 | R51 | $CH_3$ | O | $C_2H_5$ | $NH(CH_3)$ |
| 216 | R51 | $CH_3$ | O | $C_2H_5$ | $N(CH_3)_2$ |
| 217 | R51 | $CH_3$ | O | $C_2H_5$ | $NH(C_6H_5)$ |
| 218 | R51 | $CH_3$ | O | $CH(CH_3)_2$ | NH—O—H |
| 219 | R51 | $CH_3$ | O | $CH(CH_3)_2$ | NH—O—$CH_3$ |
| 220 | R51 | $CH_3$ | O | $CH(CH_3)_2$ | NH—O—$C_6H_5$ |
| 221 | R51 | $CH_3$ | O | $CH(CH_3)_2$ | $NH_2$ |
| 222 | R51 | $CH_3$ | O | $CH(CH_3)_2$ | $NH(CH_3)$ |
| 223 | R51 | $CH_3$ | O | $CH(CH_3)_2$ | $N(CH_3)_2$ |
| 224 | R51 | $CH_3$ | O | $CH(CH_3)_2$ | $NH(C_6H_5)$ |
| 225 | R51 | $CH_3$ | O | $CH_2CF_3$ | NH—O—H |
| 226 | R51 | $CH_3$ | O | $CH_2CF_3$ | NH—O—$CH_3$ |
| 227 | R51 | $CH_3$ | O | $CH_2CF_3$ | NH—O—$C_6H_5$ |
| 228 | R51 | $CH_3$ | O | $CH_2CF_3$ | $NH_2$ |
| 229 | R51 | $CH_3$ | O | $CH_2CF_3$ | $NH(CH_3)$ |
| 230 | R51 | $CH_3$ | O | $CH_2CF_3$ | $N(CH_3)_2$ |
| 231 | R51 | $CH_3$ | O | $CH_2CF_3$ | $NH(C_6H_5)$ |
| 232 | R51 | $CH_3$ | O | $CH_2$-cyclo-$C_3H_5$ | NH—O—H |
| 233 | R51 | $CH_3$ | O | $CH_2$-cyclo-$C_3H_5$ | NH—O—$CH_3$ |
| 234 | R51 | $CH_3$ | O | $CH_2$-cyclo-$C_3H_5$ | NH—O—$C_6H_5$ |
| 235 | R51 | $CH_3$ | O | $CH_2$-cyclo-$C_3H_5$ | $NH_2$ |
| 236 | R51 | $CH_3$ | O | $CH_2$-cyclo-$C_3H_5$ | $NH(CH_3)$ |
| 237 | R51 | $CH_3$ | O | $CH_2$-cyclo-$C_3H_5$ | $N(CH_3)_2$ |
| 238 | R51 | $CH_3$ | O | $CH_2$-cyclo-$C_3H_5$ | $NH(C_6H_5)$ |
| 239 | R51 | $CH_3$ | O | $C_6H_5$ | NH—O—H |
| 240 | R51 | $CH_3$ | O | $C_6H_5$ | NH—O—$CH_3$ |
| 241 | R51 | $CH_3$ | O | $C_6H_5$ | NH—O—$C_6H_5$ |
| 242 | R51 | $CH_3$ | O | $C_6H_5$ | $NH_2$ |
| 243 | R51 | $CH_3$ | O | $C_6H_5$ | $NH(CH_3)$ |
| 244 | R51 | $CH_3$ | O | $C_6H_5$ | $N(CH_3)_2$ |
| 245 | R51 | $CH_3$ | O | $C_6H_5$ | $NH(C_6H_5)$ |
| 246 | R51 | $CH_3$ | NH | H | NH—O—H |
| 247 | R51 | $CH_3$ | NH | H | NH—O—$CH_3$ |
| 248 | R51 | $CH_3$ | NH | H | NH—O—$C_6H_5$ |
| 249 | R51 | $CH_3$ | NH | H | $NH_2$ |
| 250 | R51 | $CH_3$ | NH | H | $NH(CH_3)$ |
| 251 | R51 | $CH_3$ | NH | H | $N(CH_3)_2$ |
| 252 | R51 | $CH_3$ | NH | H | $NH(C_6H_5)$ |
| 253 | R51 | $CH_3$ | NH | $CH_3$ | NH—O—H |
| 254 | R51 | $CH_3$ | NH | $CH_3$ | NH—O—$CH_3$ |
| 255 | R51 | $CH_3$ | NH | $CH_3$ | NH—O—$C_6H_5$ |
| 256 | R51 | $CH_3$ | NH | $CH_3$ | $NH_2$ |
| 257 | R51 | $CH_3$ | NH | $CH_3$ | $NH(CH_3)$ |
| 258 | R51 | $CH_3$ | NH | $CH_3$ | $N(CH_3)_2$ |
| 259 | R51 | $CH_3$ | NH | $CH_3$ | $NH(C_6H_5)$ |
| 260 | R51 | $CH_3$ | NH | $C_2H_5$ | NH—O—H |
| 261 | R51 | $CH_3$ | NH | $C_2H_5$ | NH—O—$CH_3$ |
| 262 | R51 | $CH_3$ | NH | $C_2H_5$ | NH—O—$C_6H_5$ |
| 263 | R51 | $CH_3$ | NH | $C_2H_5$ | $NH_2$ |
| 264 | R51 | $CH_3$ | NH | $C_2H_5$ | $NH(CH_3)$ |
| 265 | R51 | $CH_3$ | NH | $C_2H_5$ | $N(CH_3)_2$ |
| 266 | R51 | $CH_3$ | NH | $C_2H_5$ | $NH(C_6H_5)$ |
| 267 | R51 | $CH_3$ | NH | $CH(CH_3)_2$ | NH—O—H |
| 268 | R51 | $CH_3$ | NH | $CH(CH_3)_2$ | NH—O—$CH_3$ |
| 269 | R51 | $CH_3$ | NH | $CH(CH_3)_2$ | NH—O—$C_6H_5$ |
| 270 | R51 | $CH_3$ | NH | $CH(CH_3)_2$ | $NH_2$ |
| 271 | R51 | $CH_3$ | NH | $CH(CH_3)_2$ | $NH(CH_3)$ |
| 272 | R51 | $CH_3$ | NH | $CH(CH_3)_2$ | $N(CH_3)_2$ |
| 273 | R51 | $CH_3$ | NH | $CH(CH_3)_2$ | $NH(C_6H_5)$ |
| 274 | R51 | $CH_3$ | NH | $CH_2CF_3$ | NH—O—H |
| 275 | R51 | $CH_3$ | NH | $CH_2CF_3$ | NH—O—$CH_3$ |
| 276 | R51 | $CH_3$ | NH | $CH_2CF_3$ | NH—O—$C_6H_5$ |
| 277 | R51 | $CH_3$ | NH | $CH_2CF_3$ | $NH_2$ |
| 278 | R51 | $CH_3$ | NH | $CH_2CF_3$ | $NH(CH_3)$ |
| 279 | R51 | $CH_3$ | NH | $CH_2CF_3$ | $N(CH_3)_2$ |
| 280 | R51 | $CH_3$ | NH | $CH_2CF_3$ | $NH(C_6H_5)$ |
| 281 | R51 | $CH_3$ | NH | $CH_2$-cyclo-$C_3H_5$ | NH—O—H |
| 282 | R51 | $CH_3$ | NH | $CH_2$-cyclo-$C_3H_5$ | NH—O—$CH_3$ |
| 283 | R51 | $CH_3$ | NH | $CH_2$-cyclo-$C_3H_5$ | NH—O—$C_6H_5$ |
| 284 | R51 | $CH_3$ | NH | $CH_2$-cyclo-$C_3H_5$ | $NH_2$ |

TABLE 2-continued

Compounds of formula (I-14a)

R51 is: *-CH2-(2-chloropyridin-5-yl)

R52 is: *-CH2-(2-chlorothiazol-5-yl)

R53 is: *-CH2-(tetrahydrofuran-3-yl)

| No. | R⁵ | Rq | Z | R¹ | R² |
|---|---|---|---|---|---|
| 285 | R51 | CH₃ | NH | CH₂-cyclo-C₃H₅ | NH(CH₃) |
| 286 | R51 | CH₃ | NH | CH₂-cyclo-C₃H₅ | N(CH₃)₂ |
| 287 | R51 | CH₃ | NH | CH₂-cyclo-C₃H₅ | NH(C₆H₅) |
| 288 | R51 | CH₃ | NH | C₆H₅ | NH—O—H |
| 289 | R51 | CH₃ | NH | C₆H₅ | NH—O—CH₃ |
| 290 | R51 | CH₃ | NH | C₆H₅ | NH—O—C₆H₅ |
| 291 | R51 | CH₃ | NH | C₆H₅ | NH₂ |
| 292 | R51 | CH₃ | NH | C₆H₅ | NH(CH₃) |
| 293 | R51 | CH₃ | NH | C₆H₅ | N(CH₃)₂ |
| 294 | R51 | CH₃ | NH | C₆H₅ | NH(C₆H₅) |
| 295 | R52 | H | — | H | NH—O—H |
| 296 | R52 | H | — | H | NH—O—CH₃ |
| 297 | R52 | H | — | H | NH—O—C₆H₅ |
| 298 | R52 | H | — | H | NH₂ |
| 299 | R52 | H | — | H | NH(CH₃) |
| 300 | R52 | H | — | H | N(CH₃)₂ |
| 301 | R52 | H | — | H | NH(C₆H₅) |
| 302 | R52 | H | — | CH₃ | NH—O—H |
| 303 | R52 | H | — | CH₃ | NH—O—CH₃ |
| 304 | R52 | H | — | CH₃ | NH—O—C₆H₅ |
| 305 | R52 | H | — | CH₃ | NH₂ |
| 306 | R52 | H | — | CH₃ | NH(CH₃) |
| 307 | R52 | H | — | CH₃ | N(CH₃)₂ |
| 308 | R52 | H | — | CH₃ | NH(C₆H₅) |
| 309 | R52 | H | — | C₂H₅ | NH—O—H |
| 310 | R52 | H | — | C₂H₅ | NH—O—CH₃ |
| 311 | R52 | H | — | C₂H₅ | NH—O—C₆H₅ |
| 312 | R52 | H | — | C₂H₅ | NH₂ |
| 313 | R52 | H | — | C₂H₅ | NH(CH₃) |
| 314 | R52 | H | — | C₂H₅ | N(CH₃)₂ |
| 315 | R52 | H | — | C₂H₅ | NH(C₆H₅) |
| 316 | R52 | H | — | CH(CH₃)₂ | NH—O—H |
| 317 | R52 | H | — | CH(CH₃)₂ | NH—O—CH₃ |
| 318 | R52 | H | — | CH(CH₃)₂ | NH—O—C₆H₅ |
| 319 | R52 | H | — | CH(CH₃)₂ | NH₂ |
| 320 | R52 | H | — | CH(CH₃)₂ | NH(CH₃) |
| 321 | R52 | H | — | CH(CH₃)₂ | N(CH₃)₂ |
| 322 | R52 | H | — | CH(CH₃)₂ | NH(C₆H₅) |
| 323 | R52 | H | — | CH₂CF₃ | NH—O—H |
| 324 | R52 | H | — | CH₂CF₃ | NH—O—CH₃ |
| 325 | R52 | H | — | CH₂CF₃ | NH—O—C₆H₅ |
| 326 | R52 | H | — | CH₂CF₃ | NH₂ |
| 327 | R52 | H | — | CH₂CF₃ | NH(CH₃) |
| 328 | R52 | H | — | CH₂CF₃ | N(CH₃)₂ |
| 329 | R52 | H | — | CH₂CF₃ | NH(C₆H₅) |
| 330 | R52 | H | — | CH₂-cyclo-C₃H₅ | NH—O—H |
| 331 | R52 | H | — | CH₂-cyclo-C₃H₅ | NH—O—CH₃ |
| 332 | R52 | H | — | CH₂-cyclo-C₃H₅ | NH—O—C₆H₅ |
| 333 | R52 | H | — | CH₂-cyclo-C₃H₅ | NH₂ |
| 334 | R52 | H | — | CH₂-cyclo-C₃H₅ | NH(CH₃) |
| 335 | R52 | H | — | CH₂-cyclo-C₃H₅ | N(CH₃)₂ |
| 336 | R52 | H | — | CH₂-cyclo-C₃H₅ | NH(C₆H₅) |
| 337 | R52 | H | — | C₆H₅ | NH—O—H |
| 338 | R52 | H | — | C₆H₅ | NH—O—CH₃ |
| 339 | R52 | H | — | C₆H₅ | NH—O—C₆H₅ |
| 340 | R52 | H | — | C₆H₅ | NH₂ |
| 341 | R52 | H | — | C₆H₅ | NH(CH₃) |
| 342 | R52 | H | — | C₆H₅ | N(CH₃)₂ |
| 343 | R52 | H | — | C₆H₅ | NH(C₆H₅) |
| 344 | R52 | H | O | H | NH—O—H |
| 345 | R52 | H | O | H | NH—O—CH₃ |
| 346 | R52 | H | O | H | NH—O—C₆H₅ |
| 347 | R52 | H | O | H | NH₂ |
| 348 | R52 | H | O | H | NH(CH₃) |
| 349 | R52 | H | O | H | N(CH₃)₂ |
| 350 | R52 | H | O | H | NH(C₆H₅) |
| 351 | R52 | H | O | CH₃ | NH—O—H |
| 352 | R52 | H | O | CH₃ | NH—O—CH₃ |
| 353 | R52 | H | O | CH₃ | NH—O—C₆H₅ |
| 354 | R52 | H | O | CH₃ | NH₂ |
| 355 | R52 | H | O | CH₃ | NH(CH₃) |
| 356 | R52 | H | O | CH₃ | N(CH₃)₂ |
| 357 | R52 | H | O | CH₃ | NH(C₆H₅) |
| 358 | R52 | H | O | C₂H₅ | NH—O—H |
| 359 | R52 | H | O | C₂H₅ | NH—O—CH₃ |
| 360 | R52 | H | O | C₂H₅ | NH—O—C₆H₅ |
| 361 | R52 | H | O | C₂H₅ | NH₂ |
| 362 | R52 | H | O | C₂H₅ | NH(CH₃) |
| 363 | R52 | H | O | C₂H₅ | N(CH₃)₂ |
| 364 | R52 | H | O | C₂H₅ | NH(C₆H₅) |
| 365 | R52 | H | O | CH(CH₃)₂ | NH—O—H |
| 366 | R52 | H | O | CH(CH₃)₂ | NH—O—CH₃ |
| 367 | R52 | H | O | CH(CH₃)₂ | NH—O—C₆H₅ |
| 368 | R52 | H | O | CH(CH₃)₂ | NH₂ |
| 369 | R52 | H | O | CH(CH₃)₂ | NH(CH₃) |
| 370 | R52 | H | O | CH(CH₃)₂ | N(CH₃)₂ |
| 371 | R52 | H | O | CH(CH₃)₂ | NH(C₆H₅) |
| 372 | R52 | H | O | CH₂CF₃ | NH—O—H |
| 373 | R52 | H | O | CH₂CF₃ | NH—O—CH₃ |
| 374 | R52 | H | O | CH₂CF₃ | NH—O—C₆H₅ |
| 375 | R52 | H | O | CH₂CF₃ | NH₂ |
| 376 | R52 | H | O | CH₂CF₃ | NH(CH₃) |
| 377 | R52 | H | O | CH₂CF₃ | N(CH₃)₂ |
| 378 | R52 | H | O | CH₂CF₃ | NH(C₆H₅) |
| 379 | R52 | H | O | CH₂-cyclo-C₃H₅ | NH—O—H |
| 380 | R52 | H | O | CH₂-cyclo-C₃H₅ | NH—O—CH₃ |
| 381 | R52 | H | O | CH₂-cyclo-C₃H₅ | NH—O—C₆H₅ |
| 382 | R52 | H | O | CH₂-cyclo-C₃H₅ | NH₂ |
| 383 | R52 | H | O | CH₂-cyclo-C₃H₅ | NH(CH₃) |
| 384 | R52 | H | O | CH₂-cyclo-C₃H₅ | N(CH₃)₂ |
| 385 | R52 | H | O | CH₂-cyclo-C₃H₅ | NH(C₆H₅) |
| 386 | R52 | H | O | C₆H₅ | NH—O—H |
| 387 | R52 | H | O | C₆H₅ | NH—O—CH₃ |
| 388 | R52 | H | O | C₆H₅ | NH—O—C₆H₅ |

TABLE 2-continued

Compounds of formula (I-14a)

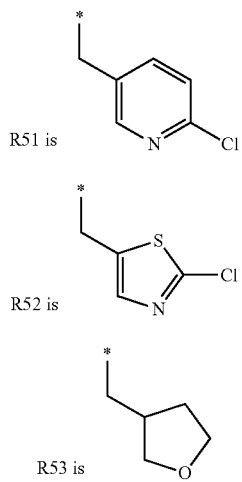

R51 is

R52 is

R53 is

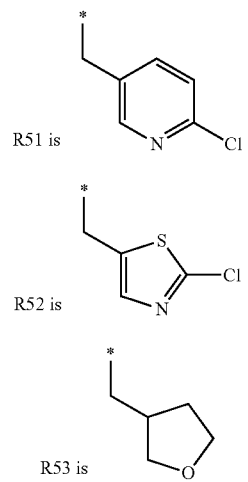

R51 is

R52 is

R53 is

| No. | R⁵ | Rq | Z | R¹ | R² |
|---|---|---|---|---|---|
| 389 | R52 | H | O | C₆H₅ | NH₂ |
| 390 | R52 | H | O | C₆H₅ | NH(CH₃) |
| 391 | R52 | H | O | C₆H₅ | N(CH₃)₂ |
| 392 | R52 | H | O | C₆H₅ | NH(C₆H₅) |
| 393 | R52 | H | NH | H | NH—O—H |
| 394 | R52 | H | NH | H | NH—O—CH₃ |
| 395 | R52 | H | NH | H | NH—O—C₆H₅ |
| 396 | R52 | H | NH | H | NH₂ |
| 397 | R52 | H | NH | H | NH(CH₃) |
| 398 | R52 | H | NH | H | N(CH₃)₂ |
| 399 | R52 | H | NH | H | NH(C₆H₅) |
| 400 | R52 | H | NH | CH₃ | NH—O—H |
| 401 | R52 | H | NH | CH₃ | NH—O—CH₃ |
| 402 | R52 | H | NH | CH₃ | NH—O—C₆H₅ |
| 403 | R52 | H | NH | CH₃ | NH₂ |
| 404 | R52 | H | NH | CH₃ | NH(CH₃) |
| 405 | R52 | H | NH | CH₃ | N(CH₃)₂ |
| 406 | R52 | H | NH | CH₃ | NH(C₆H₅) |
| 407 | R52 | H | NH | C₂H₅ | NH—O—H |
| 408 | R52 | H | NH | C₂H₅ | NH—O—CH₃ |
| 409 | R52 | H | NH | C₂H₅ | NH—O—C₆H₅ |
| 410 | R52 | H | NH | C₂H₅ | NH₂ |
| 411 | R52 | H | NH | C₂H₅ | NH(CH₃) |
| 412 | R52 | H | NH | C₂H₅ | N(CH₃)₂ |
| 413 | R52 | H | NH | C₂H₅ | NH(C₆H₅) |
| 414 | R52 | H | NH | CH(CH₃)₂ | NH—O—H |
| 415 | R52 | H | NH | CH(CH₃)₂ | NH—O—CH₃ |
| 416 | R52 | H | NH | CH(CH₃)₂ | NH—O—C₆H₅ |
| 417 | R52 | H | NH | CH(CH₃)₂ | NH₂ |
| 418 | R52 | H | NH | CH(CH₃)₂ | NH(CH₃) |
| 419 | R52 | H | NH | CH(CH₃)₂ | N(CH₃)₂ |
| 420 | R52 | H | NH | CH(CH₃)₂ | NH(C₆H₅) |
| 421 | R52 | H | NH | CH₂CF₃ | NH—O—H |
| 422 | R52 | H | NH | CH₂CF₃ | NH—O—CH₃ |
| 423 | R52 | H | NH | CH₂CF₃ | NH—O—C₆H₅ |
| 424 | R52 | H | NH | CH₂CF₃ | NH₂ |
| 425 | R52 | H | NH | CH₂CF₃ | NH(CH₃) |
| 426 | R52 | H | NH | CH₂CF₃ | N(CH₃)₂ |
| 427 | R52 | H | NH | CH₂CF₃ | NH(C₆H₅) |
| 428 | R52 | H | NH | CH₂-cyclo-C₃H₅ | NH—O—H |
| 429 | R52 | H | NH | CH₂-cyclo-C₃H₅ | NH—O—CH₃ |
| 430 | R52 | H | NH | CH₂-cyclo-C₃H₅ | NH—O—C₆H₅ |
| 431 | R52 | H | NH | CH₂-cyclo-C₃H₅ | NH₂ |
| 432 | R52 | H | NH | CH₂-cyclo-C₃H₅ | NH(CH₃) |
| 433 | R52 | H | NH | CH₂-cyclo-C₃H₅ | N(CH₃)₂ |
| 434 | R52 | H | NH | CH₂-cyclo-C₃H₅ | NH(C₆H₅) |
| 435 | R52 | H | NH | C₆H₅ | NH—O—H |
| 436 | R52 | H | NH | C₆H₅ | NH—O—CH₃ |
| 437 | R52 | H | NH | C₆H₅ | NH—O—C₆H₅ |
| 438 | R52 | H | NH | C₆H₅ | NH₂ |
| 439 | R52 | H | NH | C₆H₅ | NH(CH₃) |
| 440 | R52 | H | NH | C₆H₅ | N(CH₃)₂ |
| 441 | R52 | H | NH | C₆H₅ | NH(C₆H₅) |
| 442 | R52 | CH₃ | — | H | NH—O—H |
| 443 | R52 | CH₃ | — | H | NH—O—CH₃ |
| 444 | R52 | CH₃ | — | H | NH—O—C₆H₅ |
| 445 | R52 | CH₃ | — | H | NH₂ |
| 446 | R52 | CH₃ | — | H | NH(CH₃) |
| 447 | R52 | CH₃ | — | H | N(CH₃)₂ |
| 448 | R52 | CH₃ | — | H | NH(C₆H₅) |
| 449 | R52 | CH₃ | — | CH₃ | NH—O—H |
| 450 | R52 | CH₃ | — | CH₃ | NH—O—CH₃ |
| 451 | R52 | CH₃ | — | CH₃ | NH—O—C₆H₅ |
| 452 | R52 | CH₃ | — | CH₃ | NH₂ |
| 453 | R52 | CH₃ | — | CH₃ | NH(CH₃) |
| 454 | R52 | CH₃ | — | CH₃ | N(CH₃)₂ |
| 455 | R52 | CH₃ | — | CH₃ | NH(C₆H₅) |
| 456 | R52 | CH₃ | — | C₂H₅ | NH—O—H |
| 457 | R52 | CH₃ | — | C₂H₅ | NH—O—CH₃ |
| 458 | R52 | CH₃ | — | C₂H₅ | NH—O—C₆H₅ |
| 459 | R52 | CH₃ | — | C₂H₅ | NH₂ |
| 460 | R52 | CH₃ | — | C₂H₅ | NH(CH₃) |
| 461 | R52 | CH₃ | — | C₂H₅ | N(CH₃)₂ |
| 462 | R52 | CH₃ | — | C₂H₅ | NH(C₆H₅) |
| 463 | R52 | CH₃ | — | CH(CH₃)₂ | NH—O—H |
| 464 | R52 | CH₃ | — | CH(CH₃)₂ | NH—O—CH₃ |
| 465 | R52 | CH₃ | — | CH(CH₃)₂ | NH—O—C₆H₅ |
| 466 | R52 | CH₃ | — | CH(CH₃)₂ | NH₂ |
| 467 | R52 | CH₃ | — | CH(CH₃)₂ | NH(CH₃) |
| 468 | R52 | CH₃ | — | CH(CH₃)₂ | N(CH₃)₂ |
| 469 | R52 | CH₃ | — | CH(CH₃)₂ | NH(C₆H₅) |
| 470 | R52 | CH₃ | — | CH₂CF₃ | NH—O—H |
| 471 | R52 | CH₃ | — | CH₂CF₃ | NH—O—CH₃ |
| 472 | R52 | CH₃ | — | CH₂CF₃ | NH—O—C₆H₅ |
| 473 | R52 | CH₃ | — | CH₂CF₃ | NH₂ |
| 474 | R52 | CH₃ | — | CH₂CF₃ | NH(CH₃) |
| 475 | R52 | CH₃ | — | CH₂CF₃ | N(CH₃)₂ |
| 476 | R52 | CH₃ | — | CH₂CF₃ | NH(C₆H₅) |
| 477 | R52 | CH₃ | — | CH₂-cyclo-C₃H₅ | NH—O—H |
| 478 | R52 | CH₃ | — | CH₂-cyclo-C₃H₅ | NH—O—CH₃ |
| 479 | R52 | CH₃ | — | CH₂-cyclo-C₃H₅ | NH—O—C₆H₅ |
| 480 | R52 | CH₃ | — | CH₂-cyclo-C₃H₅ | NH₂ |
| 481 | R52 | CH₃ | — | CH₂-cyclo-C₃H₅ | NH(CH₃) |
| 482 | R52 | CH₃ | — | CH₂-cyclo-C₃H₅ | N(CH₃)₂ |
| 483 | R52 | CH₃ | — | CH₂-cyclo-C₃H₅ | NH(C₆H₅) |
| 484 | R52 | CH₃ | — | C₆H₅ | NH—O—H |
| 485 | R52 | CH₃ | — | C₆H₅ | NH—O—CH₃ |
| 486 | R52 | CH₃ | — | C₆H₅ | NH—O—C₆H₅ |
| 487 | R52 | CH₃ | — | C₆H₅ | NH₂ |
| 488 | R52 | CH₃ | — | C₆H₅ | NH(CH₃) |
| 489 | R52 | CH₃ | — | C₆H₅ | N(CH₃)₂ |
| 490 | R52 | CH₃ | — | C₆H₅ | NH(C₆H₅) |
| 491 | R52 | CH₃ | O | H | NH—O—H |
| 492 | R52 | CH₃ | O | H | NH—O—CH₃ |

TABLE 2-continued

Compounds of formula (I-14a)

R51 is: *-CH2-(pyridine with Cl at 2-position, attached at 5-position)

R52 is: *-CH2-(thiazole with S, N, Cl at 2-position, attached at 5-position)

R53 is: *-CH2-(tetrahydrofuran-3-yl)

| No. | $R^5$ | $R^q$ | Z | $R^1$ | $R^2$ |
|---|---|---|---|---|---|
| 493 | R52 | CH$_3$ | O | H | NH—O—C$_6$H$_5$ |
| 494 | R52 | CH$_3$ | O | H | NH$_2$ |
| 495 | R52 | CH$_3$ | O | H | NH(CH$_3$) |
| 496 | R52 | CH$_3$ | O | H | N(CH$_3$)$_2$ |
| 497 | R52 | CH$_3$ | O | H | NH(C$_6$H$_5$) |
| 498 | R52 | CH$_3$ | O | CH$_3$ | NH—O—H |
| 499 | R52 | CH$_3$ | O | CH$_3$ | NH—O—CH$_3$ |
| 500 | R52 | CH$_3$ | O | CH$_3$ | NH—O—C$_6$H$_5$ |
| 501 | R52 | CH$_3$ | O | CH$_3$ | NH$_2$ |
| 502 | R52 | CH$_3$ | O | CH$_3$ | NH(CH$_3$) |
| 503 | R52 | CH$_3$ | O | CH$_3$ | N(CH$_3$)$_2$ |
| 504 | R52 | CH$_3$ | O | CH$_3$ | NH(C$_6$H$_5$) |
| 505 | R52 | CH$_3$ | O | C$_2$H$_5$ | NH—O—H |
| 506 | R52 | CH$_3$ | O | C$_2$H$_5$ | NH—O—CH$_3$ |
| 507 | R52 | CH$_3$ | O | C$_2$H$_5$ | NH—O—C$_6$H$_5$ |
| 508 | R52 | CH$_3$ | O | C$_2$H$_5$ | NH$_2$ |
| 509 | R52 | CH$_3$ | O | C$_2$H$_5$ | NH(CH$_3$) |
| 510 | R52 | CH$_3$ | O | C$_2$H$_5$ | N(CH$_3$)$_2$ |
| 511 | R52 | CH$_3$ | O | C$_2$H$_5$ | NH(C$_6$H$_5$) |
| 512 | R52 | CH$_3$ | O | CH(CH$_3$)$_2$ | NH—O—H |
| 513 | R52 | CH$_3$ | O | CH(CH$_3$)$_2$ | NH—O—CH$_3$ |
| 514 | R52 | CH$_3$ | O | CH(CH$_3$)$_2$ | NH—O—C$_6$H$_5$ |
| 515 | R52 | CH$_3$ | O | CH(CH$_3$)$_2$ | NH$_2$ |
| 516 | R52 | CH$_3$ | O | CH(CH$_3$)$_2$ | NH(CH$_3$) |
| 517 | R52 | CH$_3$ | O | CH(CH$_3$)$_2$ | N(CH$_3$)$_2$ |
| 518 | R52 | CH$_3$ | O | CH(CH$_3$)$_2$ | NH(C$_6$H$_5$) |
| 519 | R52 | CH$_3$ | O | CH$_2$CF$_3$ | NH—O—H |
| 520 | R52 | CH$_3$ | O | CH$_2$CF$_3$ | NH—O—CH$_3$ |
| 521 | R52 | CH$_3$ | O | CH$_2$CF$_3$ | NH—O—C$_6$H$_5$ |
| 522 | R52 | CH$_3$ | O | CH$_2$CF$_3$ | NH$_2$ |
| 523 | R52 | CH$_3$ | O | CH$_2$CF$_3$ | NH(CH$_3$) |
| 524 | R52 | CH$_3$ | O | CH$_2$CF$_3$ | N(CH$_3$)$_2$ |
| 525 | R52 | CH$_3$ | O | CH$_2$CF$_3$ | NH(C$_6$H$_5$) |
| 526 | R52 | CH$_3$ | O | CH$_2$-cyclo-C$_3$H$_5$ | NH—O—H |
| 527 | R52 | CH$_3$ | O | CH$_2$-cyclo-C$_3$H$_5$ | NH—O—CH$_3$ |
| 528 | R52 | CH$_3$ | O | CH$_2$-cyclo-C$_3$H$_6$ | NH—O—C$_6$H$_5$ |
| 529 | R52 | CH$_3$ | O | CH$_2$-cyclo-C$_3$H$_5$ | NH$_2$ |
| 530 | R52 | CH$_3$ | O | CH$_2$-cyclo-C$_3$H$_5$ | NH(CH$_3$) |
| 531 | R52 | CH$_3$ | O | CH$_2$-cyclo-C$_3$H$_5$ | N(CH$_3$)$_2$ |
| 532 | R52 | CH$_3$ | O | CH$_2$-cyclo-C$_3$H$_5$ | NH(C$_6$H$_5$) |
| 533 | R52 | CH$_3$ | O | C$_6$H$_5$ | NH—O—H |
| 534 | R52 | CH$_3$ | O | C$_6$H$_5$ | NH—O—CH$_3$ |
| 535 | R52 | CH$_3$ | O | C$_6$H$_5$ | NH—O—C$_6$H$_5$ |
| 536 | R52 | CH$_3$ | O | C$_6$H$_5$ | NH$_2$ |
| 537 | R52 | CH$_3$ | O | C$_6$H$_5$ | NH(CH$_3$) |
| 538 | R52 | CH$_3$ | O | C$_6$H$_5$ | N(CH$_3$)$_2$ |
| 539 | R52 | CH$_3$ | O | C$_6$H$_5$ | NH(C$_6$H$_5$) |
| 540 | R52 | CH$_3$ | NH | H | NH—O—H |
| 541 | R52 | CH$_3$ | NH | H | NH—O—CH$_3$ |
| 542 | R52 | CH$_3$ | NH | H | NH—O—C$_6$H$_5$ |
| 543 | R52 | CH$_3$ | NH | H | NH$_2$ |
| 544 | R52 | CH$_3$ | NH | H | NH(CH$_3$) |
| 545 | R52 | CH$_3$ | NH | H | N(CH$_3$)$_2$ |
| 546 | R52 | CH$_3$ | NH | H | NH(C$_6$H$_5$) |
| 547 | R52 | CH$_3$ | NH | CH$_3$ | NH—O—H |
| 548 | R52 | CH$_3$ | NH | CH$_3$ | NH—O—CH$_3$ |
| 549 | R52 | CH$_3$ | NH | CH$_3$ | NH—O—C$_6$H$_5$ |
| 550 | R52 | CH$_3$ | NH | CH$_3$ | NH$_2$ |
| 551 | R52 | CH$_3$ | NH | CH$_3$ | NH(CH$_3$) |
| 552 | R52 | CH$_3$ | NH | CH$_3$ | N(CH$_3$)$_2$ |
| 553 | R52 | CH$_3$ | NH | CH$_3$ | NH(C$_6$H$_5$) |
| 554 | R52 | CH$_3$ | NH | C$_2$H$_5$ | NH—O—H |
| 555 | R52 | CH$_3$ | NH | C$_2$H$_5$ | NH—O—CH$_3$ |
| 556 | R52 | CH$_3$ | NH | C$_2$H$_5$ | NH—O—C$_6$H$_5$ |
| 557 | R52 | CH$_3$ | NH | C$_2$H$_5$ | NH$_2$ |
| 558 | R52 | CH$_3$ | NH | C$_2$H$_5$ | NH(CH$_3$) |
| 559 | R52 | CH$_3$ | NH | C$_2$H$_5$ | N(CH$_3$)$_2$ |
| 560 | R52 | CH$_3$ | NH | C$_2$H$_5$ | NH(C$_6$H$_5$) |
| 561 | R52 | CH$_3$ | NH | CH(CH$_3$)$_2$ | NH—O—H |
| 562 | R52 | CH$_3$ | NH | CH(CH$_3$)$_2$ | NH—O—CH$_3$ |
| 563 | R52 | CH$_3$ | NH | CH(CH$_3$)$_2$ | NH—O—C$_6$H$_5$ |
| 564 | R52 | CH$_3$ | NH | CH(CH$_3$)$_2$ | NH$_2$ |
| 565 | R52 | CH$_3$ | NH | CH(CH$_3$)$_2$ | NH(CH$_3$) |
| 566 | R52 | CH$_3$ | NH | CH(CH$_3$)$_2$ | N(CH$_3$)$_2$ |
| 567 | R52 | CH$_3$ | NH | CH(CH$_3$)$_2$ | NH(C$_6$H$_5$) |
| 568 | R52 | CH$_3$ | NH | CH$_2$CF$_3$ | NH—O—H |
| 569 | R52 | CH$_3$ | NH | CH$_2$CF$_3$ | NH—O—CH$_3$ |
| 570 | R52 | CH$_3$ | NH | CH$_2$CF$_3$ | NH—O—C$_6$H$_5$ |
| 571 | R52 | CH$_3$ | NH | CH$_2$CF$_3$ | NH$_2$ |
| 572 | R52 | CH$_3$ | NH | CH$_2$CF$_3$ | NH(CH$_3$) |
| 573 | R52 | CH$_3$ | NH | CH$_2$CF$_3$ | N(CH$_3$)$_2$ |
| 574 | R52 | CH$_3$ | NH | CH$_2$CF$_3$ | NH(C$_6$H$_5$) |
| 575 | R52 | CH$_3$ | NH | CH$_2$-cyclo-C$_3$H$_5$ | NH—O—H |
| 576 | R52 | CH$_3$ | NH | CH$_2$-cyclo-C$_3$H$_5$ | NH—O—CH$_3$ |
| 577 | R52 | CH$_3$ | NH | CH$_2$-cyclo-C$_3$H$_5$ | NH—O—C$_6$H$_5$ |
| 589 | R52 | CH$_3$ | NH | CH$_2$-cyclo-C$_3$H$_5$ | NH$_2$ |
| 579 | R52 | CH$_3$ | NH | CH$_2$-cyclo-C$_3$H$_5$ | NH(CH$_3$) |
| 580 | R52 | CH$_3$ | NH | CH$_2$-cyclo-C$_3$H$_5$ | N(CH$_3$)$_2$ |
| 581 | R52 | CH$_3$ | NH | CH$_2$-cyclo-C$_3$H$_5$ | NH(C$_6$H$_5$) |
| 582 | R52 | CH$_3$ | NH | C$_6$H$_5$ | NH—O—H |
| 583 | R52 | CH$_3$ | NH | C$_6$H$_5$ | NH—O—CH$_3$ |
| 584 | R52 | CH$_3$ | NH | C$_6$H$_5$ | NH—O—C$_6$H$_5$ |
| 585 | R52 | CH$_3$ | NH | C$_6$H$_5$ | NH$_2$ |
| 586 | R52 | CH$_3$ | NH | C$_6$H$_5$ | NH(CH$_3$) |
| 587 | R52 | CH$_3$ | NH | C$_6$H$_5$ | N(CH$_3$)$_2$ |
| 588 | R52 | CH$_3$ | NH | C$_6$H$_5$ | NH(C$_6$H$_5$) |
| 589 | R53 | H | — | H | NH—O—H |
| 590 | R53 | H | — | H | NH—O—CH$_3$ |
| 591 | R53 | H | — | H | NH—O—C$_6$H$_5$ |
| 592 | R53 | H | — | H | NH$_2$ |
| 593 | R53 | H | — | H | NH(CH$_3$) |
| 594 | R53 | H | — | H | N(CH$_3$)$_2$ |
| 595 | R53 | H | — | H | NH(C$_6$H$_5$) |
| 596 | R53 | H | — | CH$_3$ | NH—O—H |

TABLE 2-continued

Compounds of formula (I-14a)

R51 is 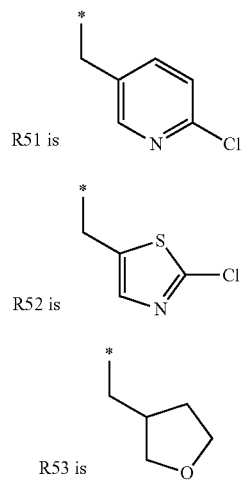

R52 is

R53 is

R51 is 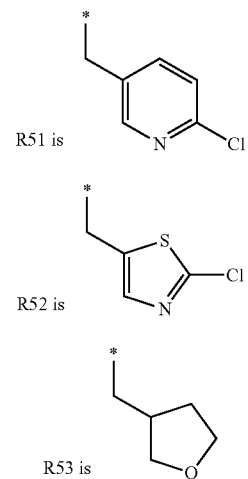

R52 is

R53 is

| No. | R⁵ | Rq | Z | R¹ | R² |
|---|---|---|---|---|---|
| 597 | R53 | H | — | CH₃ | NH—O—CH₃ |
| 598 | R53 | H | — | CH₃ | NH—O—C₆H₅ |
| 599 | R53 | H | — | CH₃ | NH₂ |
| 600 | R53 | H | — | CH₃ | NH(CH₃) |
| 601 | R53 | H | — | CH₃ | N(CH₃)₂ |
| 602 | R53 | H | — | CH₃ | NH(C₆H₅) |
| 603 | R53 | H | — | C₂H₅ | NH—O—H |
| 604 | R53 | H | — | C₂H₅ | NH—O—CH₃ |
| 605 | R53 | H | — | C₂H₅ | NH—O—C₆H₅ |
| 606 | R53 | H | — | C₂H₅ | NH₂ |
| 607 | R53 | H | — | C₂H₅ | NH(CH₃) |
| 608 | R53 | H | — | C₂H₅ | N(CH₃)₂ |
| 609 | R53 | H | — | C₂H₅ | NH(C₆H₅) |
| 610 | R53 | H | — | CH(CH₃)₂ | NH—O—H |
| 611 | R53 | H | — | CH(CH₃)₂ | NH—O—CH₃ |
| 612 | R53 | H | — | CH(CH₃)₂ | NH—O—C₆H₅ |
| 613 | R53 | H | — | CH(CH₃)₂ | NH₂ |
| 614 | R53 | H | — | CH(CH₃)₂ | NH(CH₃) |
| 615 | R53 | H | — | CH(CH₃)₂ | N(CH₃)₂ |
| 616 | R53 | H | — | CH(CH₃)₂ | NH(C₆H₅) |
| 617 | R53 | H | — | CH₂CF₃ | NH—O—H |
| 618 | R53 | H | — | CH₂CF₃ | NH—O—CH₃ |
| 619 | R53 | H | — | CH₂CF₃ | NH—O—C₆H₅ |
| 620 | R53 | H | — | CH₂CF₃ | NH₂ |
| 621 | R53 | H | — | CH₂CF₃ | NH(CH₃) |
| 622 | R53 | H | — | CH₂CF₃ | N(CH₃)₂ |
| 623 | R53 | H | — | CH₂CF₃ | NH(C₆H₅) |
| 624 | R53 | H | — | CH₂-cyclo-C₃H₅ | NH—O—H |
| 625 | R53 | H | — | CH₂-cyclo-C₃H₅ | NH—O—CH₃ |
| 626 | R53 | H | — | CH₂-cyclo-C₃H₅ | NH—O—C₆H₅ |
| 627 | R53 | H | — | CH₂-cyclo-C₃H₅ | NH₂ |
| 628 | R53 | H | — | CH₂-cyclo-C₃H₅ | NH(CH₃) |
| 629 | R53 | H | — | CH₂-cyclo-C₃H₅ | N(CH₃)₂ |
| 630 | R53 | H | — | CH₂-cyclo-C₃H₅ | NH(C₆H₅) |
| 631 | R53 | H | — | C₆H₅ | NH—O—H |
| 632 | R53 | H | — | C₆H₅ | NH—O—CH₃ |
| 633 | R53 | H | — | C₆H₅ | NH—O—C₆H₅ |
| 634 | R53 | H | — | C₆H₅ | NH₂ |
| 635 | R53 | H | — | C₆H₅ | NH(CH₃) |
| 636 | R53 | H | — | C₆H₅ | N(CH₃)₂ |
| 637 | R53 | H | — | C₆H₅ | NH(C₆H₅) |
| 638 | R53 | H | O | H | NH—O—H |
| 639 | R53 | H | O | H | NH—O—CH₃ |
| 640 | R53 | H | O | H | NH—O—C₆H₅ |
| 641 | R53 | H | O | H | NH₂ |
| 642 | R53 | H | O | H | NH(CH₃) |
| 643 | R53 | H | O | H | N(CH₃)₂ |
| 644 | R53 | H | O | H | NH(C₆H₅) |
| 645 | R53 | H | O | CH₃ | NH—O—H |
| 646 | R53 | H | O | CH₃ | NH—O—CH₃ |
| 647 | R53 | H | O | CH₃ | NH—O—C₆H₅ |
| 648 | R53 | H | O | CH₃ | NH₂ |
| 649 | R53 | H | O | CH₃ | NH(CH₃) |
| 650 | R53 | H | O | CH₃ | N(CH₃)₂ |
| 651 | R53 | H | O | CH₃ | NH(C₆H₅) |
| 652 | R53 | H | O | C₂H₅ | NH—O—H |
| 653 | R53 | H | O | C₂H₅ | NH—O—CH₃ |
| 654 | R53 | H | O | C₂H₅ | NH—O—C₆H₅ |
| 655 | R53 | H | O | C₂H₅ | NH₂ |
| 656 | R53 | H | O | C₂H₅ | NH(CH₃) |
| 657 | R53 | H | O | C₂H₅ | N(CH₃)₂ |
| 658 | R53 | H | O | C₂H₅ | NH(C₆H₅) |
| 659 | R53 | H | O | CH(CH₃)₂ | NH—O—H |
| 660 | R53 | H | O | CH(CH₃)₂ | NH—O—CH₃ |
| 661 | R53 | H | O | CH(CH₃)₂ | NH—O—C₆H₅ |
| 662 | R53 | H | O | CH(CH₃)₂ | NH₂ |
| 663 | R53 | H | O | CH(CH₃)₂ | NH(CH₃) |
| 664 | R53 | H | O | CH(CH₃)₂ | N(CH₃)₂ |
| 665 | R53 | H | O | CH(CH₃)₂ | NH(C₆H₅) |
| 666 | R53 | H | O | CH₂CF₃ | NH—O—H |
| 667 | R53 | H | O | CH₂CF₃ | NH—O—CH₃ |
| 668 | R53 | H | O | CH₂CF₃ | NH—O—C₆H₅ |
| 669 | R53 | H | O | CH₂CF₃ | NH₂ |
| 670 | R53 | H | O | CH₂CF₃ | NH(CH₃) |
| 671 | R53 | H | O | CH₂CF₃ | N(CH₃)₂ |
| 672 | R53 | H | O | CH₂CF₃ | NH(C₆H₅) |
| 673 | R53 | H | O | CH₂-cyclo-C₃H₅ | NH—O—H |
| 674 | R53 | H | O | CH₂-cyclo-C₃H₅ | NH—O—CH₃ |
| 675 | R53 | H | O | CH₂-cyclo-C₃H₅ | NH—O—C₆H₅ |
| 676 | R53 | H | O | CH₂-cyclo-C₃H₅ | NH₂ |
| 677 | R53 | H | O | CH₂-cyclo-C₃H₅ | NH(CH₃) |
| 678 | R53 | H | O | CH₂-cyclo-C₃H₅ | N(CH₃)₂ |
| 679 | R53 | H | O | CH₂-cyclo-C₃H₅ | NH(C₆H₅) |
| 680 | R53 | H | O | C₆H₅ | NH—O—H |
| 681 | R53 | H | O | C₆H₅ | NH—O—CH₃ |
| 682 | R53 | H | O | C₆H₅ | NH—O—C₆H₅ |
| 683 | R53 | H | O | C₆H₅ | NH₂ |
| 684 | R53 | H | O | C₆H₅ | NH(CH₃) |
| 685 | R53 | H | O | C₆H₅ | N(CH₃)₂ |
| 686 | R53 | H | O | C₆H₅ | NH(C₆H₅) |
| 687 | R53 | H | NH | H | NH—O—H |
| 688 | R53 | H | NH | H | NH—O—CH₃ |
| 689 | R53 | H | NH | H | NH—O—C₆H₅ |
| 690 | R53 | H | NH | H | NH₂ |
| 691 | R53 | H | NH | H | NH(CH₃) |
| 692 | R53 | H | NH | H | N(CH₃)₂ |
| 693 | R53 | H | NH | H | NH(C₆H₅) |
| 694 | R53 | H | NH | CH₃ | NH—O—H |
| 695 | R53 | H | NH | CH₃ | NH—O—CH₃ |
| 696 | R53 | H | NH | CH₃ | NH—O—C₆H₅ |
| 697 | R53 | H | NH | CH₃ | NH₂ |
| 698 | R53 | H | NH | CH₃ | NH(CH₃) |
| 699 | R53 | H | NH | CH₃ | N(CH₃)₂ |
| 700 | R53 | H | NH | CH₃ | NH(C₆H₅) |

TABLE 2-continued

Compounds of formula (I-14a)

R51 is: *-CH2-(5-pyridyl with 2-Cl)

R52 is: *-CH2-(5-thiazolyl with 2-Cl)

R53 is: *-CH2-(3-tetrahydrofuranyl)

| No. | R⁵ | Rᵍ | Z | R¹ | R² |
|---|---|---|---|---|---|
| 701 | R53 | H | NH | $C_2H_5$ | NH—O—H |
| 702 | R53 | H | NH | $C_2H_5$ | NH—O—$CH_3$ |
| 703 | R53 | H | NH | $C_2H_5$ | NH—O—$C_6H_5$ |
| 704 | R53 | H | NH | $C_2H_5$ | $NH_2$ |
| 705 | R53 | H | NH | $C_2H_5$ | $NH(CH_3)$ |
| 706 | R53 | H | NH | $C_2H_5$ | $N(CH_3)_2$ |
| 707 | R53 | H | NH | $C_2H_5$ | $NH(C_6H_5)$ |
| 708 | R53 | H | NH | $CH(CH_3)_2$ | NH—O—H |
| 709 | R53 | H | NH | $CH(CH_3)_2$ | NH—O—$CH_3$ |
| 710 | R53 | H | NH | $CH(CH_3)_2$ | NH—O—$C_6H_5$ |
| 711 | R53 | H | NH | $CH(CH_3)_2$ | $NH_2$ |
| 712 | R53 | H | NH | $CH(CH_3)_2$ | $NH(CH_3)$ |
| 713 | R53 | H | NH | $CH(CH_3)_2$ | $N(CH_3)_2$ |
| 714 | R53 | H | NH | $CH(CH_3)_2$ | $NH(C_6H_5)$ |
| 715 | R53 | H | NH | $CH_2CF_3$ | NH—O—H |
| 716 | R53 | H | NH | $CH_2CF_3$ | NH—O—$CH_3$ |
| 717 | R53 | H | NH | $CH_2CF_3$ | NH—O—$C_6H_5$ |
| 718 | R53 | H | NH | $CH_2CF_3$ | $NH_2$ |
| 719 | R53 | H | NH | $CH_2CF_3$ | $NH(CH_3)$ |
| 720 | R53 | H | NH | $CH_2CF_3$ | $N(CH_3)_2$ |
| 721 | R53 | H | NH | $CH_2CF_3$ | $NH(C_6H_5)$ |
| 722 | R53 | H | NH | $CH_2$-cyclo-$C_3H_5$ | NH—O—H |
| 723 | R53 | H | NH | $CH_2$-cyclo-$C_3H_5$ | NH—O—$CH_3$ |
| 724 | R53 | H | NH | $CH_2$-cyclo-$C_3H_5$ | NH—O—$C_6H_5$ |
| 725 | R53 | H | NH | $CH_2$-cyclo-$C_3H_5$ | $NH_2$ |
| 726 | R53 | H | NH | $CH_2$-cyclo-$C_3H_5$ | $NH(CH_3)$ |
| 727 | R53 | H | NH | $CH_2$-cyclo-$C_3H_5$ | $N(CH_3)_2$ |
| 728 | R53 | H | NH | $CH_2$-cyclo-$C_3H_5$ | $NH(C_6H_5)$ |
| 729 | R53 | H | NH | $C_6H_5$ | NH—O—H |
| 730 | R53 | H | NH | $C_6H_5$ | NH—O—$CH_3$ |
| 731 | R53 | H | NH | $C_6H_5$ | NH—O—$C_6H_5$ |
| 732 | R53 | H | NH | $C_6H_5$ | $NH_2$ |
| 733 | R53 | H | NH | $C_6H_5$ | $NH(CH_3)$ |
| 734 | R53 | H | NH | $C_6H_5$ | $N(CH_3)_2$ |
| 735 | R53 | H | NH | $C_6H_5$ | $NH(C_6H_5)$ |
| 736 | R53 | $CH_3$ | — | H | NH—O—H |
| 737 | R53 | $CH_3$ | — | H | NH—O—$CH_3$ |
| 738 | R53 | $CH_3$ | — | H | NH—O—$C_6H_5$ |
| 739 | R53 | $CH_3$ | — | H | $NH_2$ |
| 740 | R53 | $CH_3$ | — | H | $NH(CH_3)$ |
| 741 | R53 | $CH_3$ | — | H | $N(CH_3)_2$ |
| 742 | R53 | $CH_3$ | — | H | $NH(C_6H_5)$ |
| 743 | R53 | $CH_3$ | — | $CH_3$ | NH—O—H |
| 744 | R53 | $CH_3$ | — | $CH_3$ | NH—O—$CH_3$ |
| 745 | R53 | $CH_3$ | — | $CH_3$ | NH—O—$C_6H_5$ |
| 746 | R53 | $CH_3$ | — | $CH_3$ | $NH_2$ |
| 747 | R53 | $CH_3$ | — | $CH_3$ | $NH(CH_3)$ |
| 748 | R53 | $CH_3$ | — | $CH_3$ | $N(CH_3)_2$ |
| 749 | R53 | $CH_3$ | — | $CH_3$ | $NH(C_6H_5)$ |
| 750 | R53 | $CH_3$ | — | $C_2H_5$ | NH—O—H |
| 751 | R53 | $CH_3$ | — | $C_2H_5$ | NH—O—$CH_3$ |
| 752 | R53 | $CH_3$ | — | $C_2H_5$ | NH—O—$C_6H_5$ |
| 753 | R53 | $CH_3$ | — | $C_2H_5$ | $NH_2$ |
| 754 | R53 | $CH_3$ | — | $C_2H_5$ | $NH(CH_3)$ |
| 755 | R53 | $CH_3$ | — | $C_2H_5$ | $N(CH_3)_2$ |
| 756 | R53 | $CH_3$ | — | $C_2H_5$ | $NH(C_6H_5)$ |
| 757 | R53 | $CH_3$ | — | $CH(CH_3)_2$ | NH—O—H |
| 758 | R53 | $CH_3$ | — | $CH(CH_3)_2$ | NH—O—$CH_3$ |
| 759 | R53 | $CH_3$ | — | $CH(CH_3)_2$ | NH—O—$C_6H_5$ |
| 760 | R53 | $CH_3$ | — | $CH(CH_3)_2$ | $NH_2$ |
| 761 | R53 | $CH_3$ | — | $CH(CH_3)_2$ | $NH(CH_3)$ |
| 762 | R53 | $CH_3$ | — | $CH(CH_3)_2$ | $N(CH_3)_2$ |
| 763 | R53 | $CH_3$ | — | $CH(CH_3)_2$ | $NH(C_6H_5)$ |
| 764 | R53 | $CH_3$ | — | $CH_2CF_3$ | NH—O—H |
| 765 | R53 | $CH_3$ | — | $CH_2CF_3$ | NH—O—$CH_3$ |
| 766 | R53 | $CH_3$ | — | $CH_2CF_3$ | NH—O—$C_6H_5$ |
| 767 | R53 | $CH_3$ | — | $CH_2CF_3$ | $NH_2$ |
| 768 | R53 | $CH_3$ | — | $CH_2CF_3$ | $NH(CH_3)$ |
| 769 | R53 | $CH_3$ | — | $CH_2CF_3$ | $N(CH_3)_2$ |
| 770 | R53 | $CH_3$ | — | $CH_2CF_3$ | $NH(C_6H_5)$ |
| 771 | R53 | $CH_3$ | — | $CH_2$-cyclo-$C_3H_5$ | NH—O—H |
| 772 | R53 | $CH_3$ | — | $CH_2$-cyclo-$C_3H_5$ | NH—O—$CH_3$ |
| 773 | R53 | $CH_3$ | — | $CH_2$-cyclo-$C_3H_5$ | NH—O—$C_6H_5$ |
| 774 | R53 | $CH_3$ | — | $CH_2$-cyclo-$C_3H_5$ | $NH_2$ |
| 775 | R53 | $CH_3$ | — | $CH_2$-cyclo-$C_3H_5$ | $NH(CH_3)$ |
| 776 | R53 | $CH_3$ | — | $CH_2$-cyclo-$C_3H_5$ | $N(CH_3)_2$ |
| 777 | R53 | $CH_3$ | — | $CH_2$-cyclo-$C_3H_5$ | $NH(C_6H_5)$ |
| 778 | R53 | $CH_3$ | — | $C_6H_5$ | NH—O—H |
| 779 | R53 | $CH_3$ | — | $C_6H_5$ | NH—O—$CH_3$ |
| 780 | R53 | $CH_3$ | — | $C_6H_5$ | NH—O—$C_6H_5$ |
| 781 | R53 | $CH_3$ | — | $C_6H_5$ | $NH_2$ |
| 781 | R53 | $CH_3$ | — | $C_6H_5$ | $NH(CH_3)$ |
| 783 | R53 | $CH_3$ | — | $C_6H_5$ | $N(CH_3)_2$ |
| 784 | R53 | $CH_3$ | — | $C_6H_5$ | $NH(C_6H_5)$ |
| 785 | R53 | $CH_3$ | O | H | NH—O—H |
| 786 | R53 | $CH_3$ | O | H | NH—O—$CH_3$ |
| 787 | R53 | $CH_3$ | O | H | NH—O—$C_6H_5$ |
| 788 | R53 | $CH_3$ | O | H | $NH_2$ |
| 789 | R53 | $CH_3$ | O | H | $NH(CH_3)$ |
| 790 | R53 | $CH_3$ | O | H | $N(CH_3)_2$ |
| 791 | R53 | $CH_3$ | O | H | $NH(C_6H_5)$ |
| 792 | R53 | $CH_3$ | O | $CH_3$ | NH—O—H |
| 793 | R53 | $CH_3$ | O | $CH_3$ | NH—O—$CH_3$ |
| 794 | R53 | $CH_3$ | O | $CH_3$ | NH—O—$C_6H_5$ |
| 795 | R53 | $CH_3$ | O | $CH_3$ | $NH_2$ |
| 796 | R53 | $CH_3$ | O | $CH_3$ | $NH(CH_3)$ |
| 797 | R53 | $CH_3$ | O | $CH_3$ | $N(CH_3)_2$ |
| 798 | R53 | $CH_3$ | O | $CH_3$ | $NH(C_6H_5)$ |
| 799 | R53 | $CH_3$ | O | $C_2H_5$ | NH—O—H |
| 800 | R53 | $CH_3$ | O | $C_2H_5$ | NH—O—$CH_3$ |
| 801 | R53 | $CH_3$ | O | $C_2H_5$ | NH—O—$C_6H_5$ |
| 802 | R53 | $CH_3$ | O | $C_2H_5$ | $NH_2$ |
| 803 | R53 | $CH_3$ | O | $C_2H_5$ | $NH(CH_3)$ |
| 804 | R53 | $CH_3$ | O | $C_2H_5$ | $N(CH_3)_2$ |

TABLE 2-continued

Compounds of formula (I-14a)

R51 is 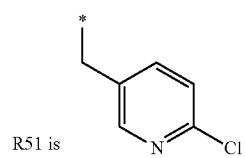

R52 is 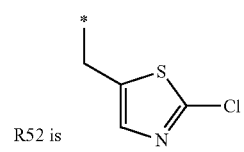

R53 is 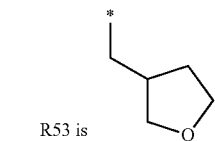

| No. | $R^5$ | $R^q$ | Z | $R^1$ | $R^2$ |
|---|---|---|---|---|---|
| 805 | R53 | $CH_3$ | O | $C_2H_5$ | $NH(C_6H_5)$ |
| 806 | R53 | $CH_3$ | O | $CH(CH_3)_2$ | NH—O—H |
| 807 | R53 | $CH_3$ | O | $CH(CH_3)_2$ | NH—O—$CH_3$ |
| 808 | R53 | $CH_3$ | O | $CH(CH_3)_2$ | NH—O—$C_6H_5$ |
| 809 | R53 | $CH_3$ | O | $CH(CH_3)_2$ | $NH_2$ |
| 810 | R53 | $CH_3$ | O | $CH(CH_3)_2$ | $NH(CH_3)$ |
| 811 | R53 | $CH_3$ | O | $CH(CH_3)_2$ | $N(CH_3)_2$ |
| 812 | R53 | $CH_3$ | O | $CH(CH_3)_2$ | $NH(C_6H_5)$ |
| 813 | R53 | $CH_3$ | O | $CH_2CF_3$ | NH—O—H |
| 814 | R53 | $CH_3$ | O | $CH_2CF_3$ | NH—O—$CH_3$ |
| 815 | R53 | $CH_3$ | O | $CH_2CF_3$ | NH—O—$C_6H_5$ |
| 816 | R53 | $CH_3$ | O | $CH_2CF_3$ | $NH_2$ |
| 817 | R53 | $CH_3$ | O | $CH_2CF_3$ | $NH(CH_3)$ |
| 818 | R53 | $CH_3$ | O | $CH_2CF_3$ | $N(CH_3)_2$ |
| 819 | R53 | $CH_3$ | O | $CH_2CF_3$ | $NH(C_6H_5)$ |
| 820 | R53 | $CH_3$ | O | $CH_2$-cyclo-$C_3H_5$ | NH—O—H |
| 821 | R53 | $CH_3$ | O | $CH_2$-cyclo-$C_3H_5$ | NH—O—$CH_3$ |
| 822 | R53 | $CH_3$ | O | $CH_2$-cyclo-$C_3H_5$ | NH—O—$C_6H_5$ |
| 823 | R53 | $CH_3$ | O | $CH_2$-cyclo-$C_3H_5$ | $NH_2$ |
| 824 | R53 | $CH_3$ | O | $CH_2$-cyclo-$C_3H_5$ | $NH(CH_3)$ |
| 825 | R53 | $CH_3$ | O | $CH_2$-cyclo-$C_3H_5$ | $N(CH_3)_2$ |
| 826 | R53 | $CH_3$ | O | $CH_2$-cyclo-$C_3H_5$ | $NH(C_6H_5)$ |
| 827 | R53 | $CH_3$ | O | $C_6H_5$ | NH—O—H |
| 828 | R53 | $CH_3$ | O | $C_6H_5$ | NH—O—$CH_3$ |
| 829 | R53 | $CH_3$ | O | $C_6H_5$ | NH—O—$C_6H_5$ |
| 830 | R53 | $CH_3$ | O | $C_6H_5$ | $NH_2$ |
| 831 | R53 | $CH_3$ | O | $C_6H_5$ | $NH(CH_3)$ |
| 832 | R53 | $CH_3$ | O | $C_6H_5$ | $N(CH_3)_2$ |
| 833 | R53 | $CH_3$ | O | $C_6H_5$ | $NH(C_6H_5)$ |
| 834 | R53 | $CH_3$ | NH | H | NH—O—H |
| 835 | R53 | $CH_3$ | NH | H | NH—O—$CH_3$ |
| 836 | R53 | $CH_3$ | NH | H | NH—O—$C_6H_5$ |
| 837 | R53 | $CH_3$ | NH | H | $NH_2$ |
| 838 | R53 | $CH_3$ | NH | H | $NH(CH_3)$ |
| 839 | R53 | $CH_3$ | NH | H | $N(CH_3)_2$ |
| 840 | R53 | $CH_3$ | NH | H | $NH(C_6H_5)$ |
| 841 | R53 | $CH_3$ | NH | $CH_3$ | NH—O—H |
| 842 | R53 | $CH_3$ | NH | $CH_3$ | NH—O—$CH_3$ |
| 843 | R53 | $CH_3$ | NH | $CH_3$ | NH—O—$C_6H_5$ |
| 844 | R53 | $CH_3$ | NH | $CH_3$ | $NH_2$ |
| 845 | R53 | $CH_3$ | NH | $CH_3$ | $NH(CH_3)$ |
| 846 | R53 | $CH_3$ | NH | $CH_3$ | $N(CH_3)_2$ |
| 847 | R53 | $CH_3$ | NH | $CH_3$ | $NH(C_6H_5)$ |
| 848 | R53 | $CH_3$ | NH | $C_2H_5$ | NH—O—H |
| 849 | R53 | $CH_3$ | NH | $C_2H_5$ | NH—O—$CH_3$ |
| 850 | R53 | $CH_3$ | NH | $C_2H_5$ | NH—O—$C_6H_5$ |
| 851 | R53 | $CH_3$ | NH | $C_2H_5$ | $NH_2$ |
| 852 | R53 | $CH_3$ | NH | $C_2H_5$ | $NH(CH_3)$ |
| 853 | R53 | $CH_3$ | NH | $C_2H_5$ | $N(CH_3)_2$ |
| 854 | R53 | $CH_3$ | NH | $C_2H_5$ | $NH(C_6H_5)$ |
| 855 | R53 | $CH_3$ | NH | $CH(CH_3)_2$ | NH—O—H |
| 856 | R53 | $CH_3$ | NH | $CH(CH_3)_2$ | NH—O—$CH_3$ |
| 857 | R53 | $CH_3$ | NH | $CH(CH_3)_2$ | NH—O—$C_6H_5$ |
| 858 | R53 | $CH_3$ | NH | $CH(CH_3)_2$ | $NH_2$ |
| 859 | R53 | $CH_3$ | NH | $CH(CH_3)_2$ | $NH(CH_3)$ |
| 860 | R53 | $CH_3$ | NH | $CH(CH_3)_2$ | $N(CH_3)_2$ |
| 861 | R53 | $CH_3$ | NH | $CH(CH_3)_2$ | $NH(C_6H_5)$ |
| 862 | R53 | $CH_3$ | NH | $CH_2CF_3$ | NH—O—H |
| 863 | R53 | $CH_3$ | NH | $CH_2CF_3$ | NH—O—$CH_3$ |
| 864 | R53 | $CH_3$ | NH | $CH_2CF_3$ | NH—O—$C_6H_5$ |
| 865 | R53 | $CH_3$ | NH | $CH_2CF_3$ | $NH_2$ |
| 866 | R53 | $CH_3$ | NH | $CH_2CF_3$ | $NH(CH_3)$ |
| 867 | R53 | $CH_3$ | NH | $CH_2CF_3$ | $N(CH_3)_2$ |
| 868 | R53 | $CH_3$ | NH | $CH_2CF_3$ | $NH(C_6H_5)$ |
| 869 | R53 | $CH_3$ | NH | $CH_2$-cyclo-$C_3H_5$ | NH—O—H |
| 870 | R53 | $CH_3$ | NH | $CH_2$-cyclo-$C_3H_5$ | NH—O—$CH_3$ |
| 871 | R53 | $CH_3$ | NH | $CH_2$-cyclo-$C_3H_5$ | NH—O—$C_6H_5$ |
| 872 | R53 | $CH_3$ | NH | $CH_2$-cyclo-$C_3H_5$ | $NH_2$ |
| 873 | R53 | $CH_3$ | NH | $CH_2$-cyclo-$C_3H_5$ | $NH(CH_3)$ |
| 874 | R53 | $CH_3$ | NH | $CH_2$-cyclo-$C_3H_5$ | $N(CH_3)_2$ |
| 875 | R53 | $CH_3$ | NH | $CH_2$-cyclo-$C_3H_5$ | $NH(C_6H_5)$ |
| 876 | R53 | $CH_3$ | NH | $C_6H_5$ | NH—O—H |
| 877 | R53 | $CH_3$ | NH | $C_6H_5$ | NH—O—$CH_3$ |
| 878 | R53 | $CH_3$ | NH | $C_6H_5$ | NH—O—$C_6H_5$ |
| 879 | R53 | $CH_3$ | NH | $C_6H_5$ | $NH_2$ |
| 880 | R53 | $CH_3$ | NH | $C_6H_5$ | $NH(CH_3)$ |
| 881 | R53 | $CH_3$ | NH | $C_6H_5$ | $N(CH_3)_2$ |
| 882 | R53 | $CH_3$ | NH | $C_6H_5$ | $NH(C_6H_5)$ |

In a further preferred embodiment, the compound of formula (I) is a compound of formula (I-15a),

(I-15a)

wherein the symbols and indices have the same meaning as in formula (I-15), in particular a compound listed in Table 3.

TABLE 3

Compounds of formula (I-15a)

R51 is 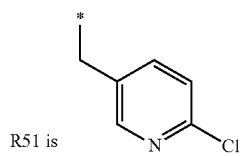

R52 is 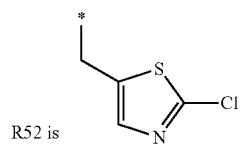

R53 is 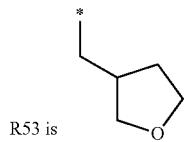

R51 is 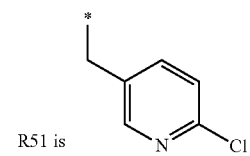

R52 is 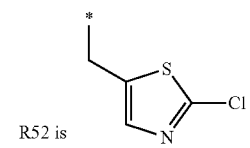

R53 is 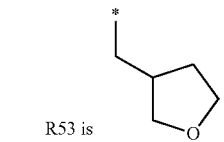

| No. | $R^5$ | $R^q$ | Z | $R^1$ | $R^2$ |
|---|---|---|---|---|---|
| 1 | R51 | H | — | H | NH—O—H |
| 2 | R51 | H | — | H | NH—O—CH$_3$ |
| 3 | R51 | H | — | H | NH—O—C$_6$H$_5$ |
| 4 | R51 | H | — | H | NH$_2$ |
| 5 | R51 | H | — | H | NH(CH$_3$) |
| 6 | R51 | H | — | H | N(CH$_3$)$_2$ |
| 7 | R51 | H | — | H | NH(C$_6$H$_5$) |
| 8 | R51 | H | — | CH$_3$ | NH—O—H |
| 9 | R51 | H | — | CH$_3$ | NH—O—CH$_3$ |
| 10 | R51 | H | — | CH$_3$ | NH—O—C$_6$H$_5$ |
| 11 | R51 | H | — | CH$_3$ | NH$_2$ |
| 12 | R51 | H | — | CH$_3$ | NH(CH$_3$) |
| 13 | R51 | H | — | CH$_3$ | N(CH$_3$)$_2$ |
| 14 | R51 | H | — | CH$_3$ | NH(C$_6$H$_5$) |
| 15 | R51 | H | — | C$_2$H$_5$ | NH—O—H |
| 16 | R51 | H | — | C$_2$H$_5$ | NH—O—CH$_3$ |
| 17 | R51 | H | — | C$_2$H$_5$ | NH—O—C$_6$H$_5$ |
| 18 | R51 | H | — | C$_2$H$_5$ | NH$_2$ |
| 19 | R51 | H | — | C$_2$H$_5$ | NH(CH$_3$) |
| 20 | R51 | H | — | C$_2$H$_5$ | N(CH$_3$)$_2$ |
| 21 | R51 | H | — | C$_2$H$_5$ | NH(C$_6$H$_5$) |
| 22 | R51 | H | — | CH(CH$_3$)$_2$ | NH—O—H |
| 23 | R51 | H | — | CH(CH$_3$)$_2$ | NH—O—CH$_3$ |
| 24 | R51 | H | — | CH(CH$_3$)$_2$ | NH—O—C$_6$H$_5$ |
| 25 | R51 | H | — | CH(CH$_3$)$_2$ | NH$_2$ |
| 26 | R51 | H | — | CH(CH$_3$)$_2$ | NH(CH$_3$) |
| 27 | R51 | H | — | CH(CH$_3$)$_2$ | N(CH$_3$)$_2$ |
| 28 | R51 | H | — | CH(CH$_3$)$_2$ | NH(C$_6$H$_5$) |
| 29 | R51 | H | — | CH$_2$CF$_3$ | NH—O—H |
| 30 | R51 | H | — | CH$_2$CF$_3$ | NH—O—CH$_3$ |
| 31 | R51 | H | — | CH$_2$CF$_3$ | NH—O—C$_6$H$_5$ |
| 32 | R51 | H | — | CH$_2$CF$_3$ | NH$_2$ |
| 33 | R51 | H | — | CH$_2$CF$_3$ | NH(CH$_3$) |
| 34 | R51 | H | — | CH$_2$CF$_3$ | N(CH$_3$)$_2$ |
| 35 | R51 | H | — | CH$_2$CF$_3$ | NH(C$_6$H$_5$) |
| 36 | R51 | H | — | CH$_2$-cyclo-C$_3$H$_5$ | NH—O—H |
| 37 | R51 | H | — | CH$_2$-cyclo-C$_3$H$_5$ | NH—O—CH$_3$ |
| 38 | R51 | H | — | CH$_2$-cyclo-C$_3$H$_5$ | NH—O—C$_6$H$_5$ |
| 39 | R51 | H | — | CH$_2$-cyclo-C$_3$H$_5$ | NH$_2$ |
| 40 | R51 | H | — | CH$_2$-cyclo-C$_3$H$_5$ | NH(CH$_3$) |
| 41 | R51 | H | — | CH$_2$-cyclo-C$_3$H$_5$ | N(CH$_3$)$_2$ |
| 42 | R51 | H | — | CH$_2$-cyclo-C$_3$H$_5$ | NH(C$_6$H$_5$) |
| 43 | R51 | H | — | C$_6$H$_5$ | NH—O—H |
| 44 | R51 | H | — | C$_6$H$_5$ | NH—O—CH$_3$ |
| 45 | R51 | H | — | C$_6$H$_5$ | NH—O—C$_6$H$_5$ |
| 46 | R51 | H | — | C$_6$H$_5$ | NH$_2$ |
| 47 | R51 | H | — | C$_6$H$_5$ | NH(CH$_3$) |
| 48 | R51 | H | — | C$_6$H$_5$ | N(CH$_3$)$_2$ |
| 49 | R51 | H | — | C$_6$H$_5$ | NH(C$_6$H$_5$) |
| 50 | R51 | H | O | H | NH—O—H |
| 51 | R51 | H | O | H | NH—O—CH$_3$ |
| 52 | R51 | H | O | H | NH—O—C$_6$H$_5$ |
| 53 | R51 | H | O | H | NH$_2$ |
| 54 | R51 | H | O | H | NH(CH$_3$) |
| 55 | R51 | H | O | H | N(CH$_3$)$_2$ |
| 56 | R51 | H | O | H | NH(C$_6$H$_5$) |
| 57 | R51 | H | O | CH$_3$ | NH—O—H |
| 58 | R51 | H | O | CH$_3$ | NH—O—CH$_3$ |
| 59 | R51 | H | O | CH$_3$ | NH—O—C$_6$H$_5$ |
| 60 | R51 | H | O | CH$_3$ | NH$_2$ |
| 61 | R51 | H | O | CH$_3$ | NH(CH$_3$) |
| 62 | R51 | H | O | CH$_3$ | N(CH$_3$)$_2$ |
| 63 | R51 | H | O | CH$_3$ | NH(C$_6$H$_5$) |
| 64 | R51 | H | O | C$_2$H$_5$ | NH—O—H |
| 65 | R51 | H | O | C$_2$H$_5$ | NH—O—CH$_3$ |
| 66 | R51 | H | O | C$_2$H$_5$ | NH—O—C$_6$H$_5$ |
| 67 | R51 | H | O | C$_2$H$_5$ | NH$_2$ |
| 68 | R51 | H | O | C$_2$H$_5$ | NH(CH$_3$) |
| 69 | R51 | H | O | C$_2$H$_5$ | N(CH$_3$)$_2$ |
| 70 | R51 | H | O | C$_2$H$_5$ | NH(C$_6$H$_5$) |
| 71 | R51 | H | O | CH(CH$_3$)$_2$ | NH—O—H |
| 72 | R51 | H | O | CH(CH$_3$)$_2$ | NH—O—CH$_3$ |
| 73 | R51 | H | O | CH(CH$_3$)$_2$ | NH—O—C$_6$H$_5$ |
| 74 | R51 | H | O | CH(CH$_3$)$_2$ | NH$_2$ |
| 75 | R51 | H | O | CH(CH$_3$)$_2$ | NH(CH$_3$) |
| 76 | R51 | H | O | CH(CH$_3$)$_2$ | N(CH$_3$)$_2$ |
| 77 | R51 | H | O | CH(CH$_3$)$_2$ | NH(C$_6$H$_5$) |
| 78 | R51 | H | O | CH$_2$CF$_3$ | NH—O—H |
| 79 | R51 | H | O | CH$_2$CF$_3$ | NH—O—CH$_3$ |
| 80 | R51 | H | O | CH$_2$CF$_3$ | NH—O—C$_6$H$_5$ |
| 81 | R51 | H | O | CH$_2$CF$_3$ | NH$_2$ |
| 82 | R51 | H | O | CH$_2$CF$_3$ | NH(CH$_3$) |
| 83 | R51 | H | O | CH$_2$CF$_3$ | N(CH$_3$)$_2$ |
| 84 | R51 | H | O | CH$_2$CF$_3$ | NH(C$_6$H$_5$) |
| 85 | R51 | H | O | CH$_2$-cyclo-C$_3$H$_5$ | NH—O—H |
| 86 | R51 | H | O | CH$_2$-cyclo-C$_3$H$_5$ | NH—O—CH$_3$ |
| 87 | R51 | H | O | CH$_2$-cyclo-C$_3$H$_5$ | NH—O—C$_6$H$_5$ |
| 88 | R51 | H | O | CH$_2$-cyclo-C$_3$H$_5$ | NH$_2$ |
| 89 | R51 | H | O | CH$_2$-cyclo-C$_3$H$_5$ | NH(CH$_3$) |
| 90 | R51 | H | O | CH$_2$-cyclo-C$_3$H$_5$ | N(CH$_3$)$_2$ |
| 91 | R51 | H | O | CH$_2$-cyclo-C$_3$H$_5$ | NH(C$_6$H$_5$) |
| 92 | R51 | H | O | C$_6$H$_5$ | NH—O—H |
| 93 | R51 | H | O | C$_6$H$_5$ | NH—O—CH$_3$ |
| 94 | R51 | H | O | C$_6$H$_5$ | NH—O—C$_6$H$_5$ |
| 95 | R51 | H | O | C$_6$H$_5$ | NH$_2$ |
| 96 | R51 | H | O | C$_6$H$_5$ | NH(CH$_3$) |
| 97 | R51 | H | O | C$_6$H$_5$ | N(CH$_3$)$_2$ |
| 98 | R51 | H | O | C$_6$H$_5$ | NH(C$_6$H$_5$) |
| 99 | R51 | H | NH | H | NH—O—H |
| 100 | R51 | H | NH | H | NH—O—CH$_3$ |
| 101 | R51 | H | NH | H | NH—O—C$_6$H$_5$ |
| 102 | R51 | H | NH | H | NH$_2$ |
| 103 | R51 | H | NH | H | NH(CH$_3$) |
| 104 | R51 | H | NH | H | N(CH$_3$)$_2$ |

TABLE 3-continued

Compounds of formula (I-15a)

R51 is 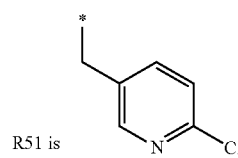

R52 is 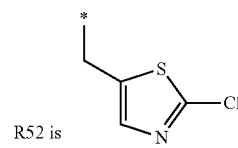

R53 is 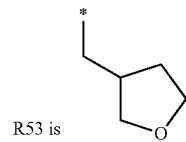

| No. | R⁵ | R$^q$ | Z | R¹ | R² |
|---|---|---|---|---|---|
| 105 | R51 | H | NH | H | NH(C₆H₅) |
| 106 | R51 | H | NH | CH₃ | NH—O—H |
| 107 | R51 | H | NH | CH₃ | NH—O—CH₃ |
| 108 | R51 | H | NH | CH₃ | NH—O—C₆H₅ |
| 109 | R51 | H | NH | CH₃ | NH₂ |
| 110 | R51 | H | NH | CH₃ | NH(CH₃) |
| 111 | R51 | H | NH | CH₃ | N(CH₃)₂ |
| 112 | R51 | H | NH | CH₃ | NH(C₆H₅) |
| 113 | R51 | H | NH | C₂H₅ | NH—O—H |
| 114 | R51 | H | NH | C₂H₅ | NH—O—CH₃ |
| 115 | R51 | H | NH | C₂H₅ | NH—O—C₆H₅ |
| 116 | R51 | H | NH | C₂H₅ | NH₂ |
| 117 | R51 | H | NH | C₂H₅ | NH(CH₃) |
| 118 | R51 | H | NH | C₂H₅ | N(CH₃)₂ |
| 119 | R51 | H | NH | C₂H₅ | NH(C₆H₅) |
| 120 | R51 | H | NH | CH(CH₃)₂ | NH—O—H |
| 121 | R51 | H | NH | CH(CH₃)₂ | NH—O—CH₃ |
| 122 | R51 | H | NH | CH(CH₃)₂ | NH—O—C₆H₅ |
| 123 | R51 | H | NH | CH(CH₃)₂ | NH₂ |
| 124 | R51 | H | NH | CH(CH₃)₂ | NH(CH₃) |
| 125 | R51 | H | NH | CH(CH₃)₂ | N(CH₃)₂ |
| 126 | R51 | H | NH | CH(CH₃)₂ | NH(C₆H₅) |
| 127 | R51 | H | NH | CH₂CF₃ | NH—O—H |
| 128 | R51 | H | NH | CH₂CF₃ | NH—O—CH₃ |
| 129 | R51 | H | NH | CH₂CF₃ | NH—O—C₆H₅ |
| 130 | R51 | H | NH | CH₂CF₃ | NH₂ |
| 131 | R51 | H | NH | CH₂CF₃ | NH(CH₃) |
| 132 | R51 | H | NH | CH₂CF₃ | N(CH₃)₂ |
| 133 | R51 | H | NH | CH₂CF₃ | NH(C₆H₅) |
| 134 | R51 | H | NH | CH₂-cyclo-C₃H₅ | NH—O—H |
| 135 | R51 | H | NH | CH₂-cyclo-C₃H₅ | NH—O—CH₃ |
| 136 | R51 | H | NH | CH₂-cyclo-C₃H₅ | NH—O—C₆H₅ |
| 137 | R51 | H | NH | CH₂-cyclo-C₃H₅ | NH₂ |
| 138 | R51 | H | NH | CH₂-cyclo-C₃H₅ | NH(CH₃) |
| 139 | R51 | H | NH | CH₂-cyclo-C₃H₅ | N(CH₃)₂ |
| 140 | R51 | H | NH | CH₂-cyclo-C₃H₅ | NH(C₆H₅) |
| 141 | R51 | H | NH | C₆H₅ | NH—O—H |
| 142 | R51 | H | NH | C₆H₅ | NH—O—CH₃ |
| 143 | R51 | H | NH | C₆H₅ | NH—O—C₆H₅ |
| 144 | R51 | H | NH | C₆H₅ | NH₂ |
| 145 | R51 | H | NH | C₆H₅ | NH(CH₃) |
| 146 | R51 | H | NH | C₆H₅ | N(CH₃)₂ |
| 147 | R51 | H | NH | C₆H₅ | NH(C₆H₅) |
| 148 | R51 | CH₃ | — | H | NH—O—H |
| 149 | R51 | CH₃ | — | H | NH—O—CH₃ |
| 150 | R51 | CH₃ | — | H | NH—O—C₆H₅ |
| 151 | R51 | CH₃ | — | H | NH₂ |
| 152 | R51 | CH₃ | — | H | NH(CH₃) |
| 153 | R51 | CH₃ | — | H | N(CH₃)₂ |
| 154 | R51 | CH₃ | — | H | NH(C₆H₅) |
| 155 | R51 | CH₃ | — | CH₃ | NH—O—H |
| 156 | R51 | CH₃ | — | CH₃ | NH—O—CH₃ |
| 157 | R51 | CH₃ | — | CH₃ | NH—O—C₆H₅ |
| 158 | R51 | CH₃ | — | CH₃ | NH₂ |
| 159 | R51 | CH₃ | — | CH₃ | NH(CH₃) |
| 160 | R51 | CH₃ | — | CH₃ | N(CH₃)₂ |
| 161 | R51 | CH₃ | — | CH₃ | NH(C₆H₅) |
| 162 | R51 | CH₃ | — | C₂H₅ | NH—O—H |
| 163 | R51 | CH₃ | — | C₂H₅ | NH—O—CH₃ |
| 164 | R51 | CH₃ | — | C₂H₅ | NH—O—C₆H₅ |
| 165 | R51 | CH₃ | — | C₂H₅ | NH₂ |
| 166 | R51 | CH₃ | — | C₂H₅ | NH(CH₃) |
| 167 | R51 | CH₃ | — | C₂H₅ | N(CH₃)₂ |
| 168 | R51 | CH₃ | — | C₂H₅ | NH(C₆H₅) |
| 169 | R51 | CH₃ | — | CH(CH₃)₂ | NH—O—H |
| 170 | R51 | CH₃ | — | CH(CH₃)₂ | NH—O—CH₃ |
| 171 | R51 | CH₃ | — | CH(CH₃)₂ | NH—O—C₆H₅ |
| 172 | R51 | CH₃ | — | CH(CH₃)₂ | NH₂ |
| 173 | R51 | CH₃ | — | CH(CH₃)₂ | NH(CH₃) |
| 174 | R51 | CH₃ | — | CH(CH₃)₂ | N(CH₃)₂ |
| 175 | R51 | CH₃ | — | CH(CH₃)₂ | NH(C₆H₅) |
| 176 | R51 | CH₃ | — | CH₂CF₃ | NH—O—H |
| 177 | R51 | CH₃ | — | CH₂CF₃ | NH—O—CH₃ |
| 178 | R51 | CH₃ | — | CH₂CF₃ | NH—O—C₆H₅ |
| 179 | R51 | CH₃ | — | CH₂CF₃ | NH₂ |
| 180 | R51 | CH₃ | — | CH₂CF₃ | NH(CH₃) |
| 181 | R51 | CH₃ | — | CH₂CF₃ | N(CH₃)₂ |
| 182 | R51 | CH₃ | — | CH₂CF₃ | NH(C₆H₅) |
| 183 | R51 | CH₃ | — | CH₂-cyclo-C₃H₅ | NH—O—H |
| 184 | R51 | CH₃ | — | CH₂-cyclo-C₃H₅ | NH—O—CH₃ |
| 185 | R51 | CH₃ | — | CH₂-cyclo-C₃H₅ | NH—O—C₆H₅ |
| 186 | R51 | CH₃ | — | CH₂-cyclo-C₃H₅ | NH₂ |
| 187 | R51 | CH₃ | — | CH₂-cyclo-C₃H₅ | NH(CH₃) |
| 188 | R51 | CH₃ | — | CH₂-cyclo-C₃H₅ | N(CH₃)₂ |
| 189 | R51 | CH₃ | — | CH₂-cyclo-C₃H₅ | NH(C₆H₅) |
| 190 | R51 | CH₃ | — | C₆H₅ | NH—O—H |
| 191 | R51 | CH₃ | — | C₆H₅ | NH—O—CH₃ |
| 192 | R51 | CH₃ | — | C₆H₅ | NH—O—C₆H₅ |
| 193 | R51 | CH₃ | — | C₆H₅ | NH₂ |
| 194 | R51 | CH₃ | — | C₆H₅ | NH(CH₃) |
| 195 | R51 | CH₃ | — | C₆H₅ | N(CH₃)₂ |
| 196 | R51 | CH₃ | — | C₆H₅ | NH(C₆H₅) |
| 197 | R51 | CH₃ | O | H | NH—O—H |
| 198 | R51 | CH₃ | O | H | NH—O—CH₃ |
| 199 | R51 | CH₃ | O | H | NH—O—C₆H₅ |
| 200 | R51 | CH₃ | O | H | NH₂ |
| 201 | R51 | CH₃ | O | H | NH(CH₃) |
| 202 | R51 | CH₃ | O | H | N(CH₃)₂ |
| 203 | R51 | CH₃ | O | H | NH(C₆H₅) |
| 204 | R51 | CH₃ | O | CH₃ | NH—O—H |
| 205 | R51 | CH₃ | O | CH₃ | NH—O—CH₃ |
| 206 | R51 | CH₃ | O | CH₃ | NH—O—C₆H₅ |
| 207 | R51 | CH₃ | O | CH₃ | NH₂ |
| 208 | R51 | CH₃ | O | CH₃ | NH(CH₃) |

TABLE 3-continued

Compounds of formula (I-15a)

R51 is: *-CH2-(5-pyridyl with 2-Cl)

R52 is: *-CH2-(5-thiazolyl with 2-Cl)

R53 is: *-CH2-(3-tetrahydrofuranyl)

| No. | R⁵ | Rq | Z | R¹ | R² |
|---|---|---|---|---|---|
| 209 | R51 | CH₃ | O | CH₃ | N(CH₃)₂ |
| 210 | R51 | CH₃ | O | CH₃ | NH(C₆H₅) |
| 211 | R51 | CH₃ | O | C₂H₅ | NH—O—H |
| 212 | R51 | CH₃ | O | C₂H₅ | NH—O—CH₃ |
| 213 | R51 | CH₃ | O | C₂H₅ | NH—O—C₆H₅ |
| 214 | R51 | CH₃ | O | C₂H₅ | NH₂ |
| 215 | R51 | CH₃ | O | C₂H₅ | NH(CH₃) |
| 216 | R51 | CH₃ | O | C₂H₅ | N(CH₃)₂ |
| 217 | R51 | CH₃ | O | C₂H₅ | NH(C₆H₅) |
| 218 | R51 | CH₃ | O | CH(CH₃)₂ | NH—O—H |
| 219 | R51 | CH₃ | O | CH(CH₃)₂ | NH—O—CH₃ |
| 220 | R51 | CH₃ | O | CH(CH₃)₂ | NH—O—C₆H₅ |
| 221 | R51 | CH₃ | O | CH(CH₃)₂ | NH₂ |
| 222 | R51 | CH₃ | O | CH(CH₃)₂ | NH(CH₃) |
| 223 | R51 | CH₃ | O | CH(CH₃)₂ | N(CH₃)₂ |
| 224 | R51 | CH₃ | O | CH(CH₃)₂ | NH(C₆H₅) |
| 225 | R51 | CH₃ | O | CH₂CF₃ | NH—O—H |
| 226 | R51 | CH₃ | O | CH₂CF₃ | NH—O—CH₃ |
| 227 | R51 | CH₃ | O | CH₂CF₃ | NH—O—C₆H₅ |
| 228 | R51 | CH₃ | O | CH₂CF₃ | NH₂ |
| 229 | R51 | CH₃ | O | CH₂CF₃ | NH(CH₃) |
| 230 | R51 | CH₃ | O | CH₂CF₃ | N(CH₃)₂ |
| 231 | R51 | CH₃ | O | CH₂CF₃ | NH(C₆H₅) |
| 232 | R51 | CH₃ | O | CH₂-cyclo-C₃H₅ | NH—O—H |
| 233 | R51 | CH₃ | O | CH₂-cyclo-C₃H₅ | NH—O—CH₃ |
| 234 | R51 | CH₃ | O | CH₂-cyclo-C₃H₅ | NH—O—C₆H₅ |
| 235 | R51 | CH₃ | O | CH₂-cyclo-C₃H₅ | NH₂ |
| 236 | R51 | CH₃ | O | CH₂-cyclo-C₃H₅ | NH(CH₃) |
| 237 | R51 | CH₃ | O | CH₂-cyclo-C₃H₅ | N(CH₃)₂ |
| 238 | R51 | CH₃ | O | CH₂-cyclo-C₃H₅ | NH(C₆H₅) |
| 239 | R51 | CH₃ | O | C₆H₅ | NH—O—H |
| 240 | R51 | CH₃ | O | C₆H₅ | NH—O—CH₃ |
| 241 | R51 | CH₃ | O | C₆H₅ | NH—O—C₆H₅ |
| 242 | R51 | CH₃ | O | C₆H₅ | NH₂ |
| 243 | R51 | CH₃ | O | C₆H₅ | NH(CH₃) |
| 244 | R51 | CH₃ | O | C₆H₅ | N(CH₃)₂ |
| 245 | R51 | CH₃ | O | C₆H₅ | NH(C₆H₅) |
| 246 | R51 | CH₃ | NH | H | NH—O—H |
| 247 | R51 | CH₃ | NH | H | NH—O—CH₃ |
| 248 | R51 | CH₃ | NH | H | NH—O—C₆H₅ |
| 249 | R51 | CH₃ | NH | H | NH₂ |
| 250 | R51 | CH₃ | NH | H | NH(CH₃) |
| 251 | R51 | CH₃ | NH | H | N(CH₃)₂ |
| 252 | R51 | CH₃ | NH | H | NH(C₆H₅) |
| 253 | R51 | CH₃ | NH | CH₃ | NH—O—H |
| 254 | R51 | CH₃ | NH | CH₃ | NH—O—CH₃ |
| 255 | R51 | CH₃ | NH | CH₃ | NH—O—C₆H₅ |
| 256 | R51 | CH₃ | NH | CH₃ | NH₂ |
| 257 | R51 | CH₃ | NH | CH₃ | NH(CH₃) |
| 258 | R51 | CH₃ | NH | CH₃ | N(CH₃)₂ |
| 259 | R51 | CH₃ | NH | CH₃ | NH(C₆H₅) |
| 260 | R51 | CH₃ | NH | C₂H₅ | NH—O—H |
| 261 | R51 | CH₃ | NH | C₂H₅ | NH—O—CH₃ |
| 262 | R51 | CH₃ | NH | C₂H₅ | NH—O—C₆H₅ |
| 263 | R51 | CH₃ | NH | C₂H₅ | NH₂ |
| 264 | R51 | CH₃ | NH | C₂H₅ | NH(CH₃) |
| 265 | R51 | CH₃ | NH | C₂H₅ | N(CH₃)₂ |
| 266 | R51 | CH₃ | NH | C₂H₅ | NH(C₆H₅) |
| 267 | R51 | CH₃ | NH | CH(CH₃)₂ | NH—O—H |
| 268 | R51 | CH₃ | NH | CH(CH₃)₂ | NH—O—CH₃ |
| 269 | R51 | CH₃ | NH | CH(CH₃)₂ | NH—O—C₆H₅ |
| 270 | R51 | CH₃ | NH | CH(CH₃)₂ | NH₂ |
| 271 | R51 | CH₃ | NH | CH(CH₃)₂ | NH(CH₃) |
| 272 | R51 | CH₃ | NH | CH(CH₃)₂ | N(CH₃)₂ |
| 273 | R51 | CH₃ | NH | CH(CH₃)₂ | NH(C₆H₅) |
| 274 | R51 | CH₃ | NH | CH₂CF₃ | NH—O—H |
| 275 | R51 | CH₃ | NH | CH₂CF₃ | NH—O—CH₃ |
| 276 | R51 | CH₃ | NH | CH₂CF₃ | NH—O—C₆H₅ |
| 277 | R51 | CH₃ | NH | CH₂CF₃ | NH₂ |
| 278 | R51 | CH₃ | NH | CH₂CF₃ | NH(CH₃) |
| 279 | R51 | CH₃ | NH | CH₂CF₃ | N(CH₃)₂ |
| 280 | R51 | CH₃ | NH | CH₂CF₃ | NH(C₆H₅) |
| 281 | R51 | CH₃ | NH | CH₂-cyclo-C₃H₅ | NH—O—H |
| 282 | R51 | CH₃ | NH | CH₂-cyclo-C₃H₅ | NH—O—CH₃ |
| 283 | R51 | CH₃ | NH | CH₂-cyclo-C₃H₅ | NH—O—C₆H₅ |
| 284 | R51 | CH₃ | NH | CH₂-cyclo-C₃H₅ | NH₂ |
| 285 | R51 | CH₃ | NH | CH₂-cyclo-C₃H₅ | NH(CH₃) |
| 286 | R51 | CH₃ | NH | CH₂-cyclo-C₃H₅ | N(CH₃)₂ |
| 287 | R51 | CH₃ | NH | CH₂-cyclo-C₃H₅ | NH(C₆H₅) |
| 288 | R51 | CH₃ | NH | C₆H₅ | NH—O—H |
| 289 | R51 | CH₃ | NH | C₆H₅ | NH—O—CH₃ |
| 290 | R51 | CH₃ | NH | C₆H₅ | NH—O—C₆H₅ |
| 291 | R51 | CH₃ | NH | C₆H₅ | NH₂ |
| 292 | R51 | CH₃ | NH | C₆H₅ | NH(CH₃) |
| 293 | R51 | CH₃ | NH | C₆H₅ | N(CH₃)₂ |
| 294 | R51 | CH₃ | NH | C₆H₅ | NH(C₆H₅) |
| 295 | R52 | H | — | H | NH—O—H |
| 296 | R52 | H | — | H | NH—O—CH₃ |
| 297 | R52 | H | — | H | NH—O—C₆H₅ |
| 298 | R52 | H | — | H | NH₂ |
| 299 | R52 | H | — | H | NH(CH₃) |
| 300 | R52 | H | — | H | N(CH₃)₂ |
| 301 | R52 | H | — | H | NH(C₆H₅) |
| 302 | R52 | H | — | CH₃ | NH—O—H |
| 303 | R52 | H | — | CH₃ | NH—O—CH₃ |
| 304 | R52 | H | — | CH₃ | NH—O—C₆H₅ |
| 305 | R52 | H | — | CH₃ | NH₂ |
| 306 | R52 | H | — | CH₃ | NH(CH₃) |
| 307 | R52 | H | — | CH₃ | N(CH₃)₂ |
| 308 | R52 | H | — | CH₃ | NH(C₆H₅) |
| 309 | R52 | H | — | C₂H₅ | NH—O—H |
| 310 | R52 | H | — | C₂H₅ | NH—O—CH₃ |
| 311 | R52 | H | — | C₂H₅ | NH—O—C₆H₅ |
| 312 | R52 | H | — | C₂H₅ | NH₂ |

TABLE 3-continued

Compounds of formula (I-15a)

R51 is 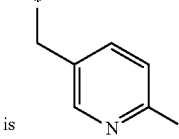

R52 is 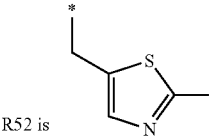

R53 is 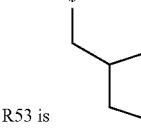

| No. | $R^5$ | $R^q$ | Z | $R^1$ | $R^2$ |
|---|---|---|---|---|---|
| 313 | R52 | H | — | $C_2H_5$ | $NH(CH_3)$ |
| 314 | R52 | H | — | $C_2H_5$ | $N(CH_3)_2$ |
| 315 | R52 | H | — | $C_2H_5$ | $NH(C_6H_5)$ |
| 316 | R52 | H | — | $CH(CH_3)_2$ | NH—O—H |
| 317 | R52 | H | — | $CH(CH_3)_2$ | NH—O—$CH_3$ |
| 318 | R52 | H | — | $CH(CH_3)_2$ | NH—O—$C_6H_5$ |
| 319 | R52 | H | — | $CH(CH_3)_2$ | $NH_2$ |
| 320 | R52 | H | — | $CH(CH_3)_2$ | $NH(CH_3)$ |
| 321 | R52 | H | — | $CH(CH_3)_2$ | $N(CH_3)_2$ |
| 322 | R52 | H | — | $CH(CH_3)_2$ | $NH(C_6H_5)$ |
| 323 | R52 | H | — | $CH_2CF_3$ | NH—O—H |
| 324 | R52 | H | — | $CH_2CF_3$ | NH—O—$CH_3$ |
| 325 | R52 | H | — | $CH_2CF_3$ | NH—O—$C_6H_5$ |
| 326 | R52 | H | — | $CH_2CF_3$ | $NH_2$ |
| 327 | R52 | H | — | $CH_2CF_3$ | $NH(CH_3)$ |
| 328 | R52 | H | — | $CH_2CF_3$ | $N(CH_3)_2$ |
| 329 | R52 | H | — | $CH_2CF_3$ | $NH(C_6H_5)$ |
| 330 | R52 | H | — | $CH_2$-cyclo-$C_3H_5$ | NH—O—H |
| 331 | R52 | H | — | $CH_2$-cyclo-$C_3H_5$ | NH—O—$CH_3$ |
| 332 | R52 | H | — | $CH_2$-cyclo-$C_3H_5$ | NH—O—$C_6H_5$ |
| 333 | R52 | H | — | $CH_2$-cyclo-$C_3H_5$ | $NH_2$ |
| 334 | R52 | H | — | $CH_2$-cyclo-$C_3H_5$ | $NH(CH_3)$ |
| 335 | R52 | H | — | $CH_2$-cyclo-$C_3H_5$ | $N(CH_3)_2$ |
| 336 | R52 | H | — | $CH_2$-cyclo-$C_3H_5$ | $NH(C_6H_5)$ |
| 337 | R52 | H | — | $C_6H_5$ | NH—O—H |
| 338 | R52 | H | — | $C_6H_5$ | NH—O—$CH_3$ |
| 339 | R52 | H | — | $C_6H_5$ | NH—O—$C_6H_5$ |
| 340 | R52 | H | — | $C_6H_5$ | $NH_2$ |
| 341 | R52 | H | — | $C_6H_5$ | $NH(CH_3)$ |
| 342 | R52 | H | — | $C_6H_5$ | $N(CH_3)_2$ |
| 343 | R52 | H | — | $C_6H_5$ | $NH(C_6H_5)$ |
| 344 | R52 | H | O | H | NH—O—H |
| 345 | R52 | H | O | H | NH—O—$CH_3$ |
| 346 | R52 | H | O | H | NH—O—$C_6H_5$ |
| 347 | R52 | H | O | H | $NH_2$ |
| 348 | R52 | H | O | H | $NH(CH_3)$ |
| 349 | R52 | H | O | H | $N(CH_3)_2$ |
| 350 | R52 | H | O | H | $NH(C_6H_5)$ |
| 351 | R52 | H | O | $CH_3$ | NH—O—H |
| 352 | R52 | H | O | $CH_3$ | NH—O—$CH_3$ |
| 353 | R52 | H | O | $CH_3$ | NH—O—$C_6H_5$ |
| 354 | R52 | H | O | $CH_3$ | $NH_2$ |
| 355 | R52 | H | O | $CH_3$ | $NH(CH_3)$ |
| 356 | R52 | H | O | $CH_3$ | $N(CH_3)_2$ |
| 357 | R52 | H | O | $CH_3$ | $NH(C_6H_5)$ |
| 358 | R52 | H | O | $C_2H_5$ | NH—O—H |
| 359 | R52 | H | O | $C_2H_5$ | NH—O—$CH_3$ |
| 360 | R52 | H | O | $C_2H_5$ | NH—O—$C_6H_5$ |
| 361 | R52 | H | O | $C_2H_5$ | $NH_2$ |
| 362 | R52 | H | O | $C_2H_5$ | $NH(CH_3)$ |
| 363 | R52 | H | O | $C_2H_5$ | $N(CH_3)_2$ |
| 364 | R52 | H | O | $C_2H_5$ | $NH(C_6H_5)$ |
| 365 | R52 | H | O | $CH(CH_3)_2$ | NH—O—H |
| 366 | R52 | H | O | $CH(CH_3)_2$ | NH—O—$CH_3$ |
| 367 | R52 | H | O | $CH(CH_3)_2$ | NH—O—$C_6H_5$ |
| 368 | R52 | H | O | $CH(CH_3)_2$ | $NH_2$ |
| 369 | R52 | H | O | $CH(CH_3)_2$ | $NH(CH_3)$ |
| 370 | R52 | H | O | $CH(CH_3)_2$ | $N(CH_3)_2$ |
| 371 | R52 | H | O | $CH(CH_3)_2$ | $NH(C_6H_5)$ |
| 372 | R52 | H | O | $CH_2CF_3$ | NH—O—H |
| 373 | R52 | H | O | $CH_2CF_3$ | NH—O—$CH_3$ |
| 374 | R52 | H | O | $CH_2CF_3$ | NH—O—$C_6H_5$ |
| 375 | R52 | H | O | $CH_2CF_3$ | $NH_2$ |
| 376 | R52 | H | O | $CH_2CF_3$ | $NH(CH_3)$ |
| 377 | R52 | H | O | $CH_2CF_3$ | $N(CH_3)_2$ |
| 378 | R52 | H | O | $CH_2CF_3$ | $NH(C_6H_5)$ |
| 379 | R52 | H | O | $CH_2$-cyclo-$C_3H_5$ | NH—O—H |
| 380 | R52 | H | O | $CH_2$-cyclo-$C_3H_5$ | NH—O—$CH_3$ |
| 381 | R52 | H | O | $CH_2$-cyclo-$C_3H_5$ | NH—O—$C_6H_5$ |
| 382 | R52 | H | O | $CH_2$-cyclo-$C_3H_5$ | $NH_2$ |
| 383 | R52 | H | O | $CH_2$-cyclo-$C_3H_5$ | $NH(CH_3)$ |
| 384 | R52 | H | O | $CH_2$-cyclo-$C_3H_5$ | $N(CH_3)_2$ |
| 385 | R52 | H | O | $CH_2$-cyclo-$C_3H_5$ | $NH(C_6H_5)$ |
| 386 | R52 | H | O | $C_6H_5$ | NH—O—H |
| 387 | R52 | H | O | $C_6H_5$ | NH—O—$CH_3$ |
| 388 | R52 | H | O | $C_6H_5$ | NH—O—$C_6H_5$ |
| 389 | R52 | H | O | $C_6H_5$ | $NH_2$ |
| 390 | R52 | H | O | $C_6H_5$ | $NH(CH_3)$ |
| 391 | R52 | H | O | $C_6H_5$ | $N(CH_3)_2$ |
| 392 | R52 | H | O | $C_6H_5$ | $NH(C_6H_5)$ |
| 393 | R52 | H | NH | H | NH—O—H |
| 394 | R52 | H | NH | H | NH—O—$CH_3$ |
| 395 | R52 | H | NH | H | NH—O—$C_6H_5$ |
| 396 | R52 | H | NH | H | $NH_2$ |
| 397 | R52 | H | NH | H | $NH(CH_3)$ |
| 398 | R52 | H | NH | H | $N(CH_3)_2$ |
| 399 | R52 | H | NH | H | $NH(C_6H_5)$ |
| 400 | R52 | H | NH | $CH_3$ | NH—O—H |
| 401 | R52 | H | NH | $CH_3$ | NH—O—$CH_3$ |
| 402 | R52 | H | NH | $CH_3$ | NH—O—$C_6H_5$ |
| 403 | R52 | H | NH | $CH_3$ | $NH_2$ |
| 404 | R52 | H | NH | $CH_3$ | $NH(CH_3)$ |
| 405 | R52 | H | NH | $CH_3$ | $N(CH_3)_2$ |
| 406 | R52 | H | NH | $CH_3$ | $NH(C_6H_5)$ |
| 407 | R52 | H | NH | $C_2H_5$ | NH—O—H |
| 408 | R52 | H | NH | $C_2H_5$ | NH—O—$CH_3$ |
| 409 | R52 | H | NH | $C_2H_5$ | NH—O—$C_6H_5$ |
| 410 | R52 | H | NH | $C_2H_5$ | $NH_2$ |
| 411 | R52 | H | NH | $C_2H_5$ | $NH(CH_3)$ |
| 412 | R52 | H | NH | $C_2H_5$ | $N(CH_3)_2$ |
| 413 | R52 | H | NH | $C_2H_5$ | $NH(C_6H_5)$ |
| 414 | R52 | H | NH | $CH(CH_3)_2$ | NH—O—H |
| 415 | R52 | H | NH | $CH(CH_3)_2$ | NH—O—$CH_3$ |
| 416 | R52 | H | NH | $CH(CH_3)_2$ | NH—O—$C_6H_5$ |

TABLE 3-continued

Compounds of formula (I-15a)

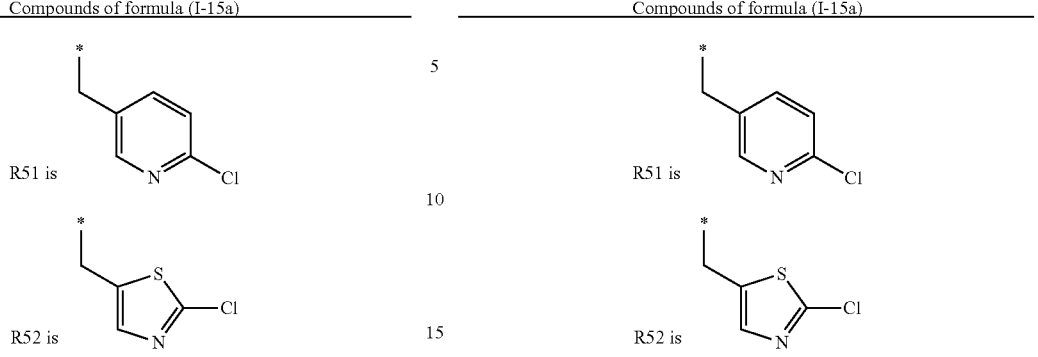

R51 is (5-methyl-2-chloropyridine)

R52 is (5-methyl-2-chlorothiazole)

R53 is (3-methyltetrahydrofuran)

| No. | R⁵ | R^q | Z | R¹ | R² |
|---|---|---|---|---|---|
| 417 | R52 | H | NH | CH(CH₃)₂ | NH₂ |
| 418 | R52 | H | NH | CH(CH₃)₂ | NH(CH₃) |
| 419 | R52 | H | NH | CH(CH₃)₂ | N(CH₃)₂ |
| 420 | R52 | H | NH | CH(CH₃)₂ | NH(C₆H₅) |
| 421 | R52 | H | NH | CH₂CF₃ | NH—O—H |
| 422 | R52 | H | NH | CH₂CF₃ | NH—O—CH₃ |
| 423 | R52 | H | NH | CH₂CF₃ | NH—O—C₆H₅ |
| 424 | R52 | H | NH | CH₂CF₃ | NH₂ |
| 425 | R52 | H | NH | CH₂CF₃ | NH(CH₃) |
| 426 | R52 | H | NH | CH₂CF₃ | N(CH₃)₂ |
| 427 | R52 | H | NH | CH₂CF₃ | NH(C₆H₅) |
| 428 | R52 | H | NH | CH₂-cyclo-C₃H₅ | NH—O—H |
| 429 | R52 | H | NH | CH₂-cyclo-C₃H₅ | NH—O—CH₃ |
| 430 | R52 | H | NH | CH₂-cyclo-C₃H₅ | NH—O—C₆H₅ |
| 431 | R52 | H | NH | CH₂-cyclo-C₃H₅ | NH₂ |
| 432 | R52 | H | NH | CH₂-cyclo-C₃H₅ | NH(CH₃) |
| 433 | R52 | H | NH | CH₂-cyclo-C₃H₅ | N(CH₃)₂ |
| 434 | R52 | H | NH | CH₂-cyclo-C₃H₅ | NH(C₆H₅) |
| 435 | R52 | H | NH | C₆H₅ | NH—O—H |
| 436 | R52 | H | NH | C₆H₅ | NH—O—CH₃ |
| 437 | R52 | H | NH | C₆H₅ | NH—O—C₆H₅ |
| 438 | R52 | H | NH | C₆H₅ | NH₂ |
| 439 | R52 | H | NH | C₆H₅ | NH(CH₃) |
| 440 | R52 | H | NH | C₆H₅ | N(CH₃)₂ |
| 441 | R52 | H | NH | C₆H₅ | NH(C₆H₅) |
| 442 | R52 | CH₃ | — | H | NH—O—H |
| 443 | R52 | CH₃ | — | H | NH—O—CH₃ |
| 444 | R52 | CH₃ | — | H | NH—O—C₆H₅ |
| 445 | R52 | CH₃ | — | H | NH₂ |
| 446 | R52 | CH₃ | — | H | NH(CH₃) |
| 447 | R52 | CH₃ | — | H | N(CH₃)₂ |
| 448 | R52 | CH₃ | — | H | NH(C₆H₅) |
| 449 | R52 | CH₃ | — | CH₃ | NH—O—H |
| 450 | R52 | CH₃ | — | CH₃ | NH—O—CH₃ |
| 451 | R52 | CH₃ | — | CH₃ | NH—O—C₆H₅ |
| 452 | R52 | CH₃ | — | CH₃ | NH₂ |
| 453 | R52 | CH₃ | — | CH₃ | NH(CH₃) |
| 454 | R52 | CH₃ | — | CH₃ | N(CH₃)₂ |
| 455 | R52 | CH₃ | — | CH₃ | NH(C₆H₅) |
| 456 | R52 | CH₃ | — | C₂H₅ | NH—O—H |
| 457 | R52 | CH₃ | — | C₂H₅ | NH—O—CH₃ |
| 458 | R52 | CH₃ | — | C₂H₅ | NH—O—C₆H₅ |
| 459 | R52 | CH₃ | — | C₂H₅ | NH₂ |
| 460 | R52 | CH₃ | — | C₂H₅ | NH(CH₃) |
| 461 | R52 | CH₃ | — | C₂H₅ | N(CH₃)₂ |
| 462 | R52 | CH₃ | — | C₂H₅ | NH(C₆H₅) |
| 463 | R52 | CH₃ | — | CH(CH₃)₂ | NH—O—H |
| 464 | R52 | CH₃ | — | CH(CH₃)₂ | NH—O—CH₃ |
| 465 | R52 | CH₃ | — | CH(CH₃)₂ | NH—O—C₆H₅ |
| 466 | R52 | CH₃ | — | CH(CH₃)₂ | NH₂ |
| 467 | R52 | CH₃ | — | CH(CH₃)₂ | NH(CH₃) |
| 468 | R52 | CH₃ | — | CH(CH₃)₂ | N(CH₃)₂ |
| 469 | R52 | CH₃ | — | CH(CH₃)₂ | NH(C₆H₅) |
| 470 | R52 | CH₃ | — | CH₂CF₃ | NH—O—H |
| 471 | R52 | CH₃ | — | CH₂CF₃ | NH—O—CH₃ |
| 472 | R52 | CH₃ | — | CH₂CF₃ | NH—O—C₆H₅ |
| 473 | R52 | CH₃ | — | CH₂CF₃ | NH₂ |
| 474 | R52 | CH₃ | — | CH₂CF₃ | NH(CH₃) |
| 475 | R52 | CH₃ | — | CH₂CF₃ | N(CH₃)₂ |
| 476 | R52 | CH₃ | — | CH₂CF₃ | NH(C₆H₅) |
| 477 | R52 | CH₃ | — | CH₂-cyclo-C₃H₅ | NH—O—H |
| 478 | R52 | CH₃ | — | CH₂-cyclo-C₃H₅ | NH—O—CH₃ |
| 479 | R52 | CH₃ | — | CH₂-cyclo-C₃H₅ | NH—O—C₆H₅ |
| 480 | R52 | CH₃ | — | CH₂-cyclo-C₃H₅ | NH₂ |
| 481 | R52 | CH₃ | — | CH₂-cyclo-C₃H₅ | NH(CH₃) |
| 482 | R52 | CH₃ | — | CH₂-cyclo-C₃H₅ | N(CH₃)₂ |
| 483 | R52 | CH₃ | — | CH₂-cyclo-C₃H₅ | NH(C₆H₅) |
| 484 | R52 | CH₃ | — | C₆H₅ | NH—O—H |
| 485 | R52 | CH₃ | — | C₆H₅ | NH—O—CH₃ |
| 486 | R52 | CH₃ | — | C₆H₅ | NH—O—C₆H₅ |
| 487 | R52 | CH₃ | — | C₆H₅ | NH₂ |
| 488 | R52 | CH₃ | — | C₆H₅ | NH(CH₃) |
| 489 | R52 | CH₃ | — | C₆H₅ | N(CH₃)₂ |
| 490 | R52 | CH₃ | — | C₆H₅ | NH(C₆H₅) |
| 491 | R52 | CH₃ | O | H | NH—O—H |
| 492 | R52 | CH₃ | O | H | NH—O—CH₃ |
| 493 | R52 | CH₃ | O | H | NH—O—C₆H₅ |
| 494 | R52 | CH₃ | O | H | NH₂ |
| 495 | R52 | CH₃ | O | H | NH(CH₃) |
| 496 | R52 | CH₃ | O | H | N(CH₃)₂ |
| 497 | R52 | CH₃ | O | H | NH(C₆H₅) |
| 498 | R52 | CH₃ | O | CH₃ | NH—O—H |
| 499 | R52 | CH₃ | O | CH₃ | NH—O—CH₃ |
| 500 | R52 | CH₃ | O | CH₃ | NH—O—C₆H₅ |
| 501 | R52 | CH₃ | O | CH₃ | NH₂ |
| 502 | R52 | CH₃ | O | CH₃ | NH(CH₃) |
| 503 | R52 | CH₃ | O | CH₃ | N(CH₃)₂ |
| 504 | R52 | CH₃ | O | CH₃ | NH(C₆H₅) |
| 505 | R52 | CH₃ | O | C₂H₅ | NH—O—H |
| 506 | R52 | CH₃ | O | C₂H₅ | NH—O—CH₃ |
| 507 | R52 | CH₃ | O | C₂H₅ | NH—O—C₆H₅ |
| 508 | R52 | CH₃ | O | C₂H₅ | NH₂ |
| 509 | R52 | CH₃ | O | C₂H₅ | NH(CH₃) |
| 510 | R52 | CH₃ | O | C₂H₅ | N(CH₃)₂ |
| 511 | R52 | CH₃ | O | C₂H₅ | NH(C₆H₅) |
| 512 | R52 | CH₃ | O | CH(CH₃)₂ | NH—O—H |
| 513 | R52 | CH₃ | O | CH(CH₃)₂ | NH—O—CH₃ |
| 514 | R52 | CH₃ | O | CH(CH₃)₂ | NH—O—C₆H₅ |
| 515 | R52 | CH₃ | O | CH(CH₃)₂ | NH₂ |
| 516 | R52 | CH₃ | O | CH(CH₃)₂ | NH(CH₃) |
| 517 | R52 | CH₃ | O | CH(CH₃)₂ | N(CH₃)₂ |
| 518 | R52 | CH₃ | O | CH(CH₃)₂ | NH(C₆H₅) |
| 519 | R52 | CH₃ | O | CH₂CF₃ | NH—O—H |
| 520 | R52 | CH₃ | O | CH₂CF₃ | NH—O—CH₃ |

TABLE 3-continued

Compounds of formula (I-15a)

R51 is 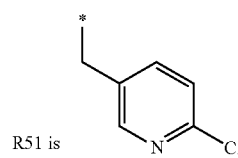

R52 is 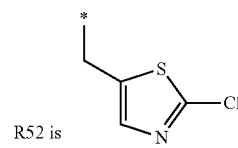

R53 is 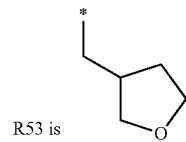

R51 is 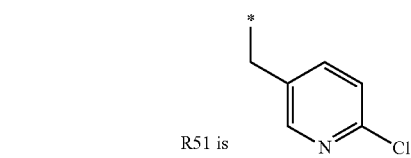

R52 is 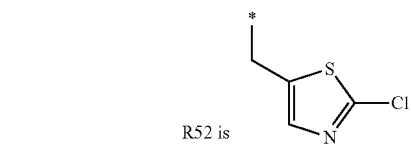

R53 is 

| No. | $R^5$ | $R^q$ | Z | $R^1$ | $R^2$ |
|---|---|---|---|---|---|
| 521 | R52 | $CH_3$ | O | $CH_2CF_3$ | $NH-O-C_6H_5$ |
| 522 | R52 | $CH_3$ | O | $CH_2CF_3$ | $NH_2$ |
| 523 | R52 | $CH_3$ | O | $CH_2CF_3$ | $NH(CH_3)$ |
| 524 | R52 | $CH_3$ | O | $CH_2CF_3$ | $N(CH_3)_2$ |
| 525 | R52 | $CH_3$ | O | $CH_2CF_3$ | $NH(C_6H_5)$ |
| 526 | R52 | $CH_3$ | O | $CH_2$-cyclo-$C_3H_5$ | $NH-O-H$ |
| 527 | R52 | $CH_3$ | O | $CH_2$-cyclo-$C_3H_5$ | $NH-O-CH_3$ |
| 528 | R52 | $CH_3$ | O | $CH_2$-cyclo-$C_3H_5$ | $NH-O-C_6H_5$ |
| 529 | R52 | $CH_3$ | O | $CH_2$-cyclo-$C_3H_5$ | $NH_2$ |
| 530 | R52 | $CH_3$ | O | $CH_2$-cyclo-$C_3H_5$ | $NH(CH_3)$ |
| 531 | R52 | $CH_3$ | O | $CH_2$-cyclo-$C_3H_5$ | $N(CH_3)_2$ |
| 532 | R52 | $CH_3$ | O | $CH_2$-cyclo-$C_3H_5$ | $NH(C_6H_5)$ |
| 533 | R52 | $CH_3$ | O | $C_6H_5$ | $NH-O-H$ |
| 534 | R52 | $CH_3$ | O | $C_6H_5$ | $NH-O-CH_3$ |
| 535 | R52 | $CH_3$ | O | $C_6H_5$ | $NH-O-C_6H_5$ |
| 536 | R52 | $CH_3$ | O | $C_6H_5$ | $NH_2$ |
| 537 | R52 | $CH_3$ | O | $C_6H_5$ | $NH(CH_3)$ |
| 538 | R52 | $CH_3$ | O | $C_6H_5$ | $N(CH_3)_2$ |
| 539 | R52 | $CH_3$ | O | $C_6H_5$ | $NH(C_6H_5)$ |
| 540 | R52 | $CH_3$ | NH | H | $NH-O-H$ |
| 541 | R52 | $CH_3$ | NH | H | $NH-O-CH_3$ |
| 542 | R52 | $CH_3$ | NH | H | $NH-O-C_6H_5$ |
| 543 | R52 | $CH_3$ | NH | H | $NH_2$ |
| 544 | R52 | $CH_3$ | NH | H | $NH(CH_3)$ |
| 545 | R52 | $CH_3$ | NH | H | $N(CH_3)_2$ |
| 546 | R52 | $CH_3$ | NH | H | $NH(C_6H_5)$ |
| 547 | R52 | $CH_3$ | NH | $CH_3$ | $NH-O-H$ |
| 548 | R52 | $CH_3$ | NH | $CH_3$ | $NH-O-CH_3$ |
| 549 | R52 | $CH_3$ | NH | $CH_3$ | $NH-O-C_6H_5$ |
| 550 | R52 | $CH_3$ | NH | $CH_3$ | $NH_2$ |
| 551 | R52 | $CH_3$ | NH | $CH_3$ | $NH(CH_3)$ |
| 552 | R52 | $CH_3$ | NH | $CH_3$ | $N(CH_3)_2$ |
| 553 | R52 | $CH_3$ | NH | $CH_3$ | $NH(C_6H_5)$ |
| 554 | R52 | $CH_3$ | NH | $C_2H_5$ | $NH-O-H$ |
| 555 | R52 | $CH_3$ | NH | $C_2H_5$ | $NH-O-CH_3$ |
| 556 | R52 | $CH_3$ | NH | $C_2H_5$ | $NH-O-C_6H_5$ |
| 557 | R52 | $CH_3$ | NH | $C_2H_5$ | $NH_2$ |
| 558 | R52 | $CH_3$ | NH | $C_2H_5$ | $NH(CH_3)$ |
| 559 | R52 | $CH_3$ | NH | $C_2H_5$ | $N(CH_3)_2$ |
| 560 | R52 | $CH_3$ | NH | $C_2H_5$ | $NH(C_6H_5)$ |
| 561 | R52 | $CH_3$ | NH | $CH(CH_3)_2$ | $NH-O-H$ |
| 562 | R52 | $CH_3$ | NH | $CH(CH_3)_2$ | $NH-O-CH_3$ |
| 563 | R52 | $CH_3$ | NH | $CH(CH_3)_2$ | $NH-O-C_6H_5$ |
| 564 | R52 | $CH_3$ | NH | $CH(CH_3)_2$ | $NH_2$ |
| 565 | R52 | $CH_3$ | NH | $CH(CH_3)_2$ | $NH(CH_3)$ |
| 566 | R52 | $CH_3$ | NH | $CH(CH_3)_2$ | $N(CH_3)_2$ |
| 567 | R52 | $CH_3$ | NH | $CH(CH_3)_2$ | $NH(C_6H_5)$ |
| 568 | R52 | $CH_3$ | NH | $CH_2CF_3$ | $NH-O-H$ |
| 569 | R52 | $CH_3$ | NH | $CH_2CF_3$ | $NH-O-CH_3$ |
| 570 | R52 | $CH_3$ | NH | $CH_2CF_3$ | $NH-O-C_6H_5$ |
| 571 | R52 | $CH_3$ | NH | $CH_2CF_3$ | $NH_2$ |
| 572 | R52 | $CH_3$ | NH | $CH_2CF_3$ | $NH(CH_3)$ |
| 573 | R52 | $CH_3$ | NH | $CH_2CF_3$ | $N(CH_3)_2$ |
| 574 | R52 | $CH_3$ | NH | $CH_2CF_3$ | $NH(C_6H_5)$ |
| 575 | R52 | $CH_3$ | NH | $CH_2$-cyclo-$C_3H_5$ | $NH-O-H$ |
| 576 | R52 | $CH_3$ | NH | $CH_2$-cyclo-$C_3H_5$ | $NH-O-CH_3$ |
| 577 | R52 | $CH_3$ | NH | $CH_2$-cyclo-$C_3H_5$ | $NH-O-C_6H_5$ |
| 589 | R52 | $CH_3$ | NH | $CH_2$-cyclo-$C_3H_5$ | $NH_2$ |
| 579 | R52 | $CH_3$ | NH | $CH_2$-cyclo-$C_3H_5$ | $NH(CH_3)$ |
| 580 | R52 | $CH_3$ | NH | $CH_2$-cyclo-$C_3H_5$ | $N(CH_3)_2$ |
| 581 | R52 | $CH_3$ | NH | $CH_2$-cyclo-$C_3H_5$ | $NH(C_6H_5)$ |
| 582 | R52 | $CH_3$ | NH | $C_6H_5$ | $NH-O-H$ |
| 583 | R52 | $CH_3$ | NH | $C_6H_5$ | $NH-O-CH_3$ |
| 584 | R52 | $CH_3$ | NH | $C_6H_5$ | $NH-O-C_6H_5$ |
| 585 | R52 | $CH_3$ | NH | $C_6H_5$ | $NH_2$ |
| 586 | R52 | $CH_3$ | NH | $C_6H_5$ | $NH(CH_3)$ |
| 587 | R52 | $CH_3$ | NH | $C_6H_5$ | $N(CH_3)_2$ |
| 588 | R52 | $CH_3$ | NH | $C_6H_5$ | $NH(C_6H_5)$ |
| 589 | R53 | H | — | H | $NH-O-H$ |
| 590 | R53 | H | — | H | $NH-O-CH_3$ |
| 591 | R53 | H | — | H | $NH-O-C_6H_5$ |
| 592 | R53 | H | — | H | $NH_2$ |
| 593 | R53 | H | — | H | $NH(CH_3)$ |
| 594 | R53 | H | — | H | $N(CH_3)_2$ |
| 595 | R53 | H | — | H | $NH(C_6H_5)$ |
| 596 | R53 | H | — | $CH_3$ | $NH-O-H$ |
| 597 | R53 | H | — | $CH_3$ | $NH-O-CH_3$ |
| 598 | R53 | H | — | $CH_3$ | $NH-O-C_6H_5$ |
| 599 | R53 | H | — | $CH_3$ | $NH_2$ |
| 600 | R53 | H | — | $CH_3$ | $NH(CH_3)$ |
| 601 | R53 | H | — | $CH_3$ | $N(CH_3)_2$ |
| 602 | R53 | H | — | $CH_3$ | $NH(C_6H_5)$ |
| 603 | R53 | H | — | $C_2H_5$ | $NH-O-H$ |
| 604 | R53 | H | — | $C_2H_5$ | $NH-O-CH_3$ |
| 605 | R53 | H | — | $C_2H_5$ | $NH-O-C_6H_5$ |
| 606 | R53 | H | — | $C_2H_5$ | $NH_2$ |
| 607 | R53 | H | — | $C_2H_5$ | $NH(CH_3)$ |
| 608 | R53 | H | — | $C_2H_5$ | $N(CH_3)_2$ |
| 609 | R53 | H | — | $C_2H_5$ | $NH(C_6H_5)$ |
| 610 | R53 | H | — | $CH(CH_3)_2$ | $NH-O-H$ |
| 611 | R53 | H | — | $CH(CH_3)_2$ | $NH-O-CH_3$ |
| 612 | R53 | H | — | $CH(CH_3)_2$ | $NH-O-C_6H_5$ |
| 613 | R53 | H | — | $CH(CH_3)_2$ | $NH_2$ |
| 614 | R53 | H | — | $CH(CH_3)_2$ | $NH(CH_3)$ |
| 615 | R53 | H | — | $CH(CH_3)_2$ | $N(CH_3)_2$ |
| 616 | R53 | H | — | $CH(CH_3)_2$ | $NH(C_6H_5)$ |
| 617 | R53 | H | — | $CH_2CF_3$ | $NH-O-H$ |
| 618 | R53 | H | — | $CH_2CF_3$ | $NH-O-CH_3$ |
| 619 | R53 | H | — | $CH_2CF_3$ | $NH-O-C_6H_5$ |
| 620 | R53 | H | — | $CH_2CF_3$ | $NH_2$ |
| 621 | R53 | H | — | $CH_2CF_3$ | $NH(CH_3)$ |
| 622 | R53 | H | — | $CH_2CF_3$ | $N(CH_3)_2$ |
| 623 | R53 | H | — | $CH_2CF_3$ | $NH(C_6H_5)$ |
| 624 | R53 | H | — | $CH_2$-cyclo-$C_3H_5$ | $NH-O-H$ |

TABLE 3-continued

Compounds of formula (I-15a)

R51 is 5-methylene-2-chloropyridine

R52 is 5-methylene-2-chlorothiazole

R53 is 3-methylene-tetrahydrofuran

| No. | R⁵ | Rq | Z | R¹ | R² |
|---|---|---|---|---|---|
| 625 | R53 | H | — | CH₂-cyclo-C₃H₅ | NH—O—CH₃ |
| 626 | R53 | H | — | CH₂-cyclo-C₃H₅ | NH—O—C₆H₅ |
| 627 | R53 | H | — | CH₂-cyclo-C₃H₅ | NH₂ |
| 628 | R53 | H | — | CH₂-cyclo-C₃H₅ | NH(CH₃) |
| 629 | R53 | H | — | CH₂-cyclo-C₃H₅ | N(CH₃)₂ |
| 630 | R53 | H | — | CH₂-cyclo-C₃H₅ | NH(C₆H₅) |
| 631 | R53 | H | — | C₆H₅ | NH—O—H |
| 632 | R53 | H | — | C₆H₅ | NH—O—CH₃ |
| 633 | R53 | H | — | C₆H₅ | NH—O—C₆H₅ |
| 634 | R53 | H | — | C₆H₅ | NH₂ |
| 635 | R53 | H | — | C₆H₅ | NH(CH₃) |
| 636 | R53 | H | — | C₆H₅ | N(CH₃)₂ |
| 637 | R53 | H | — | C₆H₅ | NH(C₆H₅) |
| 638 | R53 | H | O | H | NH—O—H |
| 639 | R53 | H | O | H | NH—O—CH₃ |
| 640 | R53 | H | O | H | NH—O—C₆H₅ |
| 641 | R53 | H | O | H | NH₂ |
| 642 | R53 | H | O | H | NH(CH₃) |
| 643 | R53 | H | O | H | N(CH₃)₂ |
| 644 | R53 | H | O | H | NH(C₆H₅) |
| 645 | R53 | H | O | CH₃ | NH—O—H |
| 646 | R53 | H | O | CH₃ | NH—O—CH₃ |
| 647 | R53 | H | O | CH₃ | NH—O—C₆H₅ |
| 648 | R53 | H | O | CH₃ | NH₂ |
| 649 | R53 | H | O | CH₃ | NH(CH₃) |
| 650 | R53 | H | O | CH₃ | N(CH₃)₂ |
| 651 | R53 | H | O | CH₃ | NH(C₆H₅) |
| 652 | R53 | H | O | C₂H₅ | NH—O—H |
| 653 | R53 | H | O | C₂H₅ | NH—O—CH₃ |
| 654 | R53 | H | O | C₂H₅ | NH—O—C₆H₅ |
| 655 | R53 | H | O | C₂H₅ | NH₂ |
| 656 | R53 | H | O | C₂H₅ | NH(CH₃) |
| 657 | R53 | H | O | C₂H₅ | N(CH₃)₂ |
| 658 | R53 | H | O | C₂H₅ | NH(C₆H₅) |
| 659 | R53 | H | O | CH(CH₃)₂ | NH—O—H |
| 660 | R53 | H | O | CH(CH₃)₂ | NH—O—CH₃ |
| 661 | R53 | H | O | CH(CH₃)₂ | NH—O—C₆H₅ |
| 662 | R53 | H | O | CH(CH₃)₂ | NH₂ |
| 663 | R53 | H | O | CH(CH₃)₂ | NH(CH₃) |
| 664 | R53 | H | O | CH(CH₃)₂ | N(CH₃)₂ |
| 665 | R53 | H | O | CH(CH₃)₂ | NH(C₆H₅) |
| 666 | R53 | H | O | CH₂CF₃ | NH—O—H |
| 667 | R53 | H | O | CH₂CF₃ | NH—O—CH₃ |
| 668 | R53 | H | O | CH₂CF₃ | NH—O—C₆H₅ |
| 669 | R53 | H | O | CH₂CF₃ | NH₂ |
| 670 | R53 | H | O | CH₂CF₃ | NH(CH₃) |
| 671 | R53 | H | O | CH₂CF₃ | N(CH₃)₂ |
| 672 | R53 | H | O | CH₂CF₃ | NH(C₆H₅) |
| 673 | R53 | H | O | CH₂-cyclo-C₃H₅ | NH—O—H |
| 674 | R53 | H | O | CH₂-cyclo-C₃H₅ | NH—O—CH₃ |
| 675 | R53 | H | O | CH₂-cyclo-C₃H₅ | NH—O—C₆H₅ |
| 676 | R53 | H | O | CH₂-cyclo-C₃H₅ | NH₂ |
| 677 | R53 | H | O | CH₂-cyclo-C₃H₅ | NH(CH₃) |
| 678 | R53 | H | O | CH₂-cyclo-C₃H₅ | N(CH₃)₂ |
| 679 | R53 | H | O | CH₂-cyclo-C₃H₅ | NH(C₆H₅) |
| 680 | R53 | H | O | C₆H₅ | NH—O—H |
| 681 | R53 | H | O | C₆H₅ | NH—O—CH₃ |
| 682 | R53 | H | O | C₆H₅ | NH—O—C₆H₅ |
| 683 | R53 | H | O | C₆H₅ | NH₂ |
| 684 | R53 | H | O | C₆H₅ | NH(CH₃) |
| 685 | R53 | H | O | C₆H₅ | N(CH₃)₂ |
| 686 | R53 | H | O | C₆H₅ | NH(C₆H₅) |
| 687 | R53 | H | NH | H | NH—O—H |
| 688 | R53 | H | NH | H | NH—O—CH₃ |
| 689 | R53 | H | NH | H | NH—O—C₆H₅ |
| 690 | R53 | H | NH | H | NH₂ |
| 691 | R53 | H | NH | H | NH(CH₃) |
| 692 | R53 | H | NH | H | N(CH₃)₂ |
| 693 | R53 | H | NH | H | NH(C₆H₅) |
| 694 | R53 | H | NH | CH₃ | NH—O—H |
| 695 | R53 | H | NH | CH₃ | NH—O—CH₃ |
| 696 | R53 | H | NH | CH₃ | NH—O—C₆H₅ |
| 697 | R53 | H | NH | CH₃ | NH₂ |
| 698 | R53 | H | NH | CH₃ | NH(CH₃) |
| 699 | R53 | H | NH | CH₃ | N(CH₃)₂ |
| 700 | R53 | H | NH | CH₃ | NH(C₆H₅) |
| 701 | R53 | H | NH | C₂H₅ | NH—O—H |
| 702 | R53 | H | NH | C₂H₅ | NH—O—CH₃ |
| 703 | R53 | H | NH | C₂H₅ | NH—O—C₆H₅ |
| 704 | R53 | H | NH | C₂H₅ | NH₂ |
| 705 | R53 | H | NH | C₂H₅ | NH(CH₃) |
| 706 | R53 | H | NH | C₂H₅ | N(CH₃)₂ |
| 707 | R53 | H | NH | C₂H₅ | NH(C₆H₅) |
| 708 | R53 | H | NH | CH(CH₃)₂ | NH—O—H |
| 709 | R53 | H | NH | CH(CH₃)₂ | NH—O—CH₃ |
| 710 | R53 | H | NH | CH(CH₃)₂ | NH—O—C₆H₅ |
| 711 | R53 | H | NH | CH(CH₃)₂ | NH₂ |
| 712 | R53 | H | NH | CH(CH₃)₂ | NH(CH₃) |
| 713 | R53 | H | NH | CH(CH₃)₂ | N(CH₃)₂ |
| 714 | R53 | H | NH | CH(CH₃)₂ | NH(C₆H₅) |
| 715 | R53 | H | NH | CH₂CF₃ | NH—O—H |
| 716 | R53 | H | NH | CH₂CF₃ | NH—O—CH₃ |
| 717 | R53 | H | NH | CH₂CF₃ | NH—O—C₆H₅ |
| 718 | R53 | H | NH | CH₂CF₃ | NH₂ |
| 719 | R53 | H | NH | CH₂CF₃ | NH(CH₃) |
| 720 | R53 | H | NH | CH₂CF₃ | N(CH₃)₂ |
| 721 | R53 | H | NH | CH₂CF₃ | NH(C₆H₅) |
| 722 | R53 | H | NH | CH₂-cyclo-C₃H₅ | NH—O—H |
| 723 | R53 | H | NH | CH₂-cyclo-C₃H₅ | NH—O—CH₃ |
| 724 | R53 | H | NH | CH₂-cyclo-C₃H₅ | NH—O—C₆H₅ |
| 725 | R53 | H | NH | CH₂-cyclo-C₃H₅ | NH₂ |
| 726 | R53 | H | NH | CH₂-cyclo-C₃H₅ | NH(CH₃) |
| 727 | R53 | H | NH | CH₂-cyclo-C₃H₅ | N(CH₃)₂ |
| 728 | R53 | H | NH | CH₂-cyclo-C₃H₅ | NH(C₆H₅) |

TABLE 3-continued

Compounds of formula (I-15a)

R51 is 5-methyl-2-chloropyridine (*-CH2- attached to pyridine with Cl at 2-position)

R52 is 5-methyl-2-chlorothiazole (*-CH2- attached to thiazole with Cl at 2-position)

R53 is *-CH2-(tetrahydrofuran-3-yl)

| No. | $R^5$ | $R^q$ | Z | $R^1$ | $R^2$ |
|---|---|---|---|---|---|
| 729 | R53 | H | NH | $C_6H_5$ | NH—O—H |
| 730 | R53 | H | NH | $C_6H_5$ | NH—O—$CH_3$ |
| 731 | R53 | H | NH | $C_6H_5$ | NH—O—$C_6H_5$ |
| 732 | R53 | H | NH | $C_6H_5$ | $NH_2$ |
| 733 | R53 | H | NH | $C_6H_5$ | $NH(CH_3)$ |
| 734 | R53 | H | NH | $C_6H_5$ | $N(CH_3)_2$ |
| 735 | R53 | H | NH | $C_6H_5$ | $NH(C_6H_5)$ |
| 736 | R53 | $CH_3$ | — | H | NH—O—H |
| 737 | R53 | $CH_3$ | — | H | NH—O—$CH_3$ |
| 738 | R53 | $CH_3$ | — | H | NH—O—$C_6H_5$ |
| 739 | R53 | $CH_3$ | — | H | $NH_2$ |
| 740 | R53 | $CH_3$ | — | H | $NH(CH_3)$ |
| 741 | R53 | $CH_3$ | — | H | $N(CH_3)_2$ |
| 742 | R53 | $CH_3$ | — | H | $NH(C_6H_5)$ |
| 743 | R53 | $CH_3$ | — | $CH_3$ | NH—O—H |
| 744 | R53 | $CH_3$ | — | $CH_3$ | NH—O—$CH_3$ |
| 745 | R53 | $CH_3$ | — | $CH_3$ | NH—O—$C_6H_5$ |
| 746 | R53 | $CH_3$ | — | $CH_3$ | $NH_2$ |
| 747 | R53 | $CH_3$ | — | $CH_3$ | $NH(CH_3)$ |
| 748 | R53 | $CH_3$ | — | $CH_3$ | $N(CH_3)_2$ |
| 749 | R53 | $CH_3$ | — | $CH_3$ | $NH(C_6H_5)$ |
| 750 | R53 | $CH_3$ | — | $C_2H_5$ | NH—O—H |
| 751 | R53 | $CH_3$ | — | $C_2H_5$ | NH—O—$CH_3$ |
| 752 | R53 | $CH_3$ | — | $C_2H_5$ | NH—O—$C_6H_5$ |
| 753 | R53 | $CH_3$ | — | $C_2H_5$ | $NH_2$ |
| 754 | R53 | $CH_3$ | — | $C_2H_5$ | $NH(CH_3)$ |
| 755 | R53 | $CH_3$ | — | $C_2H_5$ | $N(CH_3)_2$ |
| 756 | R53 | $CH_3$ | — | $C_2H_5$ | $NH(C_6H_5)$ |
| 757 | R53 | $CH_3$ | — | $CH(CH_3)_2$ | NH—O—H |
| 758 | R53 | $CH_3$ | — | $CH(CH_3)_2$ | NH—O—$CH_3$ |
| 759 | R53 | $CH_3$ | — | $CH(CH_3)_2$ | NH—O—$C_6H_5$ |
| 760 | R53 | $CH_3$ | — | $CH(CH_3)_2$ | $NH_2$ |
| 761 | R53 | $CH_3$ | — | $CH(CH_3)_2$ | $NH(CH_3)$ |
| 762 | R53 | $CH_3$ | — | $CH(CH_3)_2$ | $N(CH_3)_2$ |
| 763 | R53 | $CH_3$ | — | $CH(CH_3)_2$ | $NH(C_6H_5)$ |
| 764 | R53 | $CH_3$ | — | $CH_2CF_3$ | NH—O—H |
| 765 | R53 | $CH_3$ | — | $CH_2CF_3$ | NH—O—$CH_3$ |
| 766 | R53 | $CH_3$ | — | $CH_2CF_3$ | NH—O—$C_6H_5$ |
| 767 | R53 | $CH_3$ | — | $CH_2CF_3$ | $NH_2$ |
| 768 | R53 | $CH_3$ | — | $CH_2CF_3$ | $NH(CH_3)$ |
| 769 | R53 | $CH_3$ | — | $CH_2CF_3$ | $N(CH_3)_2$ |
| 770 | R53 | $CH_3$ | — | $CH_2CF_3$ | $NH(C_6H_5)$ |
| 771 | R53 | $CH_3$ | — | $CH_2$-cyclo-$C_3H_5$ | NH—O—H |
| 772 | R53 | $CH_3$ | — | $CH_2$-cyclo-$C_3H_5$ | NH—O—$CH_3$ |
| 773 | R53 | $CH_3$ | — | $CH_2$-cyclo-$C_3H_5$ | NH—O—$C_6H_5$ |
| 774 | R53 | $CH_3$ | — | $CH_2$-cyclo-$C_3H_5$ | $NH_2$ |
| 775 | R53 | $CH_3$ | — | $CH_2$-cyclo-$C_3H_5$ | $NH(CH_3)$ |
| 776 | R53 | $CH_3$ | — | $CH_2$-cyclo-$C_3H_5$ | $N(CH_3)_2$ |
| 777 | R53 | $CH_3$ | — | $CH_2$-cyclo-$C_3H_5$ | $NH(C_6H_5)$ |
| 778 | R53 | $CH_3$ | — | $C_6H_5$ | NH—O—H |
| 779 | R53 | $CH_3$ | — | $C_6H_5$ | NH—O—$CH_3$ |
| 780 | R53 | $CH_3$ | — | $C_6H_5$ | NH—O—$C_6H_5$ |
| 781 | R53 | $CH_3$ | — | $C_6H_5$ | $NH_2$ |
| 782 | R53 | $CH_3$ | — | $C_6H_5$ | $NH(CH_3)$ |
| 783 | R53 | $CH_3$ | — | $C_6H_5$ | $N(CH_3)_2$ |
| 784 | R53 | $CH_3$ | — | $C_6H_5$ | $NH(C_6H_5)$ |
| 785 | R53 | $CH_3$ | O | H | NH—O—H |
| 786 | R53 | $CH_3$ | O | H | NH—O—$CH_3$ |
| 787 | R53 | $CH_3$ | O | H | NH—O—$C_6H_5$ |
| 788 | R53 | $CH_3$ | O | H | $NH_2$ |
| 789 | R53 | $CH_3$ | O | H | $NH(CH_3)$ |
| 790 | R53 | $CH_3$ | O | H | $N(CH_3)_2$ |
| 791 | R53 | $CH_3$ | O | H | $NH(C_6H_5)$ |
| 792 | R53 | $CH_3$ | O | $CH_3$ | NH—O—H |
| 793 | R53 | $CH_3$ | O | $CH_3$ | NH—O—$CH_3$ |
| 794 | R53 | $CH_3$ | O | $CH_3$ | NH—O—$C_6H_5$ |
| 795 | R53 | $CH_3$ | O | $CH_3$ | $NH_2$ |
| 796 | R53 | $CH_3$ | O | $CH_3$ | $NH(CH_3)$ |
| 797 | R53 | $CH_3$ | O | $CH_3$ | $N(CH_3)_2$ |
| 798 | R53 | $CH_3$ | O | $CH_3$ | $NH(C_6H_5)$ |
| 799 | R53 | $CH_3$ | O | $C_2H_5$ | NH—O—H |
| 800 | R53 | $CH_3$ | O | $C_2H_5$ | NH—O—$CH_3$ |
| 801 | R53 | $CH_3$ | O | $C_2H_5$ | NH—O—$C_6H_5$ |
| 802 | R53 | $CH_3$ | O | $C_2H_5$ | $NH_2$ |
| 803 | R53 | $CH_3$ | O | $C_2H_5$ | $NH(CH_3)$ |
| 804 | R53 | $CH_3$ | O | $C_2H_5$ | $N(CH_3)_2$ |
| 805 | R53 | $CH_3$ | O | $C_2H_5$ | $NH(C_6H_5)$ |
| 806 | R53 | $CH_3$ | O | $CH(CH_3)_2$ | NH—O—H |
| 807 | R53 | $CH_3$ | O | $CH(CH_3)_2$ | NH—O—$CH_3$ |
| 808 | R53 | $CH_3$ | O | $CH(CH_3)_2$ | NH—O—$C_6H_5$ |
| 809 | R53 | $CH_3$ | O | $CH(CH_3)_2$ | $NH_2$ |
| 810 | R53 | $CH_3$ | O | $CH(CH_3)_2$ | $NH(CH_3)$ |
| 811 | R53 | $CH_3$ | O | $CH(CH_3)_2$ | $N(CH_3)_2$ |
| 812 | R53 | $CH_3$ | O | $CH(CH_3)_2$ | $NH(C_6H_5)$ |
| 813 | R53 | $CH_3$ | O | $CH_2CF_3$ | NH—O—H |
| 814 | R53 | $CH_3$ | O | $CH_2CF_3$ | NH—O—$CH_3$ |
| 815 | R53 | $CH_3$ | O | $CH_2CF_3$ | NH—O—$C_6H_5$ |
| 816 | R53 | $CH_3$ | O | $CH_2CF_3$ | $NH_2$ |
| 817 | R53 | $CH_3$ | O | $CH_2CF_3$ | $NH(CH_3)$ |
| 818 | R53 | $CH_3$ | O | $CH_2CF_3$ | $N(CH_3)_2$ |
| 819 | R53 | $CH_3$ | O | $CH_2CF_3$ | $NH(C_6H_5)$ |
| 820 | R53 | $CH_3$ | O | $CH_2$-cyclo-$C_3H_5$ | NH—O—H |
| 821 | R53 | $CH_3$ | O | $CH_2$-cyclo-$C_3H_5$ | NH—O—$CH_3$ |
| 822 | R53 | $CH_3$ | O | $CH_2$-cyclo-$C_3H_5$ | NH—O—$C_6H_5$ |
| 823 | R53 | $CH_3$ | O | $CH_2$-cyclo-$C_3H_5$ | $NH_2$ |
| 824 | R53 | $CH_3$ | O | $CH_2$-cyclo-$C_3H_5$ | $NH(CH_3)$ |
| 825 | R53 | $CH_3$ | O | $CH_2$-cyclo-$C_3H_5$ | $N(CH_3)_2$ |
| 826 | R53 | $CH_3$ | O | $CH_2$-cyclo-$C_3H_5$ | $NH(C_6H_5)$ |
| 827 | R53 | $CH_3$ | O | $C_6H_5$ | NH—O—H |
| 828 | R53 | $CH_3$ | O | $C_6H_5$ | NH—O—$CH_3$ |
| 829 | R53 | $CH_3$ | O | $C_6H_5$ | NH—O—$C_6H_5$ |
| 830 | R53 | $CH_3$ | O | $C_6H_5$ | $NH_2$ |
| 831 | R53 | $CH_3$ | O | $C_6H_5$ | $NH(CH_3)$ |
| 832 | R53 | $CH_3$ | O | $C_6H_5$ | $N(CH_3)_2$ |

TABLE 3-continued

Compounds of formula (I-15a)

R51 is 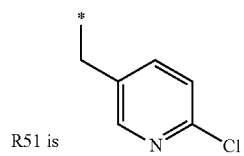

R52 is 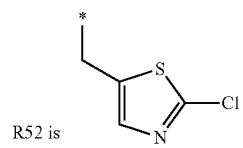

R53 is 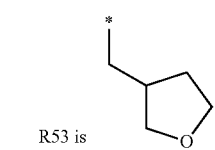

| No. | $R^5$ | $R^q$ | Z | $R^1$ | $R^2$ |
|---|---|---|---|---|---|
| 833 | R53 | $CH_3$ | O | $C_6H_5$ | $NH(C_6H_5)$ |
| 834 | R53 | $CH_3$ | NH | H | NH—O—H |
| 835 | R53 | $CH_3$ | NH | H | NH—O—$CH_3$ |
| 836 | R53 | $CH_3$ | NH | H | NH—O—$C_6H_5$ |
| 837 | R53 | $CH_3$ | NH | H | $NH_2$ |
| 838 | R53 | $CH_3$ | NH | H | $NH(CH_3)$ |
| 839 | R53 | $CH_3$ | NH | H | $N(CH_3)_2$ |
| 840 | R53 | $CH_3$ | NH | H | $NH(C_6H_5)$ |
| 841 | R53 | $CH_3$ | NH | $CH_3$ | NH—O—H |
| 842 | R53 | $CH_3$ | NH | $CH_3$ | NH—O—$CH_3$ |
| 843 | R53 | $CH_3$ | NH | $CH_3$ | NH—O—$C_6H_5$ |
| 844 | R53 | $CH_3$ | NH | $CH_3$ | $NH_2$ |
| 845 | R53 | $CH_3$ | NH | $CH_3$ | $NH(CH_3)$ |
| 846 | R53 | $CH_3$ | NH | $CH_3$ | $N(CH_3)_2$ |
| 847 | R53 | $CH_3$ | NH | $CH_3$ | $NH(C_6H_5)$ |
| 848 | R53 | $CH_3$ | NH | $C_2H_5$ | NH—O—H |
| 849 | R53 | $CH_3$ | NH | $C_2H_5$ | NH—O—$CH_3$ |
| 850 | R53 | $CH_3$ | NH | $C_2H_5$ | NH—O—$C_6H_5$ |
| 851 | R53 | $CH_3$ | NH | $C_2H_5$ | $NH_2$ |
| 852 | R53 | $CH_3$ | NH | $C_2H_5$ | $NH(CH_3)$ |
| 853 | R53 | $CH_3$ | NH | $C_2H_5$ | $N(CH_3)_2$ |
| 854 | R53 | $CH_3$ | NH | $C_2H_5$ | $NH(C_6H_5)$ |
| 855 | R53 | $CH_3$ | NH | $CH(CH_3)_2$ | NH—O—H |
| 856 | R53 | $CH_3$ | NH | $CH(CH_3)_2$ | NH—O—$CH_3$ |
| 857 | R53 | $CH_3$ | NH | $CH(CH_3)_2$ | NH—O—$C_6H_5$ |
| 858 | R53 | $CH_3$ | NH | $CH(CH_3)_2$ | $NH_2$ |
| 859 | R53 | $CH_3$ | NH | $CH(CH_3)_2$ | $NH(CH_3)$ |
| 860 | R53 | $CH_3$ | NH | $CH(CH_3)_2$ | $N(CH_3)_2$ |
| 861 | R53 | $CH_3$ | NH | $CH(CH_3)_2$ | $NH(C_6H_5)$ |
| 862 | R53 | $CH_3$ | NH | $CH_2CF_3$ | NH—O—H |
| 863 | R53 | $CH_3$ | NH | $CH_2CF_3$ | NH—O—$CH_3$ |
| 864 | R53 | $CH_3$ | NH | $CH_2CF_3$ | NH—O—$C_6H_5$ |
| 865 | R53 | $CH_3$ | NH | $CH_2CF_3$ | $NH_2$ |
| 866 | R53 | $CH_3$ | NH | $CH_2CF_3$ | $NH(CH_3)$ |
| 867 | R53 | $CH_3$ | NH | $CH_2CF_3$ | $N(CH_3)_2$ |
| 868 | R53 | $CH_3$ | NH | $CH_2CF_3$ | $NH(C_6H_5)$ |
| 869 | R53 | $CH_3$ | NH | $CH_2$-cyclo-$C_3H_5$ | NH—O—H |
| 870 | R53 | $CH_3$ | NH | $CH_2$-cyclo-$C_3H_5$ | NH—O—$CH_3$ |
| 871 | R53 | $CH_3$ | NH | $CH_2$-cyclo-$C_3H_5$ | NH—O—$C_6H_5$ |
| 872 | R53 | $CH_3$ | NH | $CH_2$-cyclo-$C_3H_5$ | $NH_2$ |
| 873 | R53 | $CH_3$ | NH | $CH_2$-cyclo-$C_3H_5$ | $NH(CH_3)$ |
| 874 | R53 | $CH_3$ | NH | $CH_2$-cyclo-$C_3H_5$ | $N(CH_3)_2$ |
| 875 | R53 | $CH_3$ | NH | $CH_2$-cyclo-$C_3H_5$ | $NH(C_6H_5)$ |
| 876 | R53 | $CH_3$ | NH | $C_6H_5$ | NH—O—H |
| 877 | R53 | $CH_3$ | NH | $C_6H_5$ | NH—O—$CH_3$ |
| 878 | R53 | $CH_3$ | NH | $C_6H_5$ | NH—O—$C_6H_5$ |
| 879 | R53 | $CH_3$ | NH | $C_6H_5$ | $NH_2$ |
| 880 | R53 | $CH_3$ | NH | $C_6H_5$ | $NH(CH_3)$ |
| 881 | R53 | $CH_3$ | NH | $C_6H_5$ | $N(CH_3)_2$ |
| 882 | R53 | $CH_3$ | NH | $C_6H_5$ | $NH(C_6H_5)$ |

In a further preferred embodiment, the compound of formula (I) is a compound of formula (I-16a),

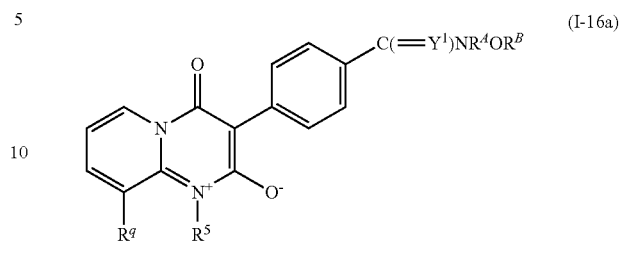

wherein the symbols and indices have the same meaning as in formula (I-16), in particular a compound listed in Table 4.

TABLE 4

Compounds of formula (I-16a)

R51 is 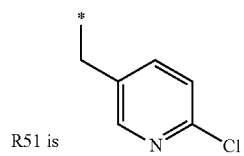

R52 is 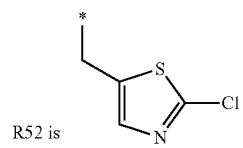

R53 is 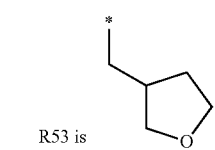

| No. | $R^5$ | $R^q$ | $Y^1$ | $R^A$ | $R^B$ |
|---|---|---|---|---|---|
| 1 | R51 | H | O | H | H |
| 2 | R51 | H | O | H | $CH_3$ |
| 3 | R51 | H | O | H | $CH_2$—$C_6H_5$ |
| 4 | R51 | H | O | H | $C_6H_5$ |
| 5 | R51 | H | O | $CH_3$ | H |
| 6 | R51 | H | O | $CH_3$ | $CH_3$ |
| 7 | R51 | H | O | $CH_3$ | $CH_2$—$C_6H_5$ |
| 8 | R51 | H | O | $CH_3$ | $C_6H_5$ |
| 9 | R51 | H | O | $CH_2$—$C_6H_5$ | H |
| 10 | R51 | H | O | $CH_2$—$C_6H_5$ | $CH_3$ |
| 11 | R51 | H | O | $CH_2$—$C_6H_5$ | $CH_2$—$C_6H_5$ |
| 12 | R51 | H | O | $CH_2$—$C_6H_5$ | $C_6H_5$ |
| 13 | R51 | H | O | $C_6H_5$ | H |
| 14 | R51 | H | O | $C_6H_5$ | $CH_3$ |
| 15 | R51 | H | O | $C_6H_5$ | $CH_2$—$C_6H_5$ |
| 16 | R51 | H | O | $C_6H_5$ | $C_6H_5$ |
| 17 | R51 | H | S | H | H |
| 18 | R51 | H | S | H | $CH_3$ |
| 19 | R51 | H | S | H | $CH_2$—$C_6H_5$ |
| 20 | R51 | H | S | H | $C_6H_5$ |
| 21 | R51 | H | S | $CH_3$ | H |
| 22 | R51 | H | S | $CH_3$ | $CH_3$ |
| 23 | R51 | H | S | $CH_3$ | $CH_2$—$C_6H_5$ |
| 24 | R51 | H | S | $CH_3$ | $C_6H_5$ |
| 25 | R51 | H | S | $CH_2$—$C_6H_5$ | H |
| 26 | R51 | H | S | $CH_2$—$C_6H_5$ | $CH_3$ |
| 27 | R51 | H | S | $CH_2$—$C_6H_5$ | $CH_2$—$C_6H_5$ |
| 28 | R51 | H | S | $CH_2$—$C_6H_5$ | $C_6H_5$ |
| 29 | R51 | H | S | $C_6H_5$ | H |
| 30 | R51 | H | S | $C_6H_5$ | $CH_3$ |

TABLE 4-continued

Compounds of formula (I-16a)

R51 is 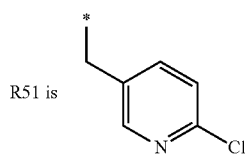

R52 is 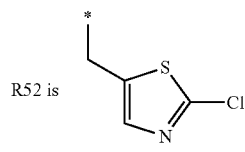

R53 is 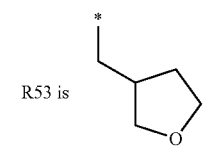

R51 is 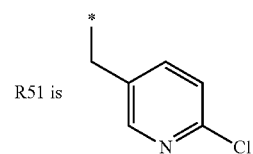

R52 is 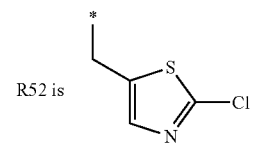

R53 is 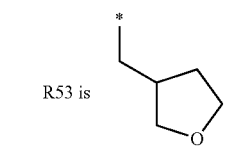

| No. | R⁵ | Rq | Y¹ | RA | RB |
|---|---|---|---|---|---|
| 31 | R51 | H | S | C₆H₅ | CH₂—C₆H₅ |
| 32 | R51 | H | S | C₆H₅ | C₆H₅ |
| 33 | R51 | CH₃ | O | H | H |
| 34 | R51 | CH₃ | O | H | CH₃ |
| 35 | R51 | CH₃ | O | H | CH₂—C₆H₅ |
| 36 | R51 | CH₃ | O | H | C₆H₅ |
| 37 | R51 | CH₃ | O | CH₃ | H |
| 38 | R51 | CH₃ | O | CH₃ | CH₃ |
| 39 | R51 | CH₃ | O | CH₃ | CH₂—C₆H₅ |
| 40 | R51 | CH₃ | O | CH₃ | C₆H₅ |
| 41 | R51 | CH₃ | O | CH₂—C₆H₅ | H |
| 42 | R51 | CH₃ | O | CH₂—C₆H₅ | CH₃ |
| 43 | R51 | CH₃ | O | CH₂—C₆H₅ | CH₂—C₆H₅ |
| 44 | R51 | CH₃ | O | CH₂—C₆H₅ | C₆H₅ |
| 45 | R51 | CH₃ | O | C₆H₅ | H |
| 46 | R51 | CH₃ | O | C₆H₅ | CH₃ |
| 47 | R51 | CH₃ | O | C₆H₅ | CH₂—C₆H₅ |
| 48 | R51 | CH₃ | O | C₆H₅ | C₆H₅ |
| 49 | R51 | CH₃ | S | H | H |
| 50 | R51 | CH₃ | S | H | CH₃ |
| 51 | R51 | CH₃ | S | H | CH₂—C₆H₅ |
| 52 | R51 | CH₃ | S | H | C₆H₅ |
| 53 | R51 | CH₃ | S | CH₃ | H |
| 54 | R51 | CH₃ | S | CH₃ | CH₃ |
| 55 | R51 | CH₃ | S | CH₃ | CH₂—C₆H₅ |
| 56 | R51 | CH₃ | S | CH₃ | C₆H₅ |
| 57 | R51 | CH₃ | S | CH₂—C₆H₅ | H |
| 58 | R51 | CH₃ | S | CH₂—C₆H₅ | CH₃ |
| 59 | R51 | CH₃ | S | CH₂—C₆H₅ | CH₂—C₆H₅ |
| 60 | R51 | CH₃ | S | CH₂—C₆H₅ | C₆H₅ |
| 61 | R51 | CH₃ | S | C₆H₅ | H |
| 62 | R51 | CH₃ | S | C₆H₅ | CH₃ |
| 63 | R51 | CH₃ | S | C₆H₅ | CH₂—C₆H₅ |
| 64 | R51 | CH₃ | S | C₆H₅ | C₆H₅ |
| 65 | R52 | H | O | H | H |
| 66 | R52 | H | O | H | CH₃ |
| 67 | R52 | H | O | H | CH₂—C₆H₅ |
| 68 | R52 | H | O | H | C₆H₅ |
| 69 | R52 | H | O | CH₃ | H |
| 70 | R52 | H | O | CH₃ | CH₃ |
| 71 | R52 | H | O | CH₃ | CH₂—C₆H₅ |
| 72 | R52 | H | O | CH₃ | C₆H₅ |
| 73 | R52 | H | O | CH₂—C₆H₅ | H |
| 74 | R52 | H | O | CH₂—C₆H₅ | CH₃ |
| 75 | R52 | H | O | CH₂—C₆H₅ | CH₂—C₆H₅ |
| 76 | R52 | H | O | CH₂—C₆H₅ | C₆H₅ |
| 77 | R52 | H | O | C₆H₅ | H |
| 78 | R52 | H | O | C₆H₅ | CH₃ |
| 79 | R52 | H | O | C₆H₅ | CH₂—C₆H₅ |
| 80 | R52 | H | O | C₆H₅ | C₆H₅ |
| 81 | R52 | H | S | H | H |
| 82 | R52 | H | S | H | CH₃ |
| 83 | R52 | H | S | H | CH₂—C₆H₅ |
| 84 | R52 | H | S | H | C₆H₅ |
| 85 | R52 | H | S | CH₃ | H |
| 86 | R52 | H | S | CH₃ | CH₃ |
| 87 | R52 | H | S | CH₃ | CH₂—C₆H₅ |
| 88 | R52 | H | S | CH₃ | C₆H₅ |
| 89 | R52 | H | S | CH₂—C₆H₅ | H |
| 90 | R52 | H | S | CH₂—C₆H₅ | CH₃ |
| 91 | R52 | H | S | CH₂—C₆H₅ | CH₂—C₆H₅ |
| 92 | R52 | H | S | CH₂—C₆H₅ | C₆H₅ |
| 93 | R52 | H | S | C₆H₅ | H |
| 94 | R52 | H | S | C₆H₅ | CH₃ |
| 95 | R52 | H | S | C₆H₅ | CH₂—C₆H₅ |
| 96 | R52 | H | S | C₆H₅ | C₆H₅ |
| 97 | R52 | CH₃ | O | H | H |
| 98 | R52 | CH₃ | O | H | CH₃ |
| 99 | R52 | CH₃ | O | H | CH₂—C₆H₅ |
| 100 | R52 | CH₃ | O | H | C₆H₅ |
| 101 | R52 | CH₃ | O | CH₃ | H |
| 102 | R52 | CH₃ | O | CH₃ | CH3 |
| 103 | R52 | CH₃ | O | CH₃ | CH₂—C₆H₅ |
| 104 | R52 | CH₃ | O | CH₃ | C₆H₅ |
| 105 | R52 | CH₃ | O | CH₂—C₆H₅ | H |
| 106 | R52 | CH₃ | O | CH₂—C₆H₅ | CH₃ |
| 107 | R52 | CH₃ | O | CH₂—C₆H₅ | CH₂—C₆H₅ |
| 108 | R52 | CH₃ | O | CH₂—C₆H₅ | C₆H₅ |
| 109 | R52 | CH₃ | O | C₆H₅ | H |
| 110 | R52 | CH₃ | O | C₆H₅ | CH₃ |
| 111 | R52 | CH₃ | O | C₆H₅ | CH₂—C₆H₅ |
| 112 | R52 | CH₃ | O | C₆H₅ | C₆H₅ |
| 113 | R52 | CH₃ | S | H | H |
| 114 | R52 | CH₃ | S | H | CH3 |
| 115 | R52 | CH₃ | S | H | CH₂—C₆H₅ |
| 116 | R52 | CH₃ | S | H | C₆H₅ |
| 117 | R52 | CH₃ | S | CH₃ | H |
| 118 | R52 | CH₃ | S | CH₃ | CH₃ |
| 119 | R52 | CH₃ | S | CH₃ | CH₂—C₆H₅ |
| 120 | R52 | CH₃ | S | CH₃ | C₆H₅ |
| 121 | R52 | CH₃ | S | CH₂—C₆H₅ | H |
| 122 | R52 | CH₃ | S | CH₂—C₆H₅ | CH₃ |
| 123 | R52 | CH₃ | S | CH₂—C₆H₅ | CH₂—C₆H₅ |
| 124 | R52 | CH₃ | S | CH₂—C₆H₅ | C₆H₅ |
| 125 | R52 | CH₃ | S | C₆H₅ | H |
| 126 | R52 | CH₃ | S | C₆H₅ | CH₃ |
| 127 | R52 | CH₃ | S | C₆H₅ | CH₂—C₆H₅ |
| 128 | R52 | CH₃ | S | C₆H₅ | C₆H₅ |
| 129 | R53 | H | O | H | H |
| 130 | R53 | H | O | H | CH₃ |
| 131 | R53 | H | O | H | CH₂—C₆H₅ |
| 132 | R53 | H | O | H | C₆H₅ |
| 133 | R53 | H | O | CH₃ | H |
| 134 | R53 | H | O | CH₃ | CH₃ |

TABLE 4-continued

Compounds of formula (I-16a)

R51 is: *-CH2-(2-chloropyridin-5-yl)

R52 is: *-CH2-(2-chlorothiazol-5-yl)

R53 is: *-CH2-(tetrahydrofuran-3-yl)

| No. | $R^5$ | $R^q$ | $Y^1$ | $R^A$ | $R^B$ |
|---|---|---|---|---|---|
| 135 | R53 | H | O | $CH_3$ | $CH_2$—$C_6H_5$ |
| 136 | R53 | H | O | $CH_3$ | $C_6H_5$ |
| 137 | R53 | H | O | $CH_2$—$C_6H_5$ | H |
| 138 | R53 | H | O | $CH_2$—$C_6H_5$ | $CH_3$ |
| 139 | R53 | H | O | $CH_2$—$C_6H_5$ | $CH_2$—$C_6H_5$ |
| 140 | R53 | H | O | $CH_2$—$C_6H_5$ | $C_6H_5$ |
| 141 | R53 | H | O | $C_6H_5$ | H |
| 142 | R53 | H | O | $C_6H_5$ | $CH_3$ |
| 143 | R53 | H | O | $C_6H_5$ | $CH_2$—$C_6H_5$ |
| 144 | R53 | H | O | $C_6H_5$ | $C_6H_5$ |
| 145 | R53 | H | S | H | H |
| 146 | R53 | H | S | H | $CH_3$ |
| 147 | R53 | H | S | H | $CH_2$—$C_6H_5$ |
| 148 | R53 | H | S | H | $C_6H_5$ |
| 149 | R53 | H | S | $CH_3$ | H |
| 150 | R53 | H | S | $CH_3$ | $CH_3$ |
| 151 | R53 | H | S | $CH_3$ | $CH_2$—$C_6H_5$ |
| 152 | R53 | H | S | $CH_3$ | $C_6H_5$ |
| 153 | R53 | H | S | $CH_2$—$C_6H_5$ | H |
| 154 | R53 | H | S | $CH_2$—$C_6H_5$ | $CH_3$ |
| 155 | R53 | H | S | $CH_2$—$C_6H_5$ | $CH_2$—$C_6H_5$ |
| 156 | R53 | H | S | $CH_2$—$C_6H_5$ | $C_6H_5$ |
| 157 | R53 | H | S | $C_6H_5$ | H |
| 158 | R53 | H | S | $C_6H_5$ | $CH_3$ |
| 159 | R53 | H | S | $C_6H_5$ | $CH_2$—$C_6H_5$ |
| 160 | R53 | H | S | $C_6H_5$ | $C_6H_5$ |
| 161 | R53 | $CH_3$ | O | H | H |
| 162 | R53 | $CH_3$ | O | H | $CH_3$ |
| 163 | R53 | $CH_3$ | O | H | $CH_2$—$C_6H_5$ |
| 164 | R53 | $CH_3$ | O | H | $C_6H_5$ |
| 165 | R53 | $CH_3$ | O | $CH_3$ | H |
| 166 | R53 | $CH_3$ | O | $CH_3$ | $CH_3$ |
| 167 | R53 | $CH_3$ | O | $CH_3$ | $CH_2$—$C_6H_5$ |
| 168 | R53 | $CH_3$ | O | $CH_3$ | $C_6H_5$ |
| 169 | R53 | $CH_3$ | O | $CH_2$—$C_6H_5$ | H |
| 170 | R53 | $CH_3$ | O | $CH_2$—$C_6H_5$ | $CH_3$ |
| 171 | R53 | $CH_3$ | O | $CH_2$—$C_6H_5$ | $CH_2$—$C_6H_5$ |
| 172 | R53 | $CH_3$ | O | $CH_2$—$C_6H_5$ | $C_6H_5$ |
| 173 | R53 | $CH_3$ | O | $C_6H_5$ | H |
| 174 | R53 | $CH_3$ | O | $C_6H_5$ | $CH_3$ |
| 175 | R53 | $CH_3$ | O | $C_6H_5$ | $CH_2$—$C_6H_5$ |
| 176 | R53 | $CH_3$ | O | $C_6H_5$ | $C_6H_5$ |
| 177 | R53 | $CH_3$ | S | H | H |
| 178 | R53 | $CH_3$ | S | H | $CH_3$ |

TABLE 4-continued

Compounds of formula (I-16a)

R51 is: *-CH2-(2-chloropyridin-5-yl)

R52 is: *-CH2-(2-chlorothiazol-5-yl)

R53 is: *-CH2-(tetrahydrofuran-3-yl)

| No. | $R^5$ | $R^q$ | $Y^1$ | $R^A$ | $R^B$ |
|---|---|---|---|---|---|
| 179 | R53 | $CH_3$ | S | H | $CH_2$—$C_6H_5$ |
| 180 | R53 | $CH_3$ | S | H | $C_6H_5$ |
| 181 | R53 | $CH_3$ | S | $CH_3$ | H |
| 182 | R53 | $CH_3$ | S | $CH_3$ | $CH_3$ |
| 183 | R53 | $CH_3$ | S | $CH_3$ | $CH_2$—$C_6H_5$ |
| 184 | R53 | $CH_3$ | S | $CH_3$ | $C_6H_5$ |
| 185 | R53 | $CH_3$ | S | $CH_2$—$C_6H_5$ | H |
| 186 | R53 | $CH_3$ | S | $CH_2$—$C_6H_5$ | $CH_3$ |
| 187 | R53 | $CH_3$ | S | $CH_2$—$C_6H_5$ | $CH_2$—$C_6H_5$ |
| 188 | R53 | $CH_3$ | S | $CH_2$—$C_6H_5$ | $C_6H_5$ |
| 189 | R53 | $CH_3$ | S | $C_6H_5$ | H |
| 190 | R53 | $CH_3$ | S | $C_6H_5$ | $CH_3$ |
| 191 | R53 | $CH_3$ | S | $C_6H_5$ | $CH_2$—$C_6H_5$ |
| 192 | R53 | $CH_3$ | S | $C_6H_5$ | $C_6H_5$ |

In a further preferred embodiment, the compound of formula (I) is a compound of formula (I-17a),

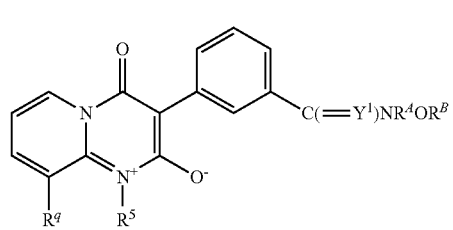

(I-17a)

wherein the symbols and indices have the same meaning as in formula (I-17), in particular a compound listed in Table 5.

TABLE 5

Compounds of formula (I-17a)

R51 is: *-CH2-(2-chloropyridin-5-yl)

R52 is: *-CH2-(2-chlorothiazol-5-yl)

R53 is: *-CH2-(tetrahydrofuran-3-yl)

| No. | R⁵ | R^q | Y¹ | R^A | R^B |
|---|---|---|---|---|---|
| 1 | R51 | H | O | H | H |
| 2 | R51 | H | O | H | CH₃ |
| 3 | R51 | H | O | H | CH₂—C₆H₅ |
| 4 | R51 | H | O | H | C₆H₅ |
| 5 | R51 | H | O | CH₃ | H |
| 6 | R51 | H | O | CH₃ | CH₃ |
| 7 | R51 | H | O | CH₃ | CH₂—C₆H₅ |
| 8 | R51 | H | O | CH₃ | C₆H₅ |
| 9 | R51 | H | O | CH₂—C₆H₅ | H |
| 10 | R51 | H | O | CH₂—C₆H₅ | CH₃ |
| 11 | R51 | H | O | CH₂—C₆H₅ | CH₂—C₆H₅ |
| 12 | R51 | H | O | CH₂—C₆H₅ | C₆H₅ |
| 13 | R51 | H | O | C₆H₅ | H |
| 14 | R51 | H | O | C₆H₅ | CH₃ |
| 15 | R51 | H | O | C₆H₅ | CH₂—C₆H |
| 16 | R51 | H | O | C₆H₅ | C₆H₅ |
| 17 | R51 | H | S | H | H |
| 18 | R51 | H | S | H | CH₃ |
| 19 | R51 | H | S | H | CH₂—CH₆H₅ |
| 20 | R51 | H | S | H | C₆H₅ |
| 21 | R51 | H | S | CH₃ | H |
| 22 | R51 | H | S | CH₃ | CH₃ |
| 23 | R51 | H | S | CH₃ | CH₂—C₆H₅ |
| 24 | R51 | H | S | CH₃ | C₆H₅ |
| 25 | R51 | H | S | CH₂—C₆H₅ | H |
| 26 | R51 | H | S | CH₂—C₆H₅ | CH₃ |
| 27 | R51 | H | S | CH₂—C₆H₅ | CH₂—C₆H₅ |
| 28 | R51 | H | S | CH₂—C₆H₅ | C₆H₅ |
| 29 | R51 | H | S | C₆H₅ | H |
| 30 | R51 | H | S | C₆H₅ | CH₃ |
| 31 | R51 | H | S | C₆H₅ | CH₂—C₆H₅ |
| 32 | R51 | H | S | C₆H₅ | C₆H₅ |
| 33 | R51 | CH₃ | O | H | H |
| 34 | R51 | CH₃ | O | H | CH₃ |
| 35 | R51 | CH₃ | O | H | CH₂—C₆H₅ |
| 36 | R51 | CH₃ | O | H | C₆H₅ |
| 37 | R51 | CH₃ | O | CH₃ | H |
| 38 | R51 | CH₃ | O | CH₃ | CH₃ |
| 39 | R51 | CH₃ | O | CH₃ | CH₂—C₆H₅ |
| 40 | R51 | CH₃ | O | CH₃ | C₆H₅ |
| 41 | R51 | CH₃ | O | CH₂—C₆H₅ | H |
| 42 | R51 | CH₃ | O | CH₂—C₆H₅ | CH₃ |
| 43 | R51 | CH₃ | O | CH₂—C₆H₅ | CH₂—C₆H₅ |
| 44 | R51 | CH₃ | O | CH₂—C₆H₅ | C₆H₅ |
| 45 | R51 | CH₃ | O | C₆H₅ | H |
| 46 | R51 | CH₃ | O | C₆H₅ | CH₃ |
| 47 | R51 | CH₃ | O | C₆H₅ | CH₂—CH₆H₅ |
| 48 | R51 | CH₃ | O | C₆H₅ | C₆H₅ |
| 49 | R51 | CH₃ | S | H | H |
| 50 | R51 | CH₃ | S | H | CH₃ |
| 51 | R51 | CH₃ | S | H | CH₂—C₆H₅ |
| 52 | R51 | CH₃ | S | H | C₆H₅ |
| 53 | R51 | CH₃ | S | CH₃ | H |
| 54 | R51 | CH₃ | S | CH₃ | CH₃ |
| 55 | R51 | CH₃ | S | CH₃ | CH₂—C₆H₅ |
| 56 | R51 | CH₃ | S | CH₃ | C₆H₅ |
| 57 | R51 | CH₃ | S | CH₂—C₆H₅ | H |
| 58 | R51 | CH₃ | S | CH₂—C₆H₅ | CH₃ |
| 59 | R51 | CH₃ | S | CH₂—C₆H₅ | CH₂—C₆H₅ |
| 60 | R51 | CH₃ | S | CH₂—C₆H₅ | C₆H₅ |
| 61 | R51 | CH₃ | S | C₆H₅ | H |
| 62 | R51 | CH₃ | S | C₆H₅ | CH₃ |
| 63 | R51 | CH₃ | S | C₆H₅ | CH₂—C₆H₅ |
| 64 | R51 | CH₃ | S | C₆H₅ | C₆H₅ |
| 65 | R52 | H | O | H | H |
| 66 | R52 | H | O | H | CH₃ |
| 67 | R52 | H | O | H | CH₂—C₆H₅ |
| 68 | R52 | H | O | H | C₆H₅ |
| 69 | R52 | H | O | CH₃ | H |
| 70 | R52 | H | O | CH₃ | CH₃ |
| 71 | R52 | H | O | CH₃ | CH₂—C₆H₅ |
| 72 | R52 | H | O | CH₃ | C₆H₅ |
| 73 | R52 | H | O | CH₂—C₆H₅ | H |
| 74 | R52 | H | O | CH₂—C₆H₅ | CH₃ |
| 75 | R52 | H | O | CH₂—C₆H₅ | CH₂—C₆H₅ |
| 76 | R52 | H | O | CH₂—C₆H₅ | C₆H₅ |
| 77 | R52 | H | O | C₆H₅ | H |
| 78 | R52 | H | O | C₆H₅ | CH₃ |
| 79 | R52 | H | O | C₆H₅ | CH₂—C₆H₅ |
| 80 | R52 | H | O | C₆H₅ | C₆H₅ |
| 81 | R52 | H | S | H | H |
| 82 | R52 | H | S | H | CH₃ |
| 83 | R52 | H | S | H | CH₂—C₆H₅ |
| 84 | R52 | H | S | H | C₆H₅ |
| 85 | R52 | H | S | CH₃ | H |
| 86 | R52 | H | S | CH₃ | CH₃ |
| 87 | R52 | H | S | CH₃ | CH₂—C₆H₅ |
| 88 | R52 | H | S | CH₃ | C₆H₅ |
| 89 | R52 | H | S | CH₂—C₆H₅ | H |
| 90 | R52 | H | S | CH₂—C₆H₅ | CH₃ |
| 91 | R52 | H | S | CH₂—C₆H₅ | CH₂—C₆H₅ |
| 92 | R52 | H | S | CH₂—C₆H₅ | C₆H₅ |
| 93 | R52 | H | S | C₆H₅ | H |
| 94 | R52 | H | S | C₆H₅ | CH₃ |
| 95 | R52 | H | S | C₆H₅ | CH₂—C₆H₅ |
| 96 | R52 | H | S | C₆H₅ | C₆H₅ |
| 97 | R52 | CH₃ | O | H | H |
| 98 | R52 | CH₃ | O | H | CH₃ |
| 99 | R52 | CH₃ | O | H | CH₂—C₆H₅ |
| 100 | R52 | CH₃ | O | H | C₆H₅ |
| 101 | R52 | CH₃ | O | CH₃ | H |
| 102 | R52 | CH₃ | O | CH₃ | CH3 |

TABLE 5-continued

Compounds of formula (I-17a)

R51 is: *-CH2-(5-pyridyl-2-Cl)

R52 is: *-CH2-(5-thiazolyl-2-Cl)

R53 is: *-CH2-(3-tetrahydrofuranyl)

| No. | $R^5$ | $R^q$ | $Y^1$ | $R^A$ | $R^B$ |
|---|---|---|---|---|---|
| 103 | R52 | CH₃ | O | CH₃ | CH₂—C₆H₅ |
| 104 | R52 | CH₃ | O | CH₃ | C₆H₅ |
| 105 | R52 | CH₃ | O | CH₂—C₆H₅ | H |
| 106 | R52 | CH₃ | O | CH₂—C₆H₅ | CH₃ |
| 107 | R52 | CH₃ | O | CH₂—C₆H₅ | CH₂—C₆H₅ |
| 108 | R52 | CH₃ | O | CH₂—C₆H₅ | C₆H₅ |
| 109 | R52 | CH₃ | O | C₆H₅ | H |
| 110 | R52 | CH₃ | O | C₆H₅ | CH₃ |
| 111 | R52 | CH₃ | O | C₆H₅ | CH₂—C₆H₅ |
| 112 | R52 | CH₃ | O | C₆H₅ | C₆H₅ |
| 113 | R52 | CH₃ | S | H | H |
| 114 | R52 | CH₃ | S | H | CH3 |
| 115 | R52 | CH₃ | S | H | CH₂—C₆H₅ |
| 116 | R52 | CH₃ | S | H | C₆H₅ |
| 117 | R52 | CH₃ | S | CH₃ | H |
| 118 | R52 | CH₃ | S | CH₃ | CH₃ |
| 119 | R52 | CH₃ | S | CH₃ | CH₂—C₆H₅ |
| 120 | R52 | CH₃ | S | CH₃ | C₆H₅ |
| 121 | R52 | CH₃ | S | CH₂—C₆H₅ | H |
| 122 | R52 | CH₃ | S | CH₂—C₆H₅ | CH₃ |
| 123 | R52 | CH₃ | S | CH₂—C₆H₅ | CH₂—C₆H₅ |
| 124 | R52 | CH₃ | S | CH₂—C₆H₅ | C₆H₅ |
| 125 | R52 | CH₃ | S | C₆H₅ | H |
| 126 | R52 | CH₃ | S | C₆H₅ | CH₃ |
| 127 | R52 | CH₃ | S | C₆H₅ | CH₂—C₆H₅ |
| 128 | R52 | CH₃ | S | C₆H₅ | C₆H₅ |
| 129 | R53 | H | O | H | H |
| 130 | R53 | H | O | H | CH₃ |
| 131 | R53 | H | O | H | CH₂—C₆H₅ |
| 132 | R53 | H | O | H | C₆H₅ |
| 133 | R53 | H | O | CH₃ | H |
| 134 | R53 | H | O | CH₃ | CH₃ |
| 135 | R53 | H | O | CH₃ | CH₂—C₆H₅ |
| 136 | R53 | H | O | CH₃ | C₆H₅ |
| 137 | R53 | H | O | CH₂—C₆H₅ | H |
| 138 | R53 | H | O | CH₂—C₆H₅ | CH₃ |
| 139 | R53 | H | O | CH₂—C₆H₅ | CH₂—C₆H₅ |
| 140 | R53 | H | O | CH₂—C₆H₅ | C₆H₅ |
| 141 | R53 | H | O | C₆H₅ | H |
| 142 | R53 | H | O | C₆H₅ | CH₃ |
| 143 | R53 | H | O | C₆H₅ | CH₂—C₆H₅ |
| 144 | R53 | H | O | C₆H₅ | C₆H₅ |
| 145 | R53 | H | S | H | H |
| 146 | R53 | H | S | H | CH₃ |
| 147 | R53 | H | S | H | CH₂—C₆H₅ |
| 148 | R53 | H | S | H | C₆H₅ |
| 149 | R53 | H | S | CH₃ | H |
| 150 | R53 | H | S | CH₃ | CH₃ |
| 151 | R53 | H | S | CH₃ | CH₂—C₆H₅ |
| 152 | R53 | H | S | CH₃ | C₆H₅ |
| 153 | R53 | H | S | CH₂—C₆H₅ | H |
| 154 | R53 | H | S | CH₂—C₆H₅ | CH₃ |
| 155 | R53 | H | S | CH₂—C₆H₅ | CH₂—C₆H₅ |
| 156 | R53 | H | S | CH₂—C₆H₅ | C₆H₅ |
| 157 | R53 | H | S | C₆H₅ | H |
| 158 | R53 | H | S | C₆H₅ | CH₃ |
| 159 | R53 | H | S | C₆H₅ | CH₂—C₆H₅ |
| 160 | R53 | H | S | C₆H₅ | C₆H₅ |
| 161 | R53 | CH₃ | O | H | H |
| 162 | R53 | CH₃ | O | H | CH₃ |
| 163 | R53 | CH₃ | O | H | CH₂—C₆H₅ |
| 164 | R53 | CH₃ | O | H | C₆H₅ |
| 165 | R53 | CH₃ | O | CH₃ | H |
| 166 | R53 | CH₃ | O | CH₃ | CH₃ |
| 167 | R53 | CH₃ | O | CH₃ | CH₂—C₆H₅ |
| 168 | R53 | CH₃ | O | CH₃ | C₆H₅ |
| 169 | R53 | CH₃ | O | CH₂—C₆H₅ | H |
| 170 | R53 | CH₃ | O | CH₂—C₆H₅ | CH₃ |
| 171 | R53 | CH₃ | O | CH₂—C₆H₅ | CH₂—C₆H₅ |
| 172 | R53 | CH₃ | O | CH₂—C₆H₅ | C₆H₅ |
| 173 | R53 | CH₃ | O | C₆H₅ | H |
| 174 | R53 | CH₃ | O | C₆H₅ | CH₃ |
| 175 | R53 | CH₃ | O | C₆H₅ | CH₂—C₆H₅ |
| 176 | R53 | CH₃ | O | C₆H₅ | C₆H₅ |
| 177 | R53 | CH₃ | S | H | H |
| 178 | R53 | CH₃ | S | H | CH₃ |
| 179 | R53 | CH₃ | S | H | CH₂—C₆H₅ |
| 180 | R53 | CH₃ | S | H | C₆H₅ |
| 181 | R53 | CH₃ | S | CH₃ | H |
| 182 | R53 | CH₃ | S | CH₃ | CH₃ |
| 183 | R53 | CH₃ | S | CH₃ | CH₂—C₆H₅ |
| 184 | R53 | CH₃ | S | CH₃ | C₆H₅ |
| 185 | R53 | CH₃ | S | CH₂—C₆H₅ | H |
| 186 | R53 | CH₃ | S | CH₂—C₆H₅ | CH₃ |
| 187 | R53 | CH₃ | S | CH₂—C₆H₅ | CH₂—C₆H₅ |
| 188 | R53 | CH₃ | S | CH₂—C₆H₅ | C₆H₅ |
| 189 | R53 | CH₃ | S | C₆H₅ | H |
| 190 | R53 | CH₃ | S | C₆H₅ | CH₃ |
| 191 | R53 | CH₃ | S | C₆H₅ | CH₂—C₆H₅ |
| 192 | R53 | CH₃ | S | C₆H₅ | C₆H₅ |

In a further preferred embodiment, the compound of formula (I) is a compound of formula (I-18a),

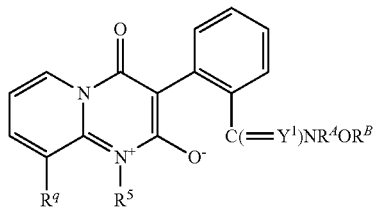

(I-18a)

wherein the symbols and indices have the same meaning as in formula (I-18), in particular a compound listed in Table 6.

TABLE 6

Compounds of formula (I-18a)

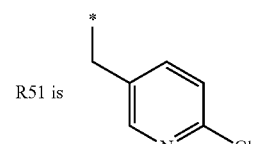

R51 is

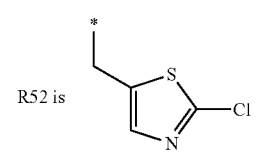

R52 is

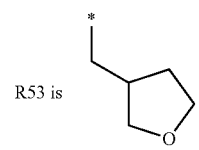

R53 is

| No. | $R^5$ | $R^q$ | $Y^1$ | $R^A$ | $R^B$ |
|---|---|---|---|---|---|
| 1 | R51 | H | O | H | H |
| 2 | R51 | H | O | H | $CH_3$ |
| 3 | R51 | H | O | H | $CH_2$—$C_6H_5$ |
| 4 | R51 | H | O | H | $C_6H_5$ |
| 5 | R51 | H | O | $CH_3$ | H |
| 6 | R51 | H | O | $CH_3$ | $CH_3$ |
| 7 | R51 | H | O | $CH_3$ | $CH_2$—$C_6H_5$ |
| 8 | R51 | H | O | $CH_3$ | $C_6H_5$ |
| 9 | R51 | H | O | $CH_2$—$C_6H_5$ | H |
| 10 | R51 | H | O | $CH_2$—$C_6H_5$ | $CH_3$ |
| 11 | R51 | H | O | $CH_2$—$C_6H_5$ | $CH_2$—$C_6H_5$ |
| 12 | R51 | H | O | $CH_2$—$C_6H_5$ | $C_6H_5$ |
| 13 | R51 | H | O | $C_6H_5$ | H |
| 14 | R51 | H | O | $C_6H_5$ | $CH_3$ |
| 15 | R51 | H | O | $C_6H_5$ | $CH_2$—$C_6H_5$ |
| 16 | R51 | H | O | $C_6H_5$ | $C_6H_5$ |
| 17 | R51 | H | S | H | H |
| 18 | R51 | H | S | H | $CH_3$ |
| 19 | R51 | H | S | H | $CH_2$—$C_6H_5$ |
| 20 | R51 | H | S | H | $C_6H_5$ |
| 21 | R51 | H | S | $CH_3$ | H |
| 22 | R51 | H | S | $CH_3$ | $CH_3$ |
| 23 | R51 | H | S | $CH_3$ | $CH_2$—$C_6H_5$ |
| 24 | R51 | H | S | $CH_3$ | $C_6H_5$ |
| 25 | R51 | H | S | $CH_2$—$C_6H_5$ | H |
| 26 | R51 | H | S | $CH_2$—$C_6H_5$ | $CH_3$ |
| 27 | R51 | H | S | $CH_2$—$C_6H_5$ | $CH_2$—$C_6H_5$ |
| 28 | R51 | H | S | $CH_2$—$C_6H_5$ | $C_6H_5$ |
| 29 | R51 | H | S | $C_6H_5$ | H |
| 30 | R51 | H | S | $C_6H_5$ | $CH_3$ |
| 31 | R51 | H | S | $C_6H_5$ | $CH_2$—$C_6H_5$ |
| 32 | R51 | H | S | $C_6H_5$ | $C_6H_5$ |
| 33 | R51 | $CH_3$ | O | H | H |
| 34 | R51 | $CH_3$ | O | H | $CH_3$ |
| 35 | R51 | $CH_3$ | O | H | $CH_2$—$C_6H_5$ |
| 36 | R51 | $CH_3$ | O | H | $C_6H_5$ |
| 37 | R51 | $CH_3$ | O | $CH_3$ | H |
| 38 | R51 | $CH_3$ | O | $CH_3$ | $CH_3$ |
| 39 | R51 | $CH_3$ | O | $CH_3$ | $CH_2$—$C_6H_5$ |
| 40 | R51 | $CH_3$ | O | $CH_3$ | $C_6H_5$ |
| 41 | R51 | $CH_3$ | O | $CH_2$—$C_6H_5$ | H |
| 42 | R51 | $CH_3$ | O | $CH_2$—$C_6H_5$ | $CH_3$ |
| 43 | R51 | $CH_3$ | O | $CH_2$—$C_6H_5$ | $CH_2$—$C_6H_5$ |
| 44 | R51 | $CH_3$ | O | $CH_2$—$C_6H_5$ | $C_6H_5$ |
| 45 | R51 | $CH_3$ | O | $C_6H_5$ | H |
| 46 | R51 | $CH_3$ | O | $C_6H_5$ | $CH_3$ |
| 47 | R51 | $CH_3$ | O | $C_6H_5$ | $CH_2$—$C_6H_5$ |
| 48 | R51 | $CH_3$ | O | $C_6H_5$ | $C_6H_5$ |
| 49 | R51 | $CH_3$ | S | H | H |
| 50 | R51 | $CH_3$ | S | H | $CH_3$ |
| 51 | R51 | $CH_3$ | S | H | $CH_2$—$C_6H_5$ |
| 52 | R51 | $CH_3$ | S | H | $C_6H_5$ |
| 53 | R51 | $CH_3$ | S | $CH_3$ | H |
| 54 | R51 | $CH_3$ | S | $CH_3$ | $CH_3$ |
| 55 | R51 | $CH_3$ | S | $CH_3$ | $CH_2$—$C_6H_5$ |
| 56 | R51 | $CH_3$ | S | $CH_3$ | $C_6H_5$ |
| 57 | R51 | $CH_3$ | S | $CH_2$—$C_6H_5$ | H |
| 58 | R51 | $CH_3$ | S | $CH_2$—$C_6H_5$ | $CH_3$ |
| 59 | R51 | $CH_3$ | S | $CH_2$—$C_6H_5$ | $CH_2$—$C_6H_5$ |
| 60 | R51 | $CH_3$ | S | $CH_2$—$C_6H_5$ | $C_6H_5$ |
| 61 | R51 | $CH_3$ | S | $C_6H_5$ | H |
| 62 | R51 | $CH_3$ | S | $C_6H_5$ | $CH_3$ |
| 63 | R51 | $CH_3$ | S | $C_6H_5$ | $CH_2$—$C_6H_5$ |
| 64 | R51 | $CH_3$ | S | $C_6H_5$ | $C_6H_5$ |
| 65 | R52 | H | O | H | H |
| 66 | R52 | H | O | H | $CH_3$ |
| 67 | R52 | H | O | H | $CH_2$—$C_6H_5$ |
| 68 | R52 | H | O | H | $C_6H_5$ |
| 69 | R52 | H | O | $CH_3$ | H |
| 70 | R52 | H | O | $CH_3$ | $CH_3$ |
| 71 | R52 | H | O | $CH_3$ | $CH_2$—$C_6H_5$ |
| 72 | R52 | H | O | $CH_3$ | $C_6H_5$ |
| 73 | R52 | H | O | $CH_2$—$C_6H_5$ | H |
| 74 | R52 | H | O | $CH_2$—$C_6H_5$ | $CH_3$ |
| 75 | R52 | H | O | $CH_2$—$C_6H_5$ | $CH_2$—$C_6H_5$ |
| 76 | R52 | H | O | $CH_2$—$C_6H_5$ | $C_6H_5$ |
| 77 | R52 | H | O | $C_6H_5$ | H |
| 78 | R52 | H | O | $C_6H_5$ | $CH_3$ |
| 79 | R52 | H | O | $C_6H_5$ | $CH_2$—$C_6H_5$ |
| 80 | R52 | H | O | $C_6H_5$ | $C_6H_5$ |
| 81 | R52 | H | S | H | H |

TABLE 6-continued

Compounds of formula (I-18a)

R51 is: *-CH2-(5-position of 2-chloropyridine)

R52 is: *-CH2-(5-position of 2-chlorothiazole)

R53 is: *-CH2-(3-position of tetrahydrofuran)

| No. | R⁵ | R^q | Y¹ | R^A | R^B |
|---|---|---|---|---|---|
| 82 | R52 | H | S | H | CH₃ |
| 83 | R52 | H | S | H | CH₂—C₆H₅ |
| 84 | R52 | H | S | H | C₆H₅ |
| 85 | R52 | H | S | CH₃ | H |
| 86 | R52 | H | S | CH₃ | CH₃ |
| 87 | R52 | H | S | CH₃ | CH₂—C₆H₅ |
| 88 | R52 | H | S | CH₃ | C₆H₅ |
| 89 | R52 | H | S | CH₂—C₆H₅ | H |
| 90 | R52 | H | S | CH₂—C₆H₅ | CH₃ |
| 91 | R52 | H | S | CH₂—C₆H₅ | CH₂—C₆H₅ |
| 92 | R52 | H | S | CH₂—C₆H₅ | C₆H₅ |
| 93 | R52 | H | S | C₆H₅ | H |
| 94 | R52 | H | S | C₆H₅ | CH₃ |
| 95 | R52 | H | S | C₆H₅ | CH₂—C₆H₅ |
| 96 | R52 | H | S | C₆H₅ | C₆H₅ |
| 97 | R52 | CH₃ | O | H | H |
| 98 | R52 | CH₃ | O | H | CH₃ |
| 99 | R52 | CH₃ | O | H | CH₂—C₆H₅ |
| 100 | R52 | CH₃ | O | H | C₆H₅ |
| 101 | R52 | CH₃ | O | CH₃ | H |
| 102 | R52 | CH₃ | O | CH₃ | CH3 |
| 103 | R52 | CH₃ | O | CH₃ | CH₂—C₆H₅ |
| 104 | R52 | CH₃ | O | CH₃ | C₆H₅ |
| 105 | R52 | CH₃ | O | CH₂—C₆H₅ | H |
| 106 | R52 | CH₃ | O | CH₂—C₆H₅ | CH₃ |
| 107 | R52 | CH₃ | O | CH₂—C₆H₅ | CH₂—C₆H₅ |
| 108 | R52 | CH₃ | O | CH₂—C₆H₅ | C₆H₅ |
| 109 | R52 | CH₃ | O | C₆H₅ | H |
| 110 | R52 | CH₃ | O | C₆H₅ | CH₃ |
| 111 | R52 | CH₃ | O | C₆H₅ | CH₂—C₆H₅ |
| 112 | R52 | CH₃ | O | C₆H₅ | C₆H₅ |
| 113 | R52 | CH₃ | S | H | H |
| 114 | R52 | CH₃ | S | H | CH3 |
| 115 | R52 | CH₃ | S | H | CH₂—C₆H₅ |
| 116 | R52 | CH₃ | S | H | C₆H₅ |
| 117 | R52 | CH₃ | S | CH₃ | H |
| 118 | R52 | CH₃ | S | CH₃ | CH₃ |
| 119 | R52 | CH₃ | S | CH₃ | CH₂—C₆H₅ |
| 120 | R52 | CH₃ | S | CH₃ | C₆H₅ |
| 121 | R52 | CH₃ | S | CH₂—C₆H₅ | H |
| 122 | R52 | CH₃ | S | CH₂—C₆H₅ | CH₃ |
| 123 | R52 | CH₃ | S | CH₂—C₆H₅ | CH₂—C₆H₅ |
| 124 | R52 | CH₃ | S | CH₂—C₆H₅ | C₆H₅ |
| 125 | R52 | CH₃ | S | C₆H₅ | H |
| 126 | R52 | CH₃ | S | C₆H₅ | CH₃ |
| 127 | R52 | CH₃ | S | C₆H₅ | CH₂—C₆H₅ |
| 128 | R52 | CH₃ | S | C₆H₅ | C₆H₅ |
| 129 | R53 | H | O | H | H |
| 130 | R53 | H | O | H | CH₃ |
| 131 | R53 | H | O | H | CH₂—C₆H₅ |
| 132 | R53 | H | O | H | C₆H₅ |
| 133 | R53 | H | O | CH₃ | H |
| 134 | R53 | H | O | CH₃ | CH₃ |
| 135 | R53 | H | O | CH₃ | CH₂—C₆H₅ |
| 136 | R53 | H | O | CH₃ | C₆H₅ |
| 137 | R53 | H | O | CH₂—C₆H₅ | H |
| 138 | R53 | H | O | CH₂—C₆H₅ | CH₃ |
| 139 | R53 | H | O | CH₂—C₆H₅ | CH₂—C₆H₅ |
| 140 | R53 | H | O | CH₂—C₆H₅ | C₆H₅ |
| 141 | R53 | H | O | C₆H₅ | H |
| 142 | R53 | H | O | C₆H₅ | CH₃ |
| 143 | R53 | H | O | C₆H₅ | CH₂—C₆H₅ |
| 144 | R53 | H | O | C₆H₅ | C₆H₅ |
| 145 | R53 | H | S | H | H |
| 146 | R53 | H | S | H | CH₃ |
| 147 | R53 | H | S | H | CH₂—C₆H₅ |
| 148 | R53 | H | S | H | C₆H₅ |
| 149 | R53 | H | S | CH₃ | H |
| 150 | R53 | H | S | CH₃ | CH₃ |
| 151 | R53 | H | S | CH₃ | CH₂—C₆H₅ |
| 152 | R53 | H | S | CH₃ | C₆H₅ |
| 153 | R53 | H | S | CH₂—C₆H₅ | H |
| 154 | R53 | H | S | CH₂—C₆H₅ | CH₃ |
| 155 | R53 | H | S | CH₂—C₆H₅ | CH₂—C₆H₅ |
| 156 | R53 | H | S | CH₂—C₆H₅ | C₆H₅ |
| 157 | R53 | H | S | C₆H₅ | H |
| 158 | R53 | H | S | C₆H₅ | CH₃ |
| 159 | R53 | H | S | C₆H₅ | CH₂—C₆H₅ |
| 160 | R53 | H | S | C₆H₅ | C₆H₅ |
| 161 | R53 | CH₃ | O | H | H |
| 162 | R53 | CH₃ | O | H | CH₃ |
| 163 | R53 | CH₃ | O | H | CH₂—C₆H₅ |
| 164 | R53 | CH₃ | O | H | C₆H₅ |
| 165 | R53 | CH₃ | O | CH₃ | H |
| 166 | R53 | CH₃ | O | CH₃ | CH₃ |
| 167 | R53 | CH₃ | O | CH₃ | CH₂—C₆H₅ |
| 168 | R53 | CH₃ | O | CH₃ | C₆H₅ |
| 169 | R53 | CH₃ | O | CH₂—C₆H₅ | H |
| 170 | R53 | CH₃ | O | CH₂—C₆H₅ | CH₃ |
| 171 | R53 | CH₃ | O | CH₂—C₆H₅ | CH₂—C₆H₅ |
| 172 | R53 | CH₃ | O | CH₂—C₆H₅ | C₆H₅ |
| 173 | R53 | CH₃ | O | C₆H₅ | H |
| 174 | R53 | CH₃ | O | C₆H₅ | CH₃ |
| 175 | R53 | CH₃ | O | C₆H₅ | CH₂—C₆H₅ |
| 176 | R53 | CH₃ | O | C₆H₅ | C₆H₅ |
| 177 | R53 | CH₃ | S | H | H |
| 178 | R53 | CH₃ | S | H | CH₃ |
| 179 | R53 | CH₃ | S | H | CH₂—C₆H₅ |
| 180 | R53 | CH₃ | S | H | C₆H₅ |
| 181 | R53 | CH₃ | S | CH₃ | H |
| 182 | R53 | CH₃ | S | CH₃ | CH₃ |
| 183 | R53 | CH₃ | S | CH₃ | CH₂—C₆H₅ |

TABLE 6-continued

Compounds of formula (I-18a)

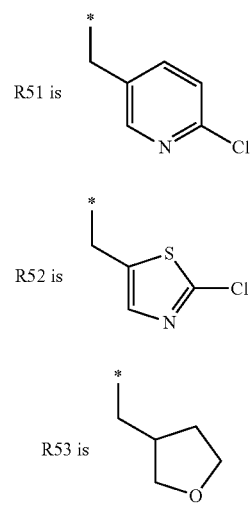

| No. | $R^5$ | $R^q$ | $Y^1$ | $R^A$ | $R^B$ |
|-----|-----|-----|-----|-----|-----|
| 184 | R53 | $CH_3$ | S | $CH_3$ | $C_6H_5$ |
| 185 | R53 | $CH_3$ | S | $CH_2—C_6H_5$ | H |
| 186 | R53 | $CH_3$ | S | $CH_2—C_6H_5$ | $CH_3$ |
| 187 | R53 | $CH_3$ | S | $CH_2—C_6H_5$ | $CH_2—C_6H_5$ |
| 188 | R53 | $CH_3$ | S | $CH_2—C_6H_5$ | $C_6H_5$ |
| 189 | R53 | $CH_3$ | S | $C_6H_5$ | H |
| 190 | R53 | $CH_3$ | S | $C_6H_5$ | $CH_3$ |
| 191 | R53 | $CH_3$ | S | $C_6H_5$ | $CH_2—C_6H_5$ |
| 192 | R53 | $CH_3$ | S | $C_6H_5$ | $C_6H_5$ |

Compounds of formula 1, 2 and 3 can be prepared as described by Holyoke et al. in WO 2009/099929 (Scheme 1).

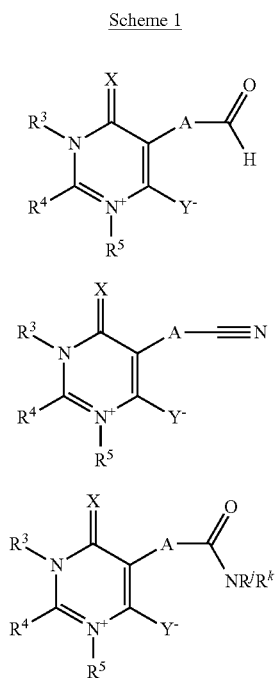

Compounds of the formula 4 can be prepared from compounds of the formula 1 by reaction with, for example, hydroxylamine hydrochloride in the presence of a base (e.g. NaOH, pyridine, triethylamine, $K_2CO_3$, NaH) as described by, for example, Sanders et al, J. Am. Chem. Soc. 2011, 133, 949-957 (Scheme 2). Compounds of the formula 5 can be prepared from compounds of the formula 4 by reaction with a chlorinating reagent (e.g. N-chlorosuccinimide, NaOCl, t-butylhypochlorite) as described by, for example, Sanders et al, J. Am. Chem. Soc. 2011, 133, 949-957. Compounds of the formula 6 can be prepared from compounds of the formula 5 by reaction with an amine nucleophile (i.e. $HNR^jR^k$) as described by, for example, Altug et al, Tetrahedron Lett. 2009, 50, 7392-7394. Compounds of the formula 7 can be prepared from compounds of the formula 6 by reaction with an electrophile (e.g. methyl iodide, cyanogen bromide, acetyl chloride etc.) in the presence of a base (e.g. NaOH, pyridine, triethylamine, $K_2CO_3$, NaH) as described by, for example, Lui et al, Pest. Manag. Sci. 2009, 65, 229-234.

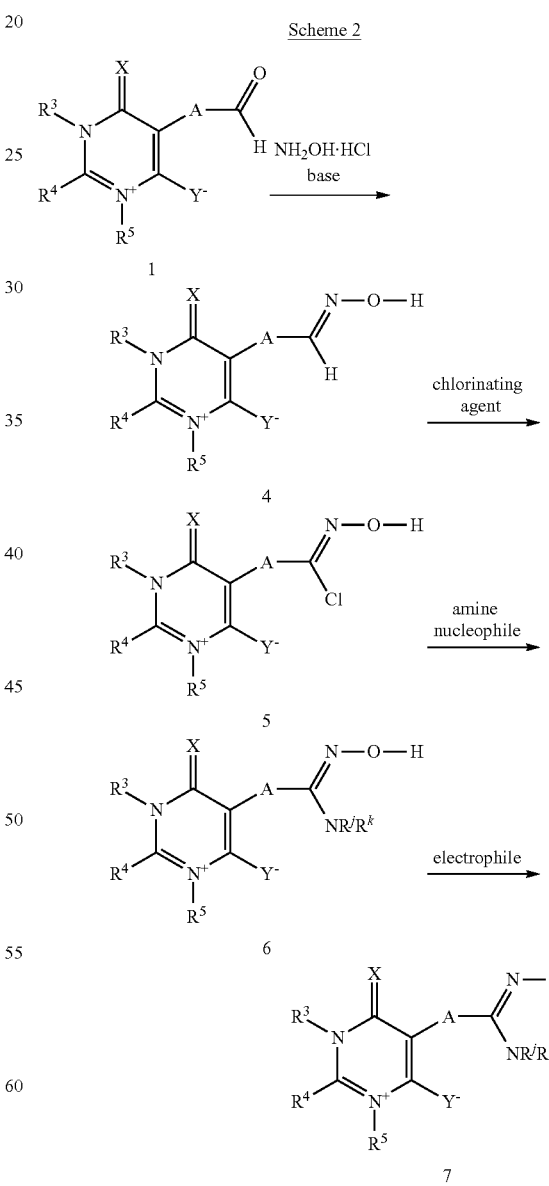

Compounds of the formula 8 can be prepared from compounds of the formula 2 by reaction with, for example, hydroxylamine hydrochloride in the presence of a base (e.g. NaOH, pyridine, triethylamine, $K_2CO_3$) as described by, for example, Neshida et al, WO 2010/065717 (Scheme 3). Compounds of the formula 9 can be prepared from compounds of the formula 8 by reaction with an electophile (e.g. methyl iodide) in the presence of a base (e.g. NaOH, pyridine, triethylamine, $K_2CO_3$, NaH) as described by, for example, Branowska et al, Bioorg. Med. Chem. Lett. 2010, 18, 3551-3558. Compounds of the formula 10 can be prepared from compounds of the formula 9 by reaction with an acylating agent (e.g. acetic anhydride) as described by, for example, Jeong et al, US 2006/0106017.

chloric acid in methanol as described by, for example, Laurent et al, Molecules, 2010, 15, 4283-4293 (Scheme 4). Compounds of the formula 12 can be prepared from compounds of the formula 11 by reaction with an amine nucleophile (i.e. $HNR^jR^k$) as described by, for example, Arnold et al, WO 2008/124849.

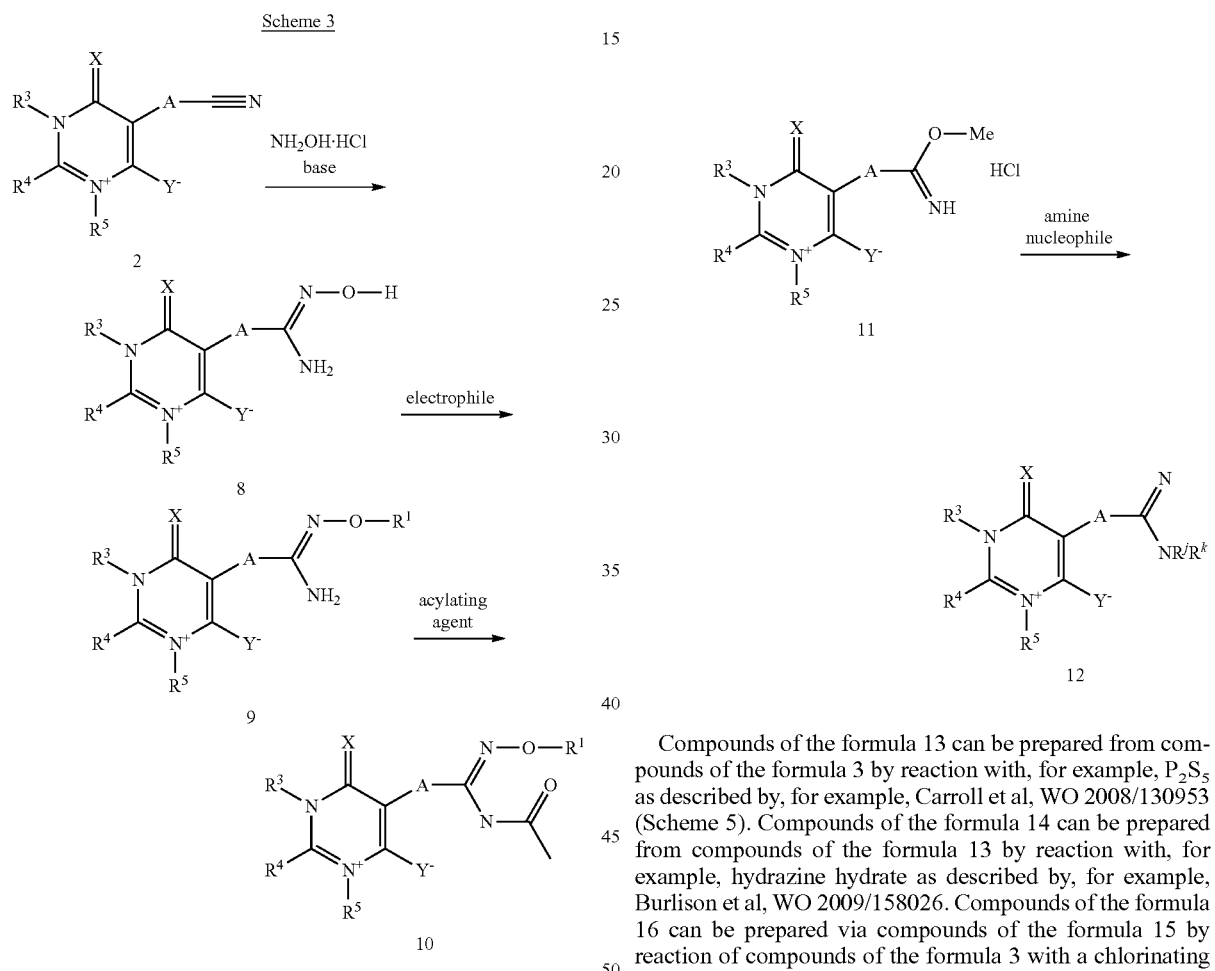

Compounds of the formula 11 can be prepared from compounds of the formula 2 by reaction with, for example, hydro- Compounds of the formula 13 can be prepared from compounds of the formula 3 by reaction with, for example, $P_2S_5$ as described by, for example, Carroll et al, WO 2008/130953 (Scheme 5). Compounds of the formula 14 can be prepared from compounds of the formula 13 by reaction with, for example, hydrazine hydrate as described by, for example, Burlison et al, WO 2009/158026. Compounds of the formula 16 can be prepared via compounds of the formula 15 by reaction of compounds of the formula 3 with a chlorinating agent (e.g. N-chlorosuccinimide, NaOCl, t-butylhypochlorite) followed by a hydrazine as described by, for example, Crimmin et al, Dalton Trans., 2011, 42, 514-522.

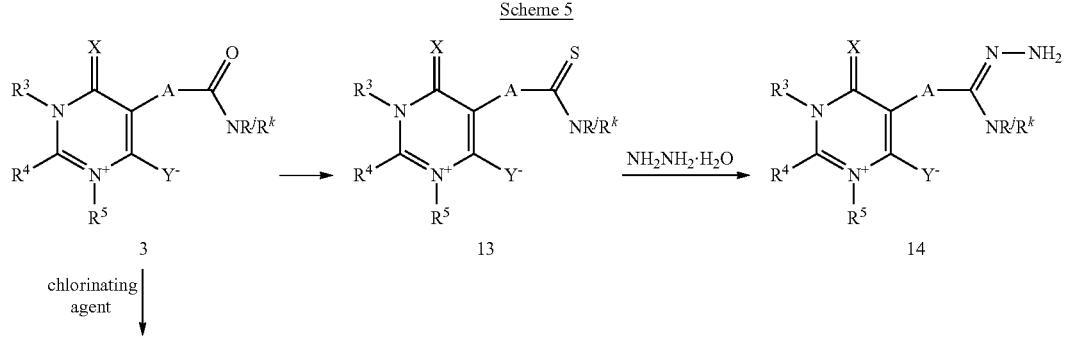

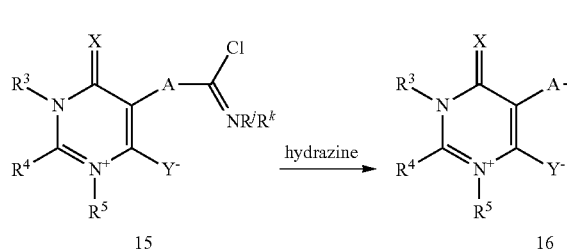

Compounds of the formula 3 where NR$^j$R$^k$ equals NR$^7$OR$^7$ (formula 18) are available from a suitable acid chloride (formula 19) and for example, a hydroxylamine NHR$^7$OR$^7$ or its hydrochloride salt in the presence of a base (e.g. NaOH, pyridine, triethylamine, K$_2$CO$_3$, NaH) as described by, for example, Wang et al, Angew. Chemie. Int. Ed, 2011, 50, 1380-1383 (Scheme II). Alternatively compounds of the formula 18 can be prepared from the corresponding carboxylic acid (formula 20) by reaction with, for example, a hydroxylamine NHR$^7$OR$^7$ or its hydrochloride salt and a coupling agent (e.g. HATU, DCC, EDCl.HCl) in the presence of a base (e.g. Et$_3$N, Hünig's Base, K$_2$CO$_3$) as described by, for example, Tae et al, Bioorg. Med. Chem. 2011, 19, 1708-1713. Furthermore compounds of the formula 18 can be prepared from compounds of the formula 20 by reaction with, for example, an alkyl chloroformate in the presence of a base (e.g. pyridine, Et$_3$N, K$_2$CO$_3$) to form mixed anhydrides of the formula 21 which are then reacted with, for example, a hydroxylamine NHR$^A$OR$^B$ or its hydrochloride salt in the presence of a base (e.g. NaOH, pyridine, triethylamine, K$_2$CO$_3$, NaH) as described by, for example, Shcherbakova et al, WO 2007/044796 (Scheme 6).

Scheme 6

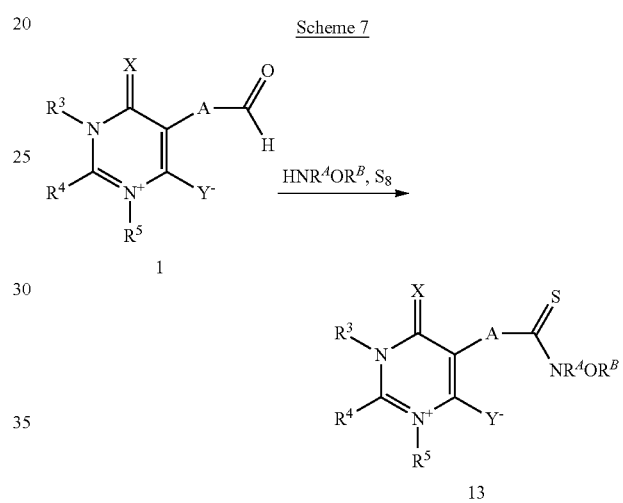

Compounds of the formula 13 can alternatively be prepared from 1 by means of the Willgerodt-Kindler reaction as exemplified by Chem et al. in WO 2009/123704 or Thompson et al. WO 2005/092304 (Scheme 7).

Scheme 7

Compounds of the formula 17 can be prepared from compounds of the formula 2 by reaction with a hydrazine (i.e. H$_2$NNR$^a$R$^1$) as described by, for example, Chambers et al, WO 2006/097766 (Scheme 8).

Scheme 8

The compounds of formula (I), N-oxides and their salts are in particular suitable for efficiently controlling arthropodal pests such as arachnids, myriapedes and insects as well as nematodes.

The compounds of formula (I), their N-oxides and their salts are especially suitable for efficiently combating the following pests:

Insects from the order of the lepidopterans (Lepidoptera), for example *Agrotis ypsilon, Agrotis segetum, Alabama* argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

beetles (Coleoptera), for example Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicomis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon coch/eariae, Phyllobius pyri, Phyllotreta chrysocephala, Phyllophaga sp., Phyllopertha horticola, Phyllotreta nemorum, Phyllotreta striolata, Popiffia japonica, Sitona lineatus and Sitophilus granaria;

flies, mosquitoes (Diptera), e.g. Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga spp., Simulium vittatum, Stomoxys calcitrans, Tabanus bovinus, Tabanus atratus, Tabanus lineola, and Tabanus similis, Tipula oleracea, and Tipula paludosa;

thrips (Thysanoptera), e.g. Dichromothrips corbetti, Dichromothrips ssp., Frankliniella fusca, Frankliniella occidentalis, Frankliniella tritici, Scirtothrips citri, Thrips oryzae, Thrips palmi and Thrips tabaci, termites (Isoptera), e.g. Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis, and Coptotermes formosanus;

cockroaches (Blattaria—Biattodea), e.g. Blattella germanica, Blattella asahinae, Periplaneta americana, Periplaneta japonica, Periplaneta brunnea, Periplaneta fuligginosa, Periplaneta austraiasiae, and Blatta orientalis;

bugs, aphids, leafhoppers, whiteflies, scale insects, cicadas (Hemiptera), e.g. Acrosternum hilare, Blissus leucopterus, Cyrtopeitis notatus, Dysdercus cingulatus, Dysdercus intermedius, Eurygaster integriceps, Euschistus impictiventris, Leptogiossus phyllopus, Lygus lineolaris, Lygus pratensis, Nezara viridula, Piesma quadrata, Solubea insularis, Thyanta perditor, Acyrthosiphon onobrychis, Adeiges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyaiopterus pruni, Hyperomyzus iactucae, Macrosiphum avenae, Macrosiphum euphorbiae, Macrosiphon rosae, Megoura viciae, Melanaphis pyrarius, Metopoiophium dirhodum, Myzus persicae, Myzus ascaionicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopaiomyzus ascaionicus, Rhopalosiphum maidis, Rhopalosiphum path, Rhopalosiphum insertum, Sappaphis mala, Sappaphis mall, Schizaphis graminum, Schizoneura ianuginosa, Sitobion avenae, Triaieurodes vaporariorum, Toxoptera aurantiiand, Viteus vitifolii, Cimex lectularius, Cimex hemipterus, Reduvius senilis, Triatoma spp., and Arilus critatus;

ants, bees, wasps, sawflies (Hymenoptera), e.g. Athalia rosae, Atta cephaiotes, Atta capiguara, Atta cephaiotes, Atta iaevigata, Atta robusta, Atta sexdens, Atta texana, Crematogaster spp., Hopiocampa minuta, Hopiocampa testudinea, Lasius niger, Monomorium pharaonis, Solenopsis geminata, Solenopsis invicta, Solenopsis richteri, Solenopsis xyioni, Pogonomyrmex barbatus, Pogonomyrmex californicus,

*Pheidoie megacephaia, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotaipa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaieus senegaiensis, Zonozerus variegatus, Hierogiyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gaffinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis; Araneida,* e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula (I) and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Compounds of formula (I) are particularly useful for controlling insects, preferably sucking or piercing insects such as insects from the genera *Thysanoptera, Diptera* and *Hemiptera,* in particular the following species:

*Thysanoptera: Frankliniella fusca, Frankliniella occidentalis, Frankliniella tritici, Scirtothrips citri, Thrips oryzae, Thrips palmi* and *Thrips tabaci, Diptera,* e.g. *Aedes aegypti, Aedes albopictus, Aedes vexans, Anastrepha ludens, Anopheles maculipennis, Anopheles crucians, Anopheles albimanus, Anopheles gambiae, Anopheles freebomi, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inomata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haem-*

*orrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

*Hemiptera*, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopalomyzus ascalonicus, Rhopalosiphum maidis, Rhopalosiphum path, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii.*

Compounds of formula (I), their N-oxides and salts are particularly useful for controlling insects of the orders *Hemiptera* and *Thysanoptera.*

Compositions (Formulations)

The invention also relates to agrochemical compositions comprising an auxiliary and at least one compound (I) or an N-oxide or salt thereof.

An agrochemical composition comprises a pesticidally effective amount of a compound (I) or an N-oxide or salt thereof. The term "effective amount" denotes an amount of the composition or of the compound (I) or an N-oxide or salt thereof, which is sufficient for controlling harmful animal pests and which does not result in a substantial damage to the treated plants. Such an amount can vary in a broad range and is dependent on various factors, such as the pest to be controlled the treated cultivated plant or material, the climatic conditions and the specific compound (I) or an N-oxide or salt thereof used.

The compounds (I), their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for Composition Types and their Preparation are
 i) Water-soluble concentrates (SL, LS)
10-60 wt % of a compound (I) or an N-oxide or salt thereof and 5-15 wt % wetting agent (e.g. alcohol alkoxylates) are dissolved in water and/or in a water-soluble solvent (e.g. alcohols) up to 100 wt %. The active substance dissolves upon dilution with water.
 ii) Dispersible concentrates (DC)
5-25 wt % of a compound (I) or an N-oxide or salt thereof and 1-10 wt % dispersant (e.g. polyvinylpyrrolidone) are dissolved in up to 100 wt % organic solvent (e.g. cyclohexanone). Dilution with water gives a dispersion.
 iii) Emulsifiable concentrates (EC)
15-70 wt % of a compound (I) or an N-oxide or salt thereof and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.
 iv) Emulsions (EW, EO, ES)
5-40 wt % of a compound (I) or an N-oxide or salt thereof and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.
 v) Suspensions (SC, OD, FS)
In an agitated ball mill, 20-60 wt % of a compound (I) or an N-oxide or salt thereof are comminuted with addition of 2-10 wt % dispersants and wetting agents (e.g. sodium lignosulfonate and alcohol ethoxylate), 0, 1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.
 vi) Water-dispersible granules and water-soluble granules (WG, SG)
50-80 wt % of a compound (I) or an N-oxide or salt thereof are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.
 vii) Water-dispersible powders and water-soluble powders (WP, SP, WS)
50-80 wt % of a compound (I) or an N-oxide or salt thereof are ground in a rotorstator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.
 viii) Gel (GW, GF)
In an agitated ball mill, 5-25 wt % of a compound (I) or an N-oxide or salt thereof are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.
 iv) Microemulsion (ME)
5-20 wt % of a compound (I) or an N-oxide or salt thereof are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.
 iv) Microcapsules (CS)
An oil phase comprising 5-50 wt % of a compound (I) or an N-oxide or salt thereof, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.
 ix) Dustable powders (DP, DS)
1-10 wt % of a compound (I) or an N-oxide or salt thereof are ground finely and mixed intimately with up to 100 wt % solid carrier, e.g. finely divided kaolin.
 x) Granules (GR, FG)
0.5-30 wt % of a compound (I) or an N-oxide or salt thereof is ground finely and associated with up to 100 wt % solid carrier (e.g. silicate). Granulation is achieved by extrusion, spray-drying or the fluidized bed.
 xi) Ultra-low volume liquids (UL)
1-50 wt % of a compound (I) or an N-oxide or salt thereof are dissolved in up to 100 wt % organic solvent, e.g. aromatic hydrocarbon.

The compositions types i) to xi) may optionally comprise further auxiliaries, such as 0, 1-1 wt % bactericides, 5-15 wt % anti-freezing agents, 0, 1-1 wt % anti-foaming agents, and 0, 1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially pre-mixed components, e.g. components comprising compounds I and/or active substances from the groups A) to O), may be mixed by the user in a spray tank and further auxiliaries and additives may be added, if appropriate.

In a further embodiment, either individual components of the composition according to the invention or partially pre-mixed components, e.g. components comprising at least one and/or compound (I) or an N-oxide or salt thereof active substances from the groups M1-M27 and FI-FXII below, can be applied jointly (e.g. after tank mix) or consecutively.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphosethyl, azinphos-methyl, chlorethoxyfos, chlorfenvinphos, chlormephos, chlorpyrifos, chlorpyrifos-methyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bio-allethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichlorophenyl)-5-trifluoromethyl-4,5-dihydro-isoxazol-3-yl]-2-methyl-N-(2,2,2-trifluoroethyl)-benzamide (M22.2), 4-[5-(3,5-Dichloro-phenyl)-5-trifluoromethyl-4,5-dihydroisoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4), 4-[5-(3,5-Dichlorophenyl)-5-trifluoromethyl-4,5-dihydro-isoxazol-3-yl]-N-[(methoxyimino)methyl]-2-methylbenzamide (M22.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydroisoxazol-3-yl]naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydroisoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropylethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide(M23.3), 5-Bromo-2-(3-chloro-pyridin-2-yl)-2H-pyrazole-3-carboxylic acid [2-bromo-4-chloro-6-(1-cyclopropylethylcarbamoyl)-phenyl]-amide(M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methylhydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethylhydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2HCF_2CF_2CF_2CH_2C(CN)_2CH_2CH_2CF_3$) (M24.1) and 2-(2,2,3,3,4,4,5,5-octafluoropentyl)-2-(3,3,4,4,4-pentafluorobutyl)-malonodinitrile ($CF_2HCF_2CF_2$—$CF_2CH_2C(CN)_2CH_2CH_2CF_2CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro-1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethylpyridazin-3-yl)-3-aza-bicyclo[3.2.1]octane(M27.3).

The commercially available compounds of the group M may be found in The Pesticide Manual, 14th Edition, British Crop Protection Council (2006) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822, 779.-AKD 1022 and its preparation have been described in U.S. Pat. No. 6,300,348.—M21.1 is known from WO 2007/ 101540.—Isoxazolines M22.1 to M22.8 have been described in e.g. WO 2005/085216, WO 2007/079162, WO 2007/ 026965, WO 2009/126668 and WO 2009/051956. Anthranilamides M23.1 to M23.6 have been described in WO 2008/ 72743 and WO 2008/72783, those M23.7 to M23.12 in WO 2007/043677. Malononitriles M24.1 and M24.2 have been described in WO 02/089579, WO 02/090320, WO 02/090321, WO 04/006677, WO 05/068423, WO 05/068432 and WO 05/063694. Aminofuranones M26.1 to M6.10 have been described eg. in WO 2007/115644. Alkynylether M27.1 is described e.g. in JP 2006131529. Organic sulfur compounds have been described in WO 2007060839. Pyripyropene derivative M27.2 has been described in WO 2008/66153 and WO 2008/108491. Pyridazin M27.3 has been described in JP 2008/115155.

The following list of active substances, in conjunction with which the compounds according to the invention can be used, is intended to illustrate the possible combinations but does not limit them:

F.I) Respiration Inhibitors
F.I-1) Inhibitors of complex III at Qo site (e.g. strobilurins)
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxyacrylic acid methyl ester and 2 (2-(3-(2,6-dichlorophenyl)-1-methyl-allylideneaminooxymethyl)phenyl)-2-methoxyimino-N methyl-acetamide;
oxazolidinediones and imidazolinones: famoxadone, fenamidone;
F.I-2) Inhibitors of complex II (e.g. carboxamides):
carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2-yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;
F.I-3) Inhibitors of complex III at Qi site: cyazofamid, amisulbrom;
F.I-4) Other respiration inhibitors (complex I, uncouplers) diflumetorim; tecnazen; ferimzone; ametoctradin; silthiofam;
nitrophenyl derivates: binapacryl, dinobuton, dinocap, fluazinam, nitrthal-isopropyl, organometal compounds: fentin salts, such as fentin-acetate, fentin chloride or fentin hydroxide;
F.II) Sterol biosynthesis inhibitors (SBI fungicides)
F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole; imidazoles: imazalil, pefurazoate, oxpoconazole, prochloraz, triflumizole; pyrimidines, pyridines and piperazines: fenarimol, nuarimol, pyrifenox, triforine;
F.II-2) Delta14-reductase initors (Amines, e.g. morpholines, piperidines) morpholines: aldimorph, dodemorph, dodemorph-acetate, fenpropimorph, tridemorph; piperidines: fenpropidin, piperalin;
spiroketalamines: spiroxamine;
F.II-3) Inhibitors of 3-keto reductase: hydroxyanilides: fenhexamid;
F.III) Nucleic acid synthesis inhibitors
F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;
F.III-2) DNA topisomerase inhibitors: oxolinic acid;
F.III-3) Nucleotide metabolism (e.g. adenosin-deaminase) hydroxy(2-amino)-pyrimidines: bupirimate;
F.IV) Inhibitors of cell division and or cytoskeleton
F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5a]pyrimidine
F.IV-2) Other cell division inhibitors
benzamides and phenyl acetamides: diethofencarb, ethaboxam, pencycuron, fluopicolide, zoxamide;
F.IV-3) Actin inhibitors: benzophenones: metrafenone;
F.V) Inhibitors of amino acid and protein synthesis
F.V-1) Mmethionine synthesis inhibitors (anilino-pyrimidines)
anilino-pyrimidines: cyprodinil, mepanipyrim, nitrapyrin, pyrimethanil;
F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;
F.VI) Signal transduction inhibitors
F.VI-1) MAP/Histidine kinase inhibitors (e.g. anilino-pyrimidines) dicarboximides: fluoroimid, iprodione, procymidone, vinclozolin;
phenylpyrroles: fenpiclonil, fludioxonil;
F.VI-2) G protein inhibitors: quinolines: quinoxyfen;
F.VII) Lipid and membrane synthesis inhibitors
F.VII-1) Phospholipid biosynthesis inhibitors organophosphorus compounds: edifenphos, iprobenfos, pyrazophos; dithiolanes: isoprothiolane;
F.VII-2) Lipid peroxidation
aromatic hydrocarbons: dicloran, quintozene, tecnazene, tolclofos-methyl, biphenyl, chloroneb, etridiazole;
F.VII-3) Carboxyl acid amides (CAA fungicides) cinnamic or mandelic acid amides: dimethomorph, flumorph, mandiproamid, pyrimorph; valinamide carbamates: benthiavalicarb, iprovalicarb, pyribencarb, valifenalate and N-(1-(1-(4-cyanophenyl)ethanesulfonyl)-but-2-yl) carbamic acid-(4-fluorophenyl) ester;
F.VII-4) Compounds affecting cell membrane permeability and fatty acides carbamates: propamocarb, propamocarb-hydrochlorid
F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: guanidine, dodine, dodine free base, guazatine, guazatineacetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-5-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethylphenoxy)-2,5-dimethyl-phenyl)-N-ethyl-N methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]-piperidin-4-yl}-thiazole-4-carboxylic acid methyl-(R)-1,2,3, 4-tetrahydro-naphthalen-1-yl-amide, methoxy-acetic acid 6-tertbutyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), Ulocladium oudemansii (e.g. the product BOTRY-ZEN from BotriZen Ltd., New Zealand), Chitosan (e.g. ARMOUR-ZEN from BotriZen Ltd., New Zealand).

Applications

The animal pest, i.e. the insects, arachnids and nematodes, the plant, soil or water in which the plant is growing can be contacted with compounds of formula (I), their N-oxides and salts or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of the invention or the pesticidal compositions comprising them may be used to protect growing plants and crops from attack or infestation by animal pests, especially insects, acaridae or arachnids by contacting the plant/crop with a pesticidally effective amount of at least one compound of the invention. The term "crop" refers both to growing and harvested crops.

The compounds of the invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of at least one compound of the invention or a composition comprising such a compound.

Moreover, animal pests may be controlled by contacting the target pest, its food supply, habitat, breeding ground or its locus with a pesticidally effective amount of at least one compound of the invention. As such, the application may be carried out before or after the infection of the locus, growing crops, or harvested crops by the pest.

The compounds of the invention can also be applied preventively to places at which occurrence of the pests is expected.

The compounds of the invention may be also used to protect growing plants from attack or infestation by pests by contacting the plant with a pesticidally effective amount of at least one compound of the invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5): 1225-35., Curr Opin Chem. Biol. 2006 October; 10(5):487-91. Epub 2006 Aug. 28, Biomaterials. 2001 March; 22(5): 405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 0 242 236, EP-A 242 246) or oxynil herbicides (see e.g. U.S. Pat. No. 5,559,024) as a result of conventional methods of breeding or genetic engineering.

Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m², preferably from 0.001 to 20 g per 100 m².

Customary application rates in the protection of materials are, for example, from 0.01 g to 1000 g of active compound per m² treated material, desirably from 0.1 g to 50 g per m².

Insecticidal compositions for use in the impregnation of materials typically contain from 0.001 to 95 weight %, preferably from 0.1 to 45 weight %, and more preferably from 1 to 25 weight % of at least one repellent and/or insecticide. For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of the invention are effective through both contact (via soil, glass, wall, bed net, carpet, plant parts or animal parts), and ingestion (bait or plant part).

The compounds of the invention may also be applied against non-crop insect pests, such as ants, termites, wasps, flies, mosquitos, crickets, or cockroaches. For use against said non-crop pests, compounds of the invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it.

The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, ° leyl ethoxylate having 3-7 mol of ethylene oxide, fatty alcohol ethoxylate, perfume oils such as ethereal oils, esters of medium fatty acids with lower alcohofs, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the invention and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula (I) and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-H-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of the invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, a compound of the invention is applied to the crops or the surrounding soil, or is directly applied to the nest of ants or the like.

Seed Treatment

The compounds of the invention are also suitable for the treatment of seeds in order to protect the seed from insect pest, in particular from soil-living insect pests and the resulting plant's roots and shoots against soil pests and foliar insects.

The compounds of the invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the invention thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the compounds of the invention may be used for treating seed from plants, which tolerate the action of herbicides or fungicides or insecticides owing to breeding, including genetic engineering methods.

For example, the compound of the invention can be employed in treatment of seeds from plants, which are resistant to herbicides from the group consisting of the sulfonylureas, imidazolinones, glufosinate-ammonium or glyphosateisopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the compound of the invention can be used for the treatment of seed from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the compound of the invention is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethylenepyrimidines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An Example of a Gelling Agent is Carrageen (Satiagel®)

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also provides to seed comprising a compound of the formula (I), or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula (I), their N-oxides and/or veterinarily acceptable salts thereof are in particular also suitable for being used for combating parasites in and on animals.

One object of the invention is therefore to provide new methods to control parasites in and on animals. Another object of the invention is to provide safer pesticides for animals. Another object of the invention is to provide pesticides for animals that may be used in lower doses than existing pesticides. Another object of the invention is to provide pesticides for animals, which provide a long residual control of parasites.

The invention also relates to compositions containing a parasiticidally effective amount of at least one compound of formula (I), N-oxide or veterinarily acceptable salt thereof and an acceptable carrier, for combating parasites in and on animals.

The invention also provides a method for treating, controlling, preventing and protecting animals against infestation and infection by parasites, which comprises orally, topically or parenterally administering or applying to the animals a parasiticidally effective amount of a compound of the invention or a composition comprising it.

The invention also provides a process for the preparation of a composition for treating, controlling, preventing or protecting animals against infestation or infection by parasites which comprises a parasiticidally effective amount of a compound of the invention or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of the invention are suitable for combating endo- and ectoparasites in and on animals.

Compounds of the invention and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the invention and compositions comprising them are suitable for systemic and/or non-systemic control of ecto- and/or endoparasites. They can be active against all or some stages of development.

The compounds of the invention are especially useful for combating ectoparasites.

The compounds of the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea,*

*Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurystemus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders *Arnblycerina* and *Ischnocerina*), e.g. *Trimenopon* spp., *Menopon* spp., *Trinoton* spp., *Bovicola* spp., *Wemeckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp, Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula (I) and compositions containing them are particularly useful for the control of pests from the orders Diptera, Siphonaptera and Ixodida.

Moreover, the use of the compounds of formula (I) and compositions containing them for combating mosquitoes is especially preferred.

The use of the compounds of the invention and compositions containing them for combating flies is a further preferred embodiment of the present invention.

Furthermore, the use of the compounds of the invention and compositions containing them for combating fleas is especially preferred.

The use of the compounds of the invention and compositions containing them for combating ticks is a further preferred embodiment of the present invention.

The compounds of the invention also are especially useful for combating endoparasites (roundworms nematoda, thorny headed worms and planarians). Administration can be carried out both prophylactically and therapeutically.

Administration of the compounds of the invention is carried out directly or in the form of suitable preparations, orally, topically/dermally or parenterally.

For oral administration to warm-blooded animals, compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with 0.01 mg/kg to 100 mg/kg of animal body weight per day of the compound of the invention, preferably with 0.5 mg/kg to 100 mg/kg of animal body weight per day.

Alternatively, the compounds of the invention may be administered to animals parenterally, for example, by intraruminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compound of the invention may be transdermally administered to animals. For parenteral administration, the dosage form chosen should provide the animal with 0.01 mg/kg to 100 mg/kg of animal body weight per day of the compound of the invention.

The compounds of the invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compound of the invention. In addition, the compounds of the invention may be formulated as ear tags for animals, particularly quadrupeds such as cattle and sheep.

Suitable Preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal. Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol. Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention generally comprisefrom about 0.001 to 95% of the compound of the invention.

Generally it is favorable to apply the compounds of the invention in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of the invention against endoparasites in concentrations of 10 ppm to 2 percent by weight, preferably of 0.05 to 0.9 percent by weight, very particularly preferably of 0.005 to 0.25 percent by weight.

In a preferred embodiment, the compositions comprising the compounds of the invention are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of the invention. A detailed list of plastics and elastomers as well as preparation procedures for the shaped articles is given e.g. in WO 03/086075.

The invention is now illustrated in further details by the following examples, without imposing any limitation thereto.

EXAMPLES

The compounds can be characterized e.g. by coupled High Performance Liquid Chromatography/mass spectrometry (HPLC/MS), by $^1$H-NMR and/or by their melting points. The following analytical procedures were employed:

Method A: Analytical HPLC column: RP-18 column Chromolith Speed ROD from Merck KgaA (Germany). Elution: acetonitrile+0.1% trifluoroacetic acid (TFA)/water+0.1% trifluoroacetic acid (TFA) in a ratio of from 5:95 to 95:5 in 5 minutes at 40° C.

Method B: Analytical UPLC column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0,8-1,0 mL/min in 1,50 minutes at 60° C.

MS-method: ESI positive.

1H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Example 1

1-[(6-chloro-3-pyridyl)methyl]-3-[4-(N'-hydroxycarbamimidoyl)phenyl]-4-oxo-pyrido[1,2-a]pyrimidin-1-ium-2-olate

Step 1: Synthesis of 1-[(6-chloro-3-pyridyl)methyl]-3-(4-cyanophenyl)-4-oxo-pyrido[1,2-a]pyrimidin-1-ium-2-olate To a mixture of 53 mg (0.36 mmol) (4-cyanophenyl)boronic acid, 100 mg (0.24 mmol) 1-[(6-chloro-3-pyridyl)methyl]-3-iodo-4-oxo-pyrido[1,2-a]pyrimidin-1-ium-2-olate (Synthesis described in WO 2009/099929), 35 mg (0.05 mmol) bis(triphenylphosphino)-palladium dichloride and 17 mg (0.05 mmol) caesium carbonate was added 160 ml of dioxane. The mixture was heated to 100° C. for 18 hours. Silica was added and the product was obtained by column chromatographie (dichloromethane/methanol) (24 mg).

Step 2: Synthesis of 1-[(6-chloro-3-pyridyl)methyl]-3-[4-(N-hydroxycarbamimidoyl)phenyl]-4-oxo-pyrido[1,2-a]pyrimidin-1-ium-2-olate 30 mg (0.08 mmol) of 1-[(6-chloro-3-pyridyl)methyl]-3-(4-cyanophenyl)-4-oxo-pyrido[1,2-a]pyrimidin-1-ium-2-olate (product of step 1) were dissolved in 2 ml DMSO. 13 mg (0.2 mmol) hydroxylammonium hydrochloride and 22 mg (0.2 mmol) potassium t-butoxide were added and the mixture was stirred at room temperature for 18 hours. The mixture was taken up with 10 ml of brine and extracted with ethyl acetate. The organic phases were dried with magnesium chloride and the solvent was removed under reduced pressure. The desired product was sufficiently pure without further purification (10 mg).
HPLC-MS: 1.74 min, M=422.5

Example 2

1-[(6-chloro-3-pyridyl)methyl]-3-[3-(N'-hydroxycarbamimidoyl)phenyl]-4-oxo-pyrido[1,2-a]pyrimidin-1-ium-2-olate

Step 1: Synthesis of 1-[(6-chloro-3-pyridyl)methyl]-3-(3-cyanophenyl)-4-oxo-pyrido[1,2-a]pyrimidin-1-ium-2-olate To a mixture of 80 mg (0.54 mmol) (3-cyanophenyl)boronic acid, 150 mg (0.36 mmol) 1-[(6-chloro-3-pyridyl)methyl]-3-iodo-4-oxo-pyrido[1,2-a]pyrimidin-1-ium-2-olate (Synthesis described in WO 2009/099929), 1.6 mg (0.07 mmol) palladium acetate, 21 mg (0.07 mmol) tri-tert-butylphosphonium tetrafluoroborate and 295 mg caesium carbonate was added 50 ml of dioxane under argon. The mixture was heated to 80° C. for 48 hours. Silica was added and the product was obtained by column chromatographie (dichloromethane/methanol) (21 mg).

Step 2: Synthesis of 1-[(6-chloro-3-pyridyl)methyl]-3-[3-(N-hydroxycarbamimidoyl)phenyl]-4-oxo-pyrido[1,2-a]pyrimidin-1-ium-2-olate 15 mg (0.04 mmol) of 1-[(6-chloro-3-pyridyl)methyl]-3-(3-cyanophenyl)-4-oxo-pyrido[1,2-a]pyrimidin-1-ium-2-olate (product of step 1) were dissolved in 2 ml DMSO. 7 mg (0.1 mmol) hydroxylammonium hydrochloride and 11 mg (0.1 mmol) potassium t-butoxide were added and the mixture was stirred at 50° C. for 48 hours. The mixture was taken up with 10 ml of brine and extracted with ethyl acetate. The organic phases were dried with magnesium chloride and the solvent was removed under reduced pressure. The desired product was sufficiently pure without further purification (5 mg). HPLC-MS: 1.75 min, M=422.5

Example 3

1-[(6-chloro-3-pyridyl)methyl]-3-[4-[hydroxy(methyl)carbamoyl]phenyl]-4-oxo-pyrido[1,2-a]pyrimidin-1-ium-2-olate (B)

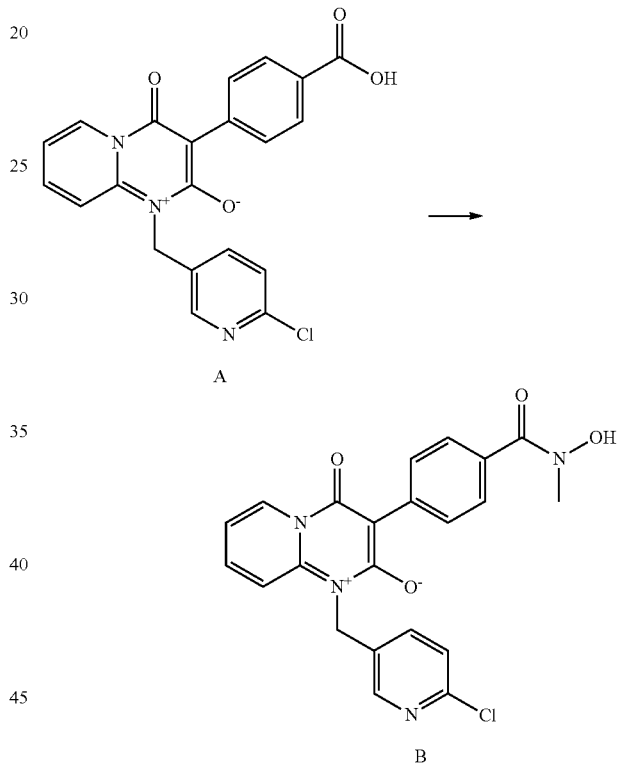

To a stirred suspension of A (100 mg, 0.25 mmol) in THF (10 mL) at room temperature was added HATU (2-(1H-7-azabenzotriazol-1-yl)-1,1,3,3-tetramethyluronium hexafluoro phosphate) (140 mg, 0.37 mmol) and DIPEA (diisopropylethylamine) (0.11 mL, 0.63 mmol). After 5 min, N-methylhydroxylamine hydrochloride (31 mg, 0.37 mmol) was added and the reaction mixture was stirred at room temperature for 16 h. The reaction mixture was then diluted with $CH_2Cl_2$ (75 mL) and washed with aq. HCl (4%, 10 mL), dried over $MgSO_4$ and concentrated to afford a bright yellow gummy solid. Purification by flash chromatography using a gradient of $CH_2Cl_2$/MeOH afforded the title compound B as a yellow foam (79 mg, 74%). $^1$H NMR (MeOD): 9.44 (d, J=5.8 Hz, 1H), 8.73 (d, 4.7 Hz, 1H), 8.48-8.40 (m, 1H), 7.84-7.73 (m, 4H), 7.66 (d, J=8.0 Hz, 2H), 7.54 (t, J=7.0 Hz, 1H), 7.43 (d, J=8.5 Hz, 1H), 5.67 (s, 2H), 3.34 (s, 3H) ppm.

Examples of the compounds of the invention are listed in the following Tables 7 and 8

TABLE 7

Compounds of formula (I-A)

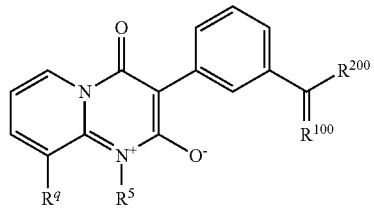
(I-A)

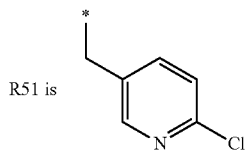
R51 is

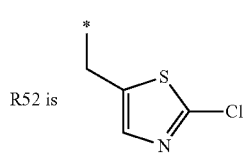
R52 is

| No. | $R^5$ | $R^q$ | $R^{100}$ | $R^{200}$ | MS Method | MS Retention time | Mass Charge Ratio | 1 H-NMR |
|---|---|---|---|---|---|---|---|---|
| 1 | $R^{51}$ | H | NH | $N(CH_3)OH$ | A | 1.92 | 436 | |
| 2 | $R^{51}$ | H | NH | $N(H)OH$ | A | 1.82 | 422 | |
| 3 | $R^{51}$ | H | NH | $NH-O-C(O)CH_3$ | A | 2.07 | 464 | |
| 4 | $R^{51}$ | H | NH | $NH-O-C(O)-CH(CH_3)_2$ | B | 0.97 | 492 | |
| 5 | $R^{51}$ | H | NH | $NH-O-C(O)$-cyclopropyl | A | 2.32 | 490 | |
| 6 | $R^{51}$ | H | NH | $NH-O-C_2H_5$ | B | 0.73 | 450 | |
| 7 | $R^{51}$ | H | NH | $NH-O-CH_2-CH=CH_2$ | B | 2.11 | 462 | |
| 8 | $R^{51}$ | H | NOH | $N(CH_3)_2$ | B | 0.71 | 450 | |
| 9 | $R^{51}$ | H | NOH | $NH(CH_3)$ | B | 0.71 | 436 | |
| 10 | $R^{51}$ | H | NOH | $NH-CH_2-CF_3$ | A | 2.23 | 405 | |
| 11 | $R^{51}$ | H | $NOCH_3$ | $N(CH_3)_2$ | B | 0.76 | 461 | |
| 12 | $R^{51}$ | H | $NOCH_3$ | $NH(CH_3)$ | A | 1.95 | 450 | |
| 13 | $R^{51}$ | H | $NOCH_3$ | NH-Phenyl | A | 2.71 | 512 | |
| 14 | $R^{52}$ | H | $NOCH_3$ | $NH-CH_2$-Phenyl | | | | 1H-NMR (CDCL3, 400 MHz): 4.33 (d, 2H), 5.55 (br, 2H), 7.2-7.4 (m, 12H), 7.61 (d, 1H), 7.89 (d, 1H), 9.45 (d, 1H) 400 MHz, CDCl3 (ppm): d = 3.86 (s 3H), 4.33 (d 2H), 5.55 (br 2H) |
| 15 | $R^{52}$ | $CH_3$ | $NOCH_3$ |  pyrrolidinyl | B | 1.21 | 511 | |
| 16 | $R^{51}$ | $CH_3$ | $NO-CH_2-CF_3$ | $N(CH_3)_2$ | B | 2.09 | 552 | |
| 17 | $R^{51}$ | H | O | $N(OH)-C(CH_3)_3$ | B | 1.03 | 479 | |
| 18 | $R^{51}$ | H | O | $N(OH)-CH(CH_3)_2$ | B | 0.97 | 465 | |
| 19 | $R^{51}$ | H | O | $N(OH)-C_2H_5$ | B | 0.82 | 451 | |
| 20 | $R^{51}$ | H | O | $N(OH)-CH_2$-Phenyl | A | 2.92 | 513 | |
| 21 | $R^{51}$ | H | O | $N(H)-O-CH_2-CF_3$ | A | 2.43 | 505 | |

TABLE 8

Compounds of formula (I-B)

(I-B)

R51 is *-CH2-(pyridine-Cl)

R52 is *-CH2-(thiazole-Cl)

| No. | $R^5$ | $R^q$ | $R^{100}$ | $R^{200}$ | MS Method | MS Retention time | Mass Charge Ratio |
|---|---|---|---|---|---|---|---|
| 22 | $R^{51}$ | H | NH | N(H)OH | A | 1.75 | 422 |
| 23 | $R^{51}$ | H | NH | N(CH$_3$)OH | A | 2.52 | 437 |
| 24 | $R^{51}$ | H | NH | NH—O—C$_2$H$_5$ | A | 1.91 | 450 |
| 25 | $R^{51}$ | H | NH | NH—O—CH$_2$—CH=CH$_2$ | A | 2.03 | 462 |
| 26 | $R^{51}$ | H | NH | NH—O—CH$_2$—C≡CH | B | 0.74 | 460 |
| 27 | $R^{51}$ | H | NH | NH—O—C$_3$H$_7$ | B | 0.77 | 464 |
| 28 | $R^{51}$ | H | NH | NH—O—C(O)—CH(CH$_3$)$_2$ | B | 0.77 | 464 |
| 29 | $R^{51}$ | H | NH | NH—O—C(O)-cyclopropyl | B | 0.88 | 404 |
| 30 | $R^{51}$ | H | NCH$_2$ | N(CH$_3$)OH | B | 0.719 | 450 |
| 31 | $R^{51}$ | H | NCH$_3$ | N(CH$_2$)OCH$_3$ | B | 0.734 | 464 |
| 32 | $R^{51}$ | H | NOH | N(CH$_3$)$_2$ | A | 1.89 | 450 |
| 33 | $R^{51}$ | H | NOH | NH(CH$_3$) | B | 0.67 | 436 |
| 34 | $R^{51}$ | H | NOH | NH—C$_2$H$_5$ | B | 0.71 | 450 |
| 35 | $R^{51}$ | H | NOH | NH—CH$_2$—CF$_3$ | B | 0.77 | 405 |
| 36 | $R^{51}$ | H | NOH | NH(CH$_3$H$_7$) | A | 2.13 | 464 |
| 37 | $R^{51}$ | H | NOH | NH—CH$_2$—CH$_2$—CF$_3$ | B | 0.79 | 518 |
| 38 | $R^{51}$ | H | NOH | pyrazolyl | A | 2.35 | 478 |
| 39 | $R^{51}$ | H | NOCH$_3$ | NH—CH$_2$—CF$_3$ | A | 2.5 | 518 |
| 40 | $R^{52}$ | CH$_3$ | NO—CH$_2$-Phenyl | N(CH$_3$)$_2$ | B | 0.93 | 560 |
| 41 | $R^{51}$ | H | NCH$_3$ | N(CH$_3$)$_2$ | B | 0.721 | 448 |
| 42 | $R^{51}$ | H | NC$_2$H$_5$ | N(CH$_2$H$_5$)$_2$ | A | 2.311 | 490 |
| 43 | $R^{51}$ | H | N-cyclopropyl | N(CH$_3$)$_2$ | B | 0.765 | 474 |
| 44 | $R^{51}$ | H | NCH$_3$ | N(CH$_3$)phenyl | B | 0.847 | 510 |
| 45 | $R^{51}$ | H | O | N(OH)CH$_3$ | | | |
| 46 | $R^{51}$ | H | O | N(OH)C$_2$H$_5$ | A | 2.05 | 451 |
| 47 | $R^{51}$ | H | O | NH—O—C$_2$H$_5$ | A | 2.06 | 451 |
| 48 | $R^{51}$ | H | O | NH—O—CH$_2$—CF$_3$ | A | 2.46 | 505 |
| 49 | $R^{51}$ | H | O | N(OH)C(CH$_3$)$_3$ | A | 2.74 | 479 |

B. Biological Examples

The activity of the compounds of formula I of the present invention could be demonstrated and evaluated in biological tests described in the following.

If not otherwise specified the test solutions are prepared as follow: The active compound is dissolved at the desired concentration in a mixture of 1:1 (vol:vol) distilled water:acteon. The test solution is prepared at the day of use and in general at concentrations of ppm (wt/vol).

B.1 Cowpea Aphid (*Aphis craccivora*)

Potted cowpea plants colonized with approximately 100-150 aphids of various stages were sprayed after the pest population has been recorded. Population reduction was assessed after 24, 72, and 120 hours.

In this test, the compounds 3, 4, 7, 11, 12, 19, 22, 23, 24 and 39 respectively, at 300 ppm showed a mortality of at least 75% in comparison with untreated controls.

B.2 Diamond Back Moth (*plutella xylostella*)

The active compound is dissolved at the desired concentration in a mixture of 1:1 (vol/vol) distilled water:aceteone. Surfactant (Alkamuls® EL 620) is added at a rate of 0.1% (vol/vol).The test solution is prepared at the day of use.

Leaves of cabbage were dipped in test solution and air-dried. Treated leaves were placed in petri dishes lined with moist filter paper and inoculated with ten 3rd instar larvae.

Mortality was recorded 72 hours after treatment. Feeding damages were also recorded using a scale of 0-100%.

In this test, the compounds 3 and 16 respectively, at 500 ppm showed a mortality of at least 75% in comparison with untreated controls.

B.3 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 28±1° C. and about 80±5% relative humidity for 5 days. Egg and larval mortality was then visually assessed.

In this test, the compounds 15, 16, 17, 23, 32, 35 and 45 respectively, at 2500 ppm showed a mortality of at least 75% in comparison with untreated controls.

B.4 Orchid *Thrips* (*dichromothrips corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant.

*Thrips* potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult thrips. The petri dishes are then covered with lids. All test arenas are held under continuous light and a temperature of about 28° C. for duration of the assay. After 4 days, the numbers of live thrips are counted on each flower, and along inner walls of each petri dish. The level of thrips mortality is extrapolated from pre-treatment thrips numbers.

In this test, the compounds 3, 4, 14, 35 and 39 respectively, at 300 ppm showed a mortality of at least 75% in comparison with untreated controls.

B.5 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was pla-ced into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 12 and 23 respectively, at 500 ppm showed a mortality of at least 75% in comparison with untreated controls.

B.6 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 2, 3, 4, 5, 8, 9, 11, 12, 13, 14, 15, 16, 17, 18, 22, 23, 24, 25, 28, 30, 31, 34, 36, 39 and 48 respectively, at 2500 ppm showed a mortality of at least 75% in comparison with untreated controls.

B.7 Tobacco Budworm (*Heliothis virescens*) I

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1, 14, 16, 17, 21, 23, 32, 34, 35, 36, 37, 45, 46, 47, 48 and 49 respectively, at 2500 ppm showed a mortality of at least 75% in comparison with untreated controls.

B.8 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, the compounds 15, 17, 18, and 23 respectively, at 2500 ppm showed a mortality of at least 75% in comparison with untreated controls.

B.9 Green Peach Aphid (*Myzus persicae*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, the compounds 3, 22, 23, 24, and 25 at 500 ppm showed a mortality of at least 75% in comparison with untreated controls.

B.10 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 3, 4, 5, 9, 11, 12, 14, 22 and 23 respectively, at 500 ppm showed a mortality of at least 75% in comparison with untreated controls.

Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 3, 5, 6, 8, 9, 11, 12, 14, 16, 22, 23, 28, 29, 33, 34, 36 and 37 respectively, at 500 ppm showed a mortality of at least 75% in comparison with untreated controls.

The invention claimed is:

1. A compound of formula (I),

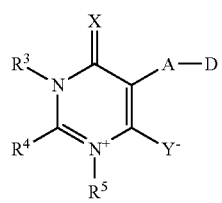

(I)

wherein
D is $C(R^2)=N-Z-R^1$ or $C(=Y^1)NR^AY^2R^B$
X is O or S;
Y, $Y^1$, $Y^2$ are independently O or S;
Z is O, $S(O)_n$, $N-R^a$ or a direct bond;
A is phenyl, naphthyl or a 5- or 6-membered heteroaromatic ring system, or a 8-10-membered heteroaromatic bicyclic ring system, each unsubstituted or substituted with up to 6 substituents $R^b$;

$R^A$ is H, $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl, $C_3$-$C_6$-cycloalkenyl, each unsubstituted or substituted with at least one substituent independently selected from $R^r$; or $Q^1$;

$R^B$ is H, $C_1$-$C_{10}$alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, $-Si(R^f)_3$, $-S(O)_mR^h$, $-S(O)_nN(R^d)_2$, $-C(=O)OR^g$, $-C(=O)N(R^d)_2$, $-C(=S)R^e$, $-C(=S)OR^g$, $-C(=S)N(R^d)_2$, $-C(=NR^d)R^e$, or $Q^1$ $R^1$ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, $-N(R^d)_2$, $-N(R^d)C(=O)R^e$, $-Si(R^f)_3$, $-OR^g$, $-SR^g$, $-S(O)_mR^h$, $-S(O)_nN(R^d)_2$, $-C(=O)R^e$, $-C(=O)OR^g$, $-C(=O)N(R^d)_2$, $-C(=S)R^e$, $-C(=S)OR^g$, $-C(=S)N(R^d)_2$, $-C(=NR^d)R^e$, or $Q^1$;

with the proviso that $R^1$ is not $-OR^g$, CN or nitro if Z is O;

$R^2$ is $NR^iR^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, $C(=O)R^e$, $-C(=O)OR^g$, $-C(=O)N(R^d)_2$, $C(=S)R^e$, $-C(=S)OR^g$, $-C(=S)N(R^d)_2$, $C(=NR^d)R^e$, halogen, cyano, O-$Q^1$ or S-$Q^1$;

or R3 and R4 together with the contiguous linking nitrogen and carbon atom to which they are bonded form any of the following substituted heterocyclic ring systems E-1 to E-9:

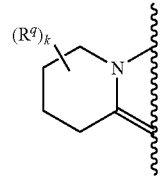

E-1

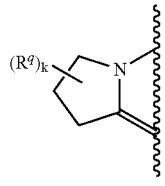

E-2

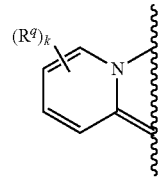

E-3

-continued

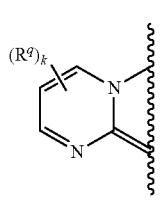
E-4

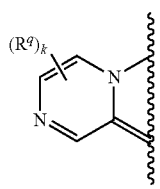
E-5

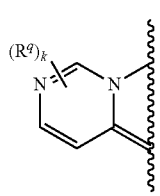
E-6

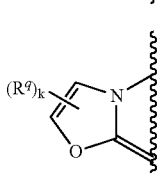
E-7

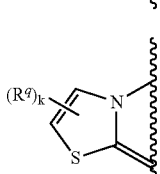
E-8

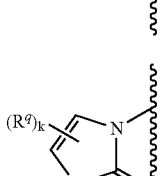
E-9

$R^5$ is $(CR^{5a}R^{5b})_a R^{5c}$ wherein a is 0, 1, 2 or 3;
or
$R^5$ is $C_3$-$C_6$ cycloalkyl unsubstituted or substituted with 1 to 4 substituents selected from the group consisting of halogen, $C_1$-$C_2$ alkyl, 1 cyclopropyl and 1 $CF_3$;

each $R^{5a}$ and $R^{5b}$ is independently H, halogen, cyano, hydroxy, amino, nitro, OCN, SCN, CHO, C(=O)OH, C(=O)NH$_2$, C(=S)NH$_2$ or SO$_2$NH$_2$, or $C_1$-$C_6$ alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{12}$-cycloalkylcycloalkyl, $C_5$-$C_8$-alkylcycloalkylalkyl, $C_3$-$C_6$-cycloalkenyl, $C_1$-$C_6$-alkoxy, $C_3$-$C_6$-cycloalkoxy, $C_4$-$C_8$-cycloalkylalkoxy, $C_2$-$C_6$-alkenyloxy or $C_2$-$C_6$-alkynyloxy, each unsubstituted or substituted with at least one substituent $R^r$;

$R^{5c}$ is H, halogen, cyano, hydroxy, amino, nitro, OCN, SCN, CHO, C(=O)OH, C(=O)NH$_2$, C(=S)NH$_2$, SO$_2$NH$_2$, C(=O)R$^l$, C(=O)OR$^l$, NHR$^l$, NR$^l$R$^l$, C(=O)NR$^l$R$^m$, C(=S)NR$^l$R$^m$, SO$_2$NR$^l$R$^m$, OR$^l$, OC(=O)R$^m$, OC(=O)OR$^l$, OC(=O)N(R$^m$)$_2$, N(R$^m$)C(=O)R$^m$, N(R$^m$)C(=O)OR$^l$, N(R$^m$)C(=O)N(R$^a$)$_2$, OSO$_2$R$^l$, OSO$_2$N(R$^a$)$_2$, NR$^m$SO$_2$R$^l$, NR$^m$SO$_2$N(R$^n$)$_2$, Si(R$_f$)$_3$, $C_1$-$C_8$-alkyl, $C_2$-$C_8$-alkenyl, $C_2$-$C_8$-alkynyl, $C_3$-$C_{10}$-cycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_3$-$C_8$-cycloalkenyl, $C_1$-$C_8$-alkylthio, $C_1$-$C_8$-alkylsulfinyl, $C_1$-$C_8$-alkylsulfonyl, $C_3$-$C_8$-cycloalkylthio, $C_3$-$C_8$-cycloalkylsulfinyl, $C_3$-$C_8$-cycloalkylsulfonyl, $C_4$-$C_{10}$-cycloalkylalkylthio, $C_4$-$C_{10}$-cycloalkylalkylsulfinyl, $C_4$-$C_{10}$-cycloalkylalkylsulfonyl, $C_2$-$C_8$-alkenylthio, $C_2$-$C_8$-alkenylsulfinyl, $C_2$-$C_8$-alkenylsulfonyl, $C_2$-$C_8$-alkynylthio, $C_2$-$C_8$-alkynylsulfinyl or $C_2$-$C_8$-alkynylsulfonyl, each unsubstituted or substituted with at least one substituent $R^r$, or $Q^2$;

each $R^a$ is independently H, CN, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —N(R$^d$)$_2$, —Si(R$^f$)$_3$, —OR$^g$, —SR$^g$, —S(O)$_m$R$^h$, —S(O)$_m$N(R$^d$)$_2$, —C(=O)R$^e$, —C(=O)R$^e$, —C(=O)N(R$^d$)$_2$, —C(=S)R$^a$, —C(=S)OR$^g$, —C(=S)N(R$^d$)$_2$, —C(=NR$^d$)R$^e$ or $Q^1$;

or $R^1$ and $R^a$ together form a group =C(R$^n$)$_2$, =S(O)$_n$R$^h$, =S(O)$_m$N(R$^d$)$_2$, =NR$^d$ or =NOR$^g$;

or $R^1$ and $R^a$ together form a $C_2$-$C_7$ alkylene chain, thus forming, together with the nitrogen atom to which they are bonded, a 3-, 4-, 5-, 6-, 7- or 8-membered ring, where the alkylene chain is optionally interrupted by 1 or 2 O, S and/or NR$^p$ and/or 1 or 2 of the CH$_2$ groups of the alkylene chain are optionally replaced by a group C=O, C=S and/or C=NR$^d$, and/or the alkylene chain is unsubstituted or substituted with one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl and $Q^1$;

each $R^b$ is independently halogen, cyano, azido, nitro, SCN, SF$_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals are unsubstituted or substituted with one or more $R^c$, Si(R$^f$)$_3$, OR$^g$, OS(O)$_n$R$^h$, —S(O)$_n$R$^h$, S(O)$_n$N(R$^d$)$_2$, N(R$^d$)$_2$, C(=O)R$^e$, C(=O)OR$^g$, —C(=NR$^d$)R$^e$, C(=O)N(R$^d$)$_2$, C(=S)N(R$^d$)$_2$ or $Q^4$;

each $R^c$ is independently, halogen, cyano, azido, nitro, —SCN, SF$_5$, $C_1$-$C_{10}$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, Si(R$^f$)$_3$, OR$^o$, OSO$_2$R$^o$, S(O)$_n$R$^n$, S(O)$_n$N(R$^p$)$_2$, NR$^p$)$_2$, C(=O)N(R$^p$)$^2$, C(=S)N(R$^p$)$_2$, C(=O)OR$^o$, or $Q^1$ or two $R^c$ present on one carbon atom together form =O, =C(R$^m$)$_2$, =S, =S(O)$_n$R$^n$, =S(O)$_m$N(R$^p$)$_2$, =NR$^p$, =NOR$^o$, =NNR$^p$, or two $R^c$ together with the carbon atoms to which the two $R^e$ are bonded to form a 3-, 4-, 5-, 6-, 7- or 8-membered saturated or partly unsaturated carbocyclic or heterocyclic ring;

each $R^d$ is independently hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $S(O)_mR^n$, —$S(O)_mN(R^p)_2$, $C(=O)R^m$, $C(=O)OR^o$, $C(=O)N(R^p)_2$, $C(=S)R^n$, $C(=S)SR^o$, $C(=S)N(R^p)_2$, $C(=NR^p)R^n$ or $Q^1$; or two $R^d$ together are a $C_2$-$C_7$ alkylene chain, forming a 3- to 8-membered saturated, partly saturated or aromatic heterocyclic ring together with the nitrogen atom they are bonded to, wherein the alkylene chain optionally contain 1 or 2 oxygen atoms, sulfur atoms or nitrogen atoms, and wherein the alkylene chain is unsubstituted or substituted with at least one substituent selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl and $Q^1$;

each $R^e$ is independently $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $Si(R^f)_3$, $OR^o$, $OSO_2R^n$, $S(O)_nR^n$, $S(O)_nN(R^p)_2$, $N(R^p)_2$, $C(=O)N(R^p)^2$, $C(=S)N(R^p)_2$, $C(=O)OR^o$ or $Q^1$;

each $R^f$ is independently hydrogen, halogen, $C_1$-$C_6$-alkyl, $C_1$-$C_6$-haloalkyl, $C_1$-$C_6$-alkoxyalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxyalkyl, $C_1$-$C_6$-haloalkoxyalkyl or phenyl which is unsubstituted or substituted with one or more substituents $R^q$;

each $R^g$ is independently H, $C_1$-$C_6$-alkyl, $C_1$-$C_6$-haloalkyl, $C_1$-$C_6$-alkylsulfinyl, $C_1$-$C_6$-alkylsulfonyl, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^f)_3$, $S(O)_nR^o$, —$S(O)_nNR^p_2$, —$C(=O)R^o$, $C(=O)N(R^p)_2$, $C(=S)N(R^p)_2$, $C(=O)OR^o$ or $Q^1$;

each $R^h$ is independently $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^f)_3$, $S(O)_nR^o$, —$S(O)_nNR^p_2$, $N(R^p)_2$, —$N=C(R^n)_2$, —$C(=O)R^o$, $C(=O)N(R^p)_2$, $C(=S)N(R^p)_2$, $C(=O)OR^o$ or $Q^1$;

$R^i$ is independently cyano, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals are unsubstituted or substituted with one or more substituents $R^c$, $N(R^d)_2$, $Si(R^f)_3$, $OR^g$, $S(O)_nR^h$, $C(=O)R^c$, $C(=O)N(R^d)_2$, $C(=O)OR^g$, $C(=S)R^c$, $C(=S)N(R^d)_2$, $C(=S)SR^g$, $C(=NR^d)R^e$ or $Q^1$;

$R^k$ is independently H or $R^i$;

or $R^i$ and $R^k$ together are =$C(R^n)_2$, =$S(O)_nR^h$, =$S(O)_nNC(R^d)_2$, =$NR^d$ or =$NOR^g$;

each $R^l$ is independently $C_1$-$C_6$-alkyl, $C_2$-$C_6$-alkenyl, $C_2$-$C_6$-alkynyl, $C_3$-$C_8$-cycloalkyl, $C_4$-$C_8$-alkylcycloalkyl, $C_4$-$C_8$-cycloalkylalkyl, $C_6$-$C_{10}$-cycloalkylcycloalkyl, $C_5$-$C_{10}$-alkylcycloalkylalkyl or $C_3$-$C_6$-cycloalkenyl, each unsubstituted or substituted with at least one substituent independently selected from $R^r$; or $Q^1$;

each $R^m$ is independently H or $R^1$;

each $R^n$ is independently $C_1$-$C_4$ alkyl, $C_1$-$C_6$ cycloalkyl, alkoxyalkyl, phenyl or benzyl;

each $R^o$ is independently H, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or may carry 1 or 2 radicals selected from 1 or 2 $C_1$-$C_4$-alkoxy groups and (=O); or is $Q^5$;

each $R^p$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals are unsubstituted, partially or fully halogenated and/or optionally carry 1 or 2 radicals selected from 1 or 2 $C_1$-$C_4$-alkoxy groups and (=O); or is $Q^5$; or two groups $R^p$ are together a $C_2$-$C_6$ alkylene chain forming a 3- to 7-membered saturated, partly saturated or unsaturated ring together with the nitrogen atom they are bonded to, wherein the alkylene chain optionally contains 1 or 2 heteroatoms selected from oxygen, sulfur, nitrogen, S(O), $S(O)_2$ and NO and is unsubstituted or substituted with one or more halogen, $C_1$-$C_4$-haloalkyl, $C_1$-$C_4$-alkoxy and $C_1$-$C_4$-haloalkoxy;

each $R^q$ is independently H, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic group and cyclo-aliphatic radicals are unsubstituted or substituted with one or more $R^t$, $Si(R^f)_3$, $OR^o$, $OS(O)_nR^o$, —$S(O)_nR^n$, $S(O)_nN(R^p)_2$, $N(R^p)_2$, $C(=O)R^o$, $C(=O)OR^o$, —$C(=NR^p)R^o$, $C(=O)N(R^p)_2$, $C(=S)N(R^p)_2$, phenyl, unsubstituted or substituted with halogen, cyano, nitro, $C_1$-$C_6$-alkyl, $C_1$-$C_6$-haloalkyl, $C_1$-$C_6$-alkoxy or $C_1$-$C_6$-haloalkoxy or is $Q^4$; or two $R^q$ together on one atom of a partly saturated heterocyclic are =O, =$C(R^n)_2$, =$S(O)_mR^n$, =$S(O)_mN(R^p)_2$, =$NR^p$, =$NOR^o$ or =$NN(R^p)_2$; or two $R^q$ on adjacent carbon atoms form a bridge selected from $CH_2CH_2CH_2CH_2$, $CH=CH-CH=CH$, $N=CH-CH=CH$, $CH=N-CH=CH$, $N=CH-N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^p$, $CH_2CH=N$, $CH=CH-NR^p$, $OCH=N$, $SCH=N$ and form together with the carbon atoms to which the two $R^q$ are bonded to a 5-membered or 6-membered partly saturated, unsaturated, aromatic carbocyclic or heterocyclic ring, wherein the ring is unsubstituted or substituted with one or two substituents selected from =O, OH, CH$_3$, OCH$_3$, halogen, halomethyl and halomethoxy;

each R$^r$ is independently halogen, cyano, nitro, CHO, C(=O)OH, C(=O)NH$_2$, C(=O)R$^s$, C(=O)OR$^s$, C(=O)N(R$^s$)$_2$, OR$^s$, S(O)$_n$R$^s$, SO$_2$N(R$^f$)$_2$, Si(R$^s$)$_3$ or Z$^1$Q$^2$;

each R$^s$ is independently C$_1$-C$_6$-alkyl, C$_2$-C$_6$-alkenyl, C$_2$-C$_6$-alkynyl, C$_3$-C$_8$-cycloalkyl, C$_4$-C$_8$-alkylcycloalkyl, C$_4$-C$_8$-cycloalkylalkyl, C$_6$-C$_{10}$-cycloalkylcycloalkyl, C$_5$-C$_{10}$-alkylcycloalkylalkyl or C$_3$-C$_6$-cycloalkenyl, each unsubstituted or substituted with at least one substituent independently selected from the group consisting of halogen, cyano, nitro, CHO, C(=O)OH, C(=O)NH$_2$, C$_1$-C$_4$ alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-cycloalkylamino, C$_2$-C$_4$-alkoxyalkyl, C$_2$-C$_4$-alkylcarbonyl, C$_2$-C$_6$-alkoxycarbonyl, C$_2$-C$_6$-alkylcarbonyloxy, C$_2$-C$_6$-alkylcarbonylthio, C$_2$-C$_6$-alkylaminocarbonyl, C$_3$-C$_8$-dialkylaminocarbonyl and C$_3$-C$_6$-trialkylsilyl; or is phenyl or a 5- or 6-membered heteroaromatic ring, each unsubstituted or substituted with at least one substituent independently selected from the group consisting of C$_1$-C$_6$-alkyl, C$_1$-C$_6$-haloalkyl, C$_2$-C$_6$-alkenyl, C$_2$-C$_6$-alkynyl, C$_3$-C$_8$-cycloalkyl, C$_4$-C$_8$-alkylcycloalkyl, C$_4$-C$_8$-cycloalkylalkyl, C$_6$-C$_{10}$-cycloalkylcycloalkyl, C$_5$-C$_{10}$-alkylcycloalkylalkyl, C$_3$-C$_6$-cycloalkenyl, halogen, cyano, nitro, CHO, C(=O)OH, C(=O)NH$_2$, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-cycloalkylamino, C$_2$-C$_4$-alkoxyalkyl, C$_2$-C$_4$-alkylcarbonyl, C$_2$-C$_6$-alkoxycarbonyl, C$_2$-C$_6$-alkylcarbonyloxy, C$_2$-C$_6$-alkylcarbonylthio, C$_2$-C$_6$-alkylaminocarbonyl, C$_3$-C$_8$-dialkylaminocarbonyl and C$_3$-C$_6$-trialkylsilyl;

each R$^t$ is independently hydrogen, halogen, cyano, nitro, OH, SH, SCN, SF$_5$, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tert-butyldimethylsilyl, C$_1$-C$_6$-alkyl, C$_2$-C$_6$-alkenyl, C$_2$-C$_6$-alkyl, C$_3$-C$_8$-cycloalkyl, wherein the four last mentioned aliphatic and cyclo-aliphatic radicals are unsubstituted, partially or fully halogenated and/or substituted with (=O) and/or carry 1 or 2 radicals selected from C$_1$-C$_4$-alkoxy; Q$^5$; or two R$^t$ present on the same carbon atom are together =O, =CH(C$_1$-C$_4$), =C(C$_1$-C$_4$-alkyl) C$_1$-C$_4$-alkyl, =N(C$_1$-C$_6$-alkyl) or =NO(C$_1$-C$_6$-alkyl);

each R$^u$ is independently C$_1$-C$_6$-alkyl, C$_2$-C$_6$-alkenyl, C$_2$-C$_6$-alkynyl, C$_3$-C$_8$-cycloalkyl, C$_4$-C$_8$-alkylcycloalkyl, C$_4$-C$_8$-cycloalkylalkyl, C$_6$-C$_{10}$-cycloalkylcycloalkyl, C$_5$-C$_{10}$-alkylcycloalkylalkyl, C$_3$-C$_6$-cycloalkenyl, C$_2$-C$_6$-alkylcarbonyl or C$_2$-C$_6$-alkoxycarbonyl, each unsubstituted or substituted with at least one substituent independently selected from the group consisting of halogen, cyano, nitro, CHO, C(=O)OH, C(=O)NH$_2$, C(=O)R$^n$, C(=O)OR$^o$, C(=O)N(R$^p$)$_2$, OR$^o$, S(O)$_n$R$^o$, SO$_2$N(R$^p$)$_2$ and Si(R$^f$)$_3$; or is H;

each R$^v$ is independently C$_1$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent R$^r$;

each Q$^1$ is independently phenyl which is unsubstituted or substituted with 1, 2, 3, 4 or 5 radicals R$^q$, or a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring is unsubstituted or substituted with one or more radicals R$^q$;

each Q$^2$ is independently a 3- to 10-membered ring or a 7- to 11-membered ring system, each ring or ring system containing ring members selected from carbon atoms and up to 4 heteroatoms independently selected from up to 2O, up to 2S, and up to 4N, wherein up to 3 carbon atom ring members are independently selected from C(=O) and C(=S) and the sulfur atom ring members are independently selected from S(=O)$_x$(=NR$^p$)$_z$, each ring or ring system unsubstituted or substituted with up to 5 substituents R$^r$ each Q$^3$ is independently a 3- to 10-membered ring or a 7- to 11-membered ring system, each ring or ring system containing ring members selected from carbon atoms and up to 4 heteroatoms independently selected from up to 2O, up to 2S, and up to 4N, wherein up to 3 carbon atom ring members are independently selected from C(=O) and C(=S) and the sulfur atom ring members are independently selected from S(=O)$_x$(=NR$^p$)$_z$, each ring or ring system unsubstituted or substituted with up to 4 substituents R$^r$;

each Q$^5$ is independently phenyl, benzyl, pyridyl, phenoxy, which are unsubstituted, partially or fully halogenated and/or carry 0, 1, 2 or 3 substituents selected from the group consisting of C$_1$-C$_6$-alkyl, C$_1$-C$_6$-haloalkyl, C$_1$-C$_6$-alkoxy, C$_1$-C$_6$-haloalkoxy, (C$_1$-C$_6$-alkoxy)carbonyl, (C$_1$-C$_6$-alkyl)amino and di-(C$_1$-C$_6$-alkyl)amino, each Z$^1$ is independently a direct bond, O, S(O)$_n$, NR$^u$, CH(R$^u$), C(R$^u$)=C(R$^u$), C=C, C(R$^u$)$_2$O, OC(R$^u$)$_2$, C(=X$^1$), C(=X$^1$)E, EC(=X$^1$), C(=NOR$^u$) or C(=NN(R$^u$)$_2$);

each X$^1$ is independently O, S or NR$^v$;

each E is independently O, S or NR$^v$;

each k is independently an integer from 0 to 6 each m is independently 1 or 2;

each n is independently 0, 1 or 2;

x and z in each case are independently 0, 1 or 2, provided that the sum x+z is 0, 1 or 2 for each ring;

or the N-oxide or salt thereof.

2. The compound of claim 1 of formula (I-1)

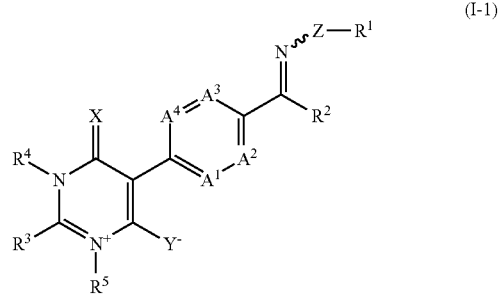

wherein
each $A^1, A^2, A^3, A^4$ is independently N or C—$R^b$,
with the proviso that no more than two of $A^1, A^2, A^3$ and $A^4$ are N.

3. The compound of claim 1 of formula (I-2)

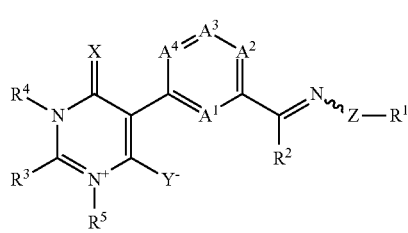

(I-2)

wherein
each $A^1, A^2, A^3, A^4$ ist independently N or C—$R^b$,
with the proviso that no more than two of $A^1, A^2, A^3$ and $A^4$ are N.

4. The compound of claim 1 of formula (I-3),

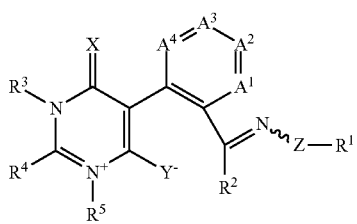

(I-3)

wherein
each $A^1, A^2, A^3, A^4$ is independently N or C—$R^b$,
with the proviso that no more than two of $A^1, A^2, A^3$ and $A^4$ are N.

5. The compound of claim 1 of formula (1-4)

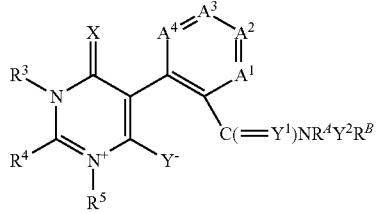

(I-4)

wherein
each $A^1, A^2, A^3, A^4$ is independently N or C—$R^b$,
with the proviso that no more than two of $A^1, A^2, A^3$ and $A^4$ are N.

6. The compound of claim 1 of formula (I-5)

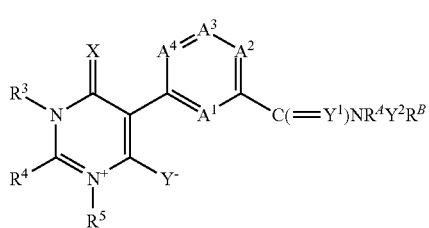

(I-5)

wherein
each $A^1, A^2, A^3, A^4$ is independently N or C—$R^b$,
with the proviso that no more than two of $A^1, A^2, A^3$ and $A^4$ are N.

7. The compound of claim 1 of formula (I-6)

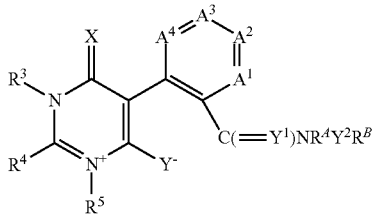

(I-6)

wherein
each $A^1, A^2, A^3, A^4$ is independently N or C—$R^b$,
with the proviso that no more than two of $A^1, A^2, A^3$ and $A^4$ are N.

8. The compound of claim 1, wherein
X is O;
Y is O and
each $A^1, A^2, A^3, A^4$ independently N or C—$R^b$,
with the proviso that no more than one of $A^1, A^2, A^3$ and $A^4$ is N.

9. The compound of claim 1, wherein
$R^5$ is $CR^{5a}R^{5b}R^{5c}$;
$R^{5a}$ is hydrogen, halogen, cyano or $C_1$-$C_4$ alkyl;
$R^{5b}$ is hydrogen, halogen or —$CH_5$;
$R^{5c}$ is a heterocyclic ring system D1-D55:

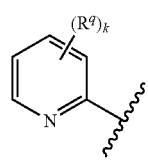

D-1

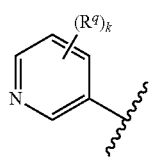

D-2

| | |
|---|---|
| 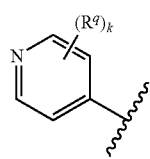 D-3 | 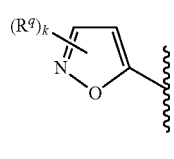 D-13 |
| 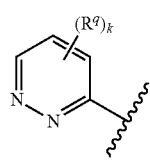 D-4 | 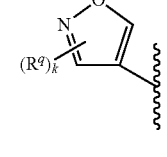 D-14 |
| 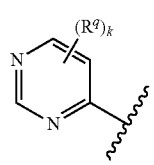 D-5 | 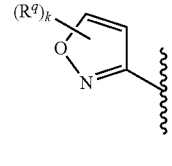 D-15 |
| 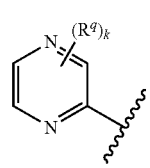 D-6 | 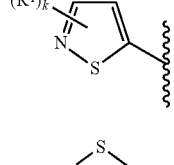 D-16 |
| 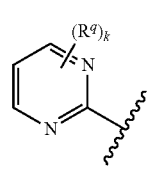 D-7 | 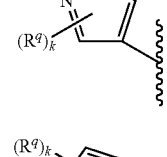 D-17 |
| 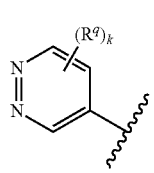 D-8 | 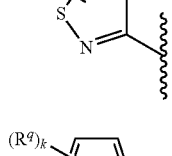 D-18 |
| 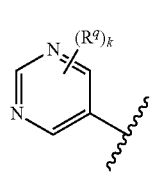 D-9 | 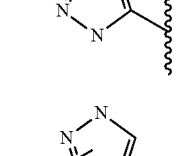 D-19 |
| 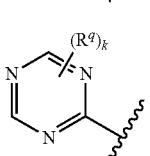 D-10 | 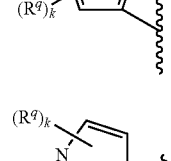 D-20 |
| 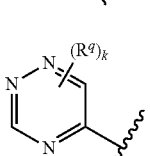 D-11 | 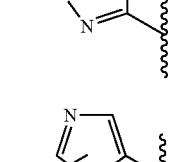 D-21 |
| 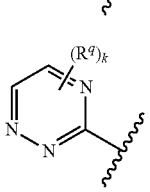 D-12 | 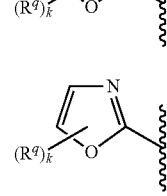 D-22, D-23 |

-continued
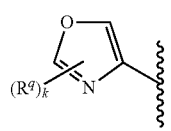 D-24
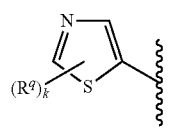 D-25
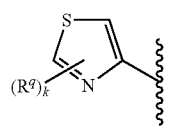 D-26
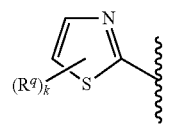 D-27
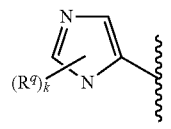 D-28
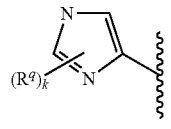 D-29
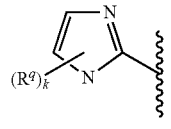 D-30
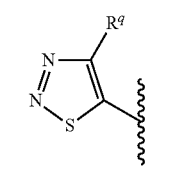 D-31
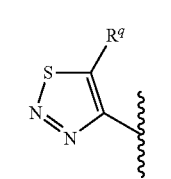 D-32
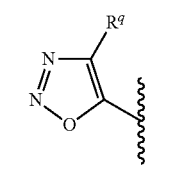 D-33
-continued
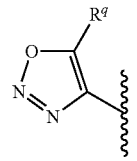 D-34
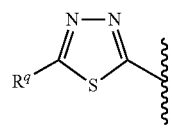 D-35
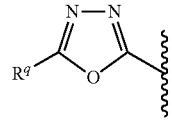 D-36
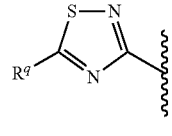 D-37
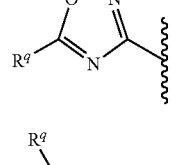 D-38
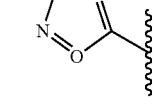 D-39
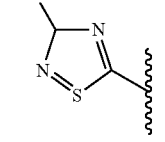 D-40
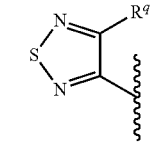 D-41
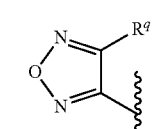 D-42
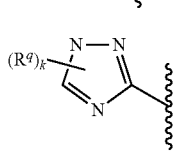 D-43
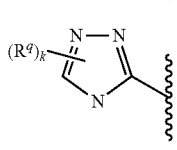 D-44

-continued
D-45 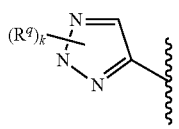
D-46 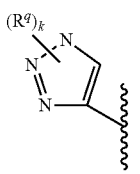
D-47 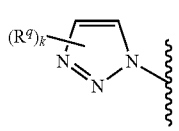
D-48 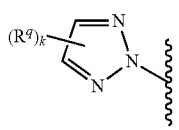
D-49 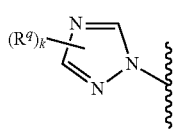
D-50 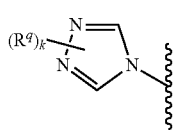
D-51 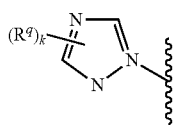
D-52 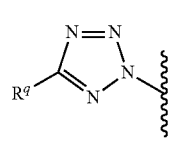
D-53 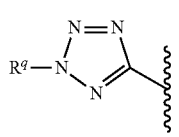
D-54 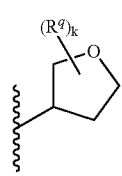
-continued
D-55 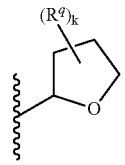
and
each k is independently 0, 1, 2, 3 or 4.
10. The compound of claim 1 of formula (I-7), (I-8), (I-9), (I-10), (I-11) or (I-12),
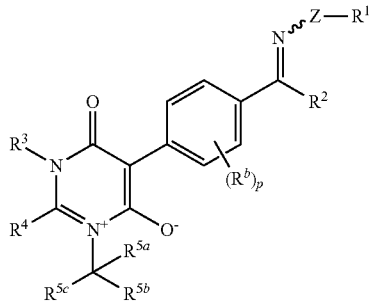
(I-7)
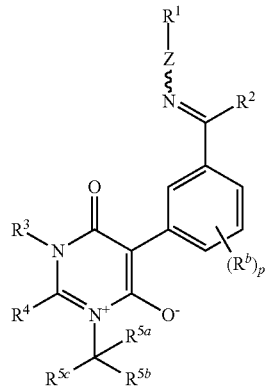
(I-8)
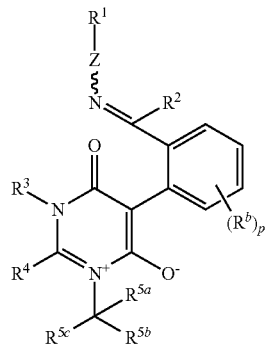
(I-9)

-continued

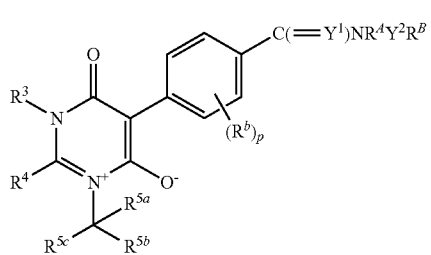
(I-10)

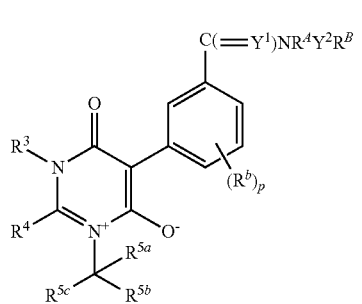
(I-11)

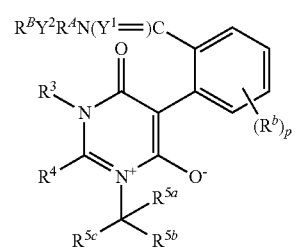
(I-12)

wherein
$Y^1$, $Y^2$ are independently O or S;
$R^A$, $R^B$ are independently H, ($C_1$-$C_6$)-alkyl, benzyl or phenyl;
Z is O, N—$R^a$ or a direct bond;
$R^1$ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$, —N($R^d$)$_2$, —N($R^d$)C(=O)$R^e$, —Si($R^f$)$_3$, —O$R^g$, —S$R^g$, —S(O)$_m$$R^h$, —S(O)$_n$N($R^d$)$_2$, —C(=O)$R^e$, —C(=O)O$R^g$, —C(=O)N($R^d$)$_2$, —C(=S)$R^e$, —C(=S)O$R^g$, —C(=S)N($R^d$)$_2$ or —C(=N$R^d$)$R^e$;
with the proviso that $R^1$ is not —O$R^g$, CN or nitro if Z is O;
$R^2$ is N$R^j$$R^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, O-$Q^1$ or S-$Q^1$;
$R^3$ and $R^4$ together with the nitrogen and carbon atom to which they are bonded, form any of the following substituted heterocyclic ring systems E-1 E-2, E-3 or E-9:

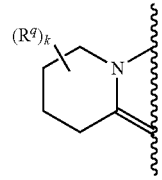
E-1

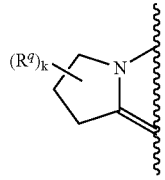
E-2

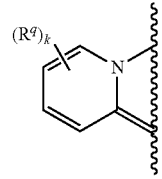
E-3

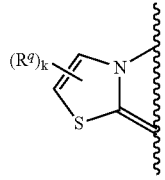
E-8

$R^{5a}$ is hydrogen, halogen, cyano or $C_1$-$C_4$ alkyl;
$R^{5b}$ is hydrogen, halogen or —CH$_3$;
$R^{5c}$ is a heterocyclic ring system:

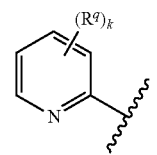
D-1

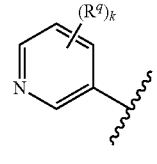
D-2

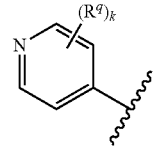
D-3

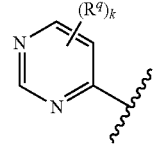
D-5

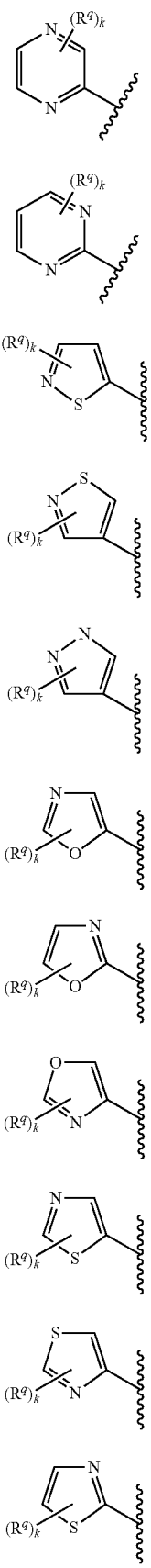

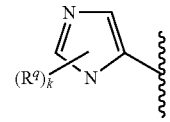
D-6

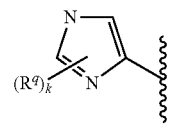
D-7

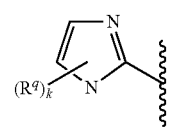
D-16

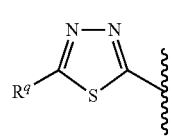
D-17

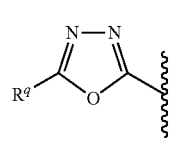
D-20

D-22

D-23

D-24

D-25

D-26

D-27

D-28

D-29

D-30

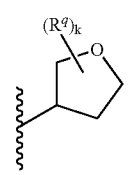
D-35

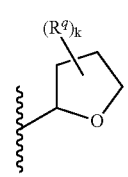
D-36

D-54

D-55

$R^a$ is hydrogen, cyano, $C_1$-$C_6$-alkyl which is unsubstituted or substituted with one or more radicals $R^c$, $C_3$-$C_6$-cycloalkyl which is unsubstituted or substituted with one or more radicals $R^c$, $C_2$-$C_6$-alkenyl which is unsubstituted or substituted with one or more radicals $R^c$, $C_2$-$C_6$-alkynyl which is unsubstituted or substituted with one or more radicals $R^c$,
—C(=O)$R^e$, —C(=O)O$R^g$, —C(=O)N($R^d$)$_2$, —C(=S)$R^e$, —C(=S)N($R^d$)$_2$, —C(=N$R^d$)$R^e$;

each $R^b$ is independently halogen, cyano, azido, nitro, SCN, SF$_5$, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals are unsubstituted or substituted with one or more $R^c$, Si($R^f$)$_3$, S$R^g$, OS(O)$_n$$R^h$, —S(O)$_n$$R^h$, S(O)$_n$N($R^d$)$_2$, N($R^d$)$_2$, C(=O)$R^e$, C(=O)O$R^g$, —C(=N$R^d$)$_2$, C(=O)N($R^d$)$_2$, C(=S)N($R^d$)$_2$; or Q$^2$;

each $R^c$ is independently hydrogen, halogen, cyano, nitro, OH, SH, SCN, SF$_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals are unsubstituted, partially or fully halogenated and/or substituted with (=O) and/or carries 1 or 2 radicals selected from $C_1$-$C_4$ alkoxy; or is $Q^5$; or two $R^c$ present on the same carbon atom are together =O, =CH($C_1$-$C_4$), =C($C_1$-$C_4$-alkyl)$C_1$-$C_4$-alkyl, =N($C_1$-$C_6$-alkyl) or =NO($C_1$-$C_6$-alkyl);

each $R^d$, $R^e$ is independently hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals are unsubstituted, partially or fully halogenated and/or carries 1 or 2 radicals selected from $C_1$-$C_4$-alkoxy, $Q^5$; or two $R^d$ are together a $C_2$-$C_6$ alkylene chain forming a 3- to 7-membered saturated, partly saturated or unsaturated ring together with the nitrogen atom they are bonded to, wherein the alkylene chain may contain 1 or 2 heteroatoms selected from the group consisting of oxygen, sulfur and nitrogen, and is unsubstituted or substituted with halogen, $C_1$-$C_4$-haloalkyl, $C_1$-$C_4$-alkoxy and/or $C_1$-$C_4$-haloalkoxy, wherein the nitrogen and/or the sulfur atom(s) of the heterocyclic ring is optionally oxidized;

each $R^e$, $R^f$ is independently $C_1$-$C_6$ alkyl or phenyl;

each $R^g$ is independently H, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from the group consisting of $C_1$-$C_4$ alkoxy, phenyl, benzyl, pyridyl, and phenoxy, wherein the last four radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^h$ is independently $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_2$-$C_6$-alkenyl, $C_2$-$C_6$-alkynyl, $C_3$-$C_8$-cycloalkyl, wherein the four last mentioned radicals are unsubstituted, partially or fully halogenated and/or oxygenated and/or carry 1 or 2 radicals selected from $C_1$-$C_4$ alkoxy,
phenyl, benzyl, pyridyl, or phenoxy, wherein the last four radicals are unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

each $R^i$ is independently hydrogen, halogen, cyano, $C_1$-$C_6$-alkoxy, $C_1$-$C_6$-haloalkoxy, $C_1$-$C_6$-alkylthio, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals are unsubstituted, partially or fully halogenated and/or oxygenated and/or carry 1 or 2 radicals selected from $C_1$-$C_4$-alkoxy,
phenyl, benzyl, pyridyl, or phenoxy, wherein the four last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy) and ($C_1$-$C_6$-alkoxy)carbonyl; or two $R^i$ present together on one atom of a partly saturated atom are =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or two $R^i$ on two adjacent carbon atoms are together a $C_2$-$C_6$ alkylene chain which forms together with the carbon atom they are bonded to a 3-, 4-, 5-, 6- or 7-membered saturated, partly saturated or unsaturated aromatic, wherein the alkylene chain may contain 1 or 2 heteroatoms selected from oxygen, sulfur and nitrogen, and is unsubstituted or substituted with halogen, $C_1$-$C_4$-haloalkyl, $C_1$-$C_4$-alkoxy and/or $C_1$-$C_4$-haloalkoxy, and wherein the nitrogen and/or the sulfur atom(s) of the heterocyclic ring are optionally oxidized;

each m is independently 1 or 2;
each n is independently 0, 1 or 2; and
each p is independently 0, 1, 2, 3 or 4; and
$Q^4$ and $Q^5$ have the meaning given above.

11. The compound of claim 1, wherein
$Y^1$, $Y^2$ are O;
$R^A$ is H, $CH_3$, $C_2H_5$, benzyl or phenyl;
$R^B$ is H or ($C_1$-$C_6$)-alkyl;
$R^1$ is H, CN, nitro, $C_1$-$C_{10}$-alkyl which is unsubstituted or substituted with one or more radicals $R^c$, $C_3$-$C_8$-cycloalkyl which is unsubstituted or substituted with one or more radicals $R^c$, $C_2$-$C_{10}$-alkenyl which is unsubstituted or substituted with one or more radicals $R^c$, $C_2$-$C_{10}$-alkynyl which is unsubstituted or substituted with one or more radicals $R^c$,
—N($R^d$)$_2$, —N($R^d$)C(=O)$R^e$, —Si($R^f$)$_3$, —O$R^g$, —S$R^g$, —S(O)$_n$$R^h$,
—S(O)$_n$N($R^d$)$_2$, —C(=O)$R^e$, —C(=O)O$R^g$, —C(=O)N($R^d$)$_2$, —C(=S)$R^d$,
—C(=S)O$R^h$, —C(=S)N($R^d$)$R^e$, —C(=N$R^d$)$R^e$;
with the proviso that $R^1$ is not —O$R^g$, CN or nitro if Z is O;
$R^2$ is $NR^iR^k$, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, O-$Q^4$ or S-$Q^4$;
$R^3$ and $R^4$ together with the nitrogen and carbon atom to which they are bound, form any of the following substituted heterocyclic ring systems E-1 E-2, E-3 or E-9:

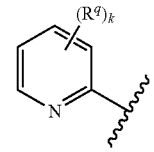

D-1

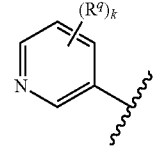

D-2

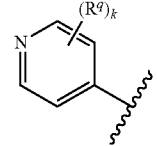

D-3

-continued

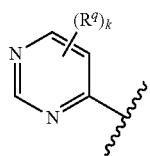
D-5

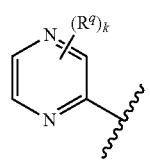
D-6

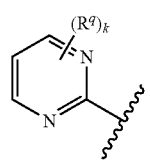
D-7

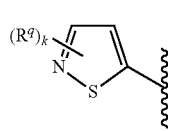
D-16

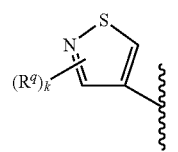
D-17

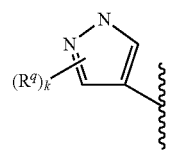
D-20

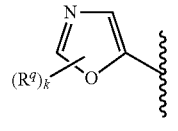
D-22

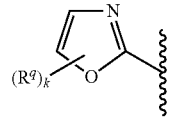
D-23

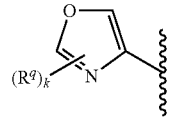
D-24

$R^5$ is $CR^{5a}R^{5b}R^{5c}$ $R^{5a}$ is hydrogen, fluoro, chloro, cyano or methyl;

$R^{5b}$ is hydrogen;

$R^{5c}$ is a substituted heterocyclic ring system:

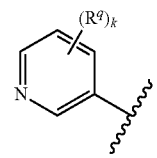
D-2

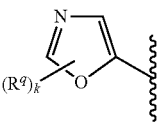
D-22

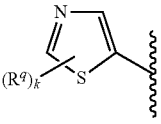
D-25

D-28

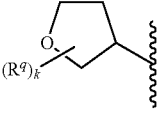
D-54

$R^a$ is hydrogen, $C_1$-$C_6$-alkyl which may be partially or fully halogenated, $C_3$-$C_6$-cycloalkyl which is unsubstituted or partially or fully halogenated, $C_2$-$C_6$-alkenyl which is unsubstituted or partially or fully halogenated, $C_2$-$C_6$-alkynyl which is unsubstituted or partially or fully halogenated, —C(=O)$R^e$, —C(=O)O$R^g$, —C(=O)N($R^d$)$_2$, —C(=S)$R^e$ or —C(=S)N($R^d$)$_2$;

each $R^b$ is independently H, CN, nitro, SCN, $C_1$-$C_6$-alkyl, $C_3$-$C_6$-cycloalkyl, $C_2$-$C_6$-alkenyl, $C_2$-$C_6$-alkynyl, wherein the carbon atoms of the aforementioned aliphatic and cyclo-aliphatic radicals are unsubstituted or partially or fully halogenated, O$R^g$, OS(O)$_n$$R^h$, —S(O)$_n$$R^h$, S(O)$_n$N($R^d$)$_2$, C(=O)$R^e$, C(=O)O$R^g$, C(=O)N($R^d$)$_2$ or C(=S)N($R^d$)$_2$.

12. The compound of claim 1, wherein $Y^1$, $Y^2$ is O;

$R^A$ is H or CH$_3$;

$R^B$ is H;

$R^1$ is H, CN, nitro, $C_1$-$C_6$-alkyl which is unsubstituted or substituted with one or more radicals $R^c$, $C_3$-$C_6$-cycloalkyl which is unsubstituted or substituted with one or more radicals $R^c$, $C_2$-$C_6$-alkenyl which is unsubstituted or substituted with one or more radicals $R^c$, $C_2$-$C_6$-alkynyl which is unsubstituted or substituted with one or more radicals $R^c$, —N($R^d$)$_2$, —N($R^d$)C(=O)$R^e$, —S(O)$_m$$R^h$, —S(O)$_n$N($R^d$)$_2$, —C(=O)$R^e$, —C(=O)O$R^g$, —C(=O)N($R^d$)$_2$, —C(=S)$R^e$, —C(=S)N($R^d$)$_2$;

$R^2$ is N$R^i$$R^k$, $R^3$ and $R^4$ together with the nitrogen and carbon atom to which they are bonded, form any of the following substituted heterocyclic ring systems E-1 E-2, E-3 or E-8:

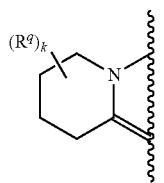 E-1

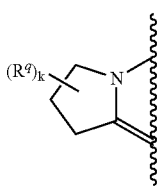 E-2

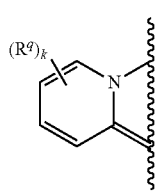 E-3

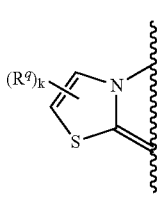 E-8

$R^5$ is $CR^{5a}R^{5b}R^{5c}$
$R^{5a}$ is hydrogen or methyl;
$R^{5b}$ is hydrogen;
$R^{5c}$ is a substituted heterocyclic ring system D-2a, D-25a or D-54a:

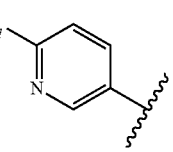 D-2a

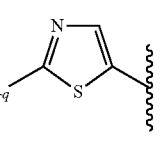 D-25a

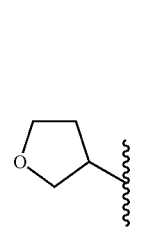 D-54a $R^a$ is hydrogen, $C_1$-$C_6$-alkyl which may be partially or fully halogenated, —C(=O)R$^e$, —C(=O)OR$^g$ or —C(=O)N(R$^d$)$_2$;
each $R^b$ is independently hydrogen, halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl or $C_1$-$C_6$-haloalkylthio;
each $R^q$ is independently H, fluoro, chloro, bromo, CN, methyl, trifluoromethyl, methoxy, difluoromethoxy, trifluoromethoxy, thiomethoxy or trifluorothiomethoxy.

13. The compound of claim 1 of formulae (I-13)-(I-18),

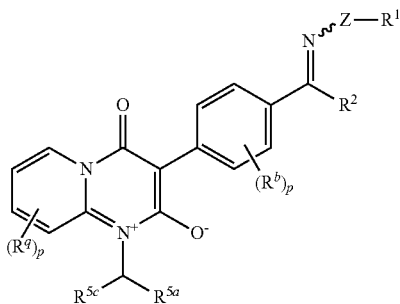 (I-13)

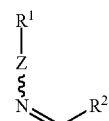 (I-14)

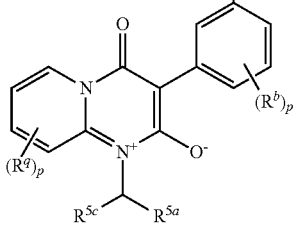 (I-15)

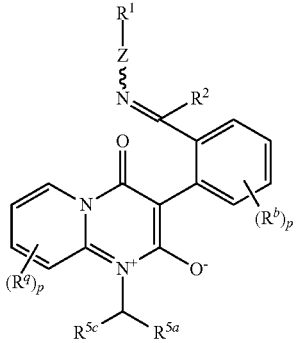 (I-16)

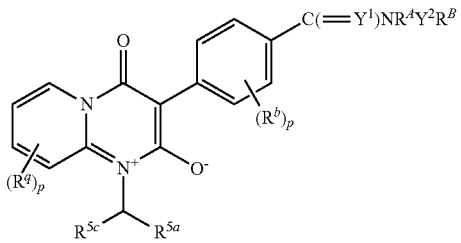

-continued

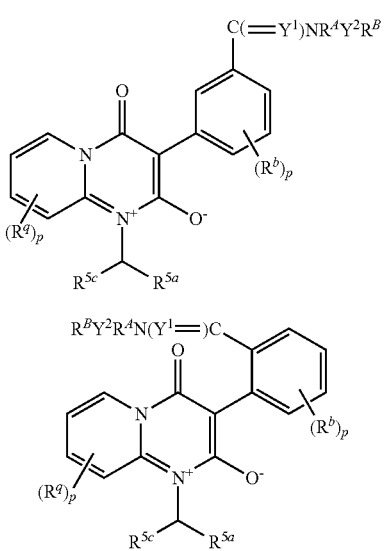

(I-17)

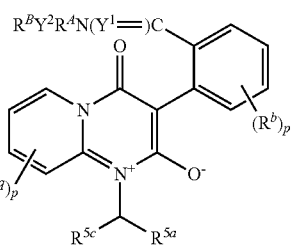

(I-18)

wherein
Y$^1$, Y$^2$ are independently O or S;
R$^A$R$^B$ are independently H, (C$_1$-C$_6$)-alkyl, benzyl or phenyl;
R$^1$ is hydrogen, cyano, nitro, C$_1$-C$_6$-alkyl which may be partially or fully halogenated and/or is unsubstituted or substituted with one or more radicals R$^c$, C$_3$-C$_6$-cycloalkyl which may be partially or fully halogenated and/or is unsubstituted or substituted with one or more radicals Re, C$_2$-C$_6$-alkenyl which may be partially or fully halogenated and/or is unsubstituted or substituted with one or more radicals R$^c$, C$_2$-C$_6$-alkynyl which may be partially or fully halogenated and/or is unsubstituted or substituted with one or more radicals R$^e$,
—N(R$^d$)$_2$, —N(R$^d$)C(=O)R$^e$, —S(O)$_m$R$^h$, —S(O)$_n$N(R$^d$)$_2$, —C(=O)R$^e$, —C(=O)OR$^h$, —C(=O)N(R$^d$)$_2$, —C(=S)R$^e$, —C(=S)N(R$^d$)$_2$;
R$^2$ is NR$^i$R$^k$;
R$^{5a}$ is hydrogen or methyl;
R$^{5c}$ is a substituted heterocyclic ring system D-2a, D-25a or D-54a;
R$^a$ is hydrogen or C$_1$-C$_4$-alkyl;
each R$^b$ is independently hydrogen, halogen, cyano, nitro, methyl, trifluoromethyl, methoxy, difluoromethoxy, trifluoromethoxy, thiomethoxy or trifluorothiomethoxy;
each R$^c$ is independently H, C$_1$-C$_6$-alkyl, C$_2$-C$_6$-alkenyl, C$_2$-C$_6$-alkynyl, C$_3$-C$_6$-cycloalkyl, wherein the four last mentioned aliphatic and cyclo-aliphatic radicals are unsubstituted or partially or fully halogenated, phenyl, benzyl, pyridyl, wherein the last three radicals are unsubstituted or partially or fully halogenated;
each R$^h$ is independently C$_1$-C$_6$-alkyl, C$_2$-C$_6$-alkenyl, C$_2$-C$_6$-alkynyl, C$_3$-C$_6$-cycloalkyl, wherein the four last mentioned aliphatic and cyclo-aliphatic radicals are unsubstituted or partially or fully halogenated, phenyl, benzyl, pyridyl, wherein the last three radicals may be unsubstituted, partially or fully halogenated;
each R$^d$ is independently hydrogen, cyano, C$_1$-C$_6$-alkoxy, C$_1$-C$_6$-haloalkoxy, C$_1$-C$_6$-alkylthio, C$_1$-C$_6$-haloalkylthio;
benzyl, C$_1$-C$_6$-alkyl, C$_2$-C$_6$-alkenyl, C$_2$-C$_6$-alkynyl, C$_3$-C$_6$-cycloalkyl, wherein the four last mentioned aliphatic and cyclo-aliphatic radicals may be unsubstituted, partially or fully halogenated;
each R$^q$ is independently hydrogen, fluoro, chloro, bromo, methyl or trifluoromethyl.

14. An agricultural and/or veterinary composition comprising at least one compound of claim 1.

15. A method of combating animal pests which comprises contacting at least one of the group consisting of animal pests, their habitat, breeding ground, food supply, plant, seed, soil, area, material or environment in which the animal pests are growing or may grow, and materials, plants, seeds, soils, surfaces or spaces to be protected from pest attack or infestation with a pesticidally effective amount of at least one compound of claim 1.

16. A method for protecting crops from attack or infestation by animal pests, which comprises contacting the crop with a pesticidally effective amount of at least one compound of claim 1.

17. A method for the protection of seeds from soil insects and of the seedlings' roots and shoots from soil and foliar insects comprising contacting the seeds before sowing and/or after pregermination with at least one compound of claim 1.

18. Seeds treated with at least one compound of claim 1.

19. A method for treating or protecting animals against infestation or infection by parasites which comprises orally, topically or parenterally administering or applying to the animals a parasitically effective amount of at least one compound of claim 1.

20. A process for the preparation of a composition for treating or protecting animals against infestation or infection by parasites which comprises mixing a parasitically effective amount of at least one compound of claim 1 and an acceptable carrier.

* * * * *